(12) United States Patent
Frandsen et al.

(10) Patent No.: US 10,519,460 B2
(45) Date of Patent: Dec. 31, 2019

(54) USE OF HETEROLOGOUS EXPRESSED POLYKETIDE SYNTHASE AND SMALL MOLECULE FOLDASES TO MAKE AROMATIC AND CYCLIC COMPOUNDS

(71) Applicants: DANMARKS TEKNISKE UNIVERSITET, Kgs. Lyngby (DK); KØBENHAVNS UNIVERSITET, Copenhagen K (DK); CHR, HANSEN NATURAL COLORS A/S, Hoersholm (DK)

(72) Inventors: Rasmus John Normand Frandsen, Allerød (DK); Uffe Hasbro Mortensen, Copenhagen N (DK); Hilde Cornelijne Coumou, Altendorf (CH); Rubini Maya Kannangara, Frederiksberg (DK); Bjørn Madsen, Helsingør (DK); Majse Nafisi, Vanløse (DK); Johan Andersen-Ranberg, Copenhagen N (DK); Kenneth Thermann Kongstad, Copenhagen V (DK); Finn Thyge Okkels, Roskilde (DK); Paiman Khorsand-Jamal, Kgs. Lyngby (DK); Dan Stærk, Lynge (DK); Birger Lindberg Møller, Brønshøj (DK)

(73) Assignees: DANMARKS TENISKE UNIVESITET, Kgs. Lyngby (DK); KØBENHAVNS UNIVERSITET, Copenhagen (DK); CHR. HANSEN NATURAL COLORS A/S, Hoersholm (DK)

( * ) Notice: Subject to any disclaimer, the term of this patent is extended or adjusted under 35 U.S.C. 154(b) by 58 days.

(21) Appl. No.: 15/735,023

(22) PCT Filed: Jun. 10, 2016

(86) PCT No.: PCT/EP2016/063331
§ 371 (c)(1),
(2) Date: Dec. 8, 2017

(87) PCT Pub. No.: WO2016/198623
PCT Pub. Date: Dec. 15, 2016

(65) Prior Publication Data
US 2018/0305709 A1    Oct. 25, 2018

(30) Foreign Application Priority Data
Jun. 10, 2015  (EP) .................................. 15171430

(51) Int. Cl.
| C12N 15/52 | (2006.01) |
| C12P 7/22 | (2006.01) |
| C12N 15/82 | (2006.01) |
| C12N 9/00 | (2006.01) |
| C12P 5/00 | (2006.01) |
| C40B 50/06 | (2006.01) |

(52) U.S. Cl.
CPC .......... *C12N 15/8257* (2013.01); *C12N 9/93* (2013.01); *C12P 5/005* (2013.01); *C12Y 203/01* (2013.01); *C12Y 604/00* (2013.01); *C40B 50/06* (2013.01)

(58) Field of Classification Search
CPC ............ C07K 4/415; C12N 15/52; C12P 7/22
See application file for complete search history.

(56) References Cited

U.S. PATENT DOCUMENTS

2012/0034661 A1*   2/2012   Stephanopoulos .. C12N 9/1029
                                                  435/125

OTHER PUBLICATIONS

Park et al. 2009; Engineering of plant-specific phenylpropanoids biosynthesis in Steptomyces venezuilae. J. Biotechnol. 141:181-188.*
Abdel-Rahman et al; "In vitro formation of the anthranoid scaffold by cell-fee extracts from yeast-extract-treated Cassia bicapsularis cell cultures". Phytochemistry, vol. 88, Feb. 8, 2013, pp. 15-24.
Ames et al; "Structural and biochemical characterization of zhul aromatase/cyclase from the R1128 polyketide pathway". Biochemistry, vol. 50, Aug. 26, 2011, pp. 8392-8406.
Gagne et al; "Identification of olivetolic acid cyclase from Cannabis sativa reveals a unique catalytic route to plant polyketides". Proceedings of the National Academy of Sciences, vol. 109, No. 31, Jul. 31, 2012, pp. 12811-12816.
Go et al; "Synthetic polyketide enzymology: Platform for biosynthesis of antimicrobial polyketides". ACS Catalysis, vol. 5, May 27, 2015, pp. 4033-4042.
Hashimoto et al; "Fungal type III polyketide synthases". Natural Product Reports, vol. 31, 2014, pp. 1306-1317.
Jadhav et al; "Polyketide synthesis in tobacco plants transformed with a Plumbago zeylanica type III hexaketide synthase". Phytochemistry, vol. 98, 2014, pp. 92-100.
Jorgensen et al; "Fusarium graminearum PKS14 is involved in orsellinic acid and orcinol synthesis". Fungal Genetics and Biology, vol. 70, Jul. 8, 2014, pp. 24-31.
Karppinen et al; "Octaketide-producing type III polyketide synthase from Hypericum perforatum is expressed in dark glands accumulating hypericins". The Febs Journal, vol. 275, 2008, pp. 4329-4342.

(Continued)

*Primary Examiner* — Karen Cochrane Carlson
(74) *Attorney, Agent, or Firm* — Casimir Jones, S.C.; Lisa V. Mueller

(57) ABSTRACT

A method for producing individual or libraries of tri- to pentadecaketide-derived aromatic compounds of interest by heterologous expression of polyketide synthase and aromatase/cyclase in a recombinant host cell.

Figure 5:
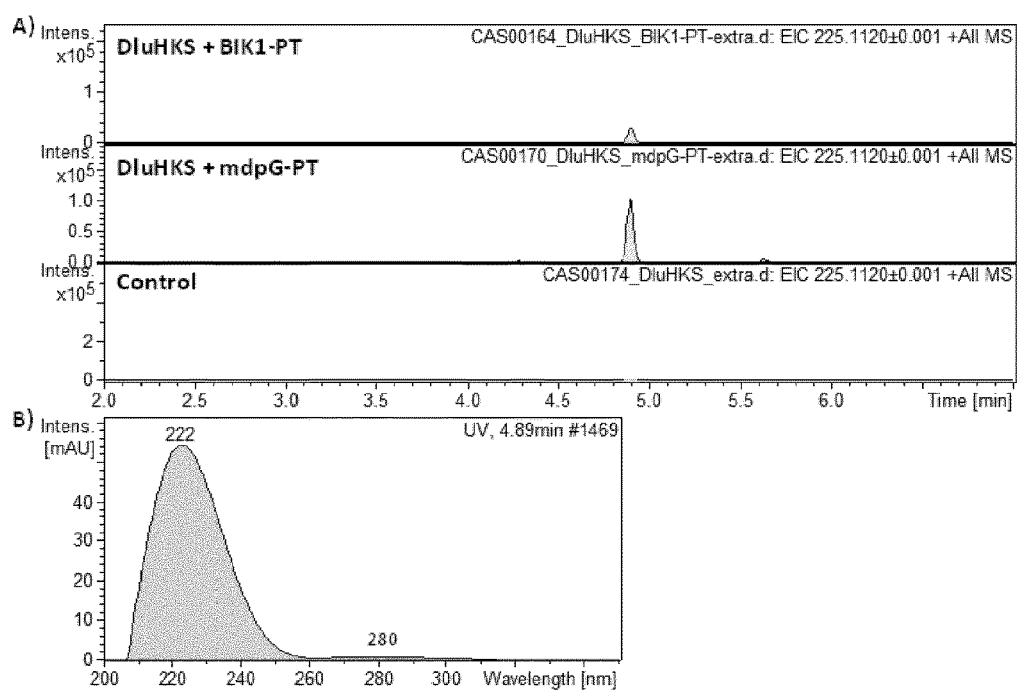

16 Claims, 15 Drawing Sheets
Specification includes a Sequence Listing.

(56) References Cited

OTHER PUBLICATIONS

Poseth, Sarah Elizabeth Cyclization modes in type III polyketide synthases and the synthetic compounds used as probes for mechanistic studies:. University of Regina, Saskatchewan Thesis, 2012, pp. Cover p. + i-Xii+1-88.

Vagstad et al; "Characterization of a Fungal Thioesterase Having Claisen Cyclase and Deacetylase Activities in Melanin Biosynthesis". Chemistry & Biology, vol. 19, 2012, pp. 1525-1534.

Yang et al; "Biosynthesis of phloroglucinol compounds in microorganisms-review". Applied Microbiology and Biotechnology, vol. 93, 2012, pp. 487-495.

Yu et al; "Type III polyketide synthases in natural product biosynthesis". IUBMB Life, vol. 53, 2012, pp. 285-295.

Zhang et al; "Investigation of early tailoring reactions in the oxytetracycline biosynthetic pathway". The Journal of Biological Chemistry, vol. 282, Aug. 31, 2007, pp. 25717-25725.

Zhang et al; "Synthesis of unnatural small molecules by plant specific polyketide synthases". Chinese Journal of Organic Chemistry, vol. 33, 2013, pp. 2469-2484.

Zhou et al; "Cyclization of aromatic polyketides from bacteria and fungi". Natural Product Reports, vol. 27, 2014, pp. 839-868.

Bach, S.S. et al; High-Throughput Testing of Terpenoid Biosynthesis CAndidate Genes Using Transient Expression in Nicotiana benthamiana; Manuel Rodriguez-Conceoción (ed.);Plant Isoprenoids, Methods in Molecular Biology, vol. 1153; 2014.

Sainsbury, F. et al.; pEAQ: versatile expression vectors for easy and quick transient expression of heterologous proteins in plants; Plant Biotechnology Journal, 2009, 7, pp. 682-693.

\* cited by examiner

Figure 1

Figure 2 A    Triacetric lactone (TAL)
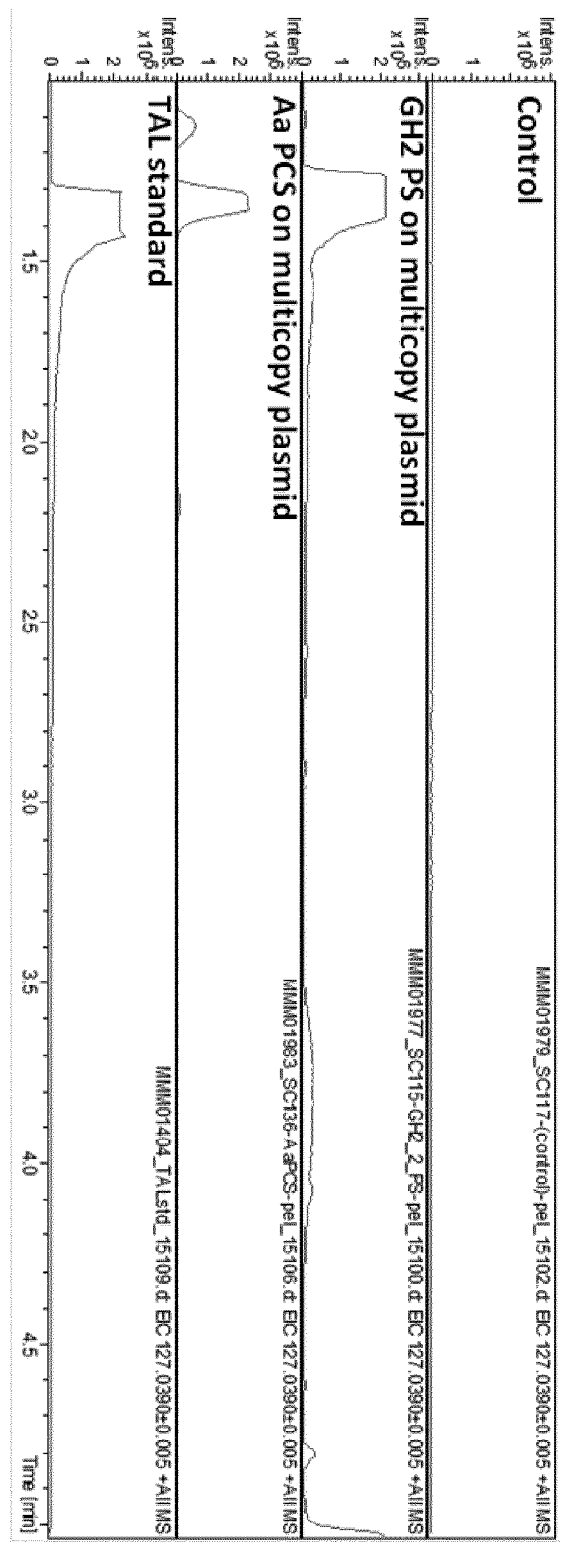

Figure 2 B 5,7-dihydroxy-2-methylchromone (pentaketidepyrone)
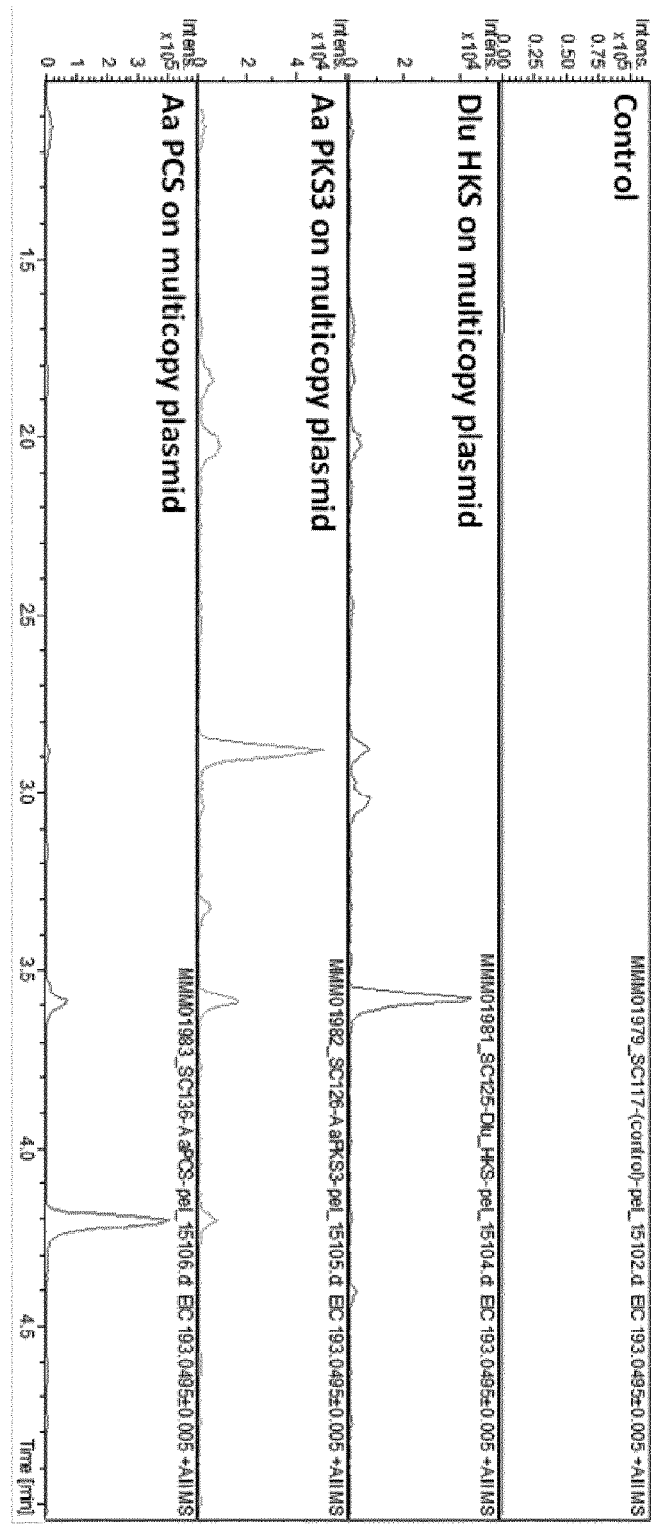

Figure 2 C  6-(2',4'-dihydroxy-6'-methylpheynyl)-4-hydroxy-2-pyrone (hexaketidepyrone)
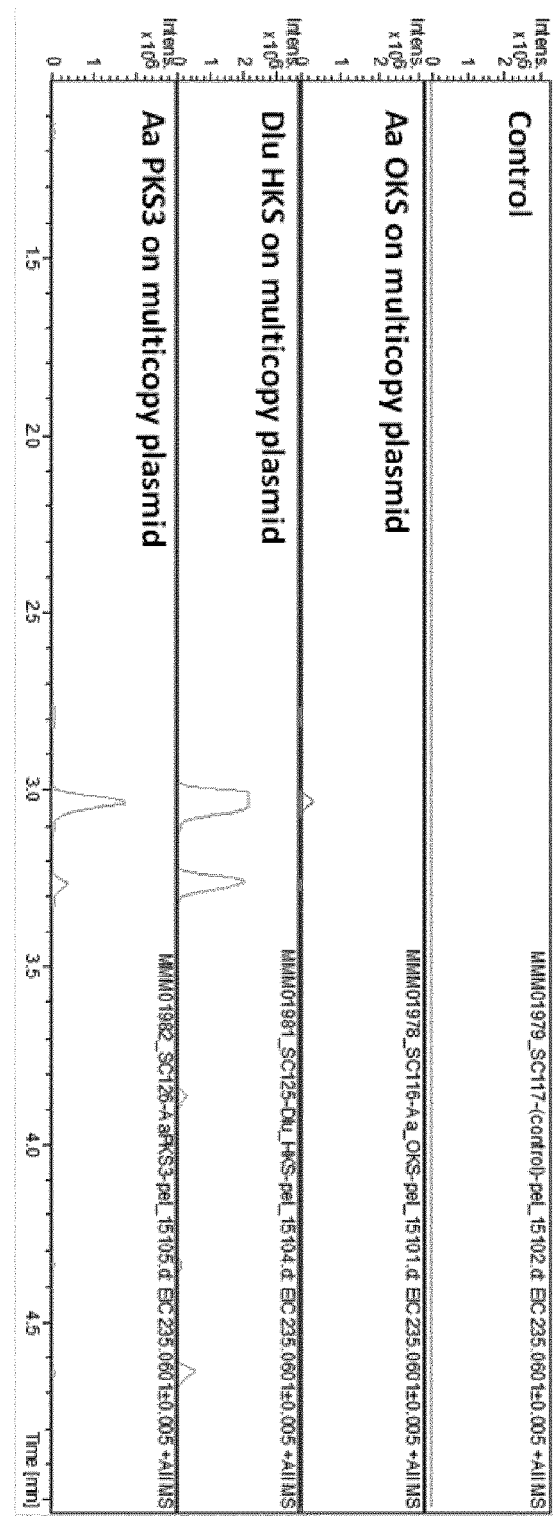

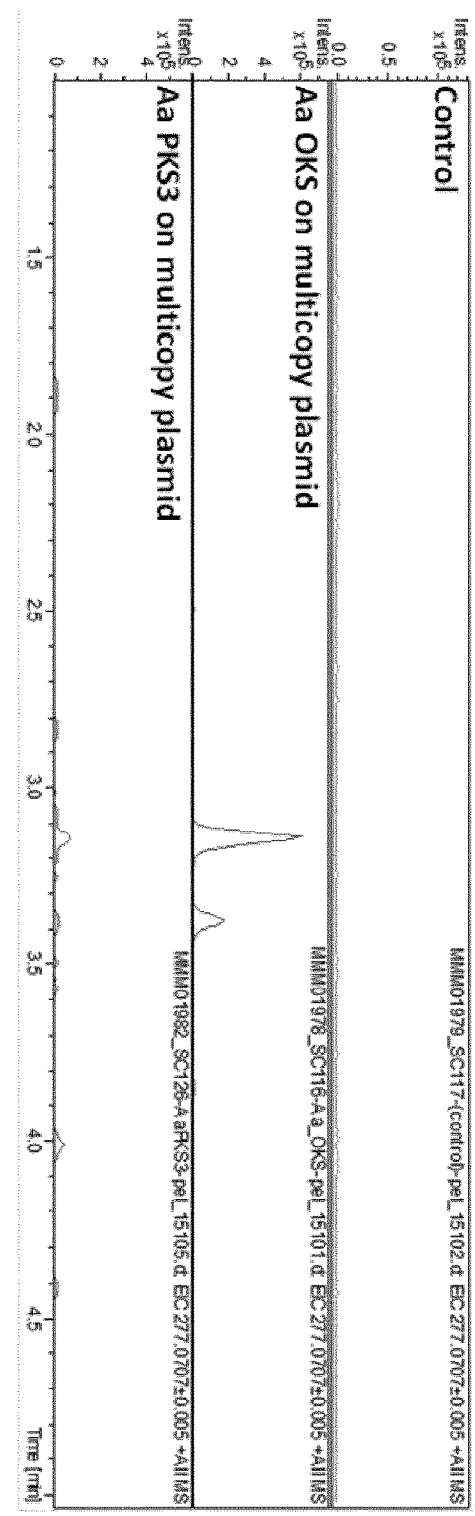
Figure 3 A  Heptaketide pyrone or TW93a

Figure 3 B  Aloesone
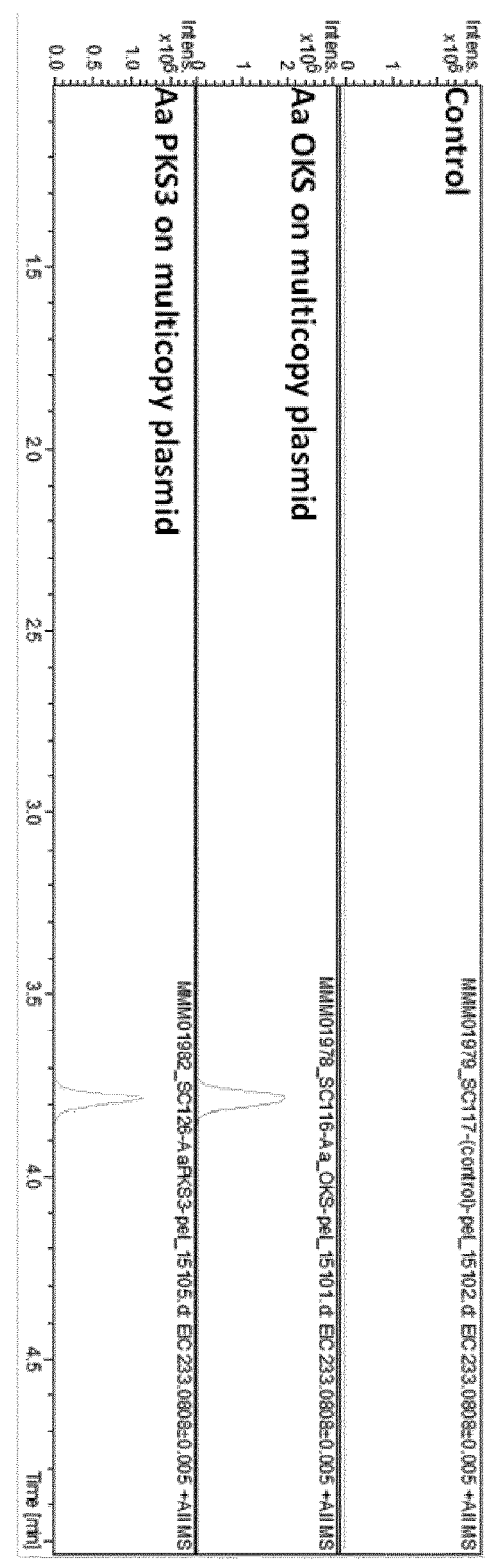

Figure 3 C  SEK4/SEK4b
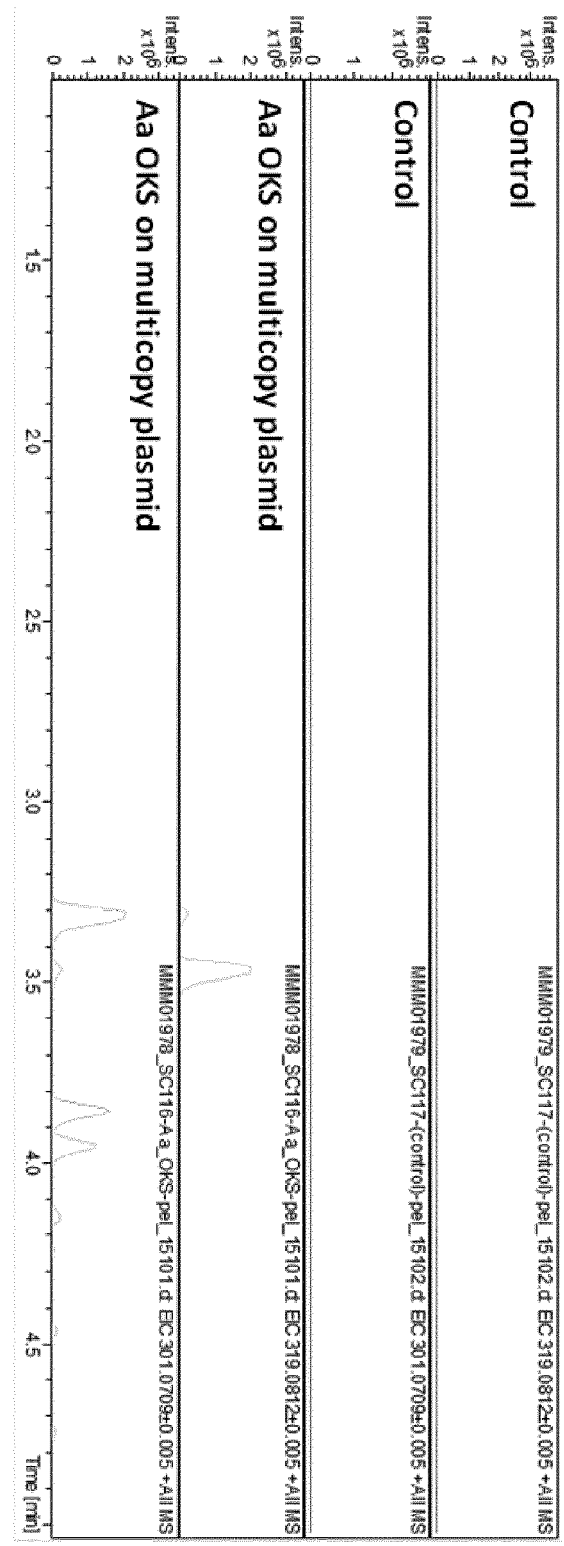

Figure 4

| | None | Cyclase α | Cyclase β | Cyclase χ | ... | Cyclase_n |
|---|---|---|---|---|---|---|
| PKS4 + Cyc1 | | | | | | |
| PKS4 + Cyc2 | | | | | | |
| PKS4 + Cyc3 | | | | | | |
| PKS4 + Cyc4 | | None | | | | |
| PKS4 + Cyc5 | | | | | | |
| ... | | | | | | |
| PKS_n | | | | | | |

Figure 11
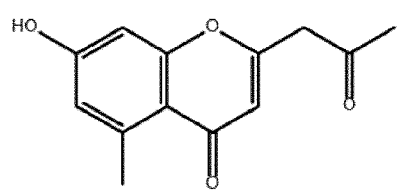
Aloesone
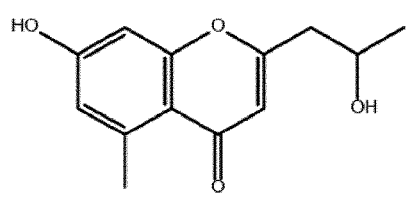
Aloesol
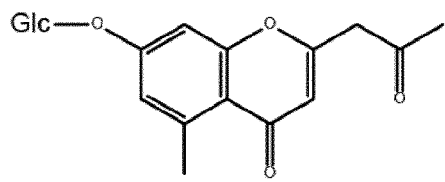
Aloesone-O-glc
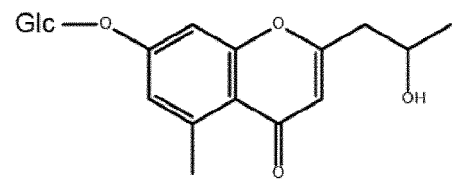
Aloesol-O-glc

USE OF HETEROLOGOUS EXPRESSED POLYKETIDE SYNTHASE AND SMALL MOLECULE FOLDASES TO MAKE AROMATIC AND CYCLIC COMPOUNDS

CROSS REFERENCE TO RELATED APPLICATIONS

This application is a U.S. National Phase Application under 35 U.S.C. 371 of International Application No. PCT/EP2016/063331 filed on Jun. 10, 2016 and published in English as WO 2016/198623 A1 on Dec. 15, 2016. This application is based on and claims the benefit of priority from European Patent Application No. 15171430.0 filed Jun. 10, 2015. The entire disclosures of all of the above applications are incorporated herein by reference.

FIELD OF THE INVENTION

The present invention relates to a method for producing individual and libraries of tri- to pentadecaketide derived aromatic and cyclic compounds of interest by heterologous expression of a polyketide synthase and one or more aromatases/cyclases in a recombinant host cell.

BACKGROUND OF THE INVENTION

Small molecules, of biological origin, often include aromatic or cyclic groups that impact their physiochemical and biological properties. Although nature is rich in aromatic compounds with different carbon skeletons, there is an urgent need for biosynthetic systems capable of producing both natural and new-to-nature aromatic compounds. Areas of specific interest are the formation of carbon skeletons that can be used medicinally (e.g. new antibiotics), or as chemical substitutes, or as food ingredients, or as precursors for the formation of more complex compounds. Among the top 100 drugs developed, 60% are small molecules (excluding proteins), and of these 82% possess aromatic motifs. Complex aromatic compounds are produced via many different biosynthetic pathways in nature, either as part of primary or secondary metabolism. One of the most versatile biosynthetic schemes for producing aromatic compounds is via the non-reducing polyketide pathways, wherein two-carbon units (—$CH_2$—CO—), referred to as ketides or 'ketide units', are polymerized into linear chains called polyketides, which subsequently can fold into aromatic structures. The formation of polyketides is dependent on an enzymes class known as polyketide synthases (PKSs).

Polyketides are synthesized by a group of enzymes which commonly is referred to as polyketide synthases (PKS). All PKSs share the ability to catalyze Claisen condensation based fusion of acyl groups by the formation of carbon-carbon bonds coupled with the release of carbon dioxide. This reaction is catalyzed by a beta-ketosynthase domain (KS). In addition to this domain/active site, synthesis can also depend on, but not exclusively, the action of Acyl-Carrier-Protein (ACP), Acyl-transferase (AT), Starter-Acyl-Transferase (SAT), Product Template (PT), ThioEsterase (TE), Chain Length Factor (CLF, also known as KSβ), CLaisen CYClase (CL-CYC), Ketoreductase (KR), DeHydratase (DH), Enoyl Reductase (ER) and C-METhyl transferase (Cmet). The substrates for polyketide synthesis are typically classified into starter and extender units, where the starter unit, e.g. but not exclusively, acetyl-CoA is the first added unit of the growing polyketide chain; and extender units, e.g. but not exclusively, malonyl-CoAs are all subsequently added carbon-carbon units. If the substrate is the standard starter (acetyl-CoA) and extender (malonyl-CoA) units, then the number of carbon atoms in the resulting polyketide chain will equal two times the number of iterations/'condensation reactions', performed by the PKS enzyme. Thus, a heptaketide synthase will perform six condensation reactions joining one starter unit (two carbons) with six extender units (six times two carbons), resulting in a polyketide consisting of seven ketide units, made up of a total of fourteen carbon atoms. However, PKSs may use alternative starter and extender units which can alter the number of carbon atoms in the final product, for example a heptaketide synthase could use p-coumarin acid (nine carbons) as a starter unit and six methyl-malonyl-CoA (six times three carbons) as extender units resulting in a heptaketide with twenty-seven carbon atoms. Each individual PKS, e.g. a heptaketide synthase, displays a different affinity for different starter and extender units, and can hence produce very different compounds which all will be categorized as heptaketides. The substrate availability in the host cell can also affect which product a given PKS produces as its preferred substrate may only be available in very limited amounts, or not at all, compared to less preferred substrates which then will outcompete the preferred substrate.

The chain length of the polyketide product is thus the result of the number of condensation reactions the PKS performs, which covalently joins one starter unit with one or more extender units together in a head-to-tail manner. A PKS that performs one iteration/condensation will produce a diketide, one that performs two iterations/condensations will produce a triketide, one that performs three iterations/condensations will produce a tetraketide, and so forth. The number of carbon atoms in the resulting polyketides will in addition be the result of which starter and extender units the enzyme utilize.

At the primary sequence level (amino acid sequence), secondary structure level (local fold), tertiary structure level (all over fold) and quaternary structure level (protein-protein interactions) the PKSs display a very large diversity, and are hence subdivided into different types.

Type I PKS systems are typically found in filamentous fungi and bacteria, where they are responsible for both the formation of aromatic, polyaromatic and reduced polyketides. Members of the type I PKS possess several active sites on the same polypeptide chain and the individual enzyme is able to catalyze the repeated condensation of two-carbon units. The minimal set of domains in type I PKS includes KS, AT and ACP. The type I PKSs are further subdivided into modular PKSs and iterative PKSs, where iterative PKSs only possess a single copy of each active site type and re-use these repeatedly until the growing polyketide chain has reached its predetermined length. Type I iterative PKSs that forms aromatic and polyaromatic compounds typically rely on endogenous PT and CL-CYC domains to direct folding of the formed non-reduced polyketide chain. Dissected PT domains have been shown to work in trans with heterologous KS-AT-ACP fragments from the type I iterative PKSs to form folded polyketide products. The PT domains typically promote the formation of several intramolecular bonds. Modular PKSs contain several copies of the same active sites, these are organized into repeated sequences of active sites which are called modules, each module is responsible for adding and modifying a single ketide unit. Each active site in the individual modules is only used once during synthesis of a single polyketide. Type I iterative PKS are typically found in fungi, while type I modular PKSs are typically found in bacteria.

Type I modular PKSs that form macrolide (macrocyclic) compounds includes a terminal CL-CYC domain.

Type II PKS systems are responsible for formation of aromatic and polyaromatic compounds in bacteria. Type II PKSs are protein complexes where individual enzymes interact transiently to form the functional PKS enzyme. The involved enzymes include activities for KS, CLF and ACP. Type II PKSs forms linear non-reduced polyketides that spontaneously folds into aromatic/cyclic compounds via the formation of intra-molecular carbon-carbon and carbon-oxygen bonds.

Types I modular (Im), type I iterative (Ii) and type II (II) are all dependent on an ACP domain(s) which is responsible for tethering the growing polyketide (acyl) chain to the enzyme during synthesis. In the ACP-dependent PKS types, the acyl group is transferred from the incoming Co-enzyme A (CoA) to the ACP domain and is subsequently condensed with another acyl group bound to the KS domain of the enzyme, resulting in a diketide bound to the ACP domain. The formed diketide is subsequently moved back to the KS domain and another ACP bound extender unit, is loaded into the enzyme.

Type III PKSs generally only consist of a KS domain, referred to as a KASIII or Chalcone synthase domain and they lack an ACP domain. Type III PKSs are self-contained enzymes that form homodimers. Their single active site in each monomer catalyzes the priming and extension reactions iteratively to form polyketide products. Type III PKS from bacteria, plant and fungi have been described. Type III PKSs (also known as Chalcone synthase) have long been known in plants, where they are responsible for formation of compounds such as flavonoids (pigments/anti-oxidants) and stilbenes, which are found in many different plant species. Formation of flavonoids and stilbenes depends on one p-coumaroyl CoA starter unit and three malonyl-CoA extender units. The products of type III PKSs often spontaneously fold into complex aromatic/cyclic compounds, e.g. flavonoids in plants. Type III PKSs that use acetyl/malonyl-CoA as starter unit and malonyl-CoA as extender units resulting in linear non-reduced polyketides have also been described in plants.

Type III enzymes do not have an 'acyl carrier protein' (ACP) functionality, but instead they rely on Co-enzyme A linking for associating the growing polyketide chain with the enzyme during the multiple catalytic cycles. In type III PKSs, the incoming acyl group remains bound to the Co-enzyme A unit, and the condensation between the two acyl groups results in a diketide bound to the incoming Co-enzyme A. The formed diketide is subsequently moved back to the KS domain and another Co-enzyme A bound extender unit, is loaded into the enzyme.

The above described unique functional and corresponding structural properties of the Type I, Type II or Type III PKS allow members of these three enzyme groups to be distinguished.

The subsequent folding and release of the polyketide chain produced by the different classes of PKS enzymes is either spontaneous, or may be catalyzed by several different enzyme families typically referred to as aromatases and/or cyclases, or by domain(s) within the PKS, such as a PT and/or CL-CYC domains. Herein these are collectively referred to as 'small molecule foldases'. This group of enzymes is characterized by catalyzing the regiospecific formation of intra-molecular carbon-carbon or carbon-oxygen bonds within a polyketide, resulting in the formation of aromatic or cyclic motifs. 'Small molecule foldases', acting on polyketides, are found in bacteria, fungi and plants.

Several examples exist where folding of the polyketide is a spontaneous process, e.g. flavonoids in plants. Though 'small molecule foldases' perform similar functions in polyketide biosynthetic pathways they are very different at the primary sequence level, and can hence be categorized based on which structural and primary sequence motifs they contain. The group of 'small molecule foldases' that act on polyketides include enzymes from the 'Cyclase', 'SRPBCC Cyclases/aromatase', 'DABB Cyclase/aromatase', 'Polyketide synthesis cyclase', 'Lactamase_B/MBL fold metallo-hydrolase', ketroreductase from Act cluster and 'Cupin_2' Superfamilies and, in addition, includes dissected PT and CL-CYC domains from type I iterative PKS from filamentous fungi.

Importantly, the Type I, Type II or Type III PKSs are further distinguished by the timing and mechanism by which the formed polyketide chain are folded into complex structures with cyclic and aromatic motifs. In Type I modular PKS, containing a CL-CYC domain, the polyketide chain remains attached to the enzyme's ACP domain, and the CL-CYC domain is both responsible for folding of the chain into a macrolide and its simultaneously release from the ACP domain and thereby also the enzyme. Type I iterative PKSs contain a PT domain and/or CL-CYC domain, that catalyse the cyclization reactions and formation of aromatic groups in the polyketide chain. The PT domain acts on the polyketide that is bound to enzyme's ACP domain, where the ACP domain influences the docking and positioning of the polyketide substrate into the active site of the PT domain and thereby the chains folding pattern. The CL-CYC domains forms cyclic structures and simultaneously releases the ACP bound product from the enzyme.

In the case of type II PKSs, polyketide folding is a post-PKS enzyme guided and catalyzed process. In this case, the KS/CLF/ACP enzyme complex forms a polyketide chain of a predetermined length, which remains bound to the ACP enzyme while it is folded by aromatase(s) and cyclase(s).

In the case of type III PKSs, the formed linear polyketide chain is released, likely following hydrolysis of the linkage to Co-enzyme A, whereafter the chain undergoes spontaneous folding into a range of sterically stable folds.

SUMMARY OF THE INVENTION

The problem solved by the present invention relates to the provision of a suitable biosynthetic pathway that forms aromatic and cyclic compounds (e.g. $C_6$-$C_{31}$ poly aromatic compounds) and/or libraries of aromatic compounds of interest in vivo.

The present invention is based on experimental results disclosed herein, which demonstrate that in vivo heterologous co-expression of a Type III polyketide synthase (PKSIII) from plants/bacteria/fungi and one or more 'small molecule foldases' from fungi/bacteria, wherein the aromatase/cyclase is from a different genus than the PKSIII, in a recombinant host cell (e.g. a yeast cell or bacterial cell), provides a suitable biosynthetic pathway for the production of aromatic compounds. The in vivo heterologously-expressed PKSIII produces a non-reduced polyketide which is converted in vivo into cyclic or/and aromatic compounds of interest by the action of the one or more heterologously-expressed 'small molecule foldases'.

Recombinant host cells expressing the PKSIII and one or more 'small molecule foldases' collectively form a programmable system for the formation of aromatic compounds, of any desirable length and fold. The natural systems do not offer such flexibility and predictability and the present invention therefore represent a major technological advance compared to existing technologies available for the creation of biosynthetic pathways that are not found in nature. The recombinant host cells may be used in a method to produce specific aromatic and cyclic compounds (e.g. $C_6$-$C_{31}$ poly aromatic compounds) and/or libraries of aromatic compounds of interest in vivo.

Accordingly, a first aspect of the present invention relates to a method of producing a library of polyketide-derived aromatic and/or polyaromatic; cyclic and/or polycyclic compounds; or any combination thereof, wherein the carbon atom chain length of the polyketide backbone of the compounds is selected from two or more of 6, 7, 8, 9, 10, 11, 12, 13, 14, 15, 16, 17, 18, 19, 20, 21, 22, 23, 24, 25, 26, 27, 28, 29, 30 and 31 carbon atoms, comprising the steps of:

a. providing one or more heterogeneous populations of recombinant cells, wherein each cell in the one or more populations comprises:
  i. a transgene encoding a heterologous type III polyketide synthase capable of forming a linear non-reduced polyketide compound, wherein the carbon atom chain length of the polyketide backbone of the formed compound is selected from 8, 9, 10, 11, 12, 13, 14, 15, 16, 17, 18, 19, 20, 21, 22, 23, 24, 25, 26, 27, 28, 29, 30 and 31 carbon atoms; and
  ii. a transgene encoding a first heterologous 'small molecule foldase' enzyme capable of catalyzing the formation of one or more region-specific intramolecular carbon-carbon or carbon-oxygen bonds in a linear non-reduced polyketide compound, wherein the carbon atom chain length of the polyketide backbone of the compound is one or more of 6, 7, 8, 9, 10, 11, 12, 13, 14, 15, 16, 17, 18, 19, 20, 21, 22, 23, 24, 25, 26, 27, 28, 29, 30 and 31 carbon atoms, and
  iii. optionally one or more transgene(s) encoding a second, third and fourth heterologous 'small molecule foldase' enzyme capable of catalyzing the formation of one or more region-specific intramolecular carbon-carbon or carbon-oxygen bonds in a non-linear polyketide,
  wherein each of the first, second, third and fourth heterologous 'small molecule foldase' enzyme is a bacterial or fungal enzyme, and wherein the genus from which said bacterial or fungal enzyme is derived is different from the genus from which the PKSIII enzyme is derived,
  wherein the one or more populations of recombinant cells comprises cells capable of producing polyketide-derived aromatic and/or polyaromatic; cyclic and/or polycyclic compounds; or any combination thereof, wherein the carbon atom chain length of the polyketide backbone of the compounds is selected from two or more of 6, 7, 8, 9, 10, 11, 12, 13, 14, 15, 16, 17, 18, 19, 20, 21, 22, 23, 24, 25, 26, 27, 28, 29, 30 and 31 carbon atoms; and
b. incubating and/or culturing the one or more heterogeneous populations of recombinant cells in a culture medium to support synthesis of the library of compounds.

A second aspect of the present invention relates to a heterogeneous population of recombinant cells capable of producing a library of polyketide-derived aromatic and/or polyaromatic; cyclic and/or polycyclic compounds; or any combination thereof, according to the method of the invention, wherein each cell in the population comprises:

a. a transgene encoding a heterologous type III PKS capable of forming a polyketide-derived aromatic, polyaromatic, cyclic or polycyclic compound, wherein the carbon atom chain length of the polyketide backbone of the formed compound is selected from among 6, 7, 8, 9, 10, 11, 12, 13, 14, 15, 16, 17, 18, 19, 20, 21, 22, 23, 24, 25, 26, 27, 28, 29, 30 and 31 carbon atoms; and
b. a transgene encoding a heterologous 'small molecule foldase' enzyme capable of catalyzing the formation of one or more specific intramolecular carbon-carbon bonds in a polyketide-derived aromatic, polyaromatic, cyclic and polycyclic compound, wherein the carbon atom chain length of the polyketide backbone of the compound is one or more of 6, 7, 8, 9, 10, 11, 12, 13, 14, 15, 16, 17, 18, 19, 20, 21, 22, 23, 24, 25, 26, 27, 28, 29, 30 and 31 carbon atoms, and
c. optionally one more transgene(s) encoding a second, third and fourth heterologous 'small molecule foldase' enzyme capable of catalyzing the formation of one or more region-specific intramolecular carbon-carbon or carbon-oxygen bonds in a non-linear polyketide,
  wherein each of the first, second, third and fourth heterologous 'small molecule foldase' enzyme is a bacterial or fungal enzyme, and wherein the genus from which said bacterial or fungal enzyme is derived is different from the genus from which the PKSIII enzyme is derived,
  wherein the population of recombinant cells comprises cells capable of producing polyketide-derived aromatic and/or polyaromatic; cyclic and/or polycyclic compounds; or any combination thereof, wherein the carbon atom chain length of the polyketide backbone of the compounds is selected from two or more of 6, 7, 8, 9, 10, 11, 12, 13, 14, 15, 16, 17, 18, 19, 20, 21, 22, 23, 24, 25, 26, 27, 28, 29, 30 and 31 carbon atoms.

It is envisaged that individual heterologous host cells capable of producing an aromatic compound of interest may be identified as a result of the screening of the library of aromatic compounds produced by the one or more populations of heterologous host cells of the invention. This, or any individual heterologous host cell (or its clonal derivatives) of the invention may be used for the production of an aromatic compound.

Accordingly, a second aspect of the present invention relates to a method of producing a polyketide-derived aromatic, polyaromatic, cyclic or polycyclic compound, wherein the carbon atom chain length of the polyketide backbone of the compound is selected from 6, 7, 8, 9, 10, 11, 12, 13, 14, 15, 16, 17, 18, 19, 20, 21, 22, 23, 24, 25, 26, 27, 28, 29, 30 and 31 carbon atoms, comprising the steps of:

a. providing a recombinant cell comprising:
  i. a transgene encoding a heterologous type III polyketide synthase capable of forming a linear non-reduced polyketide compound wherein the carbon atom chain length of the polyketide backbone of the formed compound is selected from 6, 7, 8, 9, 10, 11, 12, 13, 14, 15, 16, 17, 18, 19, 20, 21, 22, 23, 24, 25, 26, 27, 28, 29, and 31 carbon atoms; and
  ii. a transgene encoding a first heterologous 'small molecule foldase' enzyme capable of catalyzing the formation of one or more region-specific intramolecular carbon-carbon or carbon-oxygen bonds in a linear non-reduced polyketide compound, wherein the carbon atom chain length of the polyketide backbone of the compound is one or more of 6, 7, 8, 9, 10, 11, 12, 13, 14, 15, 16, 17, 18, 19, 20, 21, 22, 23, 24, 25, 26, 27, 28, 29, 30 and 31 carbon atoms, and iii. optionally one more transgene(s) encoding a second, third and fourth heterologous 'small molecule foldase' enzyme capable of catalyzing the formation of one or more region-specific intramolecular carbon-carbon or carbon-oxygen bonds in a non-linear polyketide compound,
    wherein each of the first, second, third and fourth heterologous 'small molecule foldase' enzyme is a bacterial or fungal enzyme, and wherein the genus from which said bacterial or fungal enzyme is derived is different from the genus from which the PKSIII enzyme is derived,
    wherein the recombinant cell is capable of a producing polyketide-derived aromatic, polyaromatic, cyclic or polycyclic compound, wherein the carbon atom chain length of the polyketide backbone of the compound is selected from 6, 7, 8, 9, 10, 11, 12, 13, 14, 15, 16, 17, 18, 19, 20, 21, 22, 23, 24, 25, 26, 27, 28, 29, 30 and 31 carbon atoms; and b. incubating and/or culturing the recombinant cell in a culture medium to support synthesis of the polyketide-derived aromatic, polyaromatic, cyclic or polycyclic compound.

Definitions

All definitions of herein relevant terms are in accordance of what would be understood by the skilled person in relation to the herein relevant technical context.

The term "extender units" relates to the substrates that the PKS III adds to the starter unit and the growing polyketide chain. The extender units are delivered as acyl groups bound to Co-enzyme A, such as, but not exclusively, malonyl-CoA, methylmalonyl-CoA, hydroxyl malonyl-CoA or ethyl-malonyl.

The term "heterologous host" is here defined as the situation where a gene is expressed in a recombinant host cell that is taxonomically classified as belonging to a different genus than the organism where the gene of interest was obtained from.

The term "heterologous" with respect to an enzyme encoded by a transgene that is expressed in a recombinant cell of the invention, means that the enzyme is expressed in a cell that does not normally express that enzyme; since the gene encoding the enzyme is derived from (and naturally found in) a cell from a different genetic origin (e.g. species) than the cell in which it is expressed.

The term "the genus" describes the taxonomic classification of the organism from which a bacterial or fungal 'small molecule foldase' enzyme is derived, which is different from the genus from which the PKSIII enzyme is derived, which means that the 'small molecule foldase' enzyme and the PKSIII enzyme are derived from organisms that are classified to different genera.

The term "hybridizes" in relation to a polynucleotide which hybridizes under at least medium stringency conditions with (i) a nucleic acid molecule or (ii) a complementary strand of (i), relates to the nucleotide sequence hybridizing to a labeled nucleic acid probe corresponding to a nucleotide sequence disclosed herein, or its complementary strand under medium to very high stringency conditions. Molecules to which the nucleic acid probe hybridizes under these conditions can be detected using e.g. X-ray film. Herein relevant hybridization stringency conditions are defined in J. Sambrook, E. F. Fritsch, and T. Maniatus, 1989, Molecular Cloning, A Laboratory Manual, 2d edition, Cold Spring Harbor, N.Y. According to the art—for long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

The term "in vitro" (Latin: in glass) relates to studies that are conducted using components of an organism that have been isolated from their usual biological surroundings in order to permit a more detailed or more convenient analysis than can be done with whole organisms. Colloquially, these experiments are commonly called "test tube experiments". In contrast, in vivo studies are those that are conducted with living organisms in their normal intact state.

The term "in vivo" (Latin for "within the living") relates to experimentation using living cells or a whole living organism as opposed to a partial or dead cell or organism, or an in vitro ("within the glass", e.g., in a test tube or petri dish) controlled environment.

The term "ketide" refers to a single acyl unit added during a single condensation reaction step catalyzed by a PKS. If malonyl-CoA or methyl-malonyl are used as an extender units, then the ketide unit will be —$CH_2$—CO—, and —C($CH_3$)H—CO—, respectively.

The term "non-reduced polyketide" denotes a non-reduced polyketide, characterized by the presence of the original ketone groups in the ketides (eg. —$CH_2$—CO— if malonyl-CoA has been used as the extender unit), originating from the starter or extender units, either as ketones or in the form of carbonyls in phenolic groups (—$CH_2$—CO— or its tautomeric form —CH=COH—). In the case of reduced polyketides, a single or all ketones have been reduced to alcohol (—$CH_2$—CHOH—) groups by e.g. the KR domain/enzyme, or further to an alkene group (—C=C—) by e.g. a DH domain/enzyme, or even further to an alkane group (—$CH_2$—$CH_2$—) by e.g. an ER domain/enzyme. Based on these chemical features of the formed products, the involved PKSs are categorized as either being a non-reducing PKS or a reducing PKS.

The term "non-reducing PKS" or "non-reducing polyketide synthase" denotes a PKS which does not reduce the ketone groups in the formed polyketide chain. The lack of reductions can for instance be due to (I) a lack of the necessary keto-reductase (KR) active sites in the enzyme; and/or (II) lack of tailoring enzymes capable of catalyzing the keto-reduction reaction.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention. As known in the art, control sequences include all components that are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, pro-peptide encoding sequence, promoter, signal peptide encoding sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Numbering of the carbon atoms in the polyketides, and the numbering of the individual carbon atoms found in polyketide backbone is counted from the carboxylic acid (—COOH) end of the molecule. A single or double carbon-carbon bond that links e.g. the 5 and 12 carbon atom, counted from the carboxylic acid end of the polyketide, is represented as C5-C12.

The term "pentadeca" (Greek for "fifteen") denotes a polyketide chain consisting of fifteen ketide units, meaning that the polyketide backbone consists of 30 carbon atoms.

The term "pfam####" refers to specific motif in the Wellcome Trust Sanger Institute Protein-family (pfam) online database (pfam.xfam.org) described in Finn et al. 2014 (R. D. Finn, A. Bateman, J. Clements, P. Coggill, R. Y. Eberhardt, S. R. Eddy, A. Heger, K. Hetherington, L. Holm, J. Mistry, E. L. L. Sonnhammer, J. Tate, M. Punta. (2014) The Pfam protein families database. Nucleic Acids Research (2014), Database Issue 42:D222-D230), that allows for the identification of conserved functional sequence motifs based on Hidden Markov Models and multiple sequence alignments.

The term "starter unit" relates to the first substrate that a PKS selects for incorporation into the growing polyketide chain, and hence the first ketide unit found in the polyketide chain originates from the starter units. The starter unit is delivered as acyl groups bound to Co-enzyme A, such as, but not exclusively, acetyl-CoA, malonyl-CoA, methylmalonyl-CoA, p-coumaroyl-CoA, phenylacetyl-CoA or benzoyl-CoA. Type III PKSs normally uses malonyl-CoA as extender units, but can use the other starter units.

The term "recombinant expression vector" relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites.

The term "recombinant host cell" is a cell comprising a recombinant polynucleotide (e.g. DNA) molecule and a recombinant host cell will therefore not be understood as covering a natural wildtype cell as such. Recombinant polynucleotide (e.g. DNA) molecules are polynucleotide (e.g. DNA) molecules formed by laboratory methods of genetic recombination (such as molecular cloning) to bring together genetic material from multiple sources, creating sequences that would not otherwise be found in biological organisms.

The term, 'small molecule foldases' relates to enzymes that are capable of catalyzing the formation of intra-molecular carbon-carbon or carbon-oxygen bonds within a molecule, resulting in the formation of aromatic or cyclic motifs within the molecule. These include members of the following enzyme families: pfam04199 (Cyclase superfamily domain), pfam10604 and pfam03364 (SRPBCC Cyclases/aromatases), pfam07876 (DABB Cyclases/aromatases), pfam04673 (Polyketide synthesis cyclase), pfam00753 (Lactamase_B/MBL fold metallo-hydrolase), ketoreductase from Act cluster, pfam07883 (Cupin_2) and in addition dissected PT domains from type I iterative PKS from filamentous fungi The term "Sequence Identity" relates to the relatedness between two amino acid sequences or between two nucleotide sequences. For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment).

For purposes of the present invention, the degree of sequence identity between two nucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment).

As understood by the skilled person in the present context, for both "sequence identity between two nucleotide sequences" and "sequence identity between two amino acid sequences"—the term "Length of Alignment" should be understood as the actual length of alignment between the two sequences to be compared for sequence identity.

For instance, if a reference sequence is a specific SEQ ID of e.g. 100 amino acids and the other sequence is an identical sequence with 25 amino acids less at one end (i.e. the other sequence is of a length of 75 amino acids) then will the "Length of Alignment" be 75 amino acids and the percent identity will be 100%.

Another example is for instance, if a reference sequence is a specific SEQ ID of e.g. 100 amino acids and the other sequence is an identical sequence with 25 amino acids extra at one end (i.e. the other sequence is of a length of 125 amino acids) then will the "Length of Alignment" be 100 amino acids and the percent identity will be 100%.

The term "TIGRXXX" denotes a sequence motif in the The Institute of Genomic Research's Protein family database (jcvi.org/cgi-bin/tigrfams/Terms.cgi) that allows for the identification of conserved functional sequence motifs based on Hidden Markov Models and multiple sequence alignments.

The term "a dissected product template domain from type I iterative PKS" denotes an artificially constructed enzyme that only contains the Product Template (PT) portion of a type I non-reducing iterative PKS from fungi. The PT domain can either be identified via the National Center for Biotechnology Information (NCBI) Conserved Domain Database (CDD) and the associated search tool (CD-Search), which is available via ncbi.nlm.nih.gov/Structure/cdd/wrpsb.cgi 0020. In the CDD the PT domain has accession number "TIGR04532: PT_fungal_PKS". The artificial enzyme is designed by fusing the coding sequence of the PT domain with a 5' start codon (ATG) and a 3' stop codon (TGA, TAA or TAG).

The term "triketide" (greek for "three") denotes a polyketide chain consisting of three ketide units, meaning that the polyketide backbone consists of 6 carbon atoms. The term "ketide" refers to a —CH2-CO— unit.

The term "Type III polyketide synthase (PKS)" is a self-contained enzyme that form homodimers. The single active site in each monomer catalyzes the priming and extension to form polyketide products.

DRAWINGS

Figure 1:
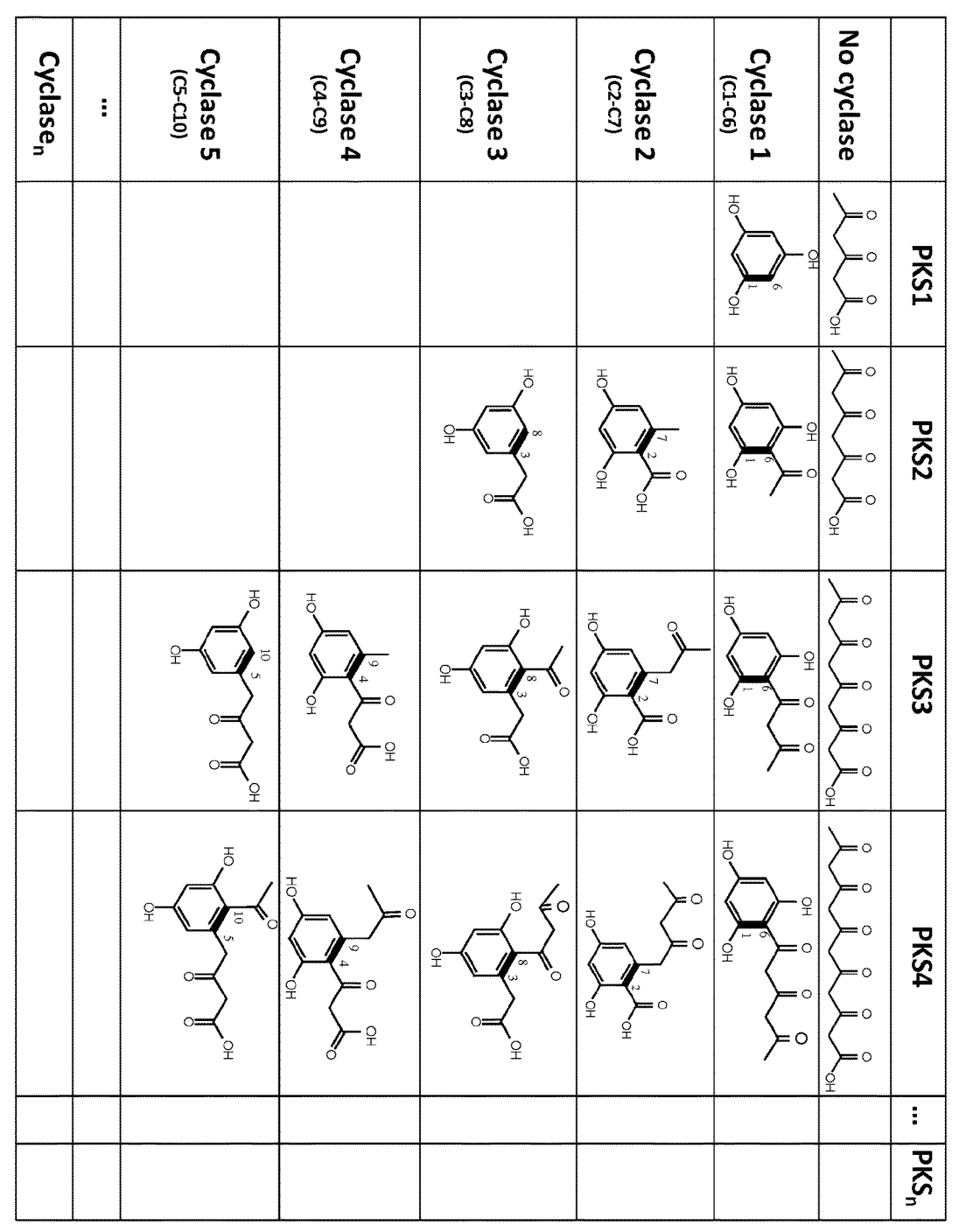

FIG. 1: Example of library of aromatic compounds made according to the invention (see working example herein). A population of PKSs (PKS1-PKS$_n$) that produces different chain lengths are combined in individual cells with 'small molecule foldases' (Cyc1 to Cyc$_n$) that catalyze different folding patters to form unique products.

FIG. 2: The figure shows Extracted Ion Chromatograms (EIC) of the novel compounds synthesized by 5 different GMO strains of S. cerevisiae comprising transgenes expressing the following type III PKSs: triketide synthase 2-PS from the plant Gerbera hybrid (GH2PS); the pentaketide synthase PCS from the plant Aloe arborescens (AaPCS); hexaketide synthase HKS from plant Drosophyllum lusitanicu (DluHKS), and the heptaketide synthase PKS3 from the plant Aloe arborescens (AaPKS3), and the octaketide synthase OKS from Aloe arborescens (AaOKS), as compared to parent control strain lacking these transgenes. Compounds that correspond to the molecular mass of the various detected compounds are: (A) Triactetic acid at EIC 127.0390+/−0.005 (including a triacetic lactone standard-TAL); (B) 5,7-dihydroxy-2-methylchromone (pentaketidepyrone) at EIC 193.0495+/−0.005; (C) 6-(2',4'-dihydroxy-6'-methylphenyl)-4-hydroxy-2-pyrone (hexaketidepyrone) at EIC 235.0601+/−0.005. Retention times, masses and compounds names can be found in table 1.

FIG. 3: The figure shows Extracted Ion Chromatograms (EIC) of the novel compounds synthesized by 2 different GMO strains of S. cerevisiae comprising transgenes expressing the following type III PKSs: the octaketide synthase OKS from Aloe arborescens (AaOKS) or the heptaketide synthase PKS3 from the plant Aloe arborescens (AaPKS3), as compared to parent control strain lacking these transgenes. Compounds that correspond to molecular mass of the various detected compounds: (A) Heptaketide pyrone (TW93a) at EIC 277.0707+/−0.005; (B) Aloesone at EIC 233.0808+/−0.005; (C) The compounds SEK4/SEK4b at EIC 319.0709 and dehydrated SEK4/SEK4B with a EIC of 319.0812. Retention times, masses and compounds names can be found in table 1.

FIG. 4: Table showing an example of a library of aromatic compounds synthesized in vivo according to the invention (see working example herein). The introduction of a second 'small molecule foldase' (Cyclase α to Cyclase$_n$) into a system that already contain a PKS and a cyclase generates novel compounds.

FIG. 5: The figure shows Extracted Ion Chromatograms (EIC) of a compound synthesized by 2 different GMO strains of S. cerevisiae comprising transgenes co-expressing: hexaketide synthase HKS, a type III PKS from plant Drosophyllum lusitanicu (DluHKS), together with a dissected product template domain (small molecule foldase), either: BIK1-PT from Fusarium graminearum or mdpG-PT from Aspergillus nidulans, as compared to a control GMO strain expressing only the type III PKS, hexaketide synthase HKS from plant Drosophyllum lusitanicu (DluHKS). The detected compound #1 corresponds to a molecular mass 225.1120 m/z eluting at 4.89 minutes. A) EIC at 225.1120 m/z for the 'DIuHKS+BIK-PT', 'DIuHKS+mdpG-PT' and control 'DIuHKS' strain. B) UV spectrum for compound #1 eluting at 4.89 minutes in the 'DluHKS+mdpG-PT' strain.

Figure 6:
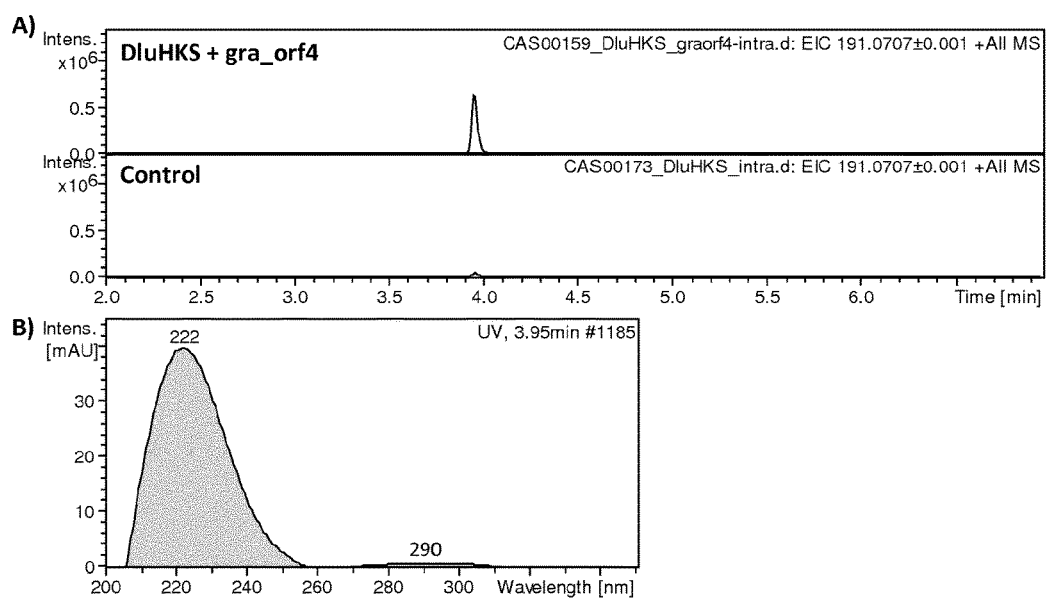

FIG. 6: The figure shows Extracted Ion Chromatograms (EIC) for a compound synthesized by a GMO strain of S. cerevisiae comprising transgenes co-expressing: hexaketide synthase HKS, a type III PKS from plant Drosophyllum lusitanicu (DluHKS), together with the cyclase (small molecule foldase) gra-orf4 from Streptomyces violaceoruber, as compared to a control GMO strain expressing only the type III PKS, hexaketide synthase HKS from plant Drosophyllum lusitanicu (DluHKS). The compound #2, corresponding to a molecular mass 191.0707 m/z, elutes at 3.95 minutes, that is just detectable in the control strain, is produced in larger amounts in the strain co-expressing the type IIIPKS and the cyclase. A) EIC at 191.0707 m/z for the 'DIuHKS+gra-orf4' and 'DIuHKS' strains. B) UV spectra for compound "2 eluting at 4.89 minutes in the 'DIuHKS+gra-orf4' strain.

Figure 7:
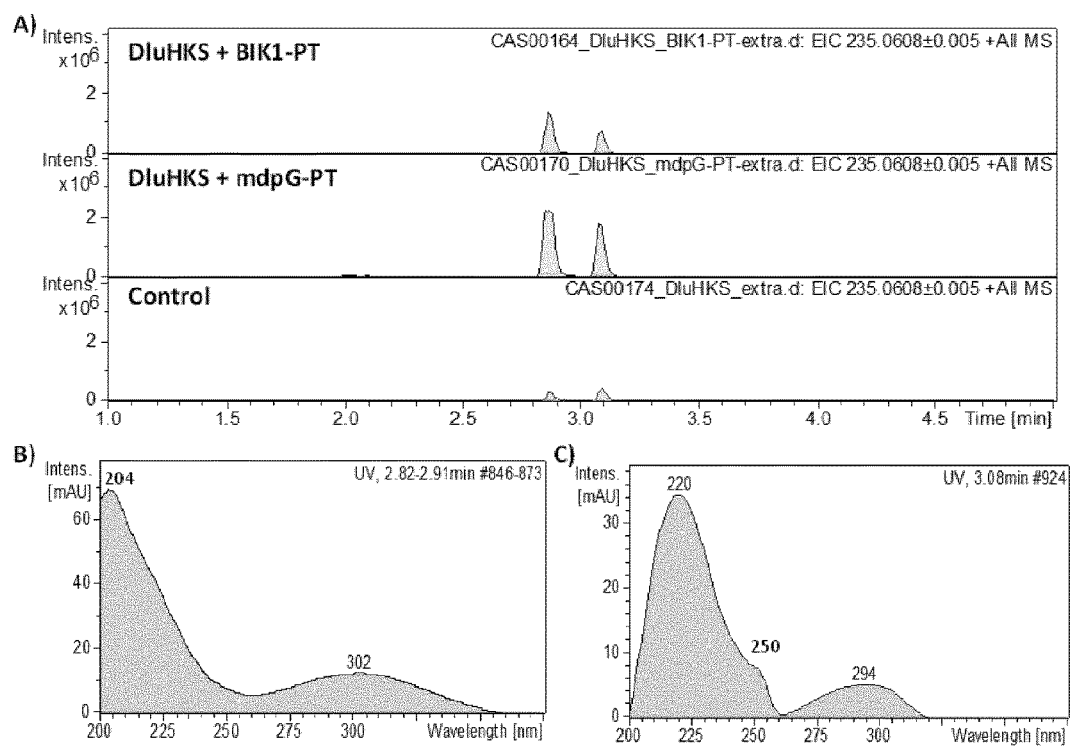

FIG. 7: The figure shows Extracted Ion Chromatograms (EIC) for two compounds synthesized by 2 different GMO strains of S. cerevisiae comprising transgenes co-expressing: hexaketide synthase HKS, a type III PKS from plant Drosophyllum lusitanicu (DluHKS), together with a dissected product template domain (small molecule foldase), either: BIK1-PT from Fusarium graminearum or mdpG-PT from Aspergillus nidulans, as compared to a control GMO strain expressing only the type III PKS, hexaketide synthase HKS from plant Drosophyllum lusitanicu (DluHKS). Detected compound #3, corresponding to a molecular mass (235.0608 m/z) elutes at 2.86 minutes and detected compound #4 (235.0608 m/z) elutes at 3.09 minutes. A) EIC at 235.0606 m/z for the "DluHKS+BIK1-PT", "DluHKS+mdpG-PT" and control "DluHKS" strains. B) UV spectra for compound #3 eluting at 2.86 m minutes in the 'DIuHKS+BIK1-PT' strain. C) UV/VIS spectrum compound #4 eluting at 3.8 minutes in the 'DIuHKS+BIK1-PT strain'.

Figure 8:
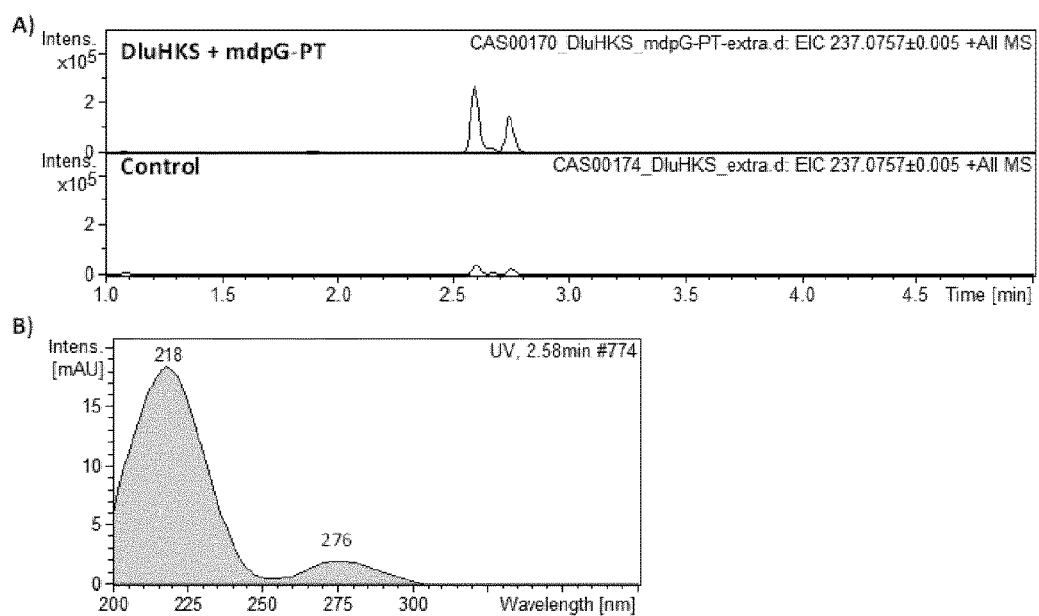

FIG. 8: The figure shows Extracted Ion Chromatograms (EIC) for a compound synthesized by a GMO strain of S. cerevisiae comprising transgenes co-expressing: hexaketide synthase HKS, a type III PKS from plant Drosophyllum lusitanicu (DluHKS), together with a dissected product template domain (small molecule foldase) mdpG-PT from Aspergillus nidulans, as compared to a control GMO strain expressing only the type III PKS, hexaketide synthase HKS from plant Drosophyllum lusitanicu (DluHKS). The detected compound #5 corresponding to a molecular mass (237.0757 m/z) elutes at 2.59 minutes, that is just detectable in the control strain, is produced in larger amounts in the strain co-expressing the type III PKS and the mdpG-PT small foldase. A) EIC at 237.0757 m/z for the 'DluHKS+mdpG-PT' and 'DluHKS' strains. B) UV spectra for compound #5 eluting at 2.59 minutes in the 'DluHKS+mdpG-PT' strain.

Figure 9:
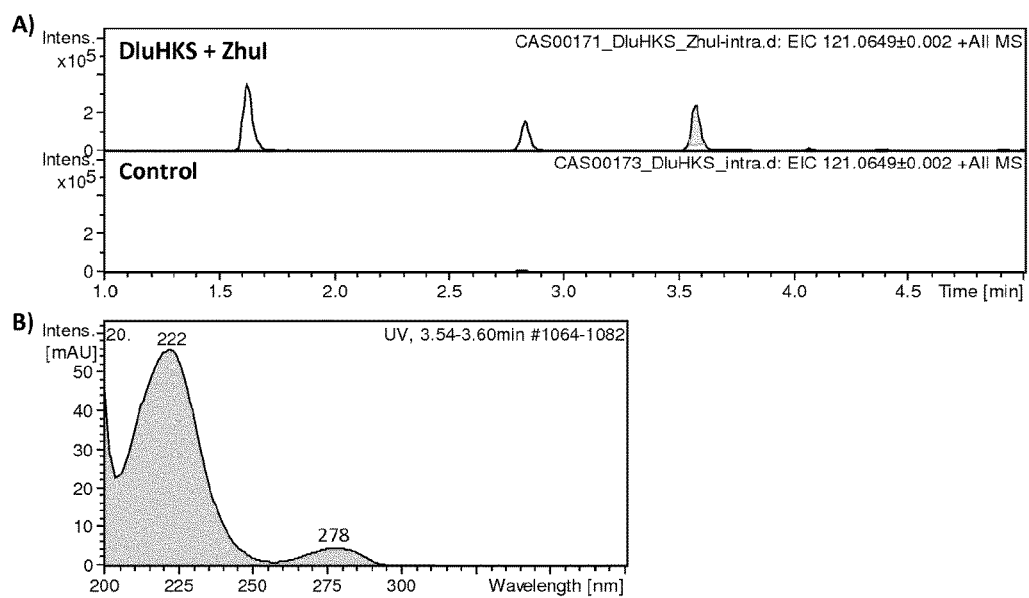

FIG. 9: The figure shows Extracted Ion Chromatograms (EIC) for a compound synthesized by a GMO strain of *S. cerevisiae* comprising transgenes co-expressing: hexaketide synthase HKS, a type III PKS from plant *Drosophyllum lusitanicu* (DluHKS), together with a cyclase ZhuI (small molecule foldase) from the bacterium *Streptomyces* sp. R1128, as compared to a control GMO strain expressing only the type III PKS, hexaketide synthase HKS from plant *Drosophyllum lusitanicu* (DluHKS). The detected compound #6, corresponding to a molecular mass 121.0649 m/z, elutes at 3.57 minutes. A) EIC at 121.0649 m/z of 'DluHKS+ZhuI' and control (DluHKS) strains. B) UV spectra for compound #6 eluting at 3.57 minutes in the 'DluHKS+ZhuI' strain.

Figure 10:
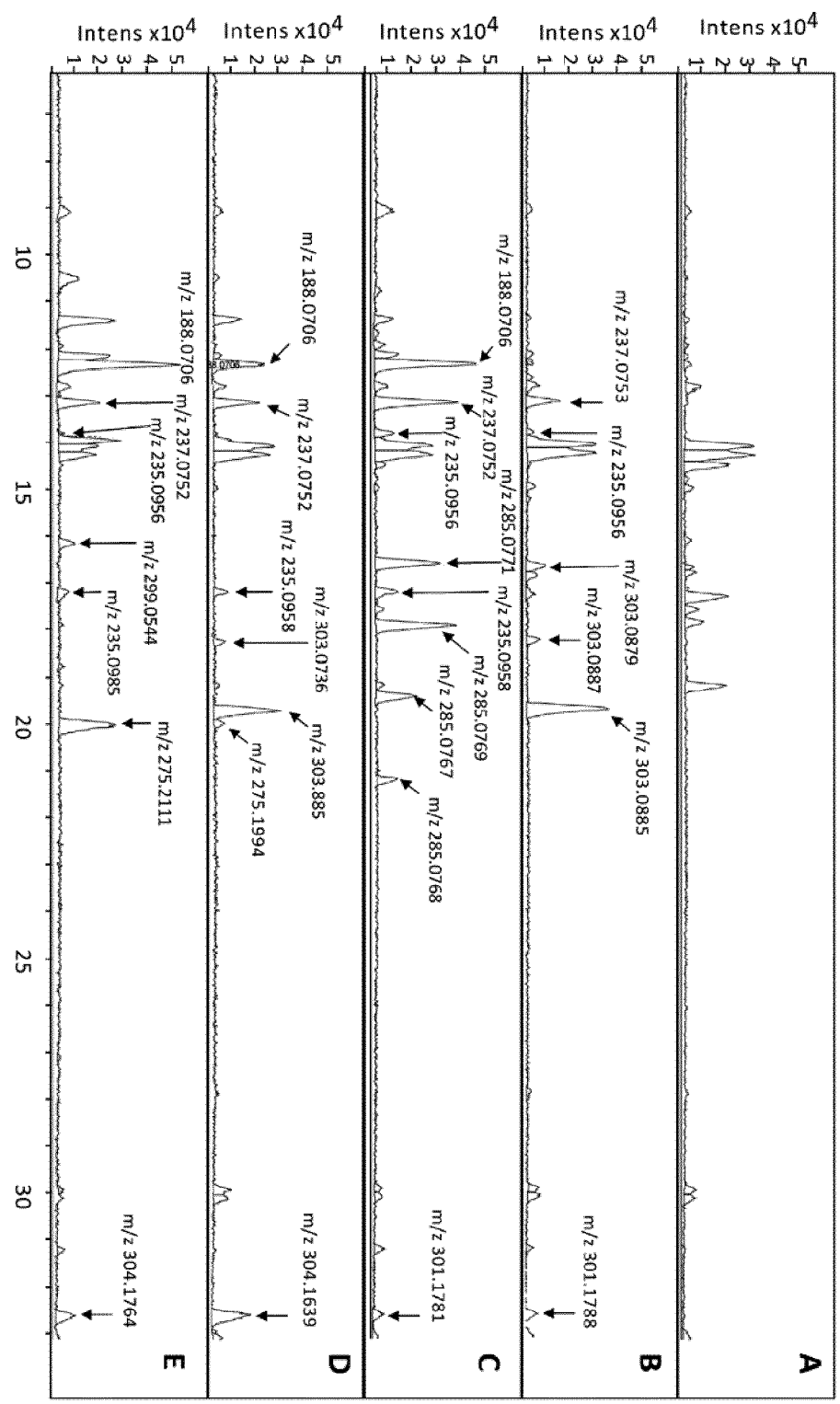

FIG. 10: The figure shows Extracted Ion Chromatograms (EIC) for compounds synthesized by GMO *Nicotiana benthamiana* lines co-expressing a type III polyketide synthase from *Aloe arborescens* (OKS), together with the cyclases/ketoreductase CYC, CYC_DH from the actinorhodin biosynthetic gene cluster in *Streptomyces coelicolor* A3 and a ketoreductase (KR) (cyclase superfamily), as compared to a control *N. benthamiana* expressing only the type III PKS (OKS). A) GMO plants expressing only type III PKS (OKS); B) GMO plants expressing type III PKS (OKS) and KR cyclase; C) GMO plants expressing type III PKS (OKS) and the cyclases/ketoreductase CYC, CYC_DH; D) GMO plants expressing type III PKS (OKS) and the cyclases/ketoreductase CYC and KR; E) GMO plants expressing type III PKS (OKS) and the cyclases/ketoreductase CYC, CYC_DH and KR.

FIG. 11: shows the structure of the heptaketides aloesone, aloesol and O-glucosylated derivatives thereof, synthesized by GMO *N. benthamiana* co-expressing a type III polyketide synthase (HpPKS2) together with several small molecule foldases.

DETAILED DESCRIPTION OF THE INVENTION

I A Method for Producing Libraries of Aromatic Compounds

The invention provides a method of producing a library of polyketide-derived aromatic, polyaromatic, cyclic and polycyclic compounds, wherein the carbon atom chain length of the polyketide backbone of the compounds is selected from two or more of 6, 7, 8, 9, 10, 11, 12, 13, 14, 15, 16, 17, 18, 19, 20, 21, 22, 23, 24, 25, 26, 27, 28, 29, 30 and 31 carbon atoms. Alternatively, the carbon atom chain length of the polyketide backbone of the compounds is selected from six, eight, ten, twelve, fourteen, sixteen, eighteen, twenty, twenty-two, and twenty-four or twenty-eight of 6, 7, 8, 9, 10, 11, 12, 13, 14, 15, 16, 17, 18, 19, 20, 21, 22, 23, 24, 25, 26, 27, 28, 29, 30 and 31 carbon atoms. The method employs recombinant cells transformed with different heterologous genes encoding enzymes in a biosynthetic pathway leading to the formation of the library of polyketide-derived aromatic, polyaromatic, cyclic and polycyclic compounds. Surprisingly, the inventors have discovered that a recombinant cell that expresses a heterologous Type III polyketide synthase (PKS) and a heterologous 'small molecule foldase' derived from a fungal/bacterial source, where the aromatase/cyclase and the PKS are derived from a different genus, is capable of producing a non-reduced polyketide which is then converted in vivo into an aromatic compound of interest. 'Small molecule foldases' of bacterial or fungal origin are only known to act on polyketides that are bound to ACP within the KS/CLF/ACP enzyme complex of type II PKS or type I PKS. The ability of 'Small molecule foldases' of bacterial or fungal origin, that in nature act on polyketides tethered to PKSI or PKSII, to guide the folding of untethered non-reduced linear polyketides products of PKSIII enzymes derived from a different genus was therefore unexpected.

Depending on the specificity of both the PKS III and the small molecule foldase type expressed in a given recombinant cell, a wide range of aromatic compounds of interest can be produced. The inventors have further discovered that a population of heterologous recombinant cells, comprising individual host cells transformed with transgenes encoding different combinations of one type of heterologous Type III polyketide synthase (PKS) and at least one type of heterologous bacterial or fungal 'small molecule foldase', is capable of a producing the library of polyketide-derived aromatic, polyaromatic, cyclic and polycyclic compounds.

Ii Recombinantly Expressed Heterologous Type III Polyketide Synthases

Despite their structural simplicity, type III PKSs are thought to contribute to the biosynthesis of a wide array of compounds in nature, such as chalcones, pyrones, acridones, phloroglucinols, stilbenes, and resorcinolic lipids. The linear non-reduced polyketides produced by type III PKSs are characterized by the presence of ketone groups in the ketides ($-CH_2-CO-$), originating from the starter or extender units, either as ketones or in the form of carbonyls in phenolic groups ($-CH_2-CO-$ or its tautomeric form $-CH=COH-$). A Type I PKS and/or a Type II PKS may be mutated to remove relevant elements (e.g. active sites) to be converted into a Type III PKS. A PKS, which by the skilled person is functionally considered to be a Type III PKS is herein understood to be a Type III PKS.

Preferably the individual type III PKS used produces products of a single chain length, i.e. only releases products after a fixed number of iterations. This will ensure that the individual recombinant cell in the library only produces one specific product which is desirable as 1) it increases the yields of the the specific product, by reducing the amount of less shunt products, and 2) it eases the identification of the active compound produced by the recombinant cell.

Preferably 80% of the formed polyketides should be of the same chain length, more preferably 90% should be of same chain length, even more preferably 95% should be of the same single chain length and most preferably 99% of the formed product should be of the same chain length.

A recombinant cell of the invention comprises a transgene encoding a heterologous Type III PKS, which may be an enzyme that is natively expressed in a bacterial, fungal or plant cell. If the encoded enzyme is of bacterial origin it is preferably selected from *Pseudomonas* or *Streptomyces*.

Alternatively, if the enzyme is of fungal origin it is preferably selected from the group consisting of: *Neurospora, Fusarium, Aspergillus*, and *Monasus*.

If the encoded enzyme is of plant origin, it is preferably selected from the group consisting of: *Gerbera* hybrid, *Aloe arborescens, Drosophyllum lusitanicum, Plumbago zeylanica, Rheum palmate, Hypericum perforatum* and *Plumbago indica*.

Preferably, a recombinant cell of the invention comprises a transgene encoding a heterologous Type III polyketide synthase selected from the members of the groups listed below, or shares high amino acid sequence identity with a member of the group. Preferably the amino acid sequence of the heterologous Type III polyketide synthase shares at least 75, 80, 85, 90, 92, 94, 96, 98, 99 or 100% sequence identity with a member of the group. The GenBank ID numbers identifying the polypeptide sequence and corresponding native nucleotide sequence for each member of the groups of Type III polyketide synthases is given in the lists below. The nucleotide sequence of a transgene encoding any member of the group of Type III polyketide synthases may, however, need to be adapted to correspond to a codon usage required for optimal expression in the host recombinant cell.

Type III polyketide synthases selected for forming triketides are preferably: 2-PS [GenBank ID number Z38097.2 (nucleotide SEQ ID NO: 1.) and GenBank ID number P48391.2 (polypeptide SEQ ID NO: 2)] from *Gerbera* hybrid.

Type III polyketide synthases selected for forming tetraketides are preferably: PhlD [GenBank ID number JN561597.1 position 2882 to 3970 (nucleotide SEQ ID NO: 3) and GenBank ID number AEW67127.1 (polypeptide SEQ ID NO: 4)] from *Pseudomonas fluorescens* for forming tetraketides.

Type III polyketide synthases selected for forming pentaketides are preferably: PCS [GenBank ID number AY823626 (nucleotide SEQ ID NO: 5) and GenBank ID number AAX35541.1 (polypeptide SEQ ID NO: 6)] from *Aloe arborescens* or ORAS GenBank ID number XM_955334.2 position 582 to 1919 (nucleotide SEQ ID NO: 7) and GenBank ID number EGZ68458 (polypeptide SEQ ID NO: 8)] from *Neurospora crassa* or 1,3,6,8-tetrahydroxynaphthalene synthase [GenBank ID number CP005080 position 7775934 to 7776986 (nucleotide SEQ ID NO: 9) and GenBank ID number AGK81780 (polypeptide SEQ ID NO: 10)] from *Streptomyces fulvissimus*.

Type III polyketide synthases selected for forming hexaketides are preferably: PinPKS [GenBank ID number AB259100 (nucleotide SEQ ID NO: 11) and GenBank ID number BAF44539 (polypeptide SEQ ID NO: 12)] from *Plumbago indica*, DluHKS [GenBank ID number EF405822 (nucleotide SEQ ID NO: 13) and GenBank ID number ABQ59603 (polypeptide SEQ ID NO:14)] from *Drosophyllum lusitanicum* or PzPKS [GenBank ID number JQ015381 (nucleotide SEQ ID NO: 15) and GenBank ID number AEX86944 (polypeptide SEQ ID NO: 16)] from *Plumbago zeylanica* for forming hexaketides.

Type III polyketide synthases selected for forming heptaketides are preferably: ALS [GenBank ID number AY517486 (nucleotide SEQ ID NO: 17) and GenBank ID number AAS87170 (polypeptide SEQ ID NO:18)] from *Rheum palmatum* or AaPKS3 [GenBank ID number EF537574 (nucleotide SEQ ID NO: 19) and GenBank ID number ABS72373 (polypeptide SEQ ID NO: 20)] from *Aloe arborescens* for forming heptaketides.

Type III polyketide synthases selected for forming octaketides are preferably: OKS [GenBank ID number AY567707 (nucleotide SEQ ID NO: 21) and GenBank ID number AAT48709.1 (polypeptide SEQ ID NO: 22)] or OKS2 [GenBank ID number FJ536166 (nucleotide SEQ ID NO: 23) and GenBank ID number ACR19997.1 (polypeptide SEQ ID NO: 24)] or OKS3 [GenBank ID number FJ536167 (nucleotide SEQ ID NO: 25) and GenBank ID number ACR19998.1 (polypeptide SEQ ID NO: 26)] from *Aloe arborescens* or HpPKS2 [GenBank ID number HQ529467 (nucleotide SEQ ID NO: 27) and GenBank ID number AEE69029 (polypeptide SEQ ID NO: 28)] from *Hypericum perforatum*.

Type III polyketide synthases selected for forming nonaketides are preferably: PCS F80A/Y82A/M207G, a mutated polypeptide—SEQ ID NO: 29 (derived from GenBank ID number AAX35541.1), from *Aloe arborescens*, having the specified triple point mutation (F80A/Y82A/M207G), and encoded by a synthetic gene.

Type III polyketide synthases selected for forming decaketides are preferably: OKS N222G a mutated polypeptide SEQ ID NO: 30 (derived from GenBank ID number AAT48709.1) from *Aloe arborescens* having the specified point mutation (N222G), and encoded by a synthetic gene.

Type III polyketide synthases selected for forming dodecaketides are preferably: OKS F66L/N222G a mutated polypeptide SEQ ID NO: 31 [derived from GenBank ID number AAT48709.1] from *Aloe arborescens* having the specified double point mutations (F66L/N222G), and encoded by a synthetic gene.

In one embodiment, the population of heterologous recombinant cells comprises host cells, or their clonal derivatives, where each individual cell comprises a transgene capable of expressing a PKS selected from a triketide synthase, tetraketide synthase, pentaketide synthase, hexaketide synthase, heptaketide synthase, octaketide synthase, nonaketide synthase, decaketide synthase, undecaketide synthase dodecaketide synthase, trideca synthase, tetradeca synthase, and pentadeca synthase. Preferably the population of heterologous recombinant cells is capable of expressing at least 2, 3, 4, 5, 6, 7, 8, 9, 10, 11, 12 or 13 members of this group.

Iii Biosynthetic Properties of the Recombinantly Expressed Heterologous Type III Polyketide Synthases The Type III polyketide synthase, expressed by the host recombinant cell is capable of converting suitable starter unit and extender units into a non-reduced polyketide under suitable incubation conditions. Suitable starter unit are acetyl-CoA or malonyl-CoA and suitable extender units are malonyl-CoA or methyl-malonyl-CoA. The biosynthesis of aromatic compounds (spontaneously folded polyketides of different chain length) by the host recombinant cell expressing a heterologous Type III polyketide synthase is exemplified in Example 1.

Iiii Recombinantly Expressed Heterologous Small Molecule Foldases

In bacterial type II PKS systems the folding of polyketide backbones is most often assisted/directed by different classes of enzymes, that act in trans (independent of the PKS enzyme) to promote a non-spontaneous fold. These enzyme classes are referred to herein as 'small molecule foldases', a group which includes aromatases and cyclases. In type II PKS systems, the formation of compounds with multiple aromatic rings typically relies on the successive action of multiple different 'small molecule foldases'. The 'small molecule foldases' can be divided into two groups based on the substrates they act on: where the first small molecule foldases only acts on linear polyketide chains and catalyze the formation of one or more aromatic/cyclic group, the second group of enzymes only accepts substrates that already contain an aromatic or cyclic group (=products from the first group of 'small molecule foldases') and catalyze the formation of additional aromatic or cyclic groups.

Surprisingly, the inventors have discovered that a bacterial/fungal 'small molecule foldase' derived from PKSI enzymes or interacting with PKSII enzymes in nature, when co-expressed with a Type III PKK in a recombinant cell, is capable of promoting a non-spontaneous fold in a non-reduced linear polyketide synthesized by the Type III PKK, thereby preventing its spontaneous folding/aromatization that it would otherwise undergo in vivo. Accordingly, the 'small molecule foldase' enzyme has a trans-acting catalytic activity that allows in vivo conversion of the non-reduced polyketide into an aromatic compound of interest. The 'small molecule foldase' enzyme is heterologous with respect to the host cell in which it is expressed, and is derived from a different genus than from which the PKS III is derived. The biosynthesis of a range of different aromatic compounds by the host recombinant cell co-expressing a heterologous Type III polyketide synthase and a heterologous bacterial/fungal small molecule foldase (where the genus from which the foldase is derived is different from the genus from which the PKSIII are derived), is exemplified in Example 2, 3 and 4.

Preferably, a recombinant cell of the invention co-expresses a Type III PKS together with a "small molecule foldase" that is an aromatase/cyclase belonging to a family selected from the group: Cyclase superfamily domain pfam04199; SRPBCC cyclase/aromatase superfamily pfam10604 and/or pfam03364, or DABB cyclase/aromatase superfamily pfam07876; Polyketide synthesis cyclase superfamily pfam04673; Lactamase_B/MBL fold metallo-hydrolase superfamily pfam00753; ketroreductase from Act cluster; Cupin-2 superfamily pfam07883; and a dissected product template domain from type I iterative PKS originating from filamentous fungi.

Preferably, a recombinant cell of the invention comprises at least one transgene encoding a heterologous 'small molecule foldase' selected from the members of the groups listed below, or shares high amino acid sequence identity with a member of the group. Preferably the amino acid sequence of the heterologous small molecule foldase shares at least 75, 80, 85, 90, 92, 94, 96, 98, 99 or 100% sequence identity with a member of the group. The GenBank ID numbers identifying the polypeptide sequence and corresponding native nucleotide sequence for each member of the groups of small molecule foldase is given in the lists below. The nucleotide sequence of a transgene encoding any member of the group of 'small molecule foldase' may, however, need to be adapted to correspond to a codon usage required for optimal expression in the host recombinant cell.

A 'first heterologous small molecule foldase' capable of acting on the linear polyketide product of the type III PKK to form a first ring (and capable of introducing a fold at the given positions in the chain) is preferably selected from the group consisting of:

ZhuI (type: SRPBCC) [GenBank ID number AF293442.1 (nucleotide SEQ ID NO: 32) and GenBank ID number AAG30197.1 (polypeptide SEQ ID NO: 33)] from *Streptomyces* sp. R1128 to form a C7-C12 fold in the linear non-reduced polyketide chain;

pdmD (type: SRPBCC) [GenBank ID number EF151801.1 Position 23865 to 24326 (nucleotide SEQ ID NO: 34) and GenBank ID number ABM21750.1 (polypeptide SEQ ID NO: 35)] from *Actinomadura hibisca* to form C9-C14+C7-C16 folds;

sanI (type: SRPBCC) [GenBank ID number GU937384.1 position 11996 to 12451 (nucleotide SEQ ID NO: 36) and GenBank ID number ADG86318.1 (polypeptide SEQ ID NO: 37)] from *Streptomyces* sp. SANK 61196;

pnxD (type: SRPBCC) [GenBank ID number AB469194.1 position 16730 to 17203 (nucleotide SEQ ID NO: 38) and GenBank ID number BAJ52684.1 (polypeptide SEQ ID NO: 39)] from *Streptomyces* sp. TA-0256;

IlpCI (type: SRPBCC) [GenBank ID number AM492533.1 position 8866 to 9333 (nucleotide SEQ ID NO: 40) and GenBank ID number CAM34342.1 (polypeptide SEQ ID NO: 41)] from *Streptomyces tendae*;

gra-orf4 (type: 2×SRPBCC) [GenBank ID number AJ011500.1 position 32006 to 32980 (nucleotide SEQ ID NO: 42) and GenBank ID number CAA09656.1 (polypeptide SEQ ID NO: 43)] from *Streptomyces violaceoruber* to form a C9-C14 fold;

schP4/SFUL_4006 (type: 2×SRPBCC) [GenBank ID number CP005080.1 Position 4477979 to 4478932 (nucleotide SEQ ID NO: 44) and GenBank ID number AGK78908.1 (polypeptide SEQ ID NO: 45)] from *Streptomyces fulvissimus* DSM 40593 to form C7-C12;

Erd4 (bifunc) (type: 2×SRPBCC) [GenBank ID number FJ719113.1 Position 3913 to 4863 (nucleotide SEQ ID NO: 46) and GenBank ID number ACX83620.1 (polypeptide SEQ ID NO: 47)] from uncultured soil bacterium V167 to form a C7-C12 fold;

med-ORF19 (type: 2×SRPBCC) [GenBank ID number AB103463.1 Position 13942 to 14898 (nucleotide SEQ ID NO: 48) and GenBank ID number BAC79027.1 (polypeptide SEQ ID NO: 49)] from *Streptomyces* sp. AM-7161 to form a C7-C12 fold;

ssfY1 (type: 2×SRPBCC) [GenBank ID number GQ409537.1 Position 9830 to 10774 (nucleotide SEQ ID NO: 50) and GenBank ID number ADE34490.1 (polypeptide SEQ ID NO: 51)] from *Streptomyces* sp. SF2575 to form a C7-C12 fold;

oxyK (type: 2×SRPBCC) [GenBank ID number DQ143963.2 Position 11443 to 12396 (nucleotide SEQ ID NO: 52) and GenBank ID number AAZ78334.2 (polypeptide SEQ ID NO: 53)] from *Streptomyces rimosus* to form a C7-C12 fold;

Act_ARO-CYC_actVII (type: 2×SRPBCC) [GenBank ID number AL939122.1 Position 162706 to 163656 (nucleotide SEQ ID NO: 54) and GenBank ID number Q02055.1 (polypeptide SEQ ID NO: 55)] from *Streptomyces coelicolor* A3(2) to form a C7-C12 fold;

wA-PT (type: PT domain) [GenBank ID number None—synthetic (nucleotide SEQ ID NO: 58) and GenBank ID number CAA46695 position 1276 to 1651 (polypeptide SEQ ID NO: 59)] from *Aspergillus nidulan* to form C7-C12+C1-C10 folds;

BIK1-PT (type: PT domain) [GenBank ID number None—synthetic (nucleotide SEQ ID NO: 60) and GenBank ID number CAB92399 Position 1252 to 1632 (polypeptide SEQ ID NO: 61)] from *Fusarium fujikuroi* to form C7-C12+C1-C10+C12-C17 folds;

PGL1_PT (type: PT domain) [GenBank ID number None—synthetic (nucleotide SEQ ID NO: 62) and GenBank ID number EYB26831 position 1225 to 1655 (polypeptide SEQ ID NO: 63)] from *Fusarium graminearum* to form C4-C9+C2-C11 folds;

mpdG_PT (type: PT domain) [GenBank ID number None—synthetic (nucleotide SEQ ID NO: 64) and GenBank ID number XP_657754.1 position 1335 to 1739 (polypeptide SEQ ID NO: 65)] from *Aspergillus nidulans* to form C6-C1+C4-C13+C2-C15 folds;

ZhuI-1 (type: SRPBCC) [GenBank ID number ANIA_10642 (nucleotide SEQ ID NO: 66) and GenBank ID number CBF80957.1 (polypeptide SEQ ID NO: 67)] from *Aspergillus nidulans*;

ZhuI-2 (type: SRPBCC) [GenBank ID number AN3000.2 (nucleotide SEQ ID NO: 68) and GenBank ID number XP_660604.1 (polypeptide SEQ ID NO: 69)] from *Aspergillus nidulans*;

AOC-1 (type: Dabb) [GenBank ID number AN8584.2 (nucleotide SEQ ID NO: 70) and GenBank ID number XP_681853.1 (polypeptide SEQ ID NO: 71)] from *Aspergillus nidulans;*

AOC-2 (type: Dabb) [GenBank ID number ANIA_01204 (nucleotide SEQ ID NO: 72) and GenBank ID number CBF87939.1 (polypeptide SEQ ID NO: 73)] from *Aspergillus nidulans;*

AOC-3 (type: Dabb) [GenBank ID number ANIA_10997 (nucleotide SEQ ID NO: 74) and GenBank ID number CBF79774.1 (polypeptide SEQ ID NO: 75)] from *Aspergillus nidulans;*

AOC-4 (type: Dabb) [GenBank ID number ANIA_11021 (nucleotide SEQ ID NO: 76) and GenBank ID number CBF80167.1 (polypeptide SEQ ID NO: 77)] from *Aspergillus nidulans;*

AOC-5 (type: Dabb) [GenBank ID number AN1979.2 (nucleotide SEQ ID NO: 78) and GenBank ID number XP_659583.1 (polypeptide SEQ ID NO: 79)] from *Aspergillus nidulans.*

Iiv. Additional Populations of Heterologous Recombinant Cells for Producing a Library of Aromatic Compounds The inventors have further discovered that the diversity of aromatic compounds produced by the heterologous recombinant cells of the invention can be extended by transforming each cell of the first population of heterologous recombinant cells with a second, optionally also a third, and optionally also a fourth transgene, where each of the second, third and fourth transgenes encodes a different heterologous 'small molecule foldase'.

The second 'small molecule foldase' is capable of acting on the aromatic polyketide product of the 'first small foldase' to form an additional aromatic group(s), while the third and fourth 'small molecule foldases' are capable of forming additional aromatic groups in an iterative synthesis (and capable of introducing a fold at the given positions in the chain). The biosynthesis of a range of different aromatic compounds by the host recombinant cell co-expressing a heterologous Type III polyketide synthase and one or more heterologous bacterial/fungal small molecule foldases (where the genus from which the foldase is derived is different from the genus from which the PKSIII are derived), is exemplified in Examples 3 and 4.

Preferably, the second, third, and fourth heterologous 'small molecule foldase' is one selected from the members of the groups listed below, or shares high amino acid sequence identity with a member of this group. Preferably the amino acid sequence of the second, third, and fourth heterologous 'small molecule foldase' shares at least 75, 80, 85, 90, 92, 94, 96, 98, 99 or 100% sequence identity with a member of this group. The GenBank ID numbers identifying the polypeptide sequence and corresponding native nucleotide sequence for each member of the groups of 'small molecule foldase' is given in the lists below. The nucleotide sequence of a transgene encoding any member of the group of 'small molecule foldase' may, however, need to be adapted to correspond to a codon usage required for optimal expression in the host recombinant cell are preferably selected from the group consisting of:

ZhuJ (type: Cyclase) [GenBank ID number AF293442.1 (nucleotide SEQ ID NO: 80) and GenBank ID number AAG30196.1 (polypeptide SEQ ID NO: 81)] from *Streptomyces* sp. R1128 to form a C5-C14 fold;

oxyN (type: Cyclase) [GenBank ID number DQ143963.2 position 14855 to 15628 (nucleotide SEQ ID NO: 82) and GenBank ID number AAZ78337.1 (polypeptide SEQ ID NO: 83)] from *Streptomyces rimosus* to form C5-C14+C3-C16 folds;

jadI (type: Polyketide synthesis cyclase) [GenBank ID number AAD37852.1 position 2020 to 2349 (nucleotide SEQ ID NO: 84) and GenBank ID number AF126429.1 (polypeptide SEQ ID NO: 85)] from *Streptomyces venezuelae* to form C4-C17 folds;

LndF (type: Polyketide synthesis cyclase) [GenBank ID number AY659997.1 (nucleotide SEQ ID NO: 86) and GenBank ID number AAU04837.1 (polypeptide SEQ ID NO: 87)] from *Streptomyces globisporus* to form C4-C17+C2-C19 folds;

pgaF (type: Polyketide synthesis cyclase) [GenBank ID number AHGS01000054.1 position 6389 to 6724 (nucleotide SEQ ID NO: 88) and GenBank ID number EHN79050.1 (polypeptide SEQ ID NO: 89)] from *Streptomyces coelicoflavus* to form C2-C19 folds;

Act_CYC (type: Lactamase) [GenBank ID number X63449.1 Position 3830 to 4723 (nucleotide SEQ ID NO: 90) and GenBank ID number CAA45047.1 (polypeptide SEQ ID NO: 91)] from *Streptomyces coelicolor* A3(2);

sanE (type: None) [GenBank ID number AF228524.1 position 15 to 584 (nucleotide SEQ ID NO: 92) and GenBank ID number AAF61923.1 (polypeptide SEQ ID NO: 93)] from *Streptomyces ansochromogenes;* pnxK (type: Polyketide synthesis cyclase) [GenBank ID number AB469194.1 position 13057 to 13380 (nucleotide SEQ ID NO: 94) and GenBank ID number BAJ52679.1 (polypeptide SEQ ID NO: 95)] from *Streptomyces* sp. TA-0256;

pnxL (type: Cupin_2) [GenBank ID number AB469194.1 position 13377 to 13901 (nucleotide SEQ ID NO: 95) and GenBank ID number BAJ52680.1 (polypeptide SEQ ID NO: 97)] from *Streptomyces* sp. TA-0256;

llpCIII (type: Cupin-2) [GenBank ID number AM492533.1 position 12120 to 12548 (nucleotide SEQ ID NO: 98) and GenBank ID number CAM34346.1 (polypeptide SEQ ID NO: 99)] from *Streptomyces tendae;* llpCIII (type: Polyketide synthesis cyclase) [GenBank ID number AM492533.1 position 12545 to 12880 (nucleotide SEQ ID NO: 100) and GenBank ID number CAM34347.1 (polypeptide SEQ ID NO: 101)] from *Streptomyces tendae;*

ZhuJ-1 (type: Cyclase) [GenBank ID number AN5060.2 (nucleotide SEQ ID NO: 102) and GenBank ID number XP_662664.1 (polypeptide SEQ ID NO: 103)] from *Aspergillus nidulans;*

ZhuJ-2 (type: Cyclase) [GenBank ID number ANIA_11053 (nucleotide SEQ ID NO: 104) and GenBank ID number CBF74060.1 (polypeptide SEQ ID NO: 105)] from *Aspergillus nidulans;*

ZhuJ-3 (type: Cyclase) [GenBank ID number ANIA_10146 (nucleotide SEQ ID NO: 106) and GenBank ID number CBF88175.1 (polypeptide SEQ ID NO: 107)] from *Aspergillus nidulans;*

ZhuJ-4 (type: Cyclase) [GenBank ID number AN5068.2 (nucleotide SEQ ID NO: 108) and GenBank ID number XP_662672.1 (polypeptide SEQ ID NO: 109)] from *Aspergillus nidulans;*

Iv Aromatic Compounds Produced by the Recombinant Cells of the Invention

In a preferred embodiment, the library of aromatic compounds may include aromatic compounds in the size range of $C_6$-$C_{31}$. The library of aromatic compounds produced by the method of the invention will comprise two to $10^6$ different compounds.

Ivi A Recombinant Cell

The term "recombinant cell" used in the method of the invention may be a eukaryotic cell [e.g. filamentous fungal cell, a yeast cell or a plant cell] or a prokaryotic cell.

Preferably the cell is a yeast cell, that may be selected from the group consisting of Ascomycetes, Basidiomycetes and fungi imperfecti, more preferably an Ascomycete.

Preferably, the Ascomycetes yeast cell is selected from the group consisting of Ashbya, Botryoascus, Debaryomyces, *Hansenula*, Kluveromyces, Lipomyces, *Saccharomyces* spp e.g. *Saccharomyces cerevisiae, Pichia* spp., *Schizosaccharomyces* spp.

Most preferably, the yeast cell is a yeast cell selected from the group consisting of *Saccharomyces* spp e.g. *Saccharomyces cerevisiae*, and *Pichia* spp.

The recombinant host cell may be a cell selected from the group consisting of a filamentous fungal cell. Filamentous fungi include all filamentous forms of the subdivision Eumycota and Oomycota (as defined by Hawksworth et al., 1995, supra). Preferably the filamentous fungal cell is a species of *Acremonium, Aspergillus, Fusarium, Humicola, Mucor, Myceliophthora, Neurospora, Penicillium, Thielavia, Tolypocladium*, and *Trichoderma* or a teleomorph or synonym thereof. For example, the filamentous fungal cell may be an *Aspergillus* cell, in particular *Aspergillus niger, Aspergillus oryzae* or *Aspergillus nidulans*.

When the recombinant cell is a bacterial cell, it is preferably selected from the group consisting of: *Bacillus, Streptomyces, Corynebacterium, Pseudomonas*, lactic acid bacteria and an *E. coli* cell. A preferred *Bacillus* cell is *B. subtilis, B. amyloliquefaciens* or *B. licheniformis*. A preferred *Streptomyces* cell is *S. setonii* or *S. coelicolor*. A preferred *Corynebacterium* cell is *C. glutamicum*. A preferred *Pseudomonas* cell is *P. putida* or *P. fluorescens*.

Ivii Production of the Library of Aromatic Compounds by the Heterogeneous Populations of Recombinant Cells The one or more heterogeneous populations of recombinant cells are incubated and/or cultivated under conditions that support synthesis of the library of polyketide-derived aromatic, polyaromatic, cyclic and polycyclic compounds. Suitable cultivation conditions depend on the nature of the host recombinant cell. When the host recombinant cell is a yeast, filamentous fungal or bacterial cell, the cultivation medium (aqueous liquid or solid medium) will comprise nutrients (carbon source, minerals, essential vitamins and substrates for polyketide biosynthesis, e.g. but not exclusively acetate and malonate) necessary for the biosynthetic activity of the host cell and for host cell growth. When the host cell is a plant cell, the cultivation medium may provide a source of water and light.

Iviii Screening the Library of Aromatic Compounds

The method of producing a library of polyketide-derived, polyaromatic, cyclic and polycyclic compounds, may include the step of screening the compounds produced by the population of heterologous recombinant cells, wherein each recombinant cell clone present in the one or more heterogeneous population of recombinant cells is grown individually on a solid support, or individually in a liquid culture. Screening for compounds with antibiotic properties may be performed by growing the individual member on the recombinant cell library on a surface of bacteria and then observing the formation of clearing zones around the recombinant cells/colonies. Alternatively, the screen may be based on a light or color forming reaction that the formed compound promotes or inhibits. Alternatively the screen may be performed using in cell assays, build into the recombinant host cells prior to construction of the libraries.

Iix Recovery of the Library of Aromatic Compounds

The method of producing a library of polyketide-derived, polyaromatic, cyclic and polycyclic compounds, may include the step of recovering the polyketide-derived aromatic, polyaromatic, cyclic and polycyclic compounds produced by the one or more heterogeneous populations of recombinant cells or produced by one or more of the recombinant cell clones present in the one or more heterogeneous populations of recombinant cells. Recovery may be performed by dilution plating or by re-streaking the population onto selective solid media.

II One or More Populations of Heterologous Recombinant Cells for Production of a Library of Aromatic Compounds The invention provides one or more populations of heterologous recombinant cells, comprising cells capable of producing polyketide-derived aromatic, polyaromatic, cyclic and polycyclic compounds, wherein the carbon atom chain length of the polyketide backbone of the compounds is selected from two or more of 6, 7, 8, 9, 10, 11, 12, 13, 14, 15, 16, 17, 18, 19, 20, 21, 22, 23, 24, 25, 26, 27, 28, 29, 30 and 31 carbon atoms. Maintenance and replication of the individual cells, or clonal derivatives thereof, in the one or more populations will depend on the nature of the host recombinant cells, and that are known in the art.

III a Method for the Construction of a Population of Recombinant Host Cells for Production of a Library of Aromatic Compounds The following method illustrates one way of constructing population(s) of recombinant host cells capable of producing a library of a polyketide-derived aromatic, polyaromatic, cyclic and polycyclic compounds, wherein the carbon atom chain length of the polyketide backbone of the compounds is selected from two or more of 6, 7, 8, 9, 10, 11, 12, 13, 14, 15, 16, 17, 18, 19, 20, 21, 22, 23, 24, 25, 26, 27, 28, 29, 30 and 31 carbon atoms. Alternatively, the carbon atom chain length of the polyketide backbone of the compounds is selected from six, eight, ten, twelve, fourteen, sixteen, eighteen, twenty, twenty-two, and twenty-four or twenty-eight of 6, 7, 8, 9, 10, 11, 12, 13, 14, 15, 16, 17, 18, 19, 20, 21, 22, 23, 24, 25, 26, 27, 28, 29, 30 and 31 carbon atoms. The method involves transforming each individual member of the host cell population with a transgene encoding a heterologous type III PKS and one or more transgenes each encoding a different heterologous 'small molecule foldase(s)', as described in Section I. The method comprises the following steps:

(i) creating a library of transgenes encoding type III PKSs that is populated by different type III PKSs, where the individual type III PKS is responsible for forming a linear non-reduced polyketide chain of a specific length, wherein the carbon atom chain length of the polyketide backbone of the chain is selected from 6, 7, 8, 9, 10, 11, 12, 13, 14, 15, 16, 17, 18, 19, 20, 21, 22, 23, 24, 25, 26, 27, 28, 29, 30 and 31 carbon atoms.

(ii) Creating a library of transgenes encoding different types of 'small molecule foldase(s)' that are populated by different foldases that individually catalyze the formation of one or more specific intramolecular carbon-carbon bonds in linear non-reduced polyketides of variable length (from (i)), resulting in the formation of aromatic compounds with different and unique folding patterns.

(iii) Creating one or more libraries of transgenes encoding different types of 'small molecule foldase(s)' that are populated by different foldases that individually catalyze the formation of one or more specific intramolecular carbon-carbon bonds in non-reduced polyketides of variable length with one or more aromatic groups (from 1(ii)), resulting in the formation of aromatic compounds with different and unique folding patterns.

(iv) The libraries described in 1(i), 1(ii) and 1(iii) consist of transgenes where the sequences encoding the said genes are operationally linked to regulatory and cis-acting sequences that allows for transcription and translation in a recombinant host cell. The transgenes are preferably cloned into vectors, which can comprise one or more selection marker encoding genes and the vectors may additionally include:
  i. Sequences that allows for autosomal replication of the vector in the recombinant host cell, or
  ii. Sequences that allows for targeted integration of the vector into the genome of the recombinant host cell, or
  iii. Sequence that allows for transfer of the contents of the vectors to another organism by conjugation.

(v) Randomly combining the PKS type III library described in 1(i) with
  i. library 1(ii) or
  ii. library 1(ii) plus library 1(iii) or
  iii. library 1(ii) plus two or three members of library 1(iii).

(vi) Co-transformation of said libraries into a population of host cells, such that each individual cell comprises at least one transgene from library (i) and (ii) and optionally one or more additional transgene from library (iii).

(vii) Optionally replicating the heterologous population of transformed cells produced in step (vi); and optionally storing the population, in a manner that each transformed cell produced in step (vi) and its clonal derivatives can be recovered individually.

(viii) Optionally isolating individual recombinant host cells from the population of host cells, to establish pure (isogenetic) cultures of the isolated recombinant host cell.

An alternative to the above described method, is as follows: Each library of transgenes described in 1(i), 1(ii) and 1(iii), optionally cloned into vectors, is individually transformed into a population of host cells, such that each individual cell of the library comprises at least one transgene from library (i), or (ii), or library (iii). The transgenes from library (ii), and optionally library (iii) transformed into the respective populations of host cells, can be transferred to the host cell population comprising library (i) by conjugation, cell-cell fusion or crossing such that the each cell in the resulting population of heterologous host cells comprises at least one transgene encoding a Type III PKS and one or more transgene encoding 'small molecular foldases'.

EXAMPLES

Example 1—Library of PKSs that Produce Polyketides of Different Lengths in *S. cerevisiae*

This example aims to show how the expression of different type III PKSs in *S. cerevisiae* result in the formation of a range of different aromatic compounds in vivo. This concept is illustrated in FIG. 1.

Methods

Five different type III polyketide synthases of variable origin were selected for heterologous expression in *S. cerevisiae*; the triketide synthase 2-PS from the plant *Gerbera hybrida*, the pentaketide synthase PCS from the plant *Aloe arborescens*, hexaketide synthase HKS from the plant *Drosophyllum lusitanicum*, heptaketide synthase PKS3 from the plant *Aloe arborescens*, and the octaketide synthase OKS from *Aloe arborescens*. The genes were codon optimized for expression in *S. cerevisiae* using the GeneArt GeneOptimzer algorithm (LifeTechnologies). The de novo synthesized genes were delivered in shuttle vectors, and the coding sequences were amplified by PCR using the primers listed below:

Primerlist:
Primers used for the construction process, where dU represents 2-deoxyuridine:

```
Sc_Gh_2-PS-F
                                      SEQ ID NO: 110
5'-ATCAACGGGdUAAAAATGGGTTCCTACTCTTCTGATGATGTTG-3'

Sc_Gh_2-PS-R
                                      SEQ ID NO: 111
5'-CGTGCGAdUTTAGTTACCATTAGCAACAGCAGCAGTAACTC-3'

Sc_AaOKS-F
                                      SEQ ID NO: 112
5'-ATCAACGGGDUAAAAATGAGTAGTTTATCAAATGCCAGTCAC-3'

Sc_AaOKS-R
                                      SEQ ID NO: 113
5'-CGTGCGADUTTACATCAATGGCAAGGAATGCAATAAG-3'

Sc_Aa_PCS-F
                                      SEQ ID NO: 114
5'-ATCAACGGGdUAAAAATGTCCTCCTTGTCTAATTCCTTGC-3'

Sc_Aa_PCS-R
                                      SEQ ID NO: 115
5'-CGTGCGAdUTTACATCAAAGGCAAAGAATGCA-3'

Sc_DluHKS-F
                                      SEQ ID NO: 116
5'-ATCAACGGGdUAAAAATGGCTTTCGTTGAAGGTATGGGT-3'

Sc_DluHKS-R
                                      SEQ ID NO: 117
5'-CGTGCGAdUTTAGTTGTTGATTGGGAAGGATCTCAAGA-3'

Sc_AaPKS3/ALS-F
                                      SEQ ID NO: 118
5'-ATCAACGGGdUAAAAATGGGTTCCTTGTCTGATTCTACTCCA-3'

Sc_AaPKS3/ALS-R
                                      SEQ ID NO: 119
5'-CGTGCGAdUTTAGACTGGTGGCAAAGAATGCAACA-3'

Promoter-F
                                      SEQ ID NO: 120
5'-ACGTATCGCdUGTGAGTCGTATTACGGATCCTTG-3'

Promoter-R
                                      SEQ ID NO: 121
5'-CGTGCGAdUGCCGCTTGTTTTATATTTGTTG-3'
```

Generation of Plasmid Constructs for Expression in *S. cerevisiae*

The used primers included 5' overhangs that allowed for directional cloning into the 2-micron pBOSAL1 vector, by the Uracil-Specific Excision Reagent Cloning (USER) technique, described in Nour-Eldin et al. 2006 (Hussam H. Nour-Eldin, Bjarne G. Hansen, Morten H. H. Norholm, Jacob K. Jensen, and Barbara A. Halkier. Advancing uracil-excision based cloning towards an ideal technique for cloning PCR fragments. Nucleic Acids Res. 2006, 34(18): e122.). The PGK1 promoter was also PCR amplified from the vector pSP-G2, using the primers PGK1-d and PGKF, as described in (Mikkelsen M D, Buron L D, Salomonsen B, Olsen C E, Hansen B G, Mortensen U H. Halkier B A. Microbial production of indolylglucosinolate through engineering of a multi-gene pathway in a versatile yeast expression platform. Metab Eng. 2012; 14:104-111). The PCR amplicons were purified via 1% agarose gel electrophoresis and the Illustra 'GFX PCR DNA and gel band purification kit (GE Healthcare). The recipient vector pCfB257, was digested with AsiSI and Nb.BsmI, and the used restriction enzymes were subsequently heat inactivated. The individual purified coding sequences were combined with the digested recipient vector and the purified promoter element and treated with the USER enzyme mix (NEB) and transformed into chemical competent E. coli DH5-alpha cells, as described in Nour-Eldin et al. 2006. Directional cloning resulted in the creation of an expression cassette, as described in Mikkelsen et al. 2012. Transformants were selected for on Luria-Bertani (LB) agar supplemented with ampicillin. Plasmid DNA from colonies were purified using the GenElute kit (Sigma-Aldrich) and the size and restriction enzyme digestion pattern were analyzed and compared to the theoretical expected sizes and patterns for the individual plasmid. Final verification of the five constructed plasmids consisted of two overlapping sequencing reactions.

The validated plasmids were digested with NotI to liberate the expression/targeting cassette from each of the five plasmids. The liberated expression cassettes were transformed into the competent S. cerevisiae cells CEN.PK102-5B, mating type a via the lithium acetate/single-stranded carrier DNA/polyethylene glycol transformation method (Gietz, R. D., Schiestl, R. H., 2007. "High-efficiency yeast transformation using the LiAc/SS carrier DNA/PEG method". Nat. Protoc. 2, 31-34). Transformants were selected for by culturing on SC-Leu agar plates as described in Mikkelsen et al 2012. Correct transformants were identified by colony-PCR using the gene specific primers.

Growth of S. cerevisiae, Metabolite Extraction and LC-MS/MS Analysis

The verified S. cerevisiae strains, called Sc.CEN.PK::2m::2-PS, Sc.CEN.PK::2m::PCS, Sc.CEN.PK::2m::HKS, Sc.CEN.PK::2m::PKS3 and Sc.CEN.PK::2m::OKS, were cultured in 300 ml Erlenmeyer flasks with either 100 ml liquid SC-Ura or Yeast-Peptone-Dextrose medium (REF). The cultures were allowed to grow for 3 days at 30° C. with 150 rpm orbital shake, after which the cells were harvested by centrifugation. The produced metabolites were extracted from the cells using isopropanol:ethyl acetate (1:3 v/v) with 1% formic acid and from the medium using ethyl-acetate. The solvents were evaporated and the analytes were resuspended in HPLC grade methanol. The analytes were separated using a Dionex UltiMate 3000 UHPLC equipped with a diode array detector (DAD) system hyphenated to a Q-TOF mass spectrometer. The samples were analyzed with three different injects volumes 1 µl, 5 µl and 10 µl. For separation in the UHPLC system a reversed-phase Kinetex C18 (100 mm, 2.1 mm, 2.6 µm) column was used and the temperature was maintained at 40° C. and a flow rate of 400 µl/min. The used mobile phases consisted of MilliQ water with 20 mM formic acid (A) and acetonitrile with 20 mM formic acid (B). The analytes were eluted using a gradient starting at 10% solvent B and increased to 100% solvent B over a period of 15 minutes. The column was washed with 100% solvent B for 3 minutes and re-equilibrated for 2.4 minutes with 10% B before the next sample was injected. The analytes were detected via an online DAD (Dionex Ultimate 3000) detector from 200 to 600 nm and an online maXis 3G Qq-Oa-TOF (Bruker Daltronics GmbH). In the MS the analytes were ionized by electrospray operating in positive mode; capillary voltage at 4.5 kV, nebulizer gas at 2.4 bar, drying gas flow at 12 ml/min and a drying temperature of 220° C. The MS was used in full scan mode in the mass range of 100-1000 Da. The instrument was calibrated using sodium formate (HCOONa) (Fluka, analytical grade). The obtained data were processed and handled using Compass DataAnalysis v. 4.0 SP4 Build 281 (Bruker Daltronics). Bruker Daltronics Compass IsotopicPattern was used for calculating isotopic patterns of the pseudo-molecular ion and adducts. An in-house standard of triaceticlactone (spontaneously folded triketide) was run under the same conditions to confirm identity of the produced triketide. Identification of other aromatic prolyketids were performed via detection of the monoisotopic molecular mass ($[M+H]^+$), supported by the maximal UV absorption wavelengths (nm) for the individual compound as specified in FIG. 4 in Karppinen et al. 2008 Octaketide-producing type III polyketide synthase from Hypericum perforatum is expressed in dark glands accumulating hypericins, FEBS 275(17): 4329-4342.

Results:

Expression of the five PKSs in S. cerevisiae resulted in production of new metabolites not observed in the reference strain not expressing any of the five genes (Table 1, FIG. 2, and FIG. 3).

TABLE 1

Products produced from the heterologous expression of type III PKS in S. cerevisiae.

| RT [min] | $[M + H]^+$ | Mol. form. | Putative compound | GH 2PS | Aa PCS | Dlu HKS | Aa PKS3 | Aa OKS |
|---|---|---|---|---|---|---|---|---|
| 1.3 | 127.039 | C6H6O3 | Triacetic lactone | + | + | nd | nd | nd |
| 4.2 | 193.0495 | C10H8O4 | Pentaketide pyrone | nd | + | + | + | nd |
| 3.06 | 235.0601 | C12H10O5 | Hexaketide pyrone | nd | nd | + | + | + |
| 3.15 | 277.0707 | C14H12O6 | Heptaketide pyrone/TW93a | nd | nd | nd | + | + |
| 3.85 | 233.0808 | C13H12O4 | Aloesone | nd | nd | nd | + | + |
| 3.3 | 319.0812 | C16H14O7 | SEK4 | nd | nd | nd | nd | + |
| 3.5 | 319.0812 | C16H14O7 | SEK4b | nd | nd | nd | nd | + |

RT: retention time;
$[M + H]^+$: positive molecular ion mass;.
'+' indicates whether the given compound was detected upon expression of the given PKS.
'nd' indicates that the compound was not detected in the sample.

Conclusion:

Heterologous expression of the five different type III PKS in *S. cerevisiae* resulted in the production of novel compounds, representing spontaneously folded tri-, penta-, hexa-, hepta- and octaketides, in the individual strains. These results demonstrate that it is possible to functionally express type III PKS in *S. cerevisiae* and obtain products similar to those reported in the literature for in vitro experiments with purified enzymes. The compounds that have previously been obtained in in vitro experiments are the result of spontaneous folding/cyclization of the formed linear non-reduced polyketides. The example shows that *S. cerevisiae* does not express any endogenous enzymes capable of preventing or altering the spontaneous folding/cyclization pattern. This demonstrates that *S. cerevisiae* does not contain any enzymatic activities that will interfere with attempts to control and direct folding of the formed linear non-reduced polyketide by introducing heterologous cyclases/aromatases.

Example 2—Combining the PKS Library with a Library of 'Small Molecule Foldases' in *S. cerevisiae*

This example aims to show how different combinations of PKSs and cyclases can result in the formation of a range of different aromatic compounds. This concept is illustrated in FIG. 4.

Methods

Four different 'small molecule foldases', including three different bacterial cyclases/aromatases and two product template (PT) domains, dissected from fungal type I iterative polyketide synthases, were selected for heterologous expression in *S. cerevisiae*; ZhuI from the bacterium *Streptomyces* sp. R1128 (C7-C12), gra-orf4 from the bacterium *Streptomyces violaceoruber* (expected C9-C14), BIK1-PT from fungi *Fusarium graminearum* (expected C2-C7) and mdpG-PT from *Aspergillus nidulans* (expected C6-C11).

The genes were codon optimized for expression in *S. cerevisiae* using the GeneArt GeneOptimizer algorithm (LifeTechnologies). The de novo synthesized genes were delivered in shuttle vectors, and the coding sequences were amplified by PCR using the primers listed below:

Primers Used for the Construction Process, where dU Represents 2-Deoxyuridine:

```
Sc_ZhuI-F
                                       SEQ ID NO: 122
5'-AGCGATACGdUAAAAATGAGACACGTTGAACACACAGTTACCG-3'

Sc_ZhuI-R
                                       SEQ ID NO: 123
5'-CACGCGAdUTTATTATGCAGTTACGGTACCAACACCAC-3'

Sc_BIK1-PT-F
                                       SEQ ID NO: 124
5'-AGCGATACGUAAAAATGAGATTGTCCGATTCCGTTCACA-3'

Sc_BIK1-PT-R
                                       SEQ ID NO: 125
5'-CACGCGAUTTAAATCAAACCAGAAGCTGAACCAACTG-3'

Sc_gra-orf4-F
                                       SEQ ID NO: 126
5'-AGCGATACGdUAAAAATGGCTAGAACTGCTGCTTTGC-3'

Sc_gra-orf4-R
                                       SEQ ID NO: 127
5'-CACGCGAdUTTAACCTGCTTCAGCAGCTTCAGC-3'

Sc_mdpG-PT-F
                                       SEQ ID NO: 144
5'-AGCGATACGUAAAAATGTCTGGTTTGAGAACTTCCACCG-3'

Sc_mdpG-PT-F
                                       SEQ ID NO: 145
5'-CACGCGAUTTAGACCAAAGCTTTAGCAGCAACTGAA-3'
```

The four 'small molecule foldases' encoding genes were cloned into the pCfB389 vector as described for the five Type III PKS genes in Example 1. The used vector allows for targeted integration into the XI-2 site in the genome of *S. cerevisiae*, as described in Mikkelsen et al. 2006. The expression cassettes were transformed into the Sc.CEN.PK 111-61A mating type alpha and selected for on SC-Ura plates. Correct transformants were identified by colony-PCR using the gene specific primers. The obtained verified strains are hereafter referred to as Sc.CEN.PK::XI-2::ZhuI, Sc.CEN.PK::XI-2::gra-orf4, Sc.CEN.PK::XI-2::BIK1-PT, and Sc.CEN.PK::XI-2:: mdpG-PT respectively.

The *S. cerevisiae* strains Sc.CEN.PK::2m::HKS and Sc.CEN.PK::2m::OKS, described in Example 1, is in the present example (Example 2) used to exemplify a library of different type III PKSs that produce polyketides of different lengths.

The five foldases were crossed with the type III PKS HKS expressing strains Sc.CEN.PK::2m::HKS, to form diploids yielding five new combinatory strains each containing a PKS and a cyclase/aromatase. The Sc.CEN.PK::2m::OKS strains was crossed with the Sc.CEN.PK::XI-2::ZhuI. Mating between the PKS carrying strains (mating type a, Leu marker) and the foldase carrying strains (mating type alpha, URA3 marker) was performed by co-inoculating the respective strains combinations on YPD agar plates. The plates were incubated at 30° C. for 8 hours, after which the cultures were replica plated onto SC-leu-ura, to select for diploids containing both the selective markers, and incubated at 30° C. for four days. Colonies from the double selective plates were streaked onto fresh SC-leu-ura plates to purify them. Single colonies of the diploids containing both the PKS and a foldase were inoculated in shake flasks with 20 mL Delft Synthetic Minimal Medium lacking leucine and uracil, but with added histidine. The cultures were incubated at 30° C. with shake for 4-5 days.

The production of novel metabolites was analyzed by UHPLC-HRMS as described in Example 1.

Results:

Combining the DIuHKS (type III PKS) with the dissected product template domain from mdpG-PT or BIK1-PT resulted in the production of a novel compound with a $[M+H]^+$ 225.1120 m/z which eluted at 4.89 minutes (FIG. 5A). The UV spectrum of the compound (FIG. 5B) shows that the compound includes a conjugated bond systems (absorption maxima at 222 nm and 280 nm) similar to what is found in phenolic compounds with a single aromatic group Co-expression of DIuHKS (type III PKS) and the cyclase gra-orf4 results in the accumulation of increased concentrations (9 times) of a compound with a $[M+H]^+$ of 191.0707 at 3.95 minutes (FIG. 6A) compared to when DIuHKS is expressed alone. The absorption maxima of 222 nm and 290 nm (FIG. 6B) support that the compound includes a conjugated aromatic bond systems characteristic of aromatic compounds.

Expression of DIuHKS (type III PKS) with the dissected product template domain (PT) from mdpG or BIK1-PT resulted in a significant increase of the concentrations of two compounds with a $[M+H]^+$ of 235.0606 eluting at 2.86 minutes and 3.08 minutes (FIG. 7A). The compounds at 2.86 minutes has absorption maxima at 212 nm and 302 nm, while the compound at 3.08 minutes absorbs at 220 nm, 250 nm and 294 nm supporting that the two compounds includes aromatic conjugated bond systems (FIG. 7B).

Combining the DluHKS (type III) with the dissected product template domain (PT) from mdpG resulted in a seven fold increase in the concentration of a compounds with a $[M+H]^+$ of 237.0757 eluting at 2.58 minutes (FIG. 8A), The compound absorbs at 218 nm and 276 nm (FIG. 8B), indicative of a aromatic conjugated bond systems.

Co-expression of DluHKS (type III) with the cyclase ZhuI resulted in a six fold increase in the concentration of a compound eluting at 3.57 min and with an $[M+H]^+$ of 121.0649 (FIG. 9A). The compound exhibit absorption maxima at 222 nm and 278 nm indicating that the compound includes a aromatic conjugated bond system (FIG. 9B).

Conclusion:

These results show that co-expression of a type III PKS and a heterologous cyclase/aromatase or dissected product template domain from a type I iterative PKS in the host cell *Saccharomyces cerevisiae* results in the formation of novel compounds than what is observed when the PKS is expressed alone. In several cases the co-expression resulted in the significant increase in the formation of aromatic compounds otherwise produced at low concentrations when the PKS is expressed alone. These results surprisingly shows that 'small molecule foldases' originating from bacterial or fungal type I and type II PKS systems, which in nature act on ACP-bound polyketides, can act on free non-reduced linear polyketides produced by type III PKSs.

Example 3—Introducing a Type III Polyketide Synthase (OKS) Together with Cyclases/Ketoreductase CYC, CYC_DH and KR (Cyclase Superfamily) into *Nicotiana benthamiana* (*N. benthamiana*)

This example illustrates how the introduction of cyclases/ketoreductases, together with a type III polyketide synthase, OKS in *N. benthamiana*, can further increase the compound diversity. This concept is illustrated in FIG. 4.

Methods

Generation of Plasmid Constructs for Expression in *N. benthamiana*.

CYC (actIORF5) and CYC_DH (actIORF4) from the actinorhodin biosynthetic gene cluster in *Streptomyces coelicolor* A3 (2) (Genbank accession: X63449.1) were codon optimized for *N. benthamiana* expression, whereas KR (Genbank accession: M19536) was codon optimized for *E. coli* expression. All three genes were purchased as synthetic DNA fragments from Genscript together with the native sequence of OKS from *Aloe arborescens* (Genbank accession: AY567707). All synthetic fragments were used as PCR templates with compatible deoxyuracil(dU)-containing primers (see table 1) to generate constructs that were cloned into pEAQ-HT-USER (Sainsbury et al., 2009) by USER technology. All pEAQ-HT-USER plasmid constructs were transformed into the *Agrobacterium tumefaciens* strain, AGL-1 and infiltrated into leaves of *N. benthamiana* plants as described in (Bach, S. S., Bassard, J. E., Andersen-Ranberg, J., Moldrup, M. E., Simonsen, H. T., Hamberger, B. (2014). High-Throughput Testing of Terpenoid Biosynthesis Candidate Genes Using Transient Expression in *Nicotiana benthamiana*. In M Rodríguez Concepcién, ed, Plant Isoprenoids, Methods in Molecular Biology, Vol. 1153. Humana Press, New York.).

Primer Sequences for Amplification of Different Gene Constructs.

| Gene fragments | Primer sequence |
|---|---|
| OKS-Forward | 5'-GGCTTAA/dU/ATGAGTTCACTCTCCAACGCTTCCCATC-3' SEQ ID NO: 130 |
| OKS-Reverse | 5'-GGTTTAA/dU/TTACATGAGAGGCAGGCTGTGGAGAAGGATAGT-3' SEQ ID NO: 131 |
| ZhuI-Forward | 5'-GGCTTAA/dU/ATGAGGCATGTCGAGCAT-3' SEQ ID NO: 132 |
| ZhuI-Reverse | 5'-GGTTTAA/dU/TTATGCCGTGACAGTTCCGACAC-3' SEQ ID NO: 133 |
| ZhuJ-Forward | 5'-GGCTTAA/dU/ATGTCCGGACGTAAGACG-3' SEQ ID NO: 134 |
| ZhuJ-Reverse | 5'-GGTTTAA/dU/TTAATCTTCCTCCTCCTGTTCAA-3' SEQ ID NO: 135 |
| CYC-Forward | 5'-GGCTTAA/dU/ATGACTGTTGAAGTTCGT-3' SEQ ID NO: 136 |
| CYC-Reverse | 5'-GGTTTAA/dU/TTAAGCCAAGCAAGTAGGAAGTT-3' SEQ ID NO: 137 |
| CYC_DH-Forward | 5'-GGCTTAA/dU/ATGTCAAGACCTGGAGAA-3' SEQ ID NO: 138 |
| CYC_DH-Reverse | 5'-GGTTTAA/dU/TTAGCTTGCCGGCCCAGC-3' SEQ ID NO: 139 |
| KR-Forward | 5'-GGCTTAA/dU/ATGGCAACCCAGGATAGCGAAGTTGCAC-3' SEQ ID NO: 140 |
| KR-Reverse | 5'-GGTTTAA/dU/TTAATAGTTGCCCAGACCACCACAAACATTCAG-3' SEQ ID NO: 141 |
| HpPKS2-Forward | 5'-GGCTTAA/dU/ATGGGTTCCCTTGACAATGGT-3' SEQ ID NO: 142 |
| HpPKS2-Reverse | 5'-GGTTTAA/dU/TTAGAGAGGCACACTTCGGAGAA-3' SEQ ID NO: 143 |

Metabolite Extraction and LC-MS/MS Analysis

Compounds produced when OKS was co-expressed with CYC, CYC_DH and KR were extracted from discs (Ø=3 cm) of agroinfiltrated *N. benthamiana* leaves. Leaf discs, excised with a cork borer, were flash frozen in liquid nitrogen. 0.5 ml of extraction buffer (85% (v/v) methanol, 0.1% (v/v) formic acid), equilibrated to 50° C., were added to each frozen leaf disc followed by incubation for 1 hour at 50° C., agitating at 600 rpm. The supernatant was isolated and passed through a Multiscreen$_{HTS}$ HV 0.45 µm filter plate (Merck Milipore). The filtered supernatant was subjected to LC-MS/MS analysis which was performed on an Agilent 1200 HPLC coupled to a Bruker micrOTOF-Q II mass spectrometer equipped with an electrospray ionization source. Chromatographic separation was obtained on a Luna $C_{18}s(2)$ column (150×4.6 mm, 3 µm, 100 Å, Phenomenex) maintained at 40° C. The aqueous eluent (A) consisted of water/acetonitrile (95:5, v/v) and the organic eluent (B) consisted of water/acetonitrile (5:95, v/v); both acidified with 0.1% formic acid.

Linear gradient elution profiles were used: 0 min, 0% B; 30 min, 100% B; 33 min 100% B; 35 min, 0% B. The flow rate was maintained at 0.5 mL/min and 10 min equilibration.

Results:

Introduction and co-expression of OKS and KR together with either CYC and/or CYC_DH in *N. benthamiana*, resulted in production of novel compounds with the masses and retention time shown in the table 2 and FIG. 10.

*licolor* A3 (2) (Genbank accession: X63449.1), ZhuI (Genbank accession: AAG30197) and ZhuJ (Genbank accession: AAG30196) were codon optimized for *N. benthamiana* expression, whereas KR (Genbank accession: M19536) was codon optimized for *E. coli* expression. All five genes were purchased as synthetic DNA fragments from Genscript together with the native sequence of HpPKS2 from *Hypericum perforatum* (Genbank accession: HQ529467). All synthetic fragments were used as PCR templates with compatible deoxyuracil(dU)-containing primers (see table 1) to generate constructs that were cloned into pEAQ-HT-USER by USER technology. All pEAQ-HT-USER plasmid constructs were transformed into the *Agrobacterium tumefaciens* strain, AGL-1 and infiltrated into leafs of *N. benthamiana* plants as described in (Bach, S. S., Bassard, J. É., Andersen-Ranberg, J., Moldrup, M. E., Simonsen, H. T., Hamberger, B. (2014). High-Throughput Testing of Terpenoid Biosynthesis Candidate Genes Using Transient Expression in *Nicotiana benthamiana*. In M Rodríguez Concepción, ed, Plant Isoprenoids, Methods in Molecular Biology, Vol. 1153. Humana Press, New York.).

Metabolite Extraction and LC-MS/MS Analysis

Extraction protocol was as described in example 4.

Results

The co-expression of the type III polyketide synthase HpPKS2 together with either ZhuI, ZhuJ and/or KR in *N. benthamiana*, resulted in the production of novel polyketide-

TABLE 2

Novel compounds produced from the in vivo combination of OKS with cyclases/ketoreductases.

| RT [min] | m/z (ESI+) | Molecular formula | B: OKS + KR | C: OKS + KR + CYC_DH | D: OKS + KR + CYC | E: OKS + KR + CYC + CYC_DH |
|---|---|---|---|---|---|---|
| 12.32 | 188.0693 | C11H10NO2 | | + | + | + |
| 13.14 | 237.0754 | C12H12O5 | + | + | + | + |
| 13.81 | 235.0953 | C13H14O4 | + | + | + | + |
| 16.14 | 299.0544 | C16H11O6 | | | | + |
| 16.57 | 285.0771 | C15H12O5 | | + | | |
| 16.66 | 303.0879 | C16H14O6 | + | | | |
| 17.19 | 235.0956 | C13H14O4 | | + | | |
| 17.9 | 285.0769 | C15H12O5 | | + | | |
| 18.23 | 303.0887 | C16H14O6 | + | | + | |
| 19.4 | 285.0767 | C15H12O5 | | + | | |
| 19.69 | 303.0885 | C16H14O6 | | | + | |
| 19.97 | 275.212 | C17H26N2O | | | + | + |
| 21.19 | 285.0768 | C15H12O5 | | + | | |
| 32.58 | 301.1788 | C19H24O3 | + | + | | |

+ indicate in which combination the polyketide synthase and foldases produced specific novel polyketide-derived compounds.
LC-MS chromatograms in which the novel polyketide-derived compounds were identified from the different combinations (B-E), can be found in FIG. 3.
RT: retention time and m/z: mass-to-charge ratio and ESI+: positive electrospray ionisation.

Conclusion

The heterologous co-expression, also defined as combinations, of OKS from *Aloe arborescens* with foldases (CYC and CYC_DH) and KR from *Streptomyces coelicolor* A3 (2) gives rise to the production of novel compounds, including polyketides of different chain-length and derivatives thereof in *N. benthamiana*.

Example 4—Introducing a Type III Polyketide Synthase (HpPKS2) Together with Cyclases/Ketoreductase ZhuI, ZhuJ, CYC, CYC_DH and KR (Cyclase Superfamily) into *N. benthamiana*

Methods

Generation of Plasmid Constructs for Expression in *N. benthamiana*.

CYC (actIORF5) and CYC_DH (actIORF4) from the actinorhodin biosynthetic gene cluster in *Streptomyces coe-* derived compounds. Among these novel compounds the heptaketide aloesone, aloesol and 0-glucosylated varieties thereof were identified (FIG. 11).

Conclusion

The heterologous co-expression, also defined as combinations, of HpPKS2 with foldases (ZhuI and ZhuJ) and KR from *Streptomyces coelicolor* A3 (2) give rise to the production of novel compounds, including polyketides of different chain-lengths and derivatives thereof in *N. benthamiana*.

REFERENCES

Bach, S. S., Bassard, J. É., Andersen-Ranberg, J., Møldrup, M. E., Simonsen, H. T., Hamberger, B. (2014). High-Throughput Testing of Terpenoid Biosynthesis Candidate Genes Using Transient Expression in *Nicotiana benthamiana*. In M Rodríguez Concepción, ed, Plant Isoprenoids, Methods in Molecular Biology, Vol. 1153. Humana Press, New York.)

Sainsbury, F., Theunemann, E C., Lomonossoff, G P., (2009) pEAQ: versatile expression vectors for easy and quick transient expression of heterologous proteins in plants, Plant Biotechnology Journal 7(7): 682-693.

The invention claimed is:

1. A method of producing a polyketide-derived aromatic, polyaromatic, cyclic or polycyclic compound, wherein the carbon atom chain length of the polyketide backbone of the compounds is selected from 6-31 carbon atoms, comprising the steps of:
   a. providing a recombinant cell comprising:
      i. a transgene encoding a heterologous type III polyketide synthase capable of forming a linear non-reduced polyketide compound, wherein the carbon atom chain length of the polyketide backbone of the formed compound is selected from 6-31 carbon atoms; and
      ii. a transgene encoding a first heterologous small molecule foldase enzyme capable of catalyzing the formation of one or more region-specific intramolecular carbon-carbon or carbon-oxygen bonds in a linear non-reduced polyketide compound, wherein the carbon atom chain length of the polyketide backbone of the compound is one or more of 6-31 carbon atoms,
         wherein the heterologous small molecule foldase enzyme is a bacterial or fungal enzyme, and wherein the genus from which said bacterial or fungal enzyme is derived is different from the genus from which said PKSIII enzyme is derived, and
         wherein the recombinant cell is capable of a producing polyketide-derived aromatic, polyaromatic, cyclic or polycyclic compound, wherein the carbon atom chain length of the polyketide backbone of the compound is selected from among 6-31 carbon atoms; and
   b. incubating and/or culturing the recombinant cell in a culture medium to support synthesis of the polyketide-derived aromatic, polyaromatic, cyclic or polycyclic compound.

2. The method according to claim 1, wherein the heterologous type III polyketide synthase is selected from the group consisting of:
   a. Triketide synthase polypeptide, wherein the amino acid sequence of the polypeptide has at least 70% sequence identity to 2-PS (SEQ ID NO:2) from *Gerbera* hybrid;
   b. Tetraketide synthase polypeptide, wherein the amino acid sequence of the polypeptide has at least 70% sequence identity to PhID (SEQ ID NO:4) from *Pseudomonas fluorescens;*
   c. Pentaketide synthase polypeptide, wherein the amino acid sequence of the polypeptide has at least 70% sequence identity to a sequence selected from the group consisting of PCS (SEQ ID NO:6) from *Aloe arborescens*, ORAS (SEQ ID NO:8) from *Neurospora crassa*, and 1,3,6,8-tetrahydroxynaphthalene synthase (SEQ ID NO:10) from *Streptomyces fulvissimus;*
   d. Hexaketide synthase polypeptide, wherein the amino acid sequence of the polypeptide has at least 70% sequence identity to a sequence selected from the group consisting of PinPKS (SEQ ID NO:12) from *Plumbago indica*, DluHKS (SEQ ID NO:14) from *Drosophyllum lusitanicum*, and PzPKS (SEQ ID NO:16) from *Plumbago zeylanica;*
   e. Heptaketide synthase polypeptide, wherein the amino acid sequence of the polypeptide has at least 70% sequence identity to ALS (SEQ ID NO:18) from *Rheum palmatum* or AaPKS3 (SEQ ID NO:20) from *Aloe arborescens;*
   f. Octaktide synthase polypeptide, wherein the amino acid sequence of the polypeptide has at least 70% sequence identity to a sequence selected from the group consisting of OKS (SEQ ID NO:22), OKS2 (SEQ ID NO:24), OKS3 (SEQ ID NO:26) from *Aloe arborescens* or HpPKS2 (SEQ ID NO:28) from *Hypericum perforatum;*
   g. Nonaketide synthase polypeptide, wherein the amino acid sequence of the polypeptide has at least 70% sequence identity to PCS F80A/Y82A/M207G (SEQ ID NO:29) from *Aloe arborescens;*
   h. Decaketide synthase polypeptide, wherein the amino acid sequence of the polypeptide has at least 70% sequence identity to OKS N222G (SEQ ID NO:30) from *Aloe arborescens*; and
   i. Dodecaketide synthase polypeptide, wherein the amino acid sequence of the polypeptide has at least 70% sequence identity to OKS F66L/N222G (SEQ ID NO:31) from *Aloe arborescens.*

3. The method according to claim 1, wherein the cell comprises one or more transgene encoding a second, third and fourth heterologous small molecule foldase enzyme capable of catalyzing the formation of one or more region-specific intramolecular carbon-carbon or carbon-oxygen bonds in a non-linear polyketide compound, and
   wherein the second, third and fourth heterologous small molecule foldase enzymes are bacterial or fungal enzymes, and
   wherein the genus from which said bacterial or fungal enzymes is derived is different from the genus from which the PKSIII enzyme is derived.

4. The method according to claim 3, wherein one or more of said second, third or fourth heterologous heterologous small molecule foldase enzymes is selected from one or more of the groups consisting of:
   a. Cyclase foldase, wherein the amino acid sequence of the polypeptide has at least 70% sequence identity to a sequence selected from the group consisting of ZhuJ (SEQ ID NO:81) from *Streptomyces* sp. R1128, oxyN (SEQ ID NO:83) from *Streptomyces rimosus*, jadI (SEQ ID NO:85) from *Streptomyces venezuelae*, LndF (SEQ ID NO:86) from *Streptomyces globisporus*, pgaF (SEQ ID NO:89) from *Streptomyces coelicoflavus*, pnxK (SEQ ID NO:95) from *Streptomyces* sp., llpCIII (SEQ ID NO:101) from *Streptomyces tendae*, Act_CYC (SEQ ID NO:91) from *Streptomyces coelicolor* A3(2), sanE (SEQ ID NO:93) from *Streptomyces ansochromogenes;*
   b. Cupin foldase, wherein the amino acid sequence of the polypeptide has at least 70% sequence identity to a sequence selected from the group consisting of pnxL (SEQ ID NO:95) from *Streptomyces* sp. TA-0256, llpCII (SEQ ID NO:99) from *Streptomyces tendae*,
   c. Cyclase foldase, wherein the amino acid sequence of the polypeptide has at least 70% sequence identity to a sequence selected from the group consisting of ZhuJ-1 (SEQ ID NO:103) from *Aspergillus nidulans*, ZhuJ-2 (SEQ ID NO:105) from *Aspergillus nidulans*, ZhuJ-3 (SEQ ID NO:107) from *Aspergillus nidulans*, ZhuJ-4 (SEQ ID NO:109) from *Aspergillus nidulan.*

5. The method according to claim 3, wherein one or more of said second, third and fourth heterologous small molecule foldase enzyme has cyclase or aromatase catalytic activity and a corresponding structural domain selected from the group consisting of:

a. a pfam04199 cyclase superfamily domain;
b. a pfam10604 or pfam03364 SRPBCC superfamily domain;
c. a pfam07876 Dabb superfamily domain;
d. a pfam04673 Polyketide synthesis cyclase superfamily domain;
e. a pfam00753 Lactamase_B/MBL fold metallo-hydrolase superfamily domain;
f. a pfam07883 Cupin-2 superfamily domain;
g. Dissected Product template (TIGR04532) domains from type I iterative PKS from filamentous fungi.

6. The method according to claim 1, wherein said first heterologous small molecule foldase enzyme has cyclase or aromatase catalytic activity and a corresponding structural domain selected from the group consisting of:
   a. a pfam04199 cyclase superfamily domain;
   b. a pfam10604 or pfam03364 SRPBCC superfamily domain;
   c. a pfam07876 Dabb superfamily domain;
   d. a pfam04673 Polyketide synthesis cyclase superfamily domain;
   e. a pfam00753 Lactamase_B/MBL fold metallo-hydrolase superfamily domain;
   f. a pfam07883 Cupin-2 superfamily domain;
   g. Dissected Product template (TIGR04532) domains from type I iterative PKS from filamentous fungi.

7. The method according to claim 1, wherein said first heterologous heterologous small molecule foldase enzyme is selected from one or more of the groups consisting of:
   a. SRPBCC Foldase, wherein the amino acid sequence of the polypeptide has at least 70% sequence identity to a sequence selected from the group consisting of ZhuI (SEQ ID NO:33) from *Streptomyces* sp. R1128, pdmD (SEQ ID NO:35) from *Actinomadura hibisca*, sanI (SEQ NO:37) from *Streptomyces* sp., SANK 61196; pnxD (SEQ ID NO:39) from *Streptomyces* sp. TA-0256, llpCI (SEQ ID NO:41) from *Streptomyces tendae*; ZhuI-1 (SEQ ID NO:66) from *Aspergillus nidulans* or ZhuI-2 (SEQ ID NO:69) from *Aspergillus nidulans;*
   b. 2×SRPBCC foldase, wherein the amino acid sequence of the polypeptide has at least 70% sequence identity to a sequence selected from the group consisting of gra-orf4 (SEQ ID NO:43) from *Streptomyces violaceoruber*, schP4 (SEQ ID NO:45) from *Streptomyces fulvissimus* DSM 40593, Erd4 (SEQ ID NO:47) from uncultured soil bacterium V167, med-ORF19 (SEQ ID NO:49) from *Streptomyces* sp. AM-7161, ssfY1 (SEQ ID NO:51) from *Streptomyces* sp. SF2575, oxyK (SEQ ID NO:53) from *Streptomyces rimosus*, Act_ARO-CYC (SEQ ID NO:55) from *Streptomyces coelicolor* A3(2);
   c. Dabb foldase, wherein the amino acid sequence of the polypeptide has at least 70% sequence identity to a sequence selected from the group consisting of AOC-1 (SEQ ID NO:71) from *Aspergillus nidulans*, AOC-2 (SEQ ID NO:73) from *Aspergillus nidulans*, AOC-3 (SEQ ID NO:75) from *Aspergillus nidulans*, AOC-4 (SEQ ID NO:77) from *Aspergillus nidulans*, or AOC-5 (SEQ ID NO:79) from *Aspergillus nidulans*; and
   d. Dissected PT domain, wherein the amino acid sequence of the polypeptide has at least 70% sequence identity to a sequence selected from the group consisting of wA-PT (SEQ ID NO:59) from *Aspergillus nidulan* to form C7-C12+C1-C10, BIK1-PT (SEQ ID NO:60) from *Fusarium fujikuroi*, PGL1 PT (SEQ ID NO:63) from *Fusarium graminearum*, mpdG_PT (SEQ ID NO:65) from *Aspergillus nidulans* or curs2-PT (GenBank AGC95321.1 position 1270 to 1613) from *Aspergillus* (SEQ ID NO:146).

8. The method according to claim 1, wherein the recombinant cell or the recombinant cells in the one or more heterogeneous populations, is selected from among a bacterial cell, a filamentous fungal cell, a yeast cell and a plant cell.

9. The method according to claim 8, wherein the yeast cell is an Ascomycete selected from the group consisting of Ashbya, Botryoascus, Debaryomyces, *Hansenula*, Kluveromyces, Lipomyces, *Saccharomyces* spp and the filamentous fungal cell is selected from the group consisting of *Acremonium, Aspergillus, Fusarium, Humicola, Mucor, Myceliophthora, Neurospora, Penicillium, Thielavia, Tolypocladium,* and *Trichoderma*.

10. The method according to claim 8, wherein the bacterial cell is selected from the group consisting of: *Bacillus, Streptomyces, Corynebacterium, Pseudomonas*, lactic acid bacteria and an *E. coli* cell.

11. The method according to claim 8, wherein the recombinant host cell is a *Nicothiana benthamiana* or *Arabidopsis thaliana* plant cell.

12. A method of producing a library of polyketide-derived aromatic, polyaromatic, cyclic, and polycyclic compounds, wherein the carbon atom chain length of the polyketide backbone of the compounds is selected from two or more of 6-31 carbon atoms, comprising the steps of:
   a. providing one or more heterogeneous populations of recombinant cells, wherein each cell in the one or more populations comprises:
      i. a transgene encoding a heterologous type III polyketide synthase capable of forming a linear non-reduced polyketide compound, wherein the carbon atom chain length of the polyketide backbone of the formed compound is selected from 6-31 carbon atoms; and
      ii. a transgene encoding a first heterologous heterologous small molecule foldase enzyme capable of catalyzing the formation of one or more region-specific intramolecular carbon-carbon or carbon-oxygen bonds in a linear non-reduced polyketide compound, wherein the carbon atom chain length of the polyketide backbone of the compound is one or more of 6-31 carbon atoms,
      wherein the heterologous small molecule foldase enzyme is a bacterial or fungal enzyme, and wherein the genus from which said bacterial or fungal enzyme is derived is different from the genus from which the PKSIII enzyme is derived, and
      wherein the one or more populations of recombinant cells comprises cells capable of producing polyketide-derived aromatic, polyaromatic, cyclic, and/or polycyclic compounds, wherein the carbon atom chain length of the polyketide backbone of the compounds is selected from two or more of 6-31 carbon atoms; and
   b. incubating and/or culturing the one or more heterogeneous populations of recombinant cells in a culture medium to support synthesis of the library of polyketide-derived aromatic, polyaromatic, cyclic, and polycyclic compounds.

13. The method of claim 12, further comprising a step of:
   c. screening the library of polyketide-derived aromatic, polyaromatic, cyclic, and polycyclic compounds, wherein each recombinant cell, or its clonal derivatives, present in the one or more heterogeneous population of recombinant cells is grown individually on a solid support, or individually in a liquid culture.

14. The method of claim 12, further comprising the step of recovering the polyketide-derived aromatic, polyaromatic, cyclic, and polycyclic compounds produced by the one or more heterogeneous populations of recombinant cells or produced by one or more of the recombinant cell clones present in the one or more heterogeneous populations of recombinant cells.

15. A heterogeneous population of recombinant cells capable of producing a library of polyketide-derived aromatic, polyaromatic, cyclic, and/or polycyclic compounds, according to the method of claim 12, wherein each cell in the population comprises:
   a. a transgene encoding a heterologous type III PKS capable of forming a polyketide-derived aromatic, polyaromatic, cyclic, and/or polycyclic compound, wherein the carbon atom chain length of the polyketide backbone of the formed compound is selected from 6-31 carbon atoms; and
   b. a transgene encoding a first heterologous heterologous small molecule foldase enzyme capable of catalyzing the formation of one or more specific intramolecular carbon-carbon bonds in a polyketide-derived aromatic, polyaromatic, cyclic and polycyclic compound, wherein the carbon atom chain length of the polyketide backbone of the compound is one or more of 6-31 carbon atoms,
   wherein the heterologous small molecule foldase enzyme is a bacterial or fungal enzyme, and wherein the genus from which said bacterial or fungal enzyme is derived is different from the genus from which the PKSIII enzyme is derived,
   wherein the population of recombinant cells comprises cells capable of producing polyketide-derived aromatic, polyaromatic, cyclic, and/or polycyclic compounds, wherein the carbon atom chain length of the polyketide backbone of the compounds is selected from two or more of 6-31 carbon atoms.

16. The heterogeneous population of recombinant cells of claim 15, wherein each cell in the population further comprises one or more transgene encoding a second, third and fourth heterologous heterologous small molecule foldase enzyme capable of catalyzing the formation of one or more region-specific intramolecular carbon-carbon or carbon-oxygen bonds in a non-linear polyketide compound, and wherein the second, third and fourth heterologous small molecule foldase enzymes are bacterial or fungal enzymes, and wherein the genus from which said bacterial or fungal enzymes is derived is different from the genus from which the PKSIII enzyme is derived.

* * * * *

SEQUENCE LISTING

```
<160> NUMBER OF SEQ ID NOS: 145

<210> SEQ ID NO 1
<211> LENGTH: 1209
<212> TYPE: DNA
<213> ORGANISM: Gerbera hybrida
<220> FEATURE:
<221> NAME/KEY: CDS
<222> LOCATION: (1)..(1209)
<223> OTHER INFORMATION: 2-PS gene [GenBank ID number Z38097.2) encoding
      a  Type III triketide synthase (GenBank ID number P48391.2)

<400> SEQUENCE: 1 atg gga tct tac tca tcc gat gat gtg gag gtg att cgt gag gcc gga       48
Met Gly Ser Tyr Ser Ser Asp Asp Val Glu Val Ile Arg Glu Ala Gly
1               5                   10                  15 cgg gca caa ggt tta gcc acg att ctt gcc att ggc act gct act cct       96
Arg Ala Gln Gly Leu Ala Thr Ile Leu Ala Ile Gly Thr Ala Thr Pro
            20                  25                  30 ccc aat tgc gtc gct caa gct gat tat gca gac tat tat ttt cgt gtc      144
Pro Asn Cys Val Ala Gln Ala Asp Tyr Ala Asp Tyr Tyr Phe Arg Val
        35                  40                  45 act aag agc gaa cat atg gtt gat ctt aaa gag aaa ttt aaa cgc att      192
Thr Lys Ser Glu His Met Val Asp Leu Lys Glu Lys Phe Lys Arg Ile
    50                  55                  60 tgt gag aaa aca gcg ata aag aaa cga tac cta gcc ctc acc gaa gac      240
Cys Glu Lys Thr Ala Ile Lys Lys Arg Tyr Leu Ala Leu Thr Glu Asp
65                  70                  75                  80 tat ctg caa gag aac cca aca atg tgt gag ttc atg gct cca tcc tta      288
Tyr Leu Gln Glu Asn Pro Thr Met Cys Glu Phe Met Ala Pro Ser Leu
                85                  90                  95 aac gct cga caa gac cta gtg gtc acc ggc gtc cca atg ctt ggc aaa      336
Asn Ala Arg Gln Asp Leu Val Val Thr Gly Val Pro Met Leu Gly Lys
            100                 105                 110 gaa gcc gca gtc aag gcc att gat gaa tgg gga cta cca aaa tcc aag      384
Glu Ala Ala Val Lys Ala Ile Asp Glu Trp Gly Leu Pro Lys Ser Lys
        115                 120                 125 atc acc cac ctc atc ttc tgc acc act gct ggc gtt gac atg ccc ggt      432
Ile Thr His Leu Ile Phe Cys Thr Thr Ala Gly Val Asp Met Pro Gly
    130                 135                 140 gct gac tat caa ctc gtc aaa ctc ctt ggt ctc tcc cct tca gtc aaa      480
Ala Asp Tyr Gln Leu Val Lys Leu Leu Gly Leu Ser Pro Ser Val Lys
145                 150                 155                 160 cgc tat atg ttg tac caa cag gga tgt gcc gcc ggc ggc aca gtc ctc      528
Arg Tyr Met Leu Tyr Gln Gln Gly Cys Ala Ala Gly Gly Thr Val Leu
                165                 170                 175 cgg cta gcc aag gac ctt gct gaa aac aac aag ggc tca cga gtc ctt      576
Arg Leu Ala Lys Asp Leu Ala Glu Asn Asn Lys Gly Ser Arg Val Leu
            180                 185                 190 atc gtc tgc tcc gag atc act gct atc tta ttc cat gga ccc aat gag      624
Ile Val Cys Ser Glu Ile Thr Ala Ile Leu Phe His Gly Pro Asn Glu
        195                 200                 205 aac cac ctt gac tca ctc gtc gct caa gct tta ttc gga gac gga gct      672
Asn His Leu Asp Ser Leu Val Ala Gln Ala Leu Phe Gly Asp Gly Ala
    210                 215                 220 gca gca ctc att gtg ggt tca ggc cct cac ttg gcc gta gaa cgg cca      720
Ala Ala Leu Ile Val Gly Ser Gly Pro His Leu Ala Val Glu Arg Pro
```

```
                 225                 230                 235                 240
ata ttc gag atc gtg tca act gat caa aca atc ttg ccg gac act gag    768
Ile Phe Glu Ile Val Ser Thr Asp Gln Thr Ile Leu Pro Asp Thr Glu
                    245                 250                 255 aag gca atg aag tta cac ttg aga gag gga ggg ttg acg ttt cag ttg    816
Lys Ala Met Lys Leu His Leu Arg Glu Gly Gly Leu Thr Phe Gln Leu
                260                 265                 270 cat aga gat gta ccc ttg atg gtc gca aag aac ata gag aac gca gcg    864
His Arg Asp Val Pro Leu Met Val Ala Lys Asn Ile Glu Asn Ala Ala
            275                 280                 285 gag aaa gcg ttg tct cca cta ggg ata act gat tgg aac tca gtt ttc    912
Glu Lys Ala Leu Ser Pro Leu Gly Ile Thr Asp Trp Asn Ser Val Phe
        290                 295                 300 tgg atg gtg cac cca ggt ggt cga gcc ata ttg gac cag gtg gag cga    960
Trp Met Val His Pro Gly Gly Arg Ala Ile Leu Asp Gln Val Glu Arg
305                 310                 315                 320 aaa cta aac ctt aag gaa gat aag tta agg gct agc agg cat gtg ctt   1008
Lys Leu Asn Leu Lys Glu Asp Lys Leu Arg Ala Ser Arg His Val Leu
                325                 330                 335 agt gaa tac gga aac ctg att agc gct tgt gtg ttg ttc atc att gac   1056
Ser Glu Tyr Gly Asn Leu Ile Ser Ala Cys Val Leu Phe Ile Ile Asp
                340                 345                 350 gag gtg agg aag aga tct atg gcg gaa ggg aag agt aca acc ggt gaa   1104
Glu Val Arg Lys Arg Ser Met Ala Glu Gly Lys Ser Thr Thr Gly Glu
            355                 360                 365 ggt ttg gat tgc ggt gtt ttg ttt gga ttt gga ccg ggt atg act gtt   1152
Gly Leu Asp Cys Gly Val Leu Phe Gly Phe Gly Pro Gly Met Thr Val
        370                 375                 380 gag act gtt gtt ctt cgt agc gtc cgc gtt act gct gcg gtt gcc aat   1200
Glu Thr Val Val Leu Arg Ser Val Arg Val Thr Ala Ala Val Ala Asn
385                 390                 395                 400 gga aac tga                                                        1209
Gly Asn

<210> SEQ ID NO 2
<211> LENGTH: 402
<212> TYPE: PRT
<213> ORGANISM: Gerbera hybrida

<400> SEQUENCE: 2

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Cys Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
                85                  90                  95

Asn Ala Arg Gln Asp Leu Val Val Thr Gly Val Pro Met Leu Gly Lys
            100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140
```

```
Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
            165                 170                 175

Arg Leu Ala Lys Asp Leu Ala Glu Asn Lys Gly Ser Arg Val Leu
        180                 185                 190

Ile Val Cys Ser Glu Ile Thr Ala Ile Leu Phe His Gly Pro Asn Glu
            195                 200                 205

Asn His Leu Asp Ser Leu Val Ala Gln Ala Leu Phe Gly Asp Gly Ala
        210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
            245                 250                 255

Lys Ala Met Lys Leu His Leu Arg Glu Gly Gly Leu Thr Phe Gln Leu
        260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
290                 295                 300

Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
            325                 330                 335

Ser Glu Tyr Gly Asn Leu Ile Ser Ala Cys Val Leu Phe Ile Ile Asp
        340                 345                 350

Glu Val Arg Lys Arg Ser Met Ala Glu Gly Lys Ser Thr Thr Gly Glu
            355                 360                 365

Gly Leu Asp Cys Gly Val Leu Phe Gly Phe Gly Pro Gly Met Thr Val
        370                 375                 380

Glu Thr Val Val Leu Arg Ser Val Arg Val Thr Ala Ala Val Ala Asn
385                 390                 395                 400

Gly Asn

<210> SEQ ID NO 3
<211> LENGTH: 1089
<212> TYPE: DNA
<213> ORGANISM: Pseudomonas fluorescens
<220> FEATURE:
<221> NAME/KEY: CDS
<222> LOCATION: (1)..(1089)
<223> OTHER INFORMATION: PhlD [GenBank ID number JN561597.1 position
      2882 to 3970) encoding a Type III tetraketide synthase (GenBank
      ID number AEW67127.1)

<400> SEQUENCE: 3 atg ctt cta act tta ttg gct tct cgc cga gga ctt gtc atg tct act     48
Met Leu Leu Thr Leu Leu Ala Ser Arg Arg Gly Leu Val Met Ser Thr
1               5                   10                  15 ctt tgt aaa ccc agt ctg ttg ttt ccg caa tac aag atc acc cag caa     96
Leu Cys Lys Pro Ser Leu Leu Phe Pro Gln Tyr Lys Ile Thr Gln Gln
            20                  25                  30 caa atg atc gag cat cta gag cag ttg cat gat gat cat cca cga atg    144
Gln Met Ile Glu His Leu Glu Gln Leu His Asp Asp His Pro Arg Met
        35                  40                  45 gca ctt gcc aaa cga atg att caa aac acg cag gtg aac gaa cgg cac    192
Ala Leu Ala Lys Arg Met Ile Gln Asn Thr Gln Val Asn Glu Arg His
```

```
            50                  55                  60
ttg gtc ctg cct atc gat gaa ctg gcg gtg cac acc ggc ttc acc cac    240
Leu Val Leu Pro Ile Asp Glu Leu Ala Val His Thr Gly Phe Thr His
 65                  70                  75                  80 cgc agt atc gtt tat gag cgc gaa gcc cgc cgc atg tca tcc atc gcg    288
Arg Ser Ile Val Tyr Glu Arg Glu Ala Arg Arg Met Ser Ser Ile Ala
                 85                  90                  95 gcg cgc caa gcc atc gag aat gcc ggg ctg acc atc gat gac att cgc    336
Ala Arg Gln Ala Ile Glu Asn Ala Gly Leu Thr Ile Asp Asp Ile Arg
            100                 105                 110 atg gtc gcg gtg aca tcg tgc acc ggt ttc atg atg ccc tcg ctg aca    384
Met Val Ala Val Thr Ser Cys Thr Gly Phe Met Met Pro Ser Leu Thr
        115                 120                 125 gcc cac ttg atc aat gac ctg ggc ctg cga acg tcg acc gta caa ctg    432
Ala His Leu Ile Asn Asp Leu Gly Leu Arg Thr Ser Thr Val Gln Leu
    130                 135                 140 ccc atc gct caa ctg ggc tgc gtg gca ggc gct gcg gcg atc aat cga    480
Pro Ile Ala Gln Leu Gly Cys Val Ala Gly Ala Ala Ala Ile Asn Arg
145                 150                 155                 160 gcc aat gac ttc gcc agc cgg gcg ccg gac aac cat gtc ctc atc gtc    528
Ala Asn Asp Phe Ala Ser Arg Ala Pro Asp Asn His Val Leu Ile Val
                165                 170                 175 tcc ctg gag ttc tca tcg ctc tgc tat caa ccc cag gac acc aag ttg    576
Ser Leu Glu Phe Ser Ser Leu Cys Tyr Gln Pro Gln Asp Thr Lys Leu
            180                 185                 190 cac gcg ttc ata tca gcc gcg tta ttc ggc gat gcc gta tcg gcc tgc    624
His Ala Phe Ile Ser Ala Ala Leu Phe Gly Asp Ala Val Ser Ala Cys
        195                 200                 205 gtc atg cgc gcc gat gac cag gcg cct ggt ttc aag atc gcc aat acc    672
Val Met Arg Ala Asp Asp Gln Ala Pro Gly Phe Lys Ile Ala Asn Thr
    210                 215                 220 ggg tct tac ttc ctg cct gat agc gag cac tac att aaa tac gac gtt    720
Gly Ser Tyr Phe Leu Pro Asp Ser Glu His Tyr Ile Lys Tyr Asp Val
225                 230                 235                 240 aaa gac agc ggc ttt cat ttc acc ttg gac aag gct gtc atg aac tcc    768
Lys Asp Ser Gly Phe His Phe Thr Leu Asp Lys Ala Val Met Asn Ser
                245                 250                 255 att aaa gat gtc gca ccg atg atg gag gaa ttg aac tac gag acc ttc    816
Ile Lys Asp Val Ala Pro Met Met Glu Glu Leu Asn Tyr Glu Thr Phe
            260                 265                 270 aat caa cat tgc gct caa aat gac ttt ttc atc ttc cat acc ggc gga    864
Asn Gln His Cys Ala Gln Asn Asp Phe Phe Ile Phe His Thr Gly Gly
        275                 280                 285 cgg aaa att ctt gat gaa ctg gtc ctg caa ctg gac ttg gaa ccc ggt    912
Arg Lys Ile Leu Asp Glu Leu Val Leu Gln Leu Asp Leu Glu Pro Gly
    290                 295                 300 cgg gtc gcg cag tct cgc gac agt ttg agc gaa gcc ggg aac atc gcc    960
Arg Val Ala Gln Ser Arg Asp Ser Leu Ser Glu Ala Gly Asn Ile Ala
305                 310                 315                 320 agc gtg gtg gtc ttc gat gtg ctc aag cgc caa ttc gac agc gga cct    1008
Ser Val Val Val Phe Asp Val Leu Lys Arg Gln Phe Asp Ser Gly Pro
                325                 330                 335 gtc aat ggc gcg acg ggc atg ttg gcg gcc ttc ggc ccg ggt ttc acc    1056
Val Asn Gly Ala Thr Gly Met Leu Ala Ala Phe Gly Pro Gly Phe Thr
            340                 345                 350 gct gaa atg gcc gtg ggc aag tgg gtc gcc tga                         1089
Ala Glu Met Ala Val Gly Lys Trp Val Ala
        355                 360
```

<210> SEQ ID NO 4
<211> LENGTH: 362
<212> TYPE: PRT
<213> ORGANISM: Pseudomonas fluorescens

<400> SEQUENCE: 4

```
Met Leu Leu Thr Leu Leu Ala Ser Arg Arg Gly Leu Val Met Ser Thr
1               5                   10                  15

Leu Cys Lys Pro Ser Leu Leu Phe Pro Gln Tyr Lys Ile Thr Gln Gln
            20                  25                  30

Gln Met Ile Glu His Leu Glu Gln Leu His Asp Asp His Pro Arg Met
        35                  40                  45

Ala Leu Ala Lys Arg Met Ile Gln Asn Thr Gln Val Asn Glu Arg His
    50                  55                  60

Leu Val Leu Pro Ile Asp Glu Leu Ala Val His Thr Gly Phe Thr His
65                  70                  75                  80

Arg Ser Ile Val Tyr Glu Arg Glu Ala Arg Met Ser Ser Ile Ala
                85                  90                  95

Ala Arg Gln Ala Ile Glu Asn Ala Gly Leu Thr Ile Asp Asp Ile Arg
            100                 105                 110

Met Val Ala Val Thr Ser Cys Thr Gly Phe Met Met Pro Ser Leu Thr
        115                 120                 125

Ala His Leu Ile Asn Asp Leu Gly Leu Arg Thr Ser Thr Val Gln Leu
    130                 135                 140

Pro Ile Ala Gln Leu Gly Cys Val Ala Gly Ala Ala Ala Ile Asn Arg
145                 150                 155                 160

Ala Asn Asp Phe Ala Ser Arg Ala Pro Asp Asn His Val Leu Ile Val
                165                 170                 175

Ser Leu Glu Phe Ser Ser Leu Cys Tyr Gln Pro Gln Asp Thr Lys Leu
            180                 185                 190

His Ala Phe Ile Ser Ala Ala Leu Phe Gly Asp Ala Val Ser Ala Cys
        195                 200                 205

Val Met Arg Ala Asp Asp Gln Ala Pro Gly Phe Lys Ile Ala Asn Thr
    210                 215                 220

Gly Ser Tyr Phe Leu Pro Asp Ser Glu His Tyr Ile Lys Tyr Asp Val
225                 230                 235                 240

Lys Asp Ser Gly Phe His Phe Thr Leu Asp Lys Ala Val Met Asn Ser
                245                 250                 255

Ile Lys Asp Val Ala Pro Met Met Glu Glu Leu Asn Tyr Glu Thr Phe
            260                 265                 270

Asn Gln His Cys Ala Gln Asn Asp Phe Ile Phe His Thr Gly Gly
        275                 280                 285

Arg Lys Ile Leu Asp Glu Leu Val Leu Gln Leu Asp Leu Glu Pro Gly
    290                 295                 300

Arg Val Ala Gln Ser Arg Asp Ser Leu Ser Glu Ala Gly Asn Ile Ala
305                 310                 315                 320

Ser Val Val Val Phe Asp Val Leu Lys Arg Gln Phe Asp Ser Gly Pro
                325                 330                 335

Val Asn Gly Ala Thr Gly Met Leu Ala Ala Phe Gly Pro Gly Phe Thr
            340                 345                 350

Ala Glu Met Ala Val Gly Lys Trp Val Ala
        355                 360
```

<210> SEQ ID NO 5
<211> LENGTH: 1212

```
<212> TYPE: DNA
<213> ORGANISM: Aloe arborescens
<220> FEATURE:
<221> NAME/KEY: CDS
<222> LOCATION: (1)..(1212)
<223> OTHER INFORMATION: PCS [GenBank ID number AY823626) encoding a
      Type III pentaketide synthase (GenBank ID number AAX35541.1)

<400> SEQUENCE: 5 atg agt tca ctc tcc aac tct ctg ccg ttg atg gag gat gtg cag ggc      48
Met Ser Ser Leu Ser Asn Ser Leu Pro Leu Met Glu Asp Val Gln Gly
1               5                   10                  15 atc cga aag gcc caa aag gca gac gga act gca acc gtg atg gcc atc      96
Ile Arg Lys Ala Gln Lys Ala Asp Gly Thr Ala Thr Val Met Ala Ile
            20                  25                  30 gga aca gct cac cca cct cat atc ttt ccg cag gac act tac gct gat     144
Gly Thr Ala His Pro Pro His Ile Phe Pro Gln Asp Thr Tyr Ala Asp
        35                  40                  45 gtc tac ttc cgg gcc acc aac agc gag cac aag gtc gag ctc aag aag     192
Val Tyr Phe Arg Ala Thr Asn Ser Glu His Lys Val Glu Leu Lys Lys
    50                  55                  60 aag ttc gat cac atc tgc aag aaa aca atg ata ggg aag cgt tac ttc     240
Lys Phe Asp His Ile Cys Lys Lys Thr Met Ile Gly Lys Arg Tyr Phe
65                  70                  75                  80 aac tat gac gag gag ttc ttg aag aag tat ccc aac att act tca tat     288
Asn Tyr Asp Glu Glu Phe Leu Lys Lys Tyr Pro Asn Ile Thr Ser Tyr
                85                  90                  95 gac gag ccc agc ctc aac gac agg cag gac att tgc gtt cct ggg gtg     336
Asp Glu Pro Ser Leu Asn Asp Arg Gln Asp Ile Cys Val Pro Gly Val
            100                 105                 110 ccg gcc ctg ggg aca gaa gcg gct gtg aag gcc atc gag gaa tgg gga     384
Pro Ala Leu Gly Thr Glu Ala Ala Val Lys Ala Ile Glu Glu Trp Gly
        115                 120                 125 cgc ccg aag tct gag atc act cac ctc gtg ttc tgc acc tcc tgc ggt     432
Arg Pro Lys Ser Glu Ile Thr His Leu Val Phe Cys Thr Ser Cys Gly
    130                 135                 140 gtc gac atg cct agc gcc gat ttc cag tgc gct aag ctc ctt ggc ctc     480
Val Asp Met Pro Ser Ala Asp Phe Gln Cys Ala Lys Leu Leu Gly Leu
145                 150                 155                 160 cat gcc aat gtc aac aag tac tgc atc tac atg cag gga tgc tat gct     528
His Ala Asn Val Asn Lys Tyr Cys Ile Tyr Met Gln Gly Cys Tyr Ala
                165                 170                 175 ggt ggc acc gtc atg cgg tat gcc aag gat ctg gcc gag aac aac cgt     576
Gly Gly Thr Val Met Arg Tyr Ala Lys Asp Leu Ala Glu Asn Asn Arg
            180                 185                 190 ggt gct cgc gtt ctt gtg gtg tgc gcg gag ctc acc atc atg atg ctt     624
Gly Ala Arg Val Leu Val Val Cys Ala Glu Leu Thr Ile Met Met Leu
        195                 200                 205 cgc gcc ccc aac gag acc cat ctc gac aat gcc atc ggc atc tct cta     672
Arg Ala Pro Asn Glu Thr His Leu Asp Asn Ala Ile Gly Ile Ser Leu
    210                 215                 220 ttt gga gat gga gct gct gca ctg atc att ggg tcg gac ccc atc att     720
Phe Gly Asp Gly Ala Ala Ala Leu Ile Ile Gly Ser Asp Pro Ile Ile
225                 230                 235                 240 ggt gtc gag aag ccc atg ttc gag att gtg tgc acc aag caa act gtg     768
Gly Val Glu Lys Pro Met Phe Glu Ile Val Cys Thr Lys Gln Thr Val
                245                 250                 255 atc cca aac act gaa gat gtt atc cat ctc cac ttg agg gag acg ggt     816
Ile Pro Asn Thr Glu Asp Val Ile His Leu His Leu Arg Glu Thr Gly
            260                 265                 270 atg atg ttc tac cta agc aag ggc agt ccc atg acc atc tcc aat aac     864
```

```
Met Met Phe Tyr Leu Ser Lys Gly Ser Pro Met Thr Ile Ser Asn Asn
            275                 280                 285 gta gag gcc tgc ctt att gat gtg ttc aag tcg gtg ggg ata act cct    912
Val Glu Ala Cys Leu Ile Asp Val Phe Lys Ser Val Gly Ile Thr Pro
        290                 295                 300 cca gag gac tgg aac tct ctc ttc tgg atc cct cat ccc ggt ggt cgg    960
Pro Glu Asp Trp Asn Ser Leu Phe Trp Ile Pro His Pro Gly Gly Arg
305                 310                 315                 320 gct atc ctc gac caa gtt gag gcc aag cta aag ctt cgc ccc gag aag   1008
Ala Ile Leu Asp Gln Val Glu Ala Lys Leu Lys Leu Arg Pro Glu Lys
                325                 330                 335 ttc agg gcg gct cga act gtt ctg tgg gat tac ggc aac atg gtg agc   1056
Phe Arg Ala Ala Arg Thr Val Leu Trp Asp Tyr Gly Asn Met Val Ser
            340                 345                 350 gca agt gtg ggc tac ata tta gat gag atg aga aga aaa tct gct gct   1104
Ala Ser Val Gly Tyr Ile Leu Asp Glu Met Arg Arg Lys Ser Ala Ala
        355                 360                 365 aaa ggg tta gaa acc tat gga gag gga tta gag tgg ggt gtc tta ctt   1152
Lys Gly Leu Glu Thr Tyr Gly Glu Gly Leu Glu Trp Gly Val Leu Leu
370                 375                 380 ggt ttt ggt cca ggg ata act gtt gaa act atc ctt ctt cac agc ctg   1200
Gly Phe Gly Pro Gly Ile Thr Val Glu Thr Ile Leu Leu His Ser Leu
385                 390                 395                 400 cct ctc atg taa                                                    1212
Pro Leu Met <210> SEQ ID NO 6
<211> LENGTH: 403
<212> TYPE: PRT
<213> ORGANISM: Aloe arborescens

<400> SEQUENCE: 6

Met Ser Ser Leu Ser Asn Ser Leu Pro Leu Met Glu Asp Val Gln Gly
1               5                   10                  15

Ile Arg Lys Ala Gln Lys Ala Asp Gly Thr Ala Thr Val Met Ala Ile
            20                  25                  30

Gly Thr Ala His Pro Pro His Ile Phe Pro Gln Asp Thr Tyr Ala Asp
        35                  40                  45

Val Tyr Phe Arg Ala Thr Asn Ser Glu His Lys Val Glu Leu Lys Lys
    50                  55                  60

Lys Phe Asp His Ile Cys Lys Lys Thr Met Ile Gly Lys Arg Tyr Phe
65                  70                  75                  80

Asn Tyr Asp Glu Glu Phe Leu Lys Lys Tyr Pro Asn Ile Thr Ser Tyr
                85                  90                  95

Asp Glu Pro Ser Leu Asn Asp Arg Gln Asp Ile Cys Val Pro Gly Val
            100                 105                 110

Pro Ala Leu Gly Thr Glu Ala Ala Val Lys Ala Ile Glu Glu Trp Gly
        115                 120                 125

Arg Pro Lys Ser Glu Ile Thr His Leu Val Phe Cys Thr Ser Cys Gly
    130                 135                 140

Val Asp Met Pro Ser Ala Asp Phe Gln Cys Ala Lys Leu Leu Gly Leu
145                 150                 155                 160

His Ala Asn Val Asn Lys Tyr Cys Ile Tyr Met Gln Gly Cys Tyr Ala
                165                 170                 175

Gly Gly Thr Val Met Arg Tyr Ala Lys Asp Leu Ala Glu Asn Asn Arg
            180                 185                 190

Gly Ala Arg Val Leu Val Val Cys Ala Glu Leu Thr Ile Met Met Leu
```

```
                195                 200                 205
Arg Ala Pro Asn Glu Thr His Leu Asp Asn Ala Ile Gly Ile Ser Leu
            210                 215                 220

Phe Gly Asp Gly Ala Ala Leu Ile Ile Gly Ser Asp Pro Ile Ile
225                 230                 235                 240

Gly Val Glu Lys Pro Met Phe Glu Ile Val Cys Thr Lys Gln Thr Val
                245                 250                 255

Ile Pro Asn Thr Glu Asp Val Ile His Leu His Leu Arg Glu Thr Gly
            260                 265                 270

Met Met Phe Tyr Leu Ser Lys Gly Ser Pro Met Thr Ile Ser Asn Asn
            275                 280                 285

Val Glu Ala Cys Leu Ile Asp Val Phe Lys Ser Val Gly Ile Thr Pro
290                 295                 300

Pro Glu Asp Trp Asn Ser Leu Phe Trp Ile Pro His Pro Gly Gly Arg
305                 310                 315                 320

Ala Ile Leu Asp Gln Val Glu Ala Lys Leu Lys Leu Arg Pro Glu Lys
                325                 330                 335

Phe Arg Ala Ala Arg Thr Val Leu Trp Asp Tyr Gly Asn Met Val Ser
            340                 345                 350

Ala Ser Val Gly Tyr Ile Leu Asp Glu Met Arg Arg Lys Ser Ala Ala
            355                 360                 365

Lys Gly Leu Glu Thr Tyr Gly Glu Gly Leu Glu Trp Gly Val Leu Leu
370                 375                 380

Gly Phe Gly Pro Gly Ile Thr Val Glu Thr Ile Leu Leu His Ser Leu
385                 390                 395                 400

Pro Leu Met

<210> SEQ ID NO 7
<211> LENGTH: 1338
<212> TYPE: DNA
<213> ORGANISM: Neurospora crassa
<220> FEATURE:
<221> NAME/KEY: CDS
<222> LOCATION: (1)..(1338)
<223> OTHER INFORMATION: ORAS gene (GenBank ID number XM_955334.2
      position 582 to 1919) encoding a Type III pentaketide synthase
      (GenBank ID number EGZ68458)

<400> SEQUENCE: 7 atg gct gct tca act gtt gcc ggg gag ctg ggg ctc tcc atc acg ggc      48
Met Ala Ala Ser Thr Val Ala Gly Glu Leu Gly Leu Ser Ile Thr Gly
1               5                   10                  15 ttg gga gtc cag tat cct cca tac agc ctt ggt cca gac gct atc gac      96
Leu Gly Val Gln Tyr Pro Pro Tyr Ser Leu Gly Pro Asp Ala Ile Asp
                20                  25                  30 att ctc agc aag aga tac cac cca gag tcc cca gcc atg aag aag gtc     144
Ile Leu Ser Lys Arg Tyr His Pro Glu Ser Pro Ala Met Lys Lys Val
            35                  40                  45 ctc gcc atc aac cga tac acg ggc att gat cag cgc tcc tcg ata gga     192
Leu Ala Ile Asn Arg Tyr Thr Gly Ile Asp Gln Arg Ser Ser Ile Gly
        50                  55                  60 aac cct gac cac ccg ctc gtg aac aag ccc aac cca cct acc gtc aaa     240
Asn Pro Asp His Pro Leu Val Asn Lys Pro Asn Pro Pro Thr Val Lys
65                  70                  75                  80 gaa ctt cat gag gtc ttc atg tcc gat ggt gtc cct ctt gct gta gaa     288
Glu Leu His Glu Val Phe Met Ser Asp Gly Val Pro Leu Ala Val Glu
                85                  90                  95 gcc tcg cga aag gct atg gcc gaa gcg cgg cta gta ccg gct cag atc     336
```

```
Ala Ser Arg Lys Ala Met Ala Glu Ala Arg Leu Val Pro Ala Gln Ile
            100                 105                 110 aca cac atg gtc tcg acg aca tgc acc gac tcg gcc aac ccg ggc tac       384
Thr His Met Val Ser Thr Thr Cys Thr Asp Ser Ala Asn Pro Gly Tyr
        115                 120                 125 gac cat tac gtc gca aaa gag ctc ggt ctc agt gac cgc ctg gag aag       432
Asp His Tyr Val Ala Lys Glu Leu Gly Leu Ser Asp Arg Leu Glu Lys
    130                 135                 140 gtc ctc ctc cac ggc atc ggc tgc agt ggt ggt ctc gcc gcc ctt cgc       480
Val Leu Leu His Gly Ile Gly Cys Ser Gly Gly Leu Ala Ala Leu Arg
145                 150                 155                 160 aca gcg gcg aat ctc tgt ctg ggc cac aca gcg cgc ggc aag cca gcc       528
Thr Ala Ala Asn Leu Cys Leu Gly His Thr Ala Arg Gly Lys Pro Ala
                165                 170                 175 cgg att ctg gtc ctc gcg ctc gaa gtc tcc acg acc atg gtc cgc agc       576
Arg Ile Leu Val Leu Ala Leu Glu Val Ser Thr Thr Met Val Arg Ser
            180                 185                 190 gag cta gaa agc atc gac gct ttg caa gaa acg cgc att ggc atc gcc       624
Glu Leu Glu Ser Ile Asp Ala Leu Gln Glu Thr Arg Ile Gly Ile Ala
        195                 200                 205 ttg ttc agc gac tgc gct agc gcc gtg atc ctg tcc aac ggc atc ggc       672
Leu Phe Ser Asp Cys Ala Ser Ala Val Ile Leu Ser Asn Gly Ile Gly
    210                 215                 220 gag gca ccg ggc aag ccc gcg atc tac gac ctc ttg ggt tgg gaa aac       720
Glu Ala Pro Gly Lys Pro Ala Ile Tyr Asp Leu Leu Gly Trp Glu Asn
225                 230                 235                 240 cgc gtg atc ccg gac tcc gaa cac gac ctc ggc ttc gac gtc gac cca       768
Arg Val Ile Pro Asp Ser Glu His Asp Leu Gly Phe Asp Val Asp Pro
                245                 250                 255 atg ggg tgg aaa gtc gtc ttg tcg ccc cga gtc cca gta cta gcc aaa       816
Met Gly Trp Lys Val Val Leu Ser Pro Arg Val Pro Val Leu Ala Lys
            260                 265                 270 gcc tcc ctc caa cca acc tac gcc gac ctc cta tcc tct ctc caa gac       864
Ala Ser Leu Gln Pro Thr Tyr Ala Asp Leu Leu Ser Ser Leu Gln Asp
        275                 280                 285 caa ctc cct tcg tcg tac cag aaa cct gcc gat ttc gac tgg gca atg       912
Gln Leu Pro Ser Ser Tyr Gln Lys Pro Ala Asp Phe Asp Trp Ala Met
    290                 295                 300 cac ccc ggc ggc gcc acc atc ctg tcc ggc gcc gaa agc gcc atg ggt       960
His Pro Gly Gly Ala Thr Ile Leu Ser Gly Ala Glu Ser Ala Met Gly
305                 310                 315                 320 ttg aca cca gag cac atg cgc gcc tcc tac gac agg tac atc aac cac      1008
Leu Thr Pro Glu His Met Arg Ala Ser Tyr Asp Arg Tyr Ile Asn His
                325                 330                 335 ggc aac tcg agc tcc gca acc atc ttc agc gtt ctc aac cgg ctc agg      1056
Gly Asn Ser Ser Ser Ala Thr Ile Phe Ser Val Leu Asn Arg Leu Arg
            340                 345                 350 gaa aag gac atg gat gca ctg gcg ccc ggc ggc aaa gta aag gag tat      1104
Glu Lys Asp Met Asp Ala Leu Ala Pro Gly Gly Lys Val Lys Glu Tyr
        355                 360                 365 gtc gtc ggt tgc gcg ttc gga ccg ggg atc aac gtc gag atg tgt atg      1152
Val Val Gly Cys Ala Phe Gly Pro Gly Ile Asn Val Glu Met Cys Met
    370                 375                 380 ttg aag cgg aga atg aac gcg cca gca agg acg acg acg ggt ttg gac      1200
Leu Lys Arg Arg Met Asn Ala Pro Ala Arg Thr Thr Thr Gly Leu Asp
385                 390                 395                 400 aca ccg ccg gag acg gat gat agc gag ggg ccg ggg ccg ggg tcg agt      1248
Thr Pro Pro Glu Thr Asp Asp Ser Glu Gly Pro Gly Pro Gly Ser Ser
                405                 410                 415
```

```
gcg  ggg  agt  gac  gat  ggg  gag  tcg  ata  gaa  ggg  ggc  gag  aag  gag  gag       1296
Ala  Gly  Ser  Asp  Asp  Gly  Glu  Ser  Ile  Glu  Gly  Gly  Glu  Lys  Glu  Glu
               420                 425                      430 aag  ttt  att  aat  gag  gcg  ttg  gac  aat  gtt  gaa  ctg  gat  tga                 1338
Lys  Phe  Ile  Asn  Glu  Ala  Leu  Asp  Asn  Val  Glu  Leu  Asp
               435                      440                 445
```

<210> SEQ ID NO 8
<211> LENGTH: 445
<212> TYPE: PRT
<213> ORGANISM: Neurospora crassa

<400> SEQUENCE: 8

```
Met Ala Ala Ser Thr Val Ala Gly Glu Leu Gly Leu Ser Ile Thr Gly
1               5                   10                  15

Leu Gly Val Gln Tyr Pro Pro Tyr Ser Leu Gly Pro Asp Ala Ile Asp
                20                  25                  30

Ile Leu Ser Lys Arg Tyr His Pro Glu Ser Pro Ala Met Lys Lys Val
            35                  40                  45

Leu Ala Ile Asn Arg Tyr Thr Gly Ile Asp Gln Arg Ser Ser Ile Gly
        50                  55                  60

Asn Pro Asp His Pro Leu Val Asn Lys Pro Asn Pro Thr Val Lys
65                  70                  75                  80

Glu Leu His Glu Val Phe Met Ser Asp Gly Val Pro Leu Ala Val Glu
                85                  90                  95

Ala Ser Arg Lys Ala Met Ala Glu Ala Arg Leu Val Pro Ala Gln Ile
                100                 105                 110

Thr His Met Val Ser Thr Thr Cys Thr Asp Ser Ala Asn Pro Gly Tyr
            115                 120                 125

Asp His Tyr Val Ala Lys Glu Leu Gly Leu Ser Asp Arg Leu Glu Lys
        130                 135                 140

Val Leu Leu His Gly Ile Gly Cys Ser Gly Gly Leu Ala Ala Leu Arg
145                 150                 155                 160

Thr Ala Ala Asn Leu Cys Leu Gly His Thr Ala Arg Gly Lys Pro Ala
                165                 170                 175

Arg Ile Leu Val Leu Ala Leu Glu Val Ser Thr Thr Met Val Arg Ser
                180                 185                 190

Glu Leu Glu Ser Ile Asp Ala Leu Gln Glu Thr Arg Ile Gly Ile Ala
            195                 200                 205

Leu Phe Ser Asp Cys Ala Ser Ala Val Ile Leu Ser Asn Gly Ile Gly
        210                 215                 220

Glu Ala Pro Gly Lys Pro Ala Ile Tyr Asp Leu Leu Gly Trp Glu Asn
225                 230                 235                 240

Arg Val Ile Pro Asp Ser Glu His Asp Leu Gly Phe Asp Val Asp Pro
                245                 250                 255

Met Gly Trp Lys Val Val Leu Ser Pro Arg Val Pro Val Leu Ala Lys
                260                 265                 270

Ala Ser Leu Gln Pro Thr Tyr Ala Asp Leu Leu Ser Ser Leu Gln Asp
            275                 280                 285

Gln Leu Pro Ser Ser Tyr Gln Lys Pro Ala Asp Phe Asp Trp Ala Met
        290                 295                 300

His Pro Gly Gly Ala Thr Ile Leu Ser Gly Ala Glu Ser Ala Met Gly
305                 310                 315                 320

Leu Thr Pro Glu His Met Arg Ala Ser Tyr Asp Arg Tyr Ile Asn His
                325                 330                 335
```

```
Gly Asn Ser Ser Ser Ala Thr Ile Phe Ser Val Leu Asn Arg Leu Arg
            340                 345                 350

Glu Lys Asp Met Asp Ala Leu Ala Pro Gly Gly Lys Val Lys Glu Tyr
        355                 360                 365

Val Val Gly Cys Ala Phe Gly Pro Gly Ile Asn Val Glu Met Cys Met
    370                 375                 380

Leu Lys Arg Arg Met Asn Ala Pro Ala Arg Thr Thr Thr Gly Leu Asp
385                 390                 395                 400

Thr Pro Pro Glu Thr Asp Ser Glu Gly Pro Gly Pro Gly Ser Ser
                405                 410                 415

Ala Gly Ser Asp Asp Gly Glu Ser Ile Glu Gly Gly Glu Lys Glu Glu
            420                 425                 430

Lys Phe Ile Asn Glu Ala Leu Asp Asn Val Glu Leu Asp
        435                 440                 445

<210> SEQ ID NO 9
<211> LENGTH: 1050
<212> TYPE: DNA
<213> ORGANISM: Streptomyces fulvissimus
<220> FEATURE:
<221> NAME/KEY: CDS
<222> LOCATION: (1)..(1050)
<223> OTHER INFORMATION: 1,3,6,8-tetrahydroxynaphthalene synthase gene
      [GenBank ID number CP005080 position 7775934 to 7776986)encoding a
      Type III pentaketide synthase (GenBank ID number AGK81780)

<400> SEQUENCE: 9
```

| | | | | | | | | | | | | | | | | |
|---|---|---|---|---|---|---|---|---|---|---|---|---|---|---|---|---|
| atg | acc | cgg | atc | gcc | gcg | gtc | cac | ggg | gcc | ctg | ccg | ccc | cac | cgc | cac | 48 |
| Met | Thr | Arg | Ile | Ala | Ala | Val | His | Gly | Ala | Leu | Pro | Pro | His | Arg | His | |
| 1 | | | | 5 | | | | | 10 | | | | | 15 | | |
| acc | cag | cca | gag | gtc | acc | gac | atg | gtg | gcc | gac | acc | tgt | ctg | ccg | ccc | 96 |
| Thr | Gln | Pro | Glu | Val | Thr | Asp | Met | Val | Ala | Asp | Thr | Cys | Leu | Pro | Pro | |
| | | | 20 | | | | | 25 | | | | | 30 | | | |
| ggc | gcc | gac | cgc | cgc | gtc | ctg | gac | cgg | ctc | cac | gag | aac | gcc | cgc | gtc | 144 |
| Gly | Ala | Asp | Arg | Arg | Val | Leu | Asp | Arg | Leu | His | Glu | Asn | Ala | Arg | Val | |
| | | | 35 | | | | | 40 | | | | | 45 | | | |
| cgc | acc | cgg | cac | acc | gtg | ctg | ccg | ctc | gac | gga | tac | cgt | gac | ctg | gac | 192 |
| Arg | Thr | Arg | His | Thr | Val | Leu | Pro | Leu | Asp | Gly | Tyr | Arg | Asp | Leu | Asp | |
| 50 | | | | | 55 | | | | | 60 | | | | | | |
| ggc | ttc | ggc | gcc | gcc | aac | gac | gtg | ttc | atc | cgc | tcg | gcc | gtc | gac | ctc | 240 |
| Gly | Phe | Gly | Ala | Ala | Asn | Asp | Val | Phe | Ile | Arg | Ser | Ala | Val | Asp | Leu | |
| 65 | | | | | 70 | | | | | 75 | | | | | 80 | |
| ggc | ggc | cag | gcc | gta | cgc | ggc | gca | ctg | cgg | gcg | gcg | ggg | ctg | cgg | ccc | 288 |
| Gly | Gly | Gln | Ala | Val | Arg | Gly | Ala | Leu | Arg | Ala | Ala | Gly | Leu | Arg | Pro | |
| | | | | 85 | | | | | 90 | | | | | 95 | | |
| acc | gat | gtg | gac | ctg | ctg | atg | ttc | acc | tcc | gtc | acc | ggt | atc | gcg | gcc | 336 |
| Thr | Asp | Val | Asp | Leu | Leu | Met | Phe | Thr | Ser | Val | Thr | Gly | Ile | Ala | Ala | |
| | | | | 100 | | | | | 105 | | | | | 110 | | |
| ccc | tcc | gtc | gac | gcc | cgg | ctg | gtg | gcc | cgc | ctc | ggc | ctg | cgg | tcc | gac | 384 |
| Pro | Ser | Val | Asp | Ala | Arg | Leu | Val | Ala | Arg | Leu | Gly | Leu | Arg | Ser | Asp | |
| | | | 115 | | | | | 120 | | | | | 125 | | | |
| gtg | aaa | cgg | ctg | ccg | gtc | ttc | ggc | ctc | ggc | tgt | gtc | gcc | gga | gcg | gcc | 432 |
| Val | Lys | Arg | Leu | Pro | Val | Phe | Gly | Leu | Gly | Cys | Val | Ala | Gly | Ala | Ala | |
| | 130 | | | | | 135 | | | | | 140 | | | | | |
| ggc | gtg | gcc | cgg | atc | cac | gac | tac | ctg | ctc | ggc | cac | ccg | gac | gac | gtc | 480 |
| Gly | Val | Ala | Arg | Ile | His | Asp | Tyr | Leu | Leu | Gly | His | Pro | Asp | Asp | Val | |
| 145 | | | | | 150 | | | | | 155 | | | | | 160 | |
| gcc | gtg | ctc | ctc | tcg | gtc | gaa | ctg | tgc | tcc | ctc | acc | ttc | cag | cgc | cac | 528 |
| Ala | Val | Leu | Leu | Ser | Val | Glu | Leu | Cys | Ser | Leu | Thr | Phe | Gln | Arg | His | |
| | | | | 165 | | | | | 170 | | | | | 175 | | |

```
gac gtg acg ccc gcc aac ctg gtg gcc acc gcc ctc ttc ggc gac ggg         576
Asp Val Thr Pro Ala Asn Leu Val Ala Thr Ala Leu Phe Gly Asp Gly
            180                 185                 190 gcc gcc gcg gtg gtc gcc ctc ggc ggg cga cgg gcc gtc tcc gga ccc         624
Ala Ala Ala Val Val Ala Leu Gly Gly Arg Arg Ala Val Ser Gly Pro
        195                 200                 205 gag atc gtg gcc acc cgc agc cgg atg tac ccc gag acc gag cac gtg         672
Glu Ile Val Ala Thr Arg Ser Arg Met Tyr Pro Glu Thr Glu His Val
    210                 215                 220 atg ggc tgg tcc gtc ggc tcc acc gga ttc agc gtg gtc ctc gat ccg         720
Met Gly Trp Ser Val Gly Ser Thr Gly Phe Ser Val Val Leu Asp Pro
225                 230                 235                 240 gcc gtg ccc gac gtc gta cgc cag tac ctc gcc gac gac gta cgg gag         768
Ala Val Pro Asp Val Val Arg Gln Tyr Leu Ala Asp Asp Val Arg Glu
                245                 250                 255 ttc ctc gcc gaa cac ggc ctc aaa ccg aag gac atc gcc cac tgg gtc         816
Phe Leu Ala Glu His Gly Leu Lys Pro Lys Asp Ile Ala His Trp Val
            260                 265                 270 tgc cac ccg ggc ggg ccc aag gtc ctg gag acc gtc acc gag gtc ctc         864
Cys His Pro Gly Gly Pro Lys Val Leu Glu Thr Val Thr Glu Val Leu
        275                 280                 285 gac ctg ccc gac ggg gcg ctc gac gtc acc tgg cgc tcg ctg gcc gac         912
Asp Leu Pro Asp Gly Ala Leu Asp Val Thr Trp Arg Ser Leu Ala Asp
    290                 295                 300 gtc ggc aac ctg tcc tcg tcc tcg gtc ctg cac gtc ctg cgg gac acc         960
Val Gly Asn Leu Ser Ser Ser Ser Val Leu His Val Leu Arg Asp Thr
305                 310                 315                 320 ctc gaa cac cgc cga ccc gaa ccg ggc acc cct ggg ctc ctg ctg gcc        1008
Leu Glu His Arg Arg Pro Glu Pro Gly Thr Pro Gly Leu Leu Leu Ala
                325                 330                 335 atg ggc ccc ggc ttc tgc tgc gaa ctg gtg ctg ctg cgc tgg                 1050
Met Gly Pro Gly Phe Cys Cys Glu Leu Val Leu Leu Arg Trp
            340                 345                 350

<210> SEQ ID NO 10
<211> LENGTH: 350
<212> TYPE: PRT
<213> ORGANISM: Streptomyces fulvissimus

<400> SEQUENCE: 10

Met Thr Arg Ile Ala Ala Val His Gly Ala Leu Pro Pro His Arg His
1               5                   10                  15

Thr Gln Pro Glu Val Thr Asp Met Val Ala Asp Thr Cys Leu Pro Pro
            20                  25                  30

Gly Ala Asp Arg Arg Val Leu Asp Arg Leu His Glu Asn Ala Arg Val
        35                  40                  45

Arg Thr Arg His Thr Val Leu Pro Leu Asp Gly Tyr Arg Asp Leu Asp
    50                  55                  60

Gly Phe Gly Ala Ala Asn Asp Val Phe Ile Arg Ser Ala Val Asp Leu
65                  70                  75                  80

Gly Gly Gln Ala Val Arg Gly Ala Leu Arg Ala Ala Gly Leu Arg Pro
                85                  90                  95

Thr Asp Val Asp Leu Leu Met Phe Thr Ser Val Thr Gly Ile Ala Ala
            100                 105                 110

Pro Ser Val Asp Ala Arg Leu Val Ala Arg Leu Gly Leu Arg Ser Asp
        115                 120                 125

Val Lys Arg Leu Pro Val Phe Gly Leu Gly Cys Val Ala Gly Ala Ala
    130                 135                 140
```

```
Gly Val Ala Arg Ile His Asp Tyr Leu Leu Gly His Pro Asp Asp Val
145                 150                 155                 160

Ala Val Leu Leu Ser Val Glu Leu Cys Ser Leu Thr Phe Gln Arg His
                165                 170                 175

Asp Val Thr Pro Ala Asn Leu Val Ala Thr Ala Leu Phe Gly Asp Gly
            180                 185                 190

Ala Ala Ala Val Val Ala Leu Gly Gly Arg Arg Ala Val Ser Gly Pro
        195                 200                 205

Glu Ile Val Ala Thr Arg Ser Arg Met Tyr Pro Thr Glu His Val
    210                 215                 220

Met Gly Trp Ser Val Gly Ser Thr Gly Phe Ser Val Val Leu Asp Pro
225                 230                 235                 240

Ala Val Pro Asp Val Val Arg Gln Tyr Leu Ala Asp Asp Val Arg Glu
                245                 250                 255

Phe Leu Ala Glu His Gly Leu Lys Pro Lys Asp Ile Ala His Trp Val
            260                 265                 270

Cys His Pro Gly Gly Pro Lys Val Leu Glu Thr Val Thr Glu Val Leu
        275                 280                 285

Asp Leu Pro Asp Gly Ala Leu Asp Val Thr Trp Arg Ser Leu Ala Asp
    290                 295                 300

Val Gly Asn Leu Ser Ser Ser Val Leu His Val Leu Arg Asp Thr
305                 310                 315                 320

Leu Glu His Arg Arg Pro Glu Pro Gly Thr Pro Gly Leu Leu Leu Ala
                325                 330                 335

Met Gly Pro Gly Phe Cys Cys Glu Leu Val Leu Leu Arg Trp
            340                 345                 350

<210> SEQ ID NO 11
<211> LENGTH: 1191
<212> TYPE: DNA
<213> ORGANISM: Plumbago indica
<220> FEATURE:
<221> NAME/KEY: CDS
<222> LOCATION: (1)..(1191)
<223> OTHER INFORMATION: PinPKS gene [GenBank ID number AB259100)
      encoding Type III hexaketide synthase  (GenBank ID number
      BAF44539)

<400> SEQUENCE: 11 atg gca cca gca gtt caa tct caa tct cac ggt gga gca tac cgc agc      48
Met Ala Pro Ala Val Gln Ser Gln Ser His Gly Gly Ala Tyr Arg Ser
1               5                   10                  15 aat ggt gag agg tca aaa ggg cca gcg acc gtg cta gcc att gct act      96
Asn Gly Glu Arg Ser Lys Gly Pro Ala Thr Val Leu Ala Ile Ala Thr
            20                  25                  30 gct gtg cca cca aat gta tac tat cag gat gaa tat gcc gac ttt ttc     144
Ala Val Pro Pro Asn Val Tyr Tyr Gln Asp Glu Tyr Ala Asp Phe Phe
        35                  40                  45 ttc cgc gtc acc aac agc gag cac aag act gcg atc aag gag aag ttt     192
Phe Arg Val Thr Asn Ser Glu His Lys Thr Ala Ile Lys Glu Lys Phe
    50                  55                  60 aac cga gtt tgc ggt acc tcg atg att aag aag agg cac atg tac ttc     240
Asn Arg Val Cys Gly Thr Ser Met Ile Lys Lys Arg His Met Tyr Phe
65                  70                  75                  80 acc gag aag atg ctt aac caa aac aaa aac atg tgc acc tgg gat gat     288
Thr Glu Lys Met Leu Asn Gln Asn Lys Asn Met Cys Thr Trp Asp Asp
                85                  90                  95 aaa tcc ctc aac gcc cgt cag gac atg gtg atc cca gca gtc ccc gag     336
Lys Ser Leu Asn Ala Arg Gln Asp Met Val Ile Pro Ala Val Pro Glu
            100                 105                 110
```

```
ctc ggc aaa gaa gcc gcc ttg aag gcc atc gag gag tgg gga aaa cca      384
Leu Gly Lys Glu Ala Ala Leu Lys Ala Ile Glu Glu Trp Gly Lys Pro
        115                 120                 125 ctc tct aac atc acc cac ctc atc ttc tgc acc aca gcc ggt aac gac      432
Leu Ser Asn Ile Thr His Leu Ile Phe Cys Thr Thr Ala Gly Asn Asp
130                 135                 140 gcc cct gga gca gac ttc agg cta acc cag ctc ctt gga ctg aac cca      480
Ala Pro Gly Ala Asp Phe Arg Leu Thr Gln Leu Leu Gly Leu Asn Pro
145                 150                 155                 160 tca gtg aac cgg tac atg atc tac cag cag gga tgc ttc gct gga gcc      528
Ser Val Asn Arg Tyr Met Ile Tyr Gln Gln Gly Cys Phe Ala Gly Ala
                165                 170                 175 acc gca ctc cgc ata gcc aag gac ctt gct gag aac aac aag ggt gct      576
Thr Ala Leu Arg Ile Ala Lys Asp Leu Ala Glu Asn Asn Lys Gly Ala
            180                 185                 190 cgt gtg ctc att gta tgc tgt gag atc ttt gct ttt gca ttc cgt gga      624
Arg Val Leu Ile Val Cys Cys Glu Ile Phe Ala Phe Ala Phe Arg Gly
        195                 200                 205 cct cat gag gac cac atg gac tct ttg att tgc cag ctg ctg ttt ggg      672
Pro His Glu Asp His Met Asp Ser Leu Ile Cys Gln Leu Leu Phe Gly
210                 215                 220 gat ggt gca gct gct gtc att gtc ggt ggt gat cct gac gag acc gag      720
Asp Gly Ala Ala Ala Val Ile Val Gly Gly Asp Pro Asp Glu Thr Glu
225                 230                 235                 240 aat gca ctc ttt gag ctc gag tgg gcc aac tca acc atc ata cca caa      768
Asn Ala Leu Phe Glu Leu Glu Trp Ala Asn Ser Thr Ile Ile Pro Gln
                245                 250                 255 tca gaa gag gcc atc acc ctt aga atg cgc gaa gaa ggt ctc atg atc      816
Ser Glu Glu Ala Ile Thr Leu Arg Met Arg Glu Glu Gly Leu Met Ile
            260                 265                 270 ggt ttg tcc aag gaa atc cca agg ctc cta ggc gaa cag atc gaa gac      864
Gly Leu Ser Lys Glu Ile Pro Arg Leu Leu Gly Glu Gln Ile Glu Asp
        275                 280                 285 att ttg gtc gag gct ttc aca ccc ctt gga att act gac tgg agc tca      912
Ile Leu Val Glu Ala Phe Thr Pro Leu Gly Ile Thr Asp Trp Ser Ser
290                 295                 300 ctc ttc tgg att gcc cac cca ggt ggt aag gcc atc ctt gag gca ctg      960
Leu Phe Trp Ile Ala His Pro Gly Gly Lys Ala Ile Leu Glu Ala Leu
305                 310                 315                 320 gag aag aaa atc ggc gtt gaa ggt aag ttg tgg gct tcg tgg cac gtt     1008
Glu Lys Lys Ile Gly Val Glu Gly Lys Leu Trp Ala Ser Trp His Val
                325                 330                 335 ctt aaa gaa tat gga aac ttg acc agt gct tgt gtg ctg ttc gcc atg     1056
Leu Lys Glu Tyr Gly Asn Leu Thr Ser Ala Cys Val Leu Phe Ala Met
            340                 345                 350 gac gaa atg agg aag agg tcc att aag gaa ggg aag gcc act act gga     1104
Asp Glu Met Arg Lys Arg Ser Ile Lys Glu Gly Lys Ala Thr Thr Gly
        355                 360                 365 gac gga cac gaa tat ggt gtt ctc ttc ggt gtc ggc ccg ggt ctt acc     1152
Asp Gly His Glu Tyr Gly Val Leu Phe Gly Val Gly Pro Gly Leu Thr
370                 375                 380 gtc gag aca gtt gtg cta aaa agt gtg ccg ctt aac taa                 1191
Val Glu Thr Val Val Leu Lys Ser Val Pro Leu Asn
385                 390                 395
```

<210> SEQ ID NO 12
<211> LENGTH: 396
<212> TYPE: PRT
<213> ORGANISM: Plumbago indica

<400> SEQUENCE: 12

```
Met Ala Pro Ala Val Gln Ser Gln Ser His Gly Gly Ala Tyr Arg Ser
1               5                   10                  15

Asn Gly Glu Arg Ser Lys Gly Pro Ala Thr Val Leu Ala Ile Ala Thr
            20                  25                  30

Ala Val Pro Pro Asn Val Tyr Tyr Gln Asp Glu Tyr Ala Asp Phe Phe
        35                  40                  45

Phe Arg Val Thr Asn Ser Glu His Lys Thr Ala Ile Lys Glu Lys Phe
    50                  55                  60

Asn Arg Val Cys Gly Thr Ser Met Ile Lys Lys Arg His Met Tyr Phe
65                  70                  75                  80

Thr Glu Lys Met Leu Asn Gln Asn Lys Asn Met Cys Thr Trp Asp Asp
                85                  90                  95

Lys Ser Leu Asn Ala Arg Gln Asp Met Val Ile Pro Ala Val Pro Glu
            100                 105                 110

Leu Gly Lys Glu Ala Ala Leu Lys Ala Ile Glu Glu Trp Gly Lys Pro
        115                 120                 125

Leu Ser Asn Ile Thr His Leu Ile Phe Cys Thr Thr Ala Gly Asn Asp
    130                 135                 140

Ala Pro Gly Ala Asp Phe Arg Leu Thr Gln Leu Leu Gly Leu Asn Pro
145                 150                 155                 160

Ser Val Asn Arg Tyr Met Ile Tyr Gln Gln Gly Cys Phe Ala Gly Ala
                165                 170                 175

Thr Ala Leu Arg Ile Ala Lys Asp Leu Ala Glu Asn Asn Lys Gly Ala
            180                 185                 190

Arg Val Leu Ile Val Cys Cys Glu Ile Phe Ala Phe Ala Phe Arg Gly
        195                 200                 205

Pro His Glu Asp His Met Asp Ser Leu Ile Cys Gln Leu Leu Phe Gly
    210                 215                 220

Asp Gly Ala Ala Ala Val Ile Val Gly Gly Asp Pro Asp Glu Thr Glu
225                 230                 235                 240

Asn Ala Leu Phe Glu Leu Glu Trp Ala Asn Ser Thr Ile Ile Pro Gln
                245                 250                 255

Ser Glu Glu Ala Ile Thr Leu Arg Met Arg Glu Glu Gly Leu Met Ile
            260                 265                 270

Gly Leu Ser Lys Glu Ile Pro Arg Leu Leu Gly Glu Gln Ile Glu Asp
        275                 280                 285

Ile Leu Val Glu Ala Phe Thr Pro Leu Gly Ile Thr Asp Trp Ser Ser
    290                 295                 300

Leu Phe Trp Ile Ala His Pro Gly Gly Lys Ala Ile Leu Glu Ala Leu
305                 310                 315                 320

Glu Lys Lys Ile Gly Val Glu Gly Lys Leu Trp Ala Ser Trp His Val
                325                 330                 335

Leu Lys Glu Tyr Gly Asn Leu Ser Ala Cys Val Leu Phe Ala Met
            340                 345                 350

Asp Glu Met Arg Lys Arg Ser Ile Lys Glu Gly Lys Ala Thr Thr Gly
        355                 360                 365

Asp Gly His Glu Tyr Gly Val Leu Phe Gly Val Gly Pro Gly Leu Thr
    370                 375                 380

Val Glu Thr Val Val Leu Lys Ser Val Pro Leu Asn
385                 390                 395
```

```
<210> SEQ ID NO 13
<211> LENGTH: 1170
<212> TYPE: DNA
<213> ORGANISM: Drosophyllum lusitanicum
<220> FEATURE:
<221> NAME/KEY: CDS
<222> LOCATION: (1)..(1170)
<223> OTHER INFORMATION: DluHKS gene [GenBank ID number EF405822)
      encoding Type III hexaketide synthase ( GenBank ID number
      ABQ59603)

<400> SEQUENCE: 13
```

| | | | | | | | | | | | | | | | | |
|---|---|---|---|---|---|---|---|---|---|---|---|---|---|---|---|---|
| atg | gca | ttt | gtg | gag | gga | atg | ggg | aag | aag | gca | gag | gga | cca | gcc | acc | 48 |
| Met | Ala | Phe | Val | Glu | Gly | Met | Gly | Lys | Lys | Ala | Glu | Gly | Pro | Ala | Thr | |
| 1 | | | | 5 | | | | | 10 | | | | | 15 | | |
| atc | ttg | gcc | atc | ggc | aca | gct | gtt | cca | ccc | aac | tgc | aac | ata | caa | gcc | 96 |
| Ile | Leu | Ala | Ile | Gly | Thr | Ala | Val | Pro | Pro | Asn | Cys | Asn | Ile | Gln | Ala | |
| | | | | 20 | | | | | 25 | | | | | 30 | | |
| gac | ttc | cca | gac | tac | tat | ttc | agg | gtc | aca | aac | agc | gag | cat | atg | act | 144 |
| Asp | Phe | Pro | Asp | Tyr | Tyr | Phe | Arg | Val | Thr | Asn | Ser | Glu | His | Met | Thr | |
| | | | | 35 | | | | | 40 | | | | | 45 | | |
| gat | tta | aag | gaa | aaa | ttc | aag | cgc | att | tgt | gag | aag | acc | gca | att | aaa | 192 |
| Asp | Leu | Lys | Glu | Lys | Phe | Lys | Arg | Ile | Cys | Glu | Lys | Thr | Ala | Ile | Lys | |
| 50 | | | | | 55 | | | | | 60 | | | | | | |
| aaa | cgt | tac | acc | tac | ttg | act | gag | gaa | atg | atc | aag | gag | aat | ccg | ggg | 240 |
| Lys | Arg | Tyr | Thr | Tyr | Leu | Thr | Glu | Glu | Met | Ile | Lys | Glu | Asn | Pro | Gly | |
| 65 | | | | | 70 | | | | | 75 | | | | | 80 | |
| atc | ggg | act | ttc | aat | ggt | tta | tct | ttg | aat | gcg | cgt | caa | gaa | atg | gtg | 288 |
| Ile | Gly | Thr | Phe | Asn | Gly | Leu | Ser | Leu | Asn | Ala | Arg | Gln | Glu | Met | Val | |
| | | | | 85 | | | | | 90 | | | | | 95 | | |
| atc | gcc | gaa | acc | ccg | agg | cta | ggg | aaa | gaa | gcg | gct | cta | aaa | gct | ctc | 336 |
| Ile | Ala | Glu | Thr | Pro | Arg | Leu | Gly | Lys | Glu | Ala | Ala | Leu | Lys | Ala | Leu | |
| | | | | 100 | | | | | 105 | | | | | 110 | | |
| aaa | gaa | tgg | ggt | cag | ccc | aaa | tcg | aga | ctc | act | cac | ctc | atc | ttc | tgt | 384 |
| Lys | Glu | Trp | Gly | Gln | Pro | Lys | Ser | Arg | Leu | Thr | His | Leu | Ile | Phe | Cys | |
| | | | 115 | | | | | 120 | | | | | 125 | | | |
| tcc | act | gcc | gga | gtc | gac | atg | cct | ggt | tgt | gat | tat | cag | ctc | acc | aaa | 432 |
| Ser | Thr | Ala | Gly | Val | Asp | Met | Pro | Gly | Cys | Asp | Tyr | Gln | Leu | Thr | Lys | |
| 130 | | | | | 135 | | | | | 140 | | | | | | |
| atg | ctc | ggt | ctg | aac | cct | act | atc | aat | aga | cta | atg | atc | tac | caa | caa | 480 |
| Met | Leu | Gly | Leu | Asn | Pro | Thr | Ile | Asn | Arg | Leu | Met | Ile | Tyr | Gln | Gln | |
| 145 | | | | | 150 | | | | | 155 | | | | | 160 | |
| ggt | tgt | tat | gct | ggt | ggc | acg | gtc | ctc | cgt | atc | gcc | aag | gat | gtc | gct | 528 |
| Gly | Cys | Tyr | Ala | Gly | Gly | Thr | Val | Leu | Arg | Ile | Ala | Lys | Asp | Val | Ala | |
| | | | | 165 | | | | | 170 | | | | | 175 | | |
| gaa | aac | aac | aag | gga | gca | cgt | gtt | ctc | gtg | gtg | tgc | tct | gaa | atc | aca | 576 |
| Glu | Asn | Asn | Lys | Gly | Ala | Arg | Val | Leu | Val | Val | Cys | Ser | Glu | Ile | Thr | |
| | | | 180 | | | | | 185 | | | | | 190 | | | |
| gca | att | ttt | ttc | cgc | ggg | cca | tct | gag | cac | cac | atg | gac | tcc | tta | gtc | 624 |
| Ala | Ile | Phe | Phe | Arg | Gly | Pro | Ser | Glu | His | His | Met | Asp | Ser | Leu | Val | |
| | | | | 195 | | | | | 200 | | | | | 205 | | |
| ggc | caa | act | ctt | ttc | ggc | gac | ggt | gct | gcc | gcg | ctg | atc | atc | ggt | tcc | 672 |
| Gly | Gln | Thr | Leu | Phe | Gly | Asp | Gly | Ala | Ala | Ala | Leu | Ile | Ile | Gly | Ser | |
| | | | 210 | | | | | 215 | | | | | 220 | | | |
| gac | atg | gac | gag | tcc | atc | gag | aag | ccg | ttg | tat | cag | ctt | atc | tcg | gct | 720 |
| Asp | Met | Asp | Glu | Ser | Ile | Glu | Lys | Pro | Leu | Tyr | Gln | Leu | Ile | Ser | Ala | |
| 225 | | | | | 230 | | | | | 235 | | | | | 240 | |
| agt | caa | acc | ctt | gta | ccg | gac | tcc | gag | aac | gcg | atg | gct | ttg | cat | ttg | 768 |
| Ser | Gln | Thr | Leu | Val | Pro | Asp | Ser | Glu | Asn | Ala | Met | Ala | Leu | His | Leu | |
| | | | | 245 | | | | | 250 | | | | | 255 | | |
| aaa | gaa | gag | ggt | ctc | acc | ttc | cac | ctt | tcg | aag | gat | gtt | ccc | tca | ttg | 816 |
| Lys | Glu | Glu | Gly | Leu | Thr | Phe | His | Leu | Ser | Lys | Asp | Val | Pro | Ser | Leu | |

```
                    260                 265                 270
ata tcg aag aac ata gag gac gtc ttg gag gcc gct ttt aag cct ttg        864
Ile Ser Lys Asn Ile Glu Asp Val Leu Glu Ala Ala Phe Lys Pro Leu
        275                 280                 285 ggt atc aac gac tgg aac tct cta ttt tac atc act cat ccc ggt ggt        912
Gly Ile Asn Asp Trp Asn Ser Leu Phe Tyr Ile Thr His Pro Gly Gly
290                 295                 300 agg gcg att cta gat ggg gtg gag aac aaa ctc ggt cta gac aag gat        960
Arg Ala Ile Leu Asp Gly Val Glu Asn Lys Leu Gly Leu Asp Lys Asp
305                 310                 315                 320 aaa atg aag gag agt cga tac gtg ctc agc gag tac ggt aat ttg aca       1008
Lys Met Lys Glu Ser Arg Tyr Val Leu Ser Glu Tyr Gly Asn Leu Thr
                325                 330                 335 gga gca tgt gtg ttg ttt atc tta gac gag atg agg aag cgg tcc atg       1056
Gly Ala Cys Val Leu Phe Ile Leu Asp Glu Met Arg Lys Arg Ser Met
        340                 345                 350 gag gaa ggc aag tca acc acc ggc aag gga tcg gat ttc ggt gtt ttg       1104
Glu Glu Gly Lys Ser Thr Thr Gly Lys Gly Ser Asp Phe Gly Val Leu
355                 360                 365 ctt ggg ttt ggg cca ggt atc aca gtt gaa acc gtt gta ttg cga agc       1152
Leu Gly Phe Gly Pro Gly Ile Thr Val Glu Thr Val Val Leu Arg Ser
370                 375                 380 ttc cct ata aac aac taa                                                1170
Phe Pro Ile Asn Asn
385

<210> SEQ ID NO 14
<211> LENGTH: 389
<212> TYPE: PRT
<213> ORGANISM: Drosophyllum lusitanicum

<400> SEQUENCE: 14

Met Ala Phe Val Glu Gly Met Gly Lys Lys Ala Glu Gly Pro Ala Thr
1               5                   10                  15

Ile Leu Ala Ile Gly Thr Ala Val Pro Pro Asn Cys Asn Ile Gln Ala
            20                  25                  30

Asp Phe Pro Asp Tyr Tyr Phe Arg Val Thr Asn Ser Glu His Met Thr
        35                  40                  45

Asp Leu Lys Glu Lys Phe Lys Arg Ile Cys Glu Lys Thr Ala Ile Lys
    50                  55                  60

Lys Arg Tyr Thr Tyr Leu Thr Glu Glu Met Ile Lys Glu Asn Pro Gly
65                  70                  75                  80

Ile Gly Thr Phe Asn Gly Leu Ser Leu Asn Ala Arg Gln Glu Met Val
                85                  90                  95

Ile Ala Glu Thr Pro Arg Leu Gly Lys Glu Ala Leu Lys Ala Leu
            100                 105                 110

Lys Glu Trp Gly Gln Pro Lys Ser Arg Leu Thr His Leu Ile Phe Cys
        115                 120                 125

Ser Thr Ala Gly Val Asp Met Pro Gly Cys Asp Tyr Gln Leu Thr Lys
    130                 135                 140

Met Leu Gly Leu Asn Pro Thr Ile Asn Arg Leu Met Ile Tyr Gln Gln
145                 150                 155                 160

Gly Cys Tyr Ala Gly Gly Thr Val Leu Arg Ile Ala Lys Asp Val Ala
                165                 170                 175

Glu Asn Asn Lys Gly Ala Arg Val Leu Val Val Cys Ser Glu Ile Thr
            180                 185                 190

Ala Ile Phe Phe Arg Gly Pro Ser Glu His His Met Asp Ser Leu Val
```

```
                    195                 200                 205
Gly Gln Thr Leu Phe Gly Asp Gly Ala Ala Leu Ile Ile Gly Ser
    210                 215                 220

Asp Met Asp Glu Ser Ile Glu Lys Pro Leu Tyr Gln Leu Ile Ser Ala
225                 230                 235                 240

Ser Gln Thr Leu Val Pro Asp Ser Glu Asn Ala Met Ala Leu His Leu
                245                 250                 255

Lys Glu Glu Gly Leu Thr Phe His Leu Ser Lys Asp Val Pro Ser Leu
            260                 265                 270

Ile Ser Lys Asn Ile Glu Asp Val Leu Glu Ala Ala Phe Lys Pro Leu
        275                 280                 285

Gly Ile Asn Asp Trp Asn Ser Leu Phe Tyr Ile Thr His Pro Gly Gly
    290                 295                 300

Arg Ala Ile Leu Asp Gly Val Glu Asn Lys Leu Gly Leu Asp Lys Asp
305                 310                 315                 320

Lys Met Lys Glu Ser Arg Tyr Val Leu Ser Glu Tyr Gly Asn Leu Thr
                325                 330                 335

Gly Ala Cys Val Leu Phe Ile Leu Asp Glu Met Arg Lys Arg Ser Met
            340                 345                 350

Glu Glu Gly Lys Ser Thr Thr Gly Lys Gly Ser Asp Phe Gly Val Leu
        355                 360                 365

Leu Gly Phe Gly Pro Gly Ile Thr Val Glu Thr Val Val Leu Arg Ser
    370                 375                 380

Phe Pro Ile Asn Asn
385

<210> SEQ ID NO 15
<211> LENGTH: 1185
<212> TYPE: DNA
<213> ORGANISM: Plumbago zeylanica
<220> FEATURE:
<221> NAME/KEY: CDS
<222> LOCATION: (1)..(1176)
<223> OTHER INFORMATION: PzPKS gene [GenBank ID number JQ015381)
      encoding a Type III hexaketide synthase (GenBank ID number
      AEX86944)

<400> SEQUENCE: 15 atg gca cca gca gtt caa tct gaa tct caa cgt gga gct tac cgc agc    48
Met Ala Pro Ala Val Gln Ser Glu Ser Gln Arg Gly Ala Tyr Arg Ser
1               5                   10                  15 aat ggt gag agg tca aag ggc cac gca acg gtg ctt gcc att gct act    96
Asn Gly Glu Arg Ser Lys Gly His Ala Thr Val Leu Ala Ile Ala Thr
            20                  25                  30 gct gtg cca cca aat gta tac tat caa gat gaa tat gcc gac ttt ttc   144
Ala Val Pro Pro Asn Val Tyr Tyr Gln Asp Glu Tyr Ala Asp Phe Phe
        35                  40                  45 ttc cgc gtc aca gac agc gag cac aag act gcg atc aag gag aag ttt   192
Phe Arg Val Thr Asp Ser Glu His Lys Thr Ala Ile Lys Glu Lys Phe
    50                  55                  60 aac cga gtt tgt ggt acc tca atg atc aag aag agg cac atg tac ttc   240
Asn Arg Val Cys Gly Thr Ser Met Ile Lys Lys Arg His Met Tyr Phe
65                  70                  75                  80 acc gag aag atg ctg aac caa aac aaa aac atg tgc ccc tgg gac gat   288
Thr Glu Lys Met Leu Asn Gln Asn Lys Asn Met Cys Pro Trp Asp Asp
                85                  90                  95 aaa tcc ctc aac gcc cgt cag gac atg gtc atc cca gcg gtc ccc gag   336
Lys Ser Leu Asn Ala Arg Gln Asp Met Val Ile Pro Ala Val Pro Glu
            100                 105                 110
```

```
ctc gga aaa gaa gcc gcc ttg aag gcc atc gaa gag tgg gga aaa cca      384
Leu Gly Lys Glu Ala Ala Leu Lys Ala Ile Glu Glu Trp Gly Lys Pro
        115                 120                 125 ctg tct aac atc act cac ctc atc ttc tgc acc aca gcc ggt aac gac      432
Leu Ser Asn Ile Thr His Leu Ile Phe Cys Thr Thr Ala Gly Asn Asp
    130                 135                 140 gct cct gga gcc gac ttc agg cta acc cag ctc ctt gga ctg aac cct      480
Ala Pro Gly Ala Asp Phe Arg Leu Thr Gln Leu Leu Gly Leu Asn Pro
145                 150                 155                 160 tca gtg aac cga tac atg atc tac cca cag gga tgc ttc gct gga gcc      528
Ser Val Asn Arg Tyr Met Ile Tyr Pro Gln Gly Cys Phe Ala Gly Ala
                165                 170                 175 acc gca ctc cgc ata ccc aag gac ctt gct gaa aac aac aag ggt gct      576
Thr Ala Leu Arg Ile Pro Lys Asp Leu Ala Glu Asn Asn Lys Gly Ala
            180                 185                 190 cgg gtg ctc att gtg tgc tgt gaa atc ttt gca ttc cgt gga cct cat      624
Arg Val Leu Ile Val Cys Cys Glu Ile Phe Ala Phe Arg Gly Pro His
        195                 200                 205 gag gac cac atg gac tct ttg att tgc cag ctt ctg ttt gga gat ggt      672
Glu Asp His Met Asp Ser Leu Ile Cys Gln Leu Leu Phe Gly Asp Gly
    210                 215                 220 gca gct gct gtc att gtt ggt ggt gat cct gat gag acc gag aat tcg      720
Ala Ala Ala Val Ile Val Gly Gly Asp Pro Asp Glu Thr Glu Asn Ser
225                 230                 235                 240 ctc ttt gag ctc gag tgg gcc aac tca acc atc ata cca caa tca gaa      768
Leu Phe Glu Leu Glu Trp Ala Asn Ser Thr Ile Ile Pro Gln Ser Glu
                245                 250                 255 gag gcc atc acc ctt aaa atg cgc gaa gag ggt ctc atg atc ggt ctg      816
Glu Ala Ile Thr Leu Lys Met Arg Glu Glu Gly Leu Met Ile Gly Leu
            260                 265                 270 tcc aag gaa atc cca agg ctc cta ggg gaa cag atc gaa gac att ttg      864
Ser Lys Glu Ile Pro Arg Leu Leu Gly Glu Gln Ile Glu Asp Ile Leu
        275                 280                 285 gtc gag gct ttt gca ccc ctt gga att agc gac tgg agc tca ctc ttc      912
Val Glu Ala Phe Ala Pro Leu Gly Ile Ser Asp Trp Ser Ser Leu Phe
    290                 295                 300 tgg att gct cac cca ggt ggt aag gca atc ctt gag gca ctc gag aag      960
Trp Ile Ala His Pro Gly Gly Lys Ala Ile Leu Glu Ala Leu Glu Lys
305                 310                 315                 320 aag atc ggt gtt gaa ggt aag ttg tgg gct tca tgg cac gtt ctt aaa      1008
Lys Ile Gly Val Glu Gly Lys Leu Trp Ala Ser Trp His Val Leu Lys
                325                 330                 335 gaa tat gga aac ttg acc agt gct tgt gtg ctc ttc gcc atg gac gag      1056
Glu Tyr Gly Asn Leu Thr Ser Ala Cys Val Leu Phe Ala Met Asp Glu
            340                 345                 350 atg agg aag agg tcg att aag gaa ggg aag gcc act acc gga gac gga      1104
Met Arg Lys Arg Ser Ile Lys Glu Gly Lys Ala Thr Thr Gly Asp Gly
        355                 360                 365 cac gac tac ggt gtt ctg ttc ggt gtc ggc ccg ggt ctt acc gtc gag      1152
His Asp Tyr Gly Val Leu Phe Gly Val Gly Pro Gly Leu Thr Val Glu
    370                 375                 380 aca gtt gtg cta aaa agt gtg ccg cttaactaa                            1185
Thr Val Val Leu Lys Ser Val Pro
385                 390

<210> SEQ ID NO 16
<211> LENGTH: 392
<212> TYPE: PRT
<213> ORGANISM: Plumbago zeylanica
```

<400> SEQUENCE: 16

Met Ala Pro Ala Val Gln Ser Glu Ser Gln Arg Gly Ala Tyr Arg Ser
1               5                   10                  15

Asn Gly Glu Arg Ser Lys Gly His Ala Thr Val Leu Ala Ile Ala Thr
            20                  25                  30

Ala Val Pro Pro Asn Val Tyr Tyr Gln Asp Glu Tyr Ala Asp Phe Phe
        35                  40                  45

Phe Arg Val Thr Asp Ser Glu His Lys Thr Ala Ile Lys Glu Lys Phe
    50                  55                  60

Asn Arg Val Cys Gly Thr Ser Met Ile Lys Lys Arg His Met Tyr Phe
65                  70                  75                  80

Thr Glu Lys Met Leu Asn Gln Asn Lys Asn Met Cys Pro Trp Asp Asp
                85                  90                  95

Lys Ser Leu Asn Ala Arg Gln Asp Met Val Ile Pro Ala Val Pro Glu
            100                 105                 110

Leu Gly Lys Glu Ala Ala Leu Lys Ala Ile Glu Glu Trp Gly Lys Pro
        115                 120                 125

Leu Ser Asn Ile Thr His Leu Ile Phe Cys Thr Thr Ala Gly Asn Asp
    130                 135                 140

Ala Pro Gly Ala Asp Phe Arg Leu Thr Gln Leu Leu Gly Leu Asn Pro
145                 150                 155                 160

Ser Val Asn Arg Tyr Met Ile Tyr Pro Gln Gly Cys Phe Ala Gly Ala
                165                 170                 175

Thr Ala Leu Arg Ile Pro Lys Asp Leu Ala Glu Asn Asn Lys Gly Ala
            180                 185                 190

Arg Val Leu Ile Val Cys Cys Glu Ile Phe Ala Phe Arg Gly Pro His
        195                 200                 205

Glu Asp His Met Asp Ser Leu Ile Cys Gln Leu Leu Phe Gly Asp Gly
    210                 215                 220

Ala Ala Ala Val Ile Val Gly Asp Pro Asp Glu Thr Glu Asn Ser
225                 230                 235                 240

Leu Phe Glu Leu Glu Trp Ala Asn Ser Thr Ile Ile Pro Gln Ser Glu
                245                 250                 255

Glu Ala Ile Thr Leu Lys Met Arg Glu Gly Leu Met Ile Gly Leu
            260                 265                 270

Ser Lys Glu Ile Pro Arg Leu Leu Gly Glu Gln Ile Glu Asp Ile Leu
        275                 280                 285

Val Glu Ala Phe Ala Pro Leu Gly Ile Ser Asp Trp Ser Ser Leu Phe
    290                 295                 300

Trp Ile Ala His Pro Gly Gly Lys Ala Ile Leu Glu Ala Leu Glu Lys
305                 310                 315                 320

Lys Ile Gly Val Glu Gly Lys Leu Trp Ala Ser His Val Leu Lys
                325                 330                 335

Glu Tyr Gly Asn Leu Thr Ser Ala Cys Val Leu Phe Ala Met Asp Glu
            340                 345                 350

Met Arg Lys Arg Ser Ile Lys Glu Gly Lys Ala Thr Thr Gly Asp Gly
        355                 360                 365

His Asp Tyr Gly Val Leu Phe Gly Val Gly Pro Gly Leu Thr Val Glu
    370                 375                 380

Thr Val Val Leu Lys Ser Val Pro
385                 390

<210> SEQ ID NO 17

<211> LENGTH: 1176
<212> TYPE: DNA
<213> ORGANISM: Rheum palmatum
<220> FEATURE:
<221> NAME/KEY: CDS
<222> LOCATION: (1)..(1176)
<223> OTHER INFORMATION: ALS gene [GenBank ID number AY517486] encoding
      Type III heptaketide synthase (GenBank ID number AAS87170)

<400> SEQUENCE: 17

```
atg gca gat gtc ctg cag gag atc cgc aac tcg cag aag gcg agc ggg        48
Met Ala Asp Val Leu Gln Glu Ile Arg Asn Ser Gln Lys Ala Ser Gly
1               5                   10                  15 ccc gcc acg gtg ctc gcc atc ggc act gcc cat cca ccg acg tgc tac        96
Pro Ala Thr Val Leu Ala Ile Gly Thr Ala His Pro Pro Thr Cys Tyr
                20                  25                  30 cct cag gcc gac tac ccc gac ttc tac ttc cga gtt tgc aag agc gag       144
Pro Gln Ala Asp Tyr Pro Asp Phe Tyr Phe Arg Val Cys Lys Ser Glu
            35                  40                  45 cac atg acc aaa ctc aag aag aaa atg caa ttc att tgt gac aga tcg       192
His Met Thr Lys Leu Lys Lys Lys Met Gln Phe Ile Cys Asp Arg Ser
        50                  55                  60 ggg ata agg cag cgg ttt atg ttc cac acg gaa gag aac ctg ggg aag       240
Gly Ile Arg Gln Arg Phe Met Phe His Thr Glu Glu Asn Leu Gly Lys
65                  70                  75                  80 aac ccg ggg atg tgc aca ttc gac ggg cca tcg ctg aac gcg cgg cag       288
Asn Pro Gly Met Cys Thr Phe Asp Gly Pro Ser Leu Asn Ala Arg Gln
                85                  90                  95 gac atg ctg atc atg gaa gtg ccg aag ctg ggg gcg gag gcg gcg gag       336
Asp Met Leu Ile Met Glu Val Pro Lys Leu Gly Ala Glu Ala Ala Glu
                100                 105                 110 aag gcg atc aag gag tgg ggg cag gac aag tcc cgg atc acc cac ctc       384
Lys Ala Ile Lys Glu Trp Gly Gln Asp Lys Ser Arg Ile Thr His Leu
            115                 120                 125 atc ttc tgc acc acc acg agc aac gac atg ccc ggg gcg gac tac cag       432
Ile Phe Cys Thr Thr Thr Ser Asn Asp Met Pro Gly Ala Asp Tyr Gln
        130                 135                 140 ttc gcc acc ctg ttc ggg ctg aac ccc ggc gtg agc cgc acc atg gtc       480
Phe Ala Thr Leu Phe Gly Leu Asn Pro Gly Val Ser Arg Thr Met Val
145                 150                 155                 160 tac cag cag ggc tgc ttc gcc ggg ggc acc gtg ctg cgc ctg gtc aag       528
Tyr Gln Gln Gly Cys Phe Ala Gly Gly Thr Val Leu Arg Leu Val Lys
                165                 170                 175 gac atc gcg gag aac aac aag ggg gcg cgc gtg ctg gtg gtg tgc tcg       576
Asp Ile Ala Glu Asn Asn Lys Gly Ala Arg Val Leu Val Val Cys Ser
                180                 185                 190 gag atc gtg gcc ttc gcc ttc cgc ggg ccc cac gag gac cac atc gac       624
Glu Ile Val Ala Phe Ala Phe Arg Gly Pro His Glu Asp His Ile Asp
            195                 200                 205 tcc ctc atc ggg cag ctc ctg ttc ggg gac ggg gcc gcc gcc ctc gtg       672
Ser Leu Ile Gly Gln Leu Leu Phe Gly Asp Gly Ala Ala Ala Leu Val
        210                 215                 220 gtc ggg aca gac atc gac gag agc gtc gag agg ccc atc ttc cag atc       720
Val Gly Thr Asp Ile Asp Glu Ser Val Glu Arg Pro Ile Phe Gln Ile
225                 230                 235                 240 atg tcg gcg acc cag gcg acc atc ccc aac tcg ctg cac acc atg gct       768
Met Ser Ala Thr Gln Ala Thr Ile Pro Asn Ser Leu His Thr Met Ala
                245                 250                 255 ctc cat ctg acg gag gcg ggg ctg acc ttc cat ctc agc aag gag gtg       816
Leu His Leu Thr Glu Ala Gly Leu Thr Phe His Leu Ser Lys Glu Val
                260                 265                 270
```

```
ccc aag gtg gtg agc gac aac atg gag gag ctc atg ctc gag gcc ttc    864
Pro Lys Val Val Ser Asp Asn Met Glu Glu Leu Met Leu Glu Ala Phe
        275                 280                 285 aag ccg ctc ggg ata acc gat tgg aac tcc ata ttc tgg caa gtg cat    912
Lys Pro Leu Gly Ile Thr Asp Trp Asn Ser Ile Phe Trp Gln Val His
        290                 295                 300 ccc ggg ggt aga gcc atc ctt gac aag atc gag gag aag ctg gag ctc    960
Pro Gly Gly Arg Ala Ile Leu Asp Lys Ile Glu Glu Lys Leu Glu Leu
305                 310                 315                 320 acc aag gat aag atg cgg gat tcc cgc tac atc ttg agc gag tac ggg   1008
Thr Lys Asp Lys Met Arg Asp Ser Arg Tyr Ile Leu Ser Glu Tyr Gly
                325                 330                 335 aat ctc acc agc gcc tgt gtg ctc ttt gtc atg gac gag atg agg aag   1056
Asn Leu Thr Ser Ala Cys Val Leu Phe Val Met Asp Glu Met Arg Lys
            340                 345                 350 agg tcc ttc cgg gaa ggg aag cag acc acc gga gac ggc tac gag tgg   1104
Arg Ser Phe Arg Glu Gly Lys Gln Thr Thr Gly Asp Gly Tyr Glu Trp
        355                 360                 365 ggt gtc gcc atc gga ttg ggg ccc ggt ctt acc gtc gag acc gtt gtc   1152
Gly Val Ala Ile Gly Leu Gly Pro Gly Leu Thr Val Glu Thr Val Val
370                 375                 380 ttg cgt agc gtc ccc att ccc tga                                    1176
Leu Arg Ser Val Pro Ile Pro
385                 390

<210> SEQ ID NO 18
<211> LENGTH: 391
<212> TYPE: PRT
<213> ORGANISM: Rheum palmatum

<400> SEQUENCE: 18

Met Ala Asp Val Leu Gln Glu Ile Arg Asn Ser Gln Lys Ala Ser Gly
1               5                   10                  15

Pro Ala Thr Val Leu Ala Ile Gly Thr Ala His Pro Thr Cys Tyr
            20                  25                  30

Pro Gln Ala Asp Tyr Pro Asp Phe Tyr Phe Arg Val Cys Lys Ser Glu
        35                  40                  45

His Met Thr Lys Leu Lys Lys Lys Met Gln Phe Ile Cys Asp Arg Ser
    50                  55                  60

Gly Ile Arg Gln Arg Phe Met Phe His Thr Glu Glu Asn Leu Gly Lys
65                  70                  75                  80

Asn Pro Gly Met Cys Thr Phe Asp Gly Pro Ser Leu Asn Ala Arg Gln
                85                  90                  95

Asp Met Leu Ile Met Glu Val Pro Lys Leu Gly Ala Glu Ala Ala Glu
            100                 105                 110

Lys Ala Ile Lys Glu Trp Gly Gln Asp Lys Ser Arg Ile Thr His Leu
        115                 120                 125

Ile Phe Cys Thr Thr Thr Ser Asn Asp Met Pro Gly Ala Asp Tyr Gln
    130                 135                 140

Phe Ala Thr Leu Phe Gly Leu Asn Pro Gly Val Ser Arg Thr Met Val
145                 150                 155                 160

Tyr Gln Gln Gly Cys Phe Ala Gly Gly Thr Val Leu Arg Leu Val Lys
                165                 170                 175

Asp Ile Ala Glu Asn Asn Lys Gly Ala Arg Val Leu Val Val Cys Ser
            180                 185                 190

Glu Ile Val Ala Phe Ala Phe Arg Gly Pro His Glu Asp His Ile Asp
        195                 200                 205
```

```
Ser Leu Ile Gly Gln Leu Leu Phe Gly Asp Gly Ala Ala Leu Val
    210                 215                 220

Val Gly Thr Asp Ile Asp Glu Ser Val Glu Arg Pro Ile Phe Gln Ile
225                 230                 235                 240

Met Ser Ala Thr Gln Ala Thr Ile Pro Asn Ser Leu His Thr Met Ala
                245                 250                 255

Leu His Leu Thr Glu Ala Gly Leu Thr Phe His Leu Ser Lys Glu Val
                260                 265                 270

Pro Lys Val Val Ser Asp Asn Met Glu Glu Leu Met Leu Glu Ala Phe
            275                 280                 285

Lys Pro Leu Gly Ile Thr Asp Trp Asn Ser Ile Phe Trp Gln Val His
290                 295                 300

Pro Gly Gly Arg Ala Ile Leu Asp Lys Ile Glu Glu Lys Leu Glu Leu
305                 310                 315                 320

Thr Lys Asp Lys Met Arg Asp Ser Arg Tyr Ile Leu Ser Glu Tyr Gly
                325                 330                 335

Asn Leu Thr Ser Ala Cys Val Leu Phe Val Met Asp Glu Met Arg Lys
                340                 345                 350

Arg Ser Phe Arg Glu Gly Lys Gln Thr Thr Gly Asp Gly Tyr Glu Trp
            355                 360                 365

Gly Val Ala Ile Gly Leu Gly Pro Gly Leu Thr Val Glu Thr Val Val
370                 375                 380

Leu Arg Ser Val Pro Ile Pro
385                 390

<210> SEQ ID NO 19
<211> LENGTH: 1212
<212> TYPE: DNA
<213> ORGANISM: Aloe arborescens
<220> FEATURE:
<221> NAME/KEY: CDS
<222> LOCATION: (1)..(1212)
<223> OTHER INFORMATION: AaPKS3 gene [GenBank ID number EF537574)
      encoding a Type III heptaketide synthase (GenBank ID number
      ABS72373)

<400> SEQUENCE: 19 atg ggt tca ctc tcc gac tct acg cct ttg atg aag gat gtg cag ggc      48
Met Gly Ser Leu Ser Asp Ser Thr Pro Leu Met Lys Asp Val Gln Gly
1               5                   10                  15 atc cga aag gcc caa aag gcc gac gga act gcg acc gtg atg gcc att      96
Ile Arg Lys Ala Gln Lys Ala Asp Gly Thr Ala Thr Val Met Ala Ile
            20                  25                  30 gga aca gct cac cct cct cat atc att tcg cag gac agc tac gcg gat     144
Gly Thr Ala His Pro Pro His Ile Ile Ser Gln Asp Ser Tyr Ala Asp
        35                  40                  45 ttc tac ttc cgg gtc acc aac agc gag cac aag gtc gag ctc aag aag     192
Phe Tyr Phe Arg Val Thr Asn Ser Glu His Lys Val Glu Leu Lys Lys
    50                  55                  60 aag ttc gat cgc atc tgc aag aaa acg atg ata ggc aag cgt tac ttt     240
Lys Phe Asp Arg Ile Cys Lys Lys Thr Met Ile Gly Lys Arg Tyr Phe
65                  70                  75                  80 aac ttc gac gag gag ttc ttg aag aag tat ccc aac att act tca ttt     288
Asn Phe Asp Glu Glu Phe Leu Lys Lys Tyr Pro Asn Ile Thr Ser Phe
                85                  90                  95 gac aag ccc agc ctc aac gac agg cat gac att tgc att cct ggg gtg     336
Asp Lys Pro Ser Leu Asn Asp Arg His Asp Ile Cys Ile Pro Gly Val
            100                 105                 110 ccg gcg ctg ggg gcg gaa gcg gct gtt aaa gcc att gag gag tgg gga     384
```

| | | | | | | | | | | | | |
|---|---|---|---|---|---|---|---|---|---|---|---|---|
|Pro|Ala|Leu|Gly|Ala|Glu|Ala|Ala|Val|Lys|Ala|Ile|Glu|Glu|Trp|Gly|
| | |115| | | |120| | | |125| | | | | |

```
cgc cct aag tct gag atc act cac ctc gtc ttc tgc acc agc ggc ggt      432
Arg Pro Lys Ser Glu Ile Thr His Leu Val Phe Cys Thr Ser Gly Gly
        130                 135                 140 gtt gac atg cct agt gcc gat ttc cag tgc gct aag ctc ctt ggc ctc      480
Val Asp Met Pro Ser Ala Asp Phe Gln Cys Ala Lys Leu Leu Gly Leu
145                 150                 155                 160 cgc acc aat gtc aac aaa tac tgc atc tac atg cag gga tgc tat gct      528
Arg Thr Asn Val Asn Lys Tyr Cys Ile Tyr Met Gln Gly Cys Tyr Ala
                165                 170                 175 ggt ggc acc gtc atg cgg tat gcc aag gat ctg gcc gag aac aac cgt      576
Gly Gly Thr Val Met Arg Tyr Ala Lys Asp Leu Ala Glu Asn Asn Arg
            180                 185                 190 ggt gct cgt gtt ctg atg gtg tgc gca gag ctc acc atc att gcg ctc      624
Gly Ala Arg Val Leu Met Val Cys Ala Glu Leu Thr Ile Ile Ala Leu
        195                 200                 205 cgt ggc ccc aat gat tcc cat atc gac aat gct atc ggc aac tct ctt      672
Arg Gly Pro Asn Asp Ser His Ile Asp Asn Ala Ile Gly Asn Ser Leu
    210                 215                 220 ttc gga gat gga gct gct gcg ctg att gtt ggg tca gac ccc atc atc      720
Phe Gly Asp Gly Ala Ala Ala Leu Ile Val Gly Ser Asp Pro Ile Ile
225                 230                 235                 240 ggt gtc gag aag ccc atg ttc gag att gtc tgc gca aag cag act gtg      768
Gly Val Glu Lys Pro Met Phe Glu Ile Val Cys Ala Lys Gln Thr Val
                245                 250                 255 atc cca aac agt gaa gaa gtt atc cat ctc cac ctg agg gag tcg ggt      816
Ile Pro Asn Ser Glu Glu Val Ile His Leu His Leu Arg Glu Ser Gly
            260                 265                 270 ctg atg ttc tac atg acc aag gac agc gcc gcg acc atc tcc aat aat      864
Leu Met Phe Tyr Met Thr Lys Asp Ser Ala Ala Thr Ile Ser Asn Asn
        275                 280                 285 ata gag gcc tgc ctt gtt gat gtg ttt aag tcg gtg ggg atg act cct      912
Ile Glu Ala Cys Leu Val Asp Val Phe Lys Ser Val Gly Met Thr Pro
    290                 295                 300 ccg gag gat tgg aac tct ctc ttc tgg atc cct cat ccc ggt ggc cgg      960
Pro Glu Asp Trp Asn Ser Leu Phe Trp Ile Pro His Pro Gly Gly Arg
305                 310                 315                 320 gct atc ctc gac caa gtt gag gcc aag ctg aag ctt cgc ccc gag aag     1008
Ala Ile Leu Asp Gln Val Glu Ala Lys Leu Lys Leu Arg Pro Glu Lys
                325                 330                 335 ttt agt gcg act cga aca gtt ctc tgg gat tat ggc aac atg ata agt     1056
Phe Ser Ala Thr Arg Thr Val Leu Trp Asp Tyr Gly Asn Met Ile Ser
            340                 345                 350 gca tgt gtg ctc tat ata ctg gat gag atg aga aga aaa tct gct gct     1104
Ala Cys Val Leu Tyr Ile Leu Asp Glu Met Arg Arg Lys Ser Ala Ala
        355                 360                 365 gaa gga tta gaa acc tac gga gag ggg tta gag tgg ggt gtc ttg ctt     1152
Glu Gly Leu Glu Thr Tyr Gly Glu Gly Leu Glu Trp Gly Val Leu Leu
    370                 375                 380 ggt ttt gga cca gga atg act att gaa act atc ctt ctt cat agc ctg     1200
Gly Phe Gly Pro Gly Met Thr Ile Glu Thr Ile Leu Leu His Ser Leu
385                 390                 395                 400 cct cct gtg taa                                                     1212
Pro Pro Val <210> SEQ ID NO 20
<211> LENGTH: 403
<212> TYPE: PRT
<213> ORGANISM: Aloe arborescens
```

<400> SEQUENCE: 20

```
Met Gly Ser Leu Ser Asp Ser Thr Pro Leu Met Lys Asp Val Gln Gly
1               5                   10                  15

Ile Arg Lys Ala Gln Lys Ala Asp Gly Thr Ala Thr Val Met Ala Ile
                20                  25                  30

Gly Thr Ala His Pro Pro His Ile Ile Ser Gln Asp Ser Tyr Ala Asp
            35                  40                  45

Phe Tyr Phe Arg Val Thr Asn Ser Glu His Lys Val Glu Leu Lys Lys
50                  55                  60

Lys Phe Asp Arg Ile Cys Lys Lys Thr Met Ile Gly Lys Arg Tyr Phe
65                  70                  75                  80

Asn Phe Asp Glu Glu Phe Leu Lys Lys Tyr Pro Asn Ile Thr Ser Phe
                85                  90                  95

Asp Lys Pro Ser Leu Asn Asp Arg His Asp Ile Cys Ile Pro Gly Val
                100                 105                 110

Pro Ala Leu Gly Ala Glu Ala Ala Val Lys Ala Ile Glu Glu Trp Gly
            115                 120                 125

Arg Pro Lys Ser Glu Ile Thr His Leu Val Phe Cys Thr Ser Gly Gly
        130                 135                 140

Val Asp Met Pro Ser Ala Asp Phe Gln Cys Ala Lys Leu Leu Gly Leu
145                 150                 155                 160

Arg Thr Asn Val Asn Lys Tyr Cys Ile Tyr Met Gln Gly Cys Tyr Ala
                165                 170                 175

Gly Gly Thr Val Met Arg Tyr Ala Lys Asp Leu Ala Glu Asn Asn Arg
            180                 185                 190

Gly Ala Arg Val Leu Met Val Cys Ala Glu Leu Thr Ile Ile Ala Leu
        195                 200                 205

Arg Gly Pro Asn Asp Ser His Ile Asp Asn Ala Ile Gly Asn Ser Leu
        210                 215                 220

Phe Gly Asp Gly Ala Ala Ala Leu Ile Val Gly Ser Asp Pro Ile Ile
225                 230                 235                 240

Gly Val Glu Lys Pro Met Phe Glu Ile Val Cys Ala Lys Gln Thr Val
                245                 250                 255

Ile Pro Asn Ser Glu Glu Val Ile His Leu His Leu Arg Glu Ser Gly
                260                 265                 270

Leu Met Phe Tyr Met Thr Lys Asp Ser Ala Ala Thr Ile Ser Asn Asn
            275                 280                 285

Ile Glu Ala Cys Leu Val Asp Val Phe Lys Ser Val Gly Met Thr Pro
        290                 295                 300

Pro Glu Asp Trp Asn Ser Leu Phe Trp Ile Pro His Pro Gly Gly Arg
305                 310                 315                 320

Ala Ile Leu Asp Gln Val Glu Ala Lys Leu Lys Leu Arg Pro Glu Lys
                325                 330                 335

Phe Ser Ala Thr Arg Thr Val Leu Trp Asp Tyr Gly Asn Met Ile Ser
            340                 345                 350

Ala Cys Val Leu Tyr Ile Leu Asp Glu Met Arg Arg Lys Ser Ala Ala
        355                 360                 365

Glu Gly Leu Glu Thr Tyr Gly Glu Gly Leu Glu Trp Gly Val Leu Leu
        370                 375                 380

Gly Phe Gly Pro Gly Met Thr Ile Glu Thr Ile Leu Leu His Ser Leu
385                 390                 395                 400

Pro Pro Val
```

-continued

```
<210> SEQ ID NO 21
<211> LENGTH: 1212
<212> TYPE: DNA
<213> ORGANISM: Aloe arborescens
<220> FEATURE:
<221> NAME/KEY: CDS
<222> LOCATION: (1)..(1212)
<223> OTHER INFORMATION: OKS gene [GenBank ID number AY567707] encoding
      a Type III octaketide (GenBank ID number AAT48709.1)

<400> SEQUENCE: 21 atg agt tca ctc tcc aac gct tcc cat ctg atg gag gat gtg cag ggc      48
Met Ser Ser Leu Ser Asn Ala Ser His Leu Met Glu Asp Val Gln Gly
1               5                   10                  15 atc cgg aag gcc cag aga gcc gat ggc acg gcc acc gtc atg gcc atc      96
Ile Arg Lys Ala Gln Arg Ala Asp Gly Thr Ala Thr Val Met Ala Ile
            20                  25                  30 gga aca gct cac cct cct cat atc ttt cct cag gac acc tac gct gac     144
Gly Thr Ala His Pro Pro His Ile Phe Pro Gln Asp Thr Tyr Ala Asp
        35                  40                  45 ttc tac ttc cgc gcc acc aac agc gag cac aag gtc gag ctc aag aag     192
Phe Tyr Phe Arg Ala Thr Asn Ser Glu His Lys Val Glu Leu Lys Lys
    50                  55                  60 aag ttc gat cgc atc tgc aaa aag aca atg ata ggc aag cgc tac ttc     240
Lys Phe Asp Arg Ile Cys Lys Lys Thr Met Ile Gly Lys Arg Tyr Phe
65                  70                  75                  80 aac tac gac gag gag ttc ttg aag aaa tat ccc aat atc act tca ttc     288
Asn Tyr Asp Glu Glu Phe Leu Lys Lys Tyr Pro Asn Ile Thr Ser Phe
                85                  90                  95 gat gag ccc agc ctc aac gac cgc cag gac att tgt gtc cct ggg gtg     336
Asp Glu Pro Ser Leu Asn Asp Arg Gln Asp Ile Cys Val Pro Gly Val
            100                 105                 110 cca gcc ctg gga gcc gaa gca gct gtg aaa gcc atc gcg gaa tgg gga     384
Pro Ala Leu Gly Ala Glu Ala Ala Val Lys Ala Ile Ala Glu Trp Gly
        115                 120                 125 cgc ccc aag tct gag att act cat ctc gtg ttc tgc acc tcc tgc ggt     432
Arg Pro Lys Ser Glu Ile Thr His Leu Val Phe Cys Thr Ser Cys Gly
    130                 135                 140 gtc gac atg ccc agc gcc gac ttc cag tgc gcc aag ctc ctt ggc ctc     480
Val Asp Met Pro Ser Ala Asp Phe Gln Cys Ala Lys Leu Leu Gly Leu
145                 150                 155                 160 cgc acc aat gtc aac aag tac tgc gtc tac atg caa gga tgc tat gct     528
Arg Thr Asn Val Asn Lys Tyr Cys Val Tyr Met Gln Gly Cys Tyr Ala
                165                 170                 175 ggt ggc acc gtc atg cgg tat gcc aag gat ctg gcc gag aac aac cgt     576
Gly Gly Thr Val Met Arg Tyr Ala Lys Asp Leu Ala Glu Asn Asn Arg
            180                 185                 190 ggt gct cgt gtt ttg gtg gtg tgt gcg gag ctc acc ata atc ggg ctt     624
Gly Ala Arg Val Leu Val Val Cys Ala Glu Leu Thr Ile Ile Gly Leu
        195                 200                 205 cga ggc cct aat gag tcc cat ctc gac aac gcc atc gga aat tct ctt     672
Arg Gly Pro Asn Glu Ser His Leu Asp Asn Ala Ile Gly Asn Ser Leu
    210                 215                 220 ttc gga gat gga gct gcc gcg ttg atc gtc ggg tcg gac ccc atc atc     720
Phe Gly Asp Gly Ala Ala Ala Leu Ile Val Gly Ser Asp Pro Ile Ile
225                 230                 235                 240 ggt gtc gag aag ccc atg ttc gag atc gtg tgt gcc aag caa act gtg     768
Gly Val Glu Lys Pro Met Phe Glu Ile Val Cys Ala Lys Gln Thr Val
                245                 250                 255 atc cca aac agc gaa gac gtt atc cat ctc cac atg aga gag gca ggt     816
```

```
Ile Pro Asn Ser Glu Asp Val Ile His Leu His Met Arg Glu Ala Gly
                260                 265                 270 ctg atg ttc tac atg agc aag gac agt ccc gag acc atc tcc aat aac        864
Leu Met Phe Tyr Met Ser Lys Asp Ser Pro Glu Thr Ile Ser Asn Asn
        275                 280                 285 gta gag gct tgc ctc gtt gat gtg ttc aag tct gtg ggg atg act cct        912
Val Glu Ala Cys Leu Val Asp Val Phe Lys Ser Val Gly Met Thr Pro
290                 295                 300 ccc gag gac tgg aac tct ctc ttc tgg atc cct cac ccc ggt ggt cgc        960
Pro Glu Asp Trp Asn Ser Leu Phe Trp Ile Pro His Pro Gly Gly Arg
305                 310                 315                 320 gcc atc ctt gat caa gtt gag gcc aag ctg aag ctt cgt cct gag aag       1008
Ala Ile Leu Asp Gln Val Glu Ala Lys Leu Lys Leu Arg Pro Glu Lys
                325                 330                 335 ttc cgt gcg act cga acc gtg ctc tgg gat tgc ggt aac atg gtc agt       1056
Phe Arg Ala Thr Arg Thr Val Leu Trp Asp Cys Gly Asn Met Val Ser
                340                 345                 350 gcg tgt gtg ctc tac ata ttg gat gag atg aga aga aaa tcc gct gat       1104
Ala Cys Val Leu Tyr Ile Leu Asp Glu Met Arg Arg Lys Ser Ala Asp
                355                 360                 365 gaa gga cta gag acc tac gga gag gga cta gag tgg ggt gtc ttg ctt       1152
Glu Gly Leu Glu Thr Tyr Gly Glu Gly Leu Glu Trp Gly Val Leu Leu
370                 375                 380 gga ttt gga cca ggg atg acc gtt gaa act atc ctt ctc cac agc ctg       1200
Gly Phe Gly Pro Gly Met Thr Val Glu Thr Ile Leu Leu His Ser Leu
385                 390                 395                 400 cct ctc atg tga                                                        1212
Pro Leu Met <210> SEQ ID NO 22
<211> LENGTH: 403
<212> TYPE: PRT
<213> ORGANISM: Aloe arborescens

<400> SEQUENCE: 22

Met Ser Ser Leu Ser Asn Ala Ser His Leu Met Glu Asp Val Gln Gly
1               5                   10                  15

Ile Arg Lys Ala Gln Arg Ala Asp Gly Thr Ala Thr Val Met Ala Ile
                20                  25                  30

Gly Thr Ala His Pro Pro His Ile Phe Pro Gln Asp Thr Tyr Ala Asp
                35                  40                  45

Phe Tyr Phe Arg Ala Thr Asn Ser Glu His Lys Val Glu Leu Lys Lys
        50                  55                  60

Lys Phe Asp Arg Ile Cys Lys Lys Thr Met Ile Gly Lys Arg Tyr Phe
65                  70                  75                  80

Asn Tyr Asp Glu Glu Phe Leu Lys Lys Tyr Pro Asn Ile Thr Ser Phe
                85                  90                  95

Asp Glu Pro Ser Leu Asn Asp Arg Gln Asp Ile Cys Val Pro Gly Val
                100                 105                 110

Pro Ala Leu Gly Ala Glu Ala Ala Val Lys Ala Ile Ala Glu Trp Gly
        115                 120                 125

Arg Pro Lys Ser Glu Ile Thr His Leu Val Phe Cys Thr Ser Cys Gly
130                 135                 140

Val Asp Met Pro Ser Ala Asp Phe Gln Cys Ala Lys Leu Leu Gly Leu
145                 150                 155                 160

Arg Thr Asn Val Asn Lys Tyr Cys Val Tyr Met Gln Gly Cys Tyr Ala
                165                 170                 175
```

```
Gly Gly Thr Val Met Arg Tyr Ala Lys Asp Leu Ala Glu Asn Asn Arg
            180                 185                 190

Gly Ala Arg Val Leu Val Val Cys Ala Glu Leu Thr Ile Ile Gly Leu
        195                 200                 205

Arg Gly Pro Asn Glu Ser His Leu Asp Asn Ala Ile Gly Asn Ser Leu
    210                 215                 220

Phe Gly Asp Gly Ala Ala Leu Ile Val Gly Ser Asp Pro Ile Ile
225                 230                 235                 240

Gly Val Glu Lys Pro Met Phe Glu Ile Val Cys Ala Lys Gln Thr Val
                245                 250                 255

Ile Pro Asn Ser Glu Asp Val Ile His Leu His Met Arg Glu Ala Gly
            260                 265                 270

Leu Met Phe Tyr Met Ser Lys Asp Ser Pro Glu Thr Ile Ser Asn Asn
        275                 280                 285

Val Glu Ala Cys Leu Val Asp Val Phe Lys Ser Val Gly Met Thr Pro
    290                 295                 300

Pro Glu Asp Trp Asn Ser Leu Phe Trp Ile Pro His Pro Gly Gly Arg
305                 310                 315                 320

Ala Ile Leu Asp Gln Val Glu Ala Lys Leu Lys Leu Arg Pro Glu Lys
                325                 330                 335

Phe Arg Ala Thr Arg Thr Val Leu Trp Asp Cys Gly Asn Met Val Ser
            340                 345                 350

Ala Cys Val Leu Tyr Ile Leu Asp Glu Met Arg Arg Lys Ser Ala Asp
        355                 360                 365

Glu Gly Leu Glu Thr Tyr Gly Glu Gly Leu Glu Trp Gly Val Leu Leu
    370                 375                 380

Gly Phe Gly Pro Gly Met Thr Val Glu Thr Ile Leu Leu His Ser Leu
385                 390                 395                 400

Pro Leu Met
```

<210> SEQ ID NO 23
<211> LENGTH: 1212
<212> TYPE: DNA
<213> ORGANISM: Aloe arborescens
<220> FEATURE:
<221> NAME/KEY: CDS
<222> LOCATION: (1)..(1212)
<223> OTHER INFORMATION: OKS2 gene [GenBank ID number FJ536166) encoding a Type III octaketide synthase (GenBank ID number ACR19997.1)

<400> SEQUENCE: 23

```
atg ggt tca ctc tcc aac tac tcg cca gtg atg gag gat gtg cag gcc      48
Met Gly Ser Leu Ser Asn Tyr Ser Pro Val Met Glu Asp Val Gln Ala
1               5                   10                  15 atc cga aag gcc caa aaa gca gat gga acc gca aca gtg atg gcc atc      96
Ile Arg Lys Ala Gln Lys Ala Asp Gly Thr Ala Thr Val Met Ala Ile
                20                  25                  30 gga aca gct cac cct cct cat atc ttt cct cag gac acc tac gcc gac    144
Gly Thr Ala His Pro Pro His Ile Phe Pro Gln Asp Thr Tyr Ala Asp
            35                  40                  45 ttc tac ttc cgc gcc acc aac agc gag cac aaa gtc gag ctc aag aag    192
Phe Tyr Phe Arg Ala Thr Asn Ser Glu His Lys Val Glu Leu Lys Lys
        50                  55                  60 aaa ttc gat cgt atc tgc aaa aag aca atg ata ggc aag cgc tac ttc    240
Lys Phe Asp Arg Ile Cys Lys Lys Thr Met Ile Gly Lys Arg Tyr Phe
65                  70                  75                  80 aat tac gat gag gag ttc ctc aag aag tat ccc aac att acc tca ttc    288
Asn Tyr Asp Glu Glu Phe Leu Lys Lys Tyr Pro Asn Ile Thr Ser Phe
```

```
                             85                  90                  95
gac gag ccc agc ctc aac gac cgc cag gat att tgc gtc cct ggg gtg        336
Asp Glu Pro Ser Leu Asn Asp Arg Gln Asp Ile Cys Val Pro Gly Val
        100                 105                 110 ccg gcc ctg gga gcc gaa gca gct gtc aaa gcc atc gct gaa tgg gga        384
Pro Ala Leu Gly Ala Glu Ala Ala Val Lys Ala Ile Ala Glu Trp Gly
    115                 120                 125 cgt cca aag tct gag atc act cat ctc gtc ttc tgc acc tcc tgc ggt        432
Arg Pro Lys Ser Glu Ile Thr His Leu Val Phe Cys Thr Ser Cys Gly
130                 135                 140 gtc gac atg cct agc gcc gac ttc cag tgc gcc aag ctc ctc ggc ctc        480
Val Asp Met Pro Ser Ala Asp Phe Gln Cys Ala Lys Leu Leu Gly Leu
145                 150                 155                 160 cgc acc aat gtc aac aag tat tgc gtc tac atg cag gga tgc tat gct        528
Arg Thr Asn Val Asn Lys Tyr Cys Val Tyr Met Gln Gly Cys Tyr Ala
                165                 170                 175 ggc ggc aca gtc atg cgg tac gcc aag gat ctc gcc gag aac aac cgt        576
Gly Gly Thr Val Met Arg Tyr Ala Lys Asp Leu Ala Glu Asn Asn Arg
            180                 185                 190 ggt gct cgt gtt cta gtg gtg tgc gcc gag ctc acc atc atc ggg ctt        624
Gly Ala Arg Val Leu Val Val Cys Ala Glu Leu Thr Ile Ile Gly Leu
        195                 200                 205 cgc gga cca aat gag tcc cat ctc gac aac gcc atc ggc aac tcc ctt        672
Arg Gly Pro Asn Glu Ser His Leu Asp Asn Ala Ile Gly Asn Ser Leu
    210                 215                 220 ttc gga gac gga gct gct gcg ctg atc gtc ggg tca gac ccc atc att        720
Phe Gly Asp Gly Ala Ala Ala Leu Ile Val Gly Ser Asp Pro Ile Ile
225                 230                 235                 240 ggt gtc gag agg cct atg ttc gag atc gtg tgc gca aag cag acc gtg        768
Gly Val Glu Arg Pro Met Phe Glu Ile Val Cys Ala Lys Gln Thr Val
                245                 250                 255 atc cca aac agt gaa gat gtt atc cat ctc cac atg agg gag gcg ggt        816
Ile Pro Asn Ser Glu Asp Val Ile His Leu His Met Arg Glu Ala Gly
            260                 265                 270 cta atg ttc tac atg agc aag gac agc ccc gag acc atc tcc aac aat        864
Leu Met Phe Tyr Met Ser Lys Asp Ser Pro Glu Thr Ile Ser Asn Asn
        275                 280                 285 gta gag gca tgc ctt gtc gat gtg ttc aag tcg gtg ggg atg act cct        912
Val Glu Ala Cys Leu Val Asp Val Phe Lys Ser Val Gly Met Thr Pro
    290                 295                 300 ccc gag gac tgg aac tct ctc ttc tgg atc cct cac ccc ggc ggt cga        960
Pro Glu Asp Trp Asn Ser Leu Phe Trp Ile Pro His Pro Gly Gly Arg
305                 310                 315                 320 gct atc ctc gac cag gtt gag gcc agg ctt aag ctt cgt ccc gag aag       1008
Ala Ile Leu Asp Gln Val Glu Ala Arg Leu Lys Leu Arg Pro Glu Lys
                325                 330                 335 ttc ggc gcg act cga act gtg ctc tgg gat tgc gga aac atg gtg agc       1056
Phe Gly Ala Thr Arg Thr Val Leu Trp Asp Cys Gly Asn Met Val Ser
            340                 345                 350 gcg tgt gtt ctc tac att ttg gat gag atg aga aga aaa tct gtt gcc       1104
Ala Cys Val Leu Tyr Ile Leu Asp Glu Met Arg Arg Lys Ser Val Ala
        355                 360                 365 gac gga cta gca acc tac gga gag ggg ctg gag tgg ggt gtc ttg ctt       1152
Asp Gly Leu Ala Thr Tyr Gly Glu Gly Leu Glu Trp Gly Val Leu Leu
    370                 375                 380 ggt ttc gga cca ggg atg acc gtt gaa act atc ctt ctc cac agc ctg       1200
Gly Phe Gly Pro Gly Met Thr Val Glu Thr Ile Leu Leu His Ser Leu
385                 390                 395                 400 ccc cct gtg taa                                                       1212
```

Pro Pro Val

<210> SEQ ID NO 24
<211> LENGTH: 403
<212> TYPE: PRT
<213> ORGANISM: Aloe arborescens

<400> SEQUENCE: 24

```
Met Gly Ser Leu Ser Asn Tyr Ser Pro Val Met Glu Asp Val Gln Ala
1               5                   10                  15

Ile Arg Lys Ala Gln Lys Ala Asp Gly Thr Ala Thr Val Met Ala Ile
                20                  25                  30

Gly Thr Ala His Pro Pro His Ile Phe Pro Gln Asp Thr Tyr Ala Asp
            35                  40                  45

Phe Tyr Phe Arg Ala Thr Asn Ser Glu His Lys Val Glu Leu Lys Lys
50                  55                  60

Lys Phe Asp Arg Ile Cys Lys Lys Thr Met Ile Gly Lys Arg Tyr Phe
65                  70                  75                  80

Asn Tyr Asp Glu Glu Phe Leu Lys Lys Tyr Pro Asn Ile Thr Ser Phe
                85                  90                  95

Asp Glu Pro Ser Leu Asn Asp Arg Gln Asp Ile Cys Val Pro Gly Val
            100                 105                 110

Pro Ala Leu Gly Ala Glu Ala Ala Val Lys Ala Ile Ala Glu Trp Gly
        115                 120                 125

Arg Pro Lys Ser Glu Ile Thr His Leu Val Phe Cys Thr Ser Cys Gly
    130                 135                 140

Val Asp Met Pro Ser Ala Asp Phe Gln Cys Ala Lys Leu Leu Gly Leu
145                 150                 155                 160

Arg Thr Asn Val Asn Lys Tyr Cys Val Tyr Met Gln Gly Cys Tyr Ala
                165                 170                 175

Gly Gly Thr Val Met Arg Tyr Ala Lys Asp Leu Ala Glu Asn Asn Arg
            180                 185                 190

Gly Ala Arg Val Leu Val Val Cys Ala Glu Leu Thr Ile Ile Gly Leu
        195                 200                 205

Arg Gly Pro Asn Glu Ser His Leu Asp Asn Ala Ile Gly Asn Ser Leu
    210                 215                 220

Phe Gly Asp Gly Ala Ala Ala Leu Ile Val Gly Ser Asp Pro Ile Ile
225                 230                 235                 240

Gly Val Glu Arg Pro Met Phe Glu Ile Val Cys Ala Lys Gln Thr Val
                245                 250                 255

Ile Pro Asn Ser Glu Asp Val Ile His Leu His Met Arg Glu Ala Gly
            260                 265                 270

Leu Met Phe Tyr Met Ser Lys Asp Ser Pro Glu Thr Ile Ser Asn Asn
        275                 280                 285

Val Glu Ala Cys Leu Val Asp Val Phe Lys Ser Val Gly Met Thr Pro
    290                 295                 300

Pro Glu Asp Trp Asn Ser Leu Phe Trp Ile Pro His Pro Gly Gly Arg
305                 310                 315                 320

Ala Ile Leu Asp Gln Val Glu Ala Arg Leu Lys Leu Arg Pro Glu Lys
                325                 330                 335

Phe Gly Ala Thr Arg Thr Val Leu Trp Asp Cys Gly Asn Met Val Ser
            340                 345                 350

Ala Cys Val Leu Tyr Ile Leu Asp Glu Met Arg Arg Lys Ser Val Ala
        355                 360                 365
```

```
Asp Gly Leu Ala Thr Tyr Gly Glu Gly Leu Glu Trp Gly Val Leu Leu
370                 375                 380

Gly Phe Gly Pro Gly Met Thr Val Glu Thr Ile Leu Leu His Ser Leu
385                 390                 395                 400

Pro Pro Val

<210> SEQ ID NO 25
<211> LENGTH: 1218
<212> TYPE: DNA
<213> ORGANISM: Aloe arborescens
<220> FEATURE:
<221> NAME/KEY: CDS
<222> LOCATION: (1)..(1218)
<223> OTHER INFORMATION: OKS3 gene [GenBank ID number FJ536167) encoding
      a Type III octaketide synthase (GenBank ID number ACR19998.1)

<400> SEQUENCE: 25 atg ggt tcg atc gcc gag tct tca cca ctg atg agt agg gag aat gtg        48
Met Gly Ser Ile Ala Glu Ser Ser Pro Leu Met Ser Arg Glu Asn Val
1               5                   10                  15 gag ggc atc aga aaa gcg cag aga gct gag gga acc gca act gtg atg        96
Glu Gly Ile Arg Lys Ala Gln Arg Ala Glu Gly Thr Ala Thr Val Met
                20                  25                  30 gcc atc gga act gct cac cct ccc cat atc ttt cct cag gac acc tac       144
Ala Ile Gly Thr Ala His Pro Pro His Ile Phe Pro Gln Asp Thr Tyr
            35                  40                  45 gca gac ttc tac ttc cgc gcc acc aac agc gag cac aaa gtt gag ctc       192
Ala Asp Phe Tyr Phe Arg Ala Thr Asn Ser Glu His Lys Val Glu Leu
        50                  55                  60 aag aag aag ttc gac cga atc tgc aaa aag aca atg att ggc aaa cgc       240
Lys Lys Lys Phe Asp Arg Ile Cys Lys Lys Thr Met Ile Gly Lys Arg
65                  70                  75                  80 tac ttc aac tac gac gag gag ttc ctc aag aag tac cca aac atc aca       288
Tyr Phe Asn Tyr Asp Glu Glu Phe Leu Lys Lys Tyr Pro Asn Ile Thr
                85                  90                  95 tcc ttc gac gag ccc agc ctg aac gac cgc cag gac atc tgc gtc ccc       336
Ser Phe Asp Glu Pro Ser Leu Asn Asp Arg Gln Asp Ile Cys Val Pro
            100                 105                 110 gga gtc ccc gcc ttg ggt aag gag gcc gct ctc aaa gcc atc gag gaa       384
Gly Val Pro Ala Leu Gly Lys Glu Ala Ala Leu Lys Ala Ile Glu Glu
        115                 120                 125 tgg ggg caa cct ctg tcc aag atc acc cat ctc gtc ttc tgc acc tcc       432
Trp Gly Gln Pro Leu Ser Lys Ile Thr His Leu Val Phe Cys Thr Ser
130                 135                 140 tgc ggc gtc gac atg ccc agc gcc gat ttc cag ctc gcc aag ctc ctc       480
Cys Gly Val Asp Met Pro Ser Ala Asp Phe Gln Leu Ala Lys Leu Leu
145                 150                 155                 160 gga ctc aac acc aac gtc aac aag tac tgc gtc tac atg cag ggc tgc       528
Gly Leu Asn Thr Asn Val Asn Lys Tyr Cys Val Tyr Met Gln Gly Cys
                165                 170                 175 tac gcc ggc ggc acc gtc ctc cgc tac gcc aag gac ctc gcc gag aac       576
Tyr Ala Gly Gly Thr Val Leu Arg Tyr Ala Lys Asp Leu Ala Glu Asn
            180                 185                 190 aac cgc ggc tcc cgc gtc ctc gtc gtc tgc gcc gag ctc acc atc atc       624
Asn Arg Gly Ser Arg Val Leu Val Val Cys Ala Glu Leu Thr Ile Ile
        195                 200                 205 ggc ctc cgc ggc cca aac gag tcc cac ctc gac aac gcc atc ggg aac       672
Gly Leu Arg Gly Pro Asn Glu Ser His Leu Asp Asn Ala Ile Gly Asn
210                 215                 220 tcc ctc ttc ggc gac ggg gcc gcc gcg ctc atc gtg ggc gcc gat cct       720
Ser Leu Phe Gly Asp Gly Ala Ala Ala Leu Ile Val Gly Ala Asp Pro
```

```
                225                 230                 235                 240
att gtt ggc ata gag aag ccc atc ttc gag atc gtc tgc gca aag cag         768
Ile Val Gly Ile Glu Lys Pro Ile Phe Glu Ile Val Cys Ala Lys Gln
                245                 250                 255 acc gtc atc ccc gac agc gag gac gtc atc cac ctc cac ctc cgc gag         816
Thr Val Ile Pro Asp Ser Glu Asp Val Ile His Leu His Leu Arg Glu
                260                 265                 270 gcc ggc ctc atg ttc tac atg agc aag gac agc ccc gag acc atc tcc         864
Ala Gly Leu Met Phe Tyr Met Ser Lys Asp Ser Pro Glu Thr Ile Ser
                275                 280                 285 aac aac gtc gag ggc tgc ctc gtc gac atc ttc aag tcc gtc ggc atg         912
Asn Asn Val Glu Gly Cys Leu Val Asp Ile Phe Lys Ser Val Gly Met
                290                 295                 300 acc ccg ccc gcc gac tgg aac tcc ctc ttc tgg atc ccc cac ccc ggc         960
Thr Pro Pro Ala Asp Trp Asn Ser Leu Phe Trp Ile Pro His Pro Gly
305                 310                 315                 320 ggc cga gcc atc ctc gac gag gtc gag gcc agg ctc aag ctc cgc ccg        1008
Gly Arg Ala Ile Leu Asp Glu Val Glu Ala Arg Leu Lys Leu Arg Pro
                325                 330                 335 gag aag ttt aga gca acc agg cac gtg ctc tgg gag tac ggg aac atg        1056
Glu Lys Phe Arg Ala Thr Arg His Val Leu Trp Glu Tyr Gly Asn Met
                340                 345                 350 gtc agc gca tgc gtt ctc tac ata ctg gac gag atg agg aac aag tcc        1104
Val Ser Ala Cys Val Leu Tyr Ile Leu Asp Glu Met Arg Asn Lys Ser
                355                 360                 365 gca gcc gac gga ttg ggg acc tac gga gaa gga ctc gaa tgg ggc gtc        1152
Ala Ala Asp Gly Leu Gly Thr Tyr Gly Glu Gly Leu Glu Trp Gly Val
                370                 375                 380 ttg ctc ggt ttc gga ccc gga atg acc gtc gag acc atc ctc ctc cac        1200
Leu Leu Gly Phe Gly Pro Gly Met Thr Val Glu Thr Ile Leu Leu His
385                 390                 395                 400 agc ctg cct cct gtc taa                                                 1218
Ser Leu Pro Pro Val
                405

<210> SEQ ID NO 26
<211> LENGTH: 405
<212> TYPE: PRT
<213> ORGANISM: Aloe arborescens

<400> SEQUENCE: 26

Met Gly Ser Ile Ala Glu Ser Ser Pro Leu Met Ser Arg Glu Asn Val
1               5                   10                  15

Glu Gly Ile Arg Lys Ala Gln Arg Ala Glu Gly Thr Ala Thr Val Met
                20                  25                  30

Ala Ile Gly Thr Ala His Pro Pro His Ile Phe Pro Gln Asp Thr Tyr
            35                  40                  45

Ala Asp Phe Tyr Phe Arg Ala Thr Asn Ser Glu His Lys Val Glu Leu
        50                  55                  60

Lys Lys Lys Phe Asp Arg Ile Cys Lys Lys Thr Met Ile Gly Lys Arg
65              70                  75                  80

Tyr Phe Asn Tyr Asp Glu Glu Phe Leu Lys Lys Tyr Pro Asn Ile Thr
                85                  90                  95

Ser Phe Asp Glu Pro Ser Leu Asn Asp Arg Gln Asp Ile Cys Val Pro
            100                 105                 110

Gly Val Pro Ala Leu Gly Lys Glu Ala Ala Leu Lys Ala Ile Glu Glu
        115                 120                 125

Trp Gly Gln Pro Leu Ser Lys Ile Thr His Leu Val Phe Cys Thr Ser
```

```
                130                 135                 140
    Cys Gly Val Asp Met Pro Ser Ala Asp Phe Gln Leu Ala Lys Leu Leu
    145                 150                 155                 160
    Gly Leu Asn Thr Asn Val Asn Lys Tyr Cys Val Tyr Met Gln Gly Cys
                    165                 170                 175
    Tyr Ala Gly Gly Thr Val Leu Arg Tyr Ala Lys Asp Leu Ala Glu Asn
                180                 185                 190
    Asn Arg Gly Ser Arg Val Leu Val Cys Ala Glu Leu Thr Ile Ile
                195                 200                 205
    Gly Leu Arg Gly Pro Asn Glu Ser His Leu Asp Asn Ala Ile Gly Asn
            210                 215                 220
    Ser Leu Phe Gly Asp Gly Ala Ala Leu Ile Val Gly Ala Asp Pro
    225                 230                 235                 240
    Ile Val Gly Ile Glu Lys Pro Ile Phe Glu Ile Val Cys Ala Lys Gln
                    245                 250                 255
    Thr Val Ile Pro Asp Ser Glu Asp Val Ile His Leu His Leu Arg Glu
                260                 265                 270
    Ala Gly Leu Met Phe Tyr Met Ser Lys Asp Ser Pro Glu Thr Ile Ser
            275                 280                 285
    Asn Asn Val Glu Gly Cys Leu Val Asp Ile Phe Lys Ser Val Gly Met
    290                 295                 300
    Thr Pro Pro Ala Asp Trp Asn Ser Leu Phe Trp Ile Pro His Pro Gly
    305                 310                 315                 320
    Gly Arg Ala Ile Leu Asp Glu Val Glu Ala Arg Leu Lys Leu Arg Pro
                    325                 330                 335
    Glu Lys Phe Arg Ala Thr Arg His Val Leu Trp Glu Tyr Gly Asn Met
                340                 345                 350
    Val Ser Ala Cys Val Leu Tyr Ile Leu Asp Glu Met Arg Asn Lys Ser
            355                 360                 365
    Ala Ala Asp Gly Leu Gly Thr Tyr Gly Glu Gly Leu Glu Trp Gly Val
    370                 375                 380
    Leu Leu Gly Phe Gly Pro Gly Met Thr Val Glu Thr Ile Leu Leu His
    385                 390                 395                 400
    Ser Leu Pro Pro Val
                405

<210> SEQ ID NO 27
<211> LENGTH: 1182
<212> TYPE: DNA
<213> ORGANISM: Hypericum perforatum
<220> FEATURE:
<221> NAME/KEY: CDS
<222> LOCATION: (1)..(1182)
<223> OTHER INFORMATION: HpPKS2 gene [GenBank ID number HQ529467)
      encoding a Type III octaketide synthase (GenBank ID number
      AEE69029)

<400> SEQUENCE: 27 atg ggt tcc ctt gac aat ggt tca gct aga att aac aac cag aaa tct      48
Met Gly Ser Leu Asp Asn Gly Ser Ala Arg Ile Asn Asn Gln Lys Ser
1               5                   10                  15 aat ggg ttg gct tca att ttg gcc att gga act gca ctt ccg ccg att      96
Asn Gly Leu Ala Ser Ile Leu Ala Ile Gly Thr Ala Leu Pro Pro Ile
                20                  25                  30 tgc att aag caa gat gac tat cct gat tac tac ttc cga gtc acc aaa     144
Cys Ile Lys Gln Asp Asp Tyr Pro Asp Tyr Tyr Phe Arg Val Thr Lys
            35                  40                  45
```

```
agc gac cac aag acg caa ctg aaa gag aag ttt cgt cgc atc tgt gaa      192
Ser Asp His Lys Thr Gln Leu Lys Glu Lys Phe Arg Arg Ile Cys Glu
 50              55                  60 aag tca gga gtg aca aaa cga tac aca gta cta acc gaa gac atg atc      240
Lys Ser Gly Val Thr Lys Arg Tyr Thr Val Leu Thr Glu Asp Met Ile
 65              70                  75                  80 aag gag aac gag aac ata ata acc tac aag gct ccg tca ctg gat gct      288
Lys Glu Asn Glu Asn Ile Ile Thr Tyr Lys Ala Pro Ser Leu Asp Ala
                 85                  90                  95 cgc caa gcg atc cta cac aag gag aca ccc aag ctc gcc ata gaa gca      336
Arg Gln Ala Ile Leu His Lys Glu Thr Pro Lys Leu Ala Ile Glu Ala
            100                 105                 110 gcc ttg aag acc atc caa gaa tgg ggc caa ccc gtc tct aag atc acc      384
Ala Leu Lys Thr Ile Gln Glu Trp Gly Gln Pro Val Ser Lys Ile Thr
        115                 120                 125 cac ctg ttc ttt tgc tcc tcc tct ggc ggc tgc tat ctt ccg agc tcc      432
His Leu Phe Phe Cys Ser Ser Ser Gly Gly Cys Tyr Leu Pro Ser Ser
    130                 135                 140 gat ttt cag atc gct aag gca ctc ggc ctc gag ccg acc gtc cag agg      480
Asp Phe Gln Ile Ala Lys Ala Leu Gly Leu Glu Pro Thr Val Gln Arg
145                 150                 155                 160 tcc atg gtg ttt cct cat gga tgc tat gct gcc agt tct ggc ctg cgt      528
Ser Met Val Phe Pro His Gly Cys Tyr Ala Ala Ser Ser Gly Leu Arg
                165                 170                 175 ttg gcc aag gac att gca gag aac aac aaa gat gca cgc gtg ctg gtg      576
Leu Ala Lys Asp Ile Ala Glu Asn Asn Lys Asp Ala Arg Val Leu Val
            180                 185                 190 gtg tgc tgc gag ttg atg gtg tcg agc ttc cat gca cca tcg gag gac      624
Val Cys Cys Glu Leu Met Val Ser Ser Phe His Ala Pro Ser Glu Asp
        195                 200                 205 gcg atc gga atg cta ata ggt cat gcc atc ttc ggc gat gga gcg gcc      672
Ala Ile Gly Met Leu Ile Gly His Ala Ile Phe Gly Asp Gly Ala Ala
    210                 215                 220 tgc gca att gta gga gca gac ccg ggg cct acg gag cgc cca ata ttc      720
Cys Ala Ile Val Gly Ala Asp Pro Gly Pro Thr Glu Arg Pro Ile Phe
225                 230                 235                 240 gag cta gtg aag ggc gga cag gtg atc gtc cca gac acg gaa gac tgt      768
Glu Leu Val Lys Gly Gly Gln Val Ile Val Pro Asp Thr Glu Asp Cys
                245                 250                 255 ctg gga ggg tgg gtg atg gag atg gga tgg atc tac gat ctc aac aag      816
Leu Gly Gly Trp Val Met Glu Met Gly Trp Ile Tyr Asp Leu Asn Lys
            260                 265                 270 cgc ctt cct caa gcc cta gcc gac aac atc ctc gga gcc cta gat gac      864
Arg Leu Pro Gln Ala Leu Ala Asp Asn Ile Leu Gly Ala Leu Asp Asp
        275                 280                 285 acc ctg agg ctg aca ggt aaa agg gat gac ctc aat ggc ctt ttc tac      912
Thr Leu Arg Leu Thr Gly Lys Arg Asp Asp Leu Asn Gly Leu Phe Tyr
    290                 295                 300 gtg ctc cac ccg ggt ggg cgg gcc atc atc gac ctg ctt gag gag aag      960
Val Leu His Pro Gly Gly Arg Ala Ile Ile Asp Leu Leu Glu Glu Lys
305                 310                 315                 320 ctt gag cta aca aag gac aag ctc gag agt agc cgt cgt gtg ctc agc     1008
Leu Glu Leu Thr Lys Asp Lys Leu Glu Ser Ser Arg Arg Val Leu Ser
                325                 330                 335 aac tat ggc aac atg tgg ggc cct gcg cta gtg ttc acg ctc gac gag     1056
Asn Tyr Gly Asn Met Trp Gly Pro Ala Leu Val Phe Thr Leu Asp Glu
            340                 345                 350 atg agg agg aag tca aag gag gac aac gcc acc acc act ggt ggc ggg     1104
Met Arg Arg Lys Ser Lys Glu Asp Asn Ala Thr Thr Thr Gly Gly Gly
        355                 360                 365
```

```
tcc gag ctc ggc ctg atg atg gcg ttt gga cct ggc ctc acc acc gag    1152
Ser Glu Leu Gly Leu Met Met Ala Phe Gly Pro Gly Leu Thr Thr Glu
370                 375                 380 atc atg gtt ctc cga agt gtg cct ctc taa                            1182
Ile Met Val Leu Arg Ser Val Pro Leu
385                 390

<210> SEQ ID NO 28
<211> LENGTH: 393
<212> TYPE: PRT
<213> ORGANISM: Hypericum perforatum

<400> SEQUENCE: 28

Met Gly Ser Leu Asp Asn Gly Ser Ala Arg Ile Asn Asn Gln Lys Ser
1               5                   10                  15

Asn Gly Leu Ala Ser Ile Leu Ala Ile Gly Thr Ala Leu Pro Pro Ile
                20                  25                  30

Cys Ile Lys Gln Asp Asp Tyr Pro Asp Tyr Tyr Phe Arg Val Thr Lys
            35                  40                  45

Ser Asp His Lys Thr Gln Leu Lys Glu Lys Phe Arg Arg Ile Cys Glu
        50                  55                  60

Lys Ser Gly Val Thr Lys Arg Tyr Thr Val Leu Thr Glu Asp Met Ile
65                  70                  75                  80

Lys Glu Asn Glu Asn Ile Ile Thr Tyr Lys Ala Pro Ser Leu Asp Ala
                85                  90                  95

Arg Gln Ala Ile Leu His Lys Glu Thr Pro Lys Leu Ala Ile Glu Ala
            100                 105                 110

Ala Leu Lys Thr Ile Gln Glu Trp Gly Gln Pro Val Ser Lys Ile Thr
        115                 120                 125

His Leu Phe Phe Cys Ser Ser Gly Gly Cys Tyr Leu Pro Ser Ser
    130                 135                 140

Asp Phe Gln Ile Ala Lys Ala Leu Gly Leu Glu Pro Thr Val Gln Arg
145                 150                 155                 160

Ser Met Val Phe Pro His Gly Cys Tyr Ala Ala Ser Ser Gly Leu Arg
                165                 170                 175

Leu Ala Lys Asp Ile Ala Glu Asn Asn Lys Asp Ala Arg Val Leu Val
            180                 185                 190

Val Cys Cys Glu Leu Met Val Ser Ser Phe His Ala Pro Ser Glu Asp
        195                 200                 205

Ala Ile Gly Met Leu Ile Gly His Ala Ile Phe Gly Asp Gly Ala Ala
    210                 215                 220

Cys Ala Ile Val Gly Ala Asp Pro Gly Pro Thr Glu Arg Pro Ile Phe
225                 230                 235                 240

Glu Leu Val Lys Gly Gly Gln Val Ile Val Pro Asp Thr Glu Asp Cys
                245                 250                 255

Leu Gly Gly Trp Val Met Glu Met Gly Trp Ile Tyr Asp Leu Asn Lys
            260                 265                 270

Arg Leu Pro Gln Ala Leu Ala Asp Asn Ile Leu Gly Ala Leu Asp Asp
        275                 280                 285

Thr Leu Arg Leu Thr Gly Lys Arg Asp Asp Leu Asn Gly Leu Phe Tyr
    290                 295                 300

Val Leu His Pro Gly Gly Arg Ala Ile Ile Asp Leu Leu Glu Glu Lys
305                 310                 315                 320

Leu Glu Leu Thr Lys Asp Lys Leu Glu Ser Ser Arg Arg Val Leu Ser
                325                 330                 335
```

```
Asn Tyr Gly Asn Met Trp Gly Pro Ala Leu Val Phe Thr Leu Asp Glu
            340                 345                 350

Met Arg Arg Lys Ser Lys Glu Asp Asn Ala Thr Thr Thr Gly Gly Gly
            355                 360                 365

Ser Glu Leu Gly Leu Met Met Ala Phe Gly Pro Gly Leu Thr Thr Glu
            370                 375                 380

Ile Met Val Leu Arg Ser Val Pro Leu
385                 390
```

<210> SEQ ID NO 29
<211> LENGTH: 403
<212> TYPE: PRT
<213> ORGANISM: Aloe arborescens
<220> FEATURE:
<221> NAME/KEY: PROPEP
<222> LOCATION: (1)..(403)
<223> OTHER INFORMATION: PCS (F80A/Y82A/M207G) derived from GenBank ID
      number AAX35541.1 having nonaketide synthse activity

<400> SEQUENCE: 29

```
Met Ser Ser Leu Ser Asn Ser Leu Pro Leu Met Glu Asp Val Gln Gly
1               5                   10                  15

Ile Arg Lys Ala Gln Lys Ala Asp Gly Thr Ala Thr Val Met Ala Ile
            20                  25                  30

Gly Thr Ala His Pro Pro His Ile Phe Pro Gln Asp Thr Tyr Ala Asp
            35                  40                  45

Val Tyr Phe Arg Ala Thr Asn Ser Glu His Lys Val Glu Leu Lys Lys
    50                  55                  60

Lys Phe Asp His Ile Cys Lys Lys Thr Met Ile Gly Lys Arg Tyr Ala
65                  70                  75                  80

Asn Ala Asp Glu Glu Phe Leu Lys Lys Tyr Pro Asn Ile Thr Ser Tyr
            85                  90                  95

Asp Glu Pro Ser Leu Asn Asp Arg Gln Asp Ile Cys Val Pro Gly Val
            100                 105                 110

Pro Ala Leu Gly Thr Glu Ala Ala Val Lys Ala Ile Glu Glu Trp Gly
            115                 120                 125

Arg Pro Lys Ser Glu Ile Thr His Leu Val Phe Cys Thr Ser Cys Gly
            130                 135                 140

Val Asp Met Pro Ser Ala Asp Phe Gln Cys Ala Lys Leu Leu Gly Leu
145                 150                 155                 160

His Ala Asn Val Asn Lys Tyr Cys Ile Tyr Met Gln Gly Cys Tyr Ala
            165                 170                 175

Gly Gly Thr Val Met Arg Tyr Ala Lys Asp Leu Ala Glu Asn Asn Arg
            180                 185                 190

Gly Ala Arg Val Leu Val Cys Ala Glu Leu Thr Ile Met Gly Leu
            195                 200                 205

Arg Ala Pro Asn Glu Thr His Leu Asp Asn Ala Ile Gly Ile Ser Leu
            210                 215                 220

Phe Gly Asp Gly Ala Ala Ala Leu Ile Ile Gly Ser Asp Pro Ile Ile
225                 230                 235                 240

Gly Val Glu Lys Pro Met Phe Glu Ile Val Cys Thr Lys Gln Thr Val
            245                 250                 255

Ile Pro Asn Thr Glu Asp Val Ile His Leu His Leu Arg Glu Thr Gly
            260                 265                 270

Met Met Phe Tyr Leu Ser Lys Gly Ser Pro Met Thr Ile Ser Asn Asn
            275                 280                 285
```

```
Val Glu Ala Cys Leu Ile Asp Val Phe Lys Ser Val Gly Ile Thr Pro
    290                 295                 300

Pro Glu Asp Trp Asn Ser Leu Phe Trp Ile Pro His Pro Gly Gly Arg
305                 310                 315                 320

Ala Ile Leu Asp Gln Val Glu Ala Lys Leu Lys Leu Arg Pro Glu Lys
                325                 330                 335

Phe Arg Ala Ala Arg Thr Val Leu Trp Asp Tyr Gly Asn Met Val Ser
                340                 345                 350

Ala Ser Val Gly Tyr Ile Leu Asp Glu Met Arg Arg Lys Ser Ala Ala
                355                 360                 365

Lys Gly Leu Glu Thr Tyr Gly Glu Gly Leu Glu Trp Gly Val Leu Leu
    370                 375                 380

Gly Phe Gly Pro Gly Ile Thr Val Glu Thr Ile Leu Leu His Ser Leu
385                 390                 395                 400

Pro Leu Met
```

<210> SEQ ID NO 30
<211> LENGTH: 403
<212> TYPE: PRT
<213> ORGANISM: Aloe arborescens
<220> FEATURE:
<221> NAME/KEY: PROPEP
<222> LOCATION: (1)..(403)
<223> OTHER INFORMATION: OKS N222G mutant polypeptide (derived from GenBank ID number AAT48709.1) having decaketide synthase activity.

<400> SEQUENCE: 30

```
Met Ser Ser Leu Ser Asn Ala Ser His Leu Met Glu Asp Val Gln Gly
1               5                   10                  15

Ile Arg Lys Ala Gln Arg Ala Asp Gly Thr Ala Thr Val Met Ala Ile
                20                  25                  30

Gly Thr Ala His Pro Pro His Ile Phe Pro Gln Asp Thr Tyr Ala Asp
                35                  40                  45

Phe Tyr Phe Arg Ala Thr Asn Ser Glu His Lys Val Glu Leu Lys Lys
    50                  55                  60

Lys Phe Asp Arg Ile Cys Lys Lys Thr Met Ile Gly Lys Arg Tyr Phe
65                  70                  75                  80

Asn Tyr Asp Glu Glu Phe Leu Lys Lys Tyr Pro Asn Ile Thr Ser Phe
                85                  90                  95

Asp Glu Pro Ser Leu Asn Asp Arg Gln Asp Ile Cys Val Pro Gly Val
                100                 105                 110

Pro Ala Leu Gly Ala Glu Ala Ala Val Lys Ala Ile Ala Glu Trp Gly
            115                 120                 125

Arg Pro Lys Ser Glu Ile Thr His Leu Val Phe Cys Thr Ser Cys Gly
130                 135                 140

Val Asp Met Pro Ser Ala Asp Phe Gln Cys Ala Lys Leu Leu Gly Leu
145                 150                 155                 160

Arg Thr Asn Val Asn Lys Tyr Cys Val Tyr Met Gln Gly Cys Tyr Ala
                165                 170                 175

Gly Gly Thr Val Met Arg Tyr Ala Lys Asp Leu Ala Glu Asn Asn Arg
            180                 185                 190

Gly Ala Arg Val Leu Val Val Cys Ala Glu Leu Thr Ile Ile Gly Leu
            195                 200                 205

Arg Gly Pro Asn Glu Ser His Leu Asp Asn Ala Ile Gly Gly Ser Leu
    210                 215                 220
```

-continued

```
Phe Gly Asp Gly Ala Ala Ala Leu Ile Val Gly Ser Asp Pro Ile Ile
225                 230                 235                 240

Gly Val Glu Lys Pro Met Phe Glu Ile Val Cys Ala Lys Gln Thr Val
            245                 250                 255

Ile Pro Asn Ser Glu Asp Val Ile His Leu His Met Arg Glu Ala Gly
            260                 265                 270

Leu Met Phe Tyr Met Ser Lys Asp Ser Pro Glu Thr Ile Ser Asn Asn
        275                 280                 285

Val Glu Ala Cys Leu Val Asp Val Phe Lys Ser Val Gly Met Thr Pro
    290                 295                 300

Pro Glu Asp Trp Asn Ser Leu Phe Trp Ile Pro His Pro Gly Gly Arg
305                 310                 315                 320

Ala Ile Leu Asp Gln Val Glu Ala Lys Leu Lys Leu Arg Pro Glu Lys
                325                 330                 335

Phe Arg Ala Thr Arg Thr Val Leu Trp Asp Cys Gly Asn Met Val Ser
            340                 345                 350

Ala Cys Val Leu Tyr Ile Leu Asp Glu Met Arg Arg Lys Ser Ala Asp
        355                 360                 365

Glu Gly Leu Glu Thr Tyr Gly Glu Gly Leu Glu Trp Gly Val Leu Leu
    370                 375                 380

Gly Phe Gly Pro Gly Met Thr Val Glu Thr Ile Leu Leu His Ser Leu
385                 390                 395                 400

Pro Leu Met
```

<210> SEQ ID NO 31
<211> LENGTH: 403
<212> TYPE: PRT
<213> ORGANISM: Aloe arborescens
<220> FEATURE:
<221> NAME/KEY: PROPEP
<222> LOCATION: (1)..(403)
<223> OTHER INFORMATION: OKS mutant polypeptide (F66L/N222G) derived
      from GenBank ID number AAT48709.1 having dodecaketide synthase
      activity.

<400> SEQUENCE: 31

```
Met Ser Ser Leu Ser Asn Ala Ser His Leu Met Glu Asp Val Gln Gly
1               5                   10                  15

Ile Arg Lys Ala Gln Arg Ala Asp Gly Thr Ala Thr Val Met Ala Ile
            20                  25                  30

Gly Thr Ala His Pro Pro His Ile Phe Pro Gln Asp Thr Tyr Ala Asp
        35                  40                  45

Phe Tyr Phe Arg Ala Thr Asn Ser Glu His Lys Val Glu Leu Lys Lys
    50                  55                  60

Lys Leu Asp Arg Ile Cys Lys Lys Thr Met Ile Gly Lys Arg Tyr Phe
65                  70                  75                  80

Asn Tyr Asp Glu Glu Phe Leu Lys Lys Tyr Pro Asn Ile Thr Ser Phe
                85                  90                  95

Asp Glu Pro Ser Leu Asn Asp Arg Gln Asp Ile Cys Val Pro Gly Val
            100                 105                 110

Pro Ala Leu Gly Ala Glu Ala Ala Val Lys Ala Ile Ala Glu Trp Gly
        115                 120                 125

Arg Pro Lys Ser Glu Ile Thr His Leu Val Phe Cys Thr Ser Cys Gly
    130                 135                 140

Val Asp Met Pro Ser Ala Asp Phe Gln Cys Ala Lys Leu Leu Gly Leu
145                 150                 155                 160
```

```
Arg Thr Asn Val Asn Lys Tyr Cys Val Tyr Met Gln Gly Cys Tyr Ala
                165                 170                 175
Gly Gly Thr Val Met Arg Tyr Ala Lys Asp Leu Ala Glu Asn Asn Arg
            180                 185                 190
Gly Ala Arg Val Leu Val Val Cys Ala Glu Leu Thr Ile Ile Gly Leu
        195                 200                 205
Arg Gly Pro Asn Glu Ser His Leu Asp Asn Ala Ile Gly Gly Ser Leu
    210                 215                 220
Phe Gly Asp Gly Ala Ala Leu Ile Val Gly Ser Asp Pro Ile Ile
225                 230                 235                 240
Gly Val Glu Lys Pro Met Phe Glu Ile Val Cys Ala Lys Gln Thr Val
                245                 250                 255
Ile Pro Asn Ser Glu Asp Val Ile His Leu His Met Arg Glu Ala Gly
            260                 265                 270
Leu Met Phe Tyr Met Ser Lys Asp Ser Pro Glu Thr Ile Ser Asn Asn
        275                 280                 285
Val Glu Ala Cys Leu Val Asp Val Phe Lys Ser Val Gly Met Thr Pro
    290                 295                 300
Pro Glu Asp Trp Asn Ser Leu Phe Trp Ile Pro His Pro Gly Gly Arg
305                 310                 315                 320
Ala Ile Leu Asp Gln Val Glu Ala Lys Leu Lys Leu Arg Pro Glu Lys
                325                 330                 335
Phe Arg Ala Thr Arg Thr Val Leu Trp Asp Cys Gly Asn Met Val Ser
            340                 345                 350
Ala Cys Val Leu Tyr Ile Leu Asp Glu Met Arg Arg Lys Ser Ala Asp
        355                 360                 365
Glu Gly Leu Glu Thr Tyr Gly Glu Gly Leu Glu Trp Gly Val Leu Leu
    370                 375                 380
Gly Phe Gly Pro Gly Met Thr Val Glu Thr Ile Leu Leu His Ser Leu
385                 390                 395                 400
Pro Leu Met

<210> SEQ ID NO 32
<211> LENGTH: 510
<212> TYPE: DNA
<213> ORGANISM: Streptomyces sp. R1128
<220> FEATURE:
<221> NAME/KEY: CDS
<222> LOCATION: (1)..(510)
<223> OTHER INFORMATION: ZhuI (type: SRPBCC) [GenBank ID number
      AF293442.1] encoding a first 'small molecule foldase' [GenBank ID
      number AAG30197.1]

<400> SEQUENCE: 32 atg cgt cac gtc gaa cac acc gtc acc gta gcg gcc ccg gcc gac ctg      48
Met Arg His Val Glu His Thr Val Thr Val Ala Ala Pro Ala Asp Leu
1               5                   10                  15 gtc tgg gag gtg ctg gcc gat gtg ctc ggc tac gcc gac atc ttc ccg      96
Val Trp Glu Val Leu Ala Asp Val Leu Gly Tyr Ala Asp Ile Phe Pro
            20                  25                  30 ccg acc gag aag gtc gag atc ctc gag gag ggt cag ggc tac cag gtc     144
Pro Thr Glu Lys Val Glu Ile Leu Glu Glu Gly Gln Gly Tyr Gln Val
        35                  40                  45 gtc cgc ctg cac gtg gac gtc gcc ggc gag atc aac acc tgg acc tcg     192
Val Arg Leu His Val Asp Val Ala Gly Glu Ile Asn Thr Trp Thr Ser
    50                  55                  60 cgc cgc gac ctg gac ccg gcc cgc cgc gtc atc gcc tac cgg cag ttg     240
Arg Arg Asp Leu Asp Pro Ala Arg Arg Val Ile Ala Tyr Arg Gln Leu
```

```
              65                  70                  75                  80
gag acg gcc ccg atc gtc ggg cac atg agc ggc gag tgg cgc gcc ttc         288
Glu Thr Ala Pro Ile Val Gly His Met Ser Gly Glu Trp Arg Ala Phe
                85                  90                  95 acg ctg gac gcc gag cgc acc caa ctg gtg ctc acc cac gac ttc gtg         336
Thr Leu Asp Ala Glu Arg Thr Gln Leu Val Leu Thr His Asp Phe Val
            100                 105                 110 acg cgc gcg gcc ggc gac gac ggc ctg gtg gcc ggc aag ctc acc ccc         384
Thr Arg Ala Ala Gly Asp Asp Gly Leu Val Ala Gly Lys Leu Thr Pro
            115                 120                 125 gac gag gcg cgc gag atg ctg gag gcg gtc gtc gag cgc aac agc gtc         432
Asp Glu Ala Arg Glu Met Leu Glu Ala Val Val Glu Arg Asn Ser Val
        130                 135                 140 gcc gac ctg aac gcg gtc ctc ggc gag gcc gag cgt cgg gtg cgc gcg         480
Ala Asp Leu Asn Ala Val Leu Gly Glu Ala Glu Arg Arg Val Arg Ala
145                 150                 155                 160 gcc ggc ggc gtc ggg acg gtg acc gcg tga                                 510
Ala Gly Gly Val Gly Thr Val Thr Ala
                165

<210> SEQ ID NO 33
<211> LENGTH: 169
<212> TYPE: PRT
<213> ORGANISM: Streptomyces sp. R1128

<400> SEQUENCE: 33

Met Arg His Val Glu His Thr Val Thr Val Ala Ala Pro Ala Asp Leu
1               5                   10                  15

Val Trp Glu Val Leu Ala Asp Val Leu Gly Tyr Ala Asp Ile Phe Pro
            20                  25                  30

Pro Thr Glu Lys Val Glu Ile Leu Glu Glu Gly Gln Gly Tyr Gln Val
        35                  40                  45

Val Arg Leu His Val Asp Val Ala Gly Glu Ile Asn Thr Trp Thr Ser
    50                  55                  60

Arg Arg Asp Leu Asp Pro Ala Arg Arg Val Ile Ala Tyr Arg Gln Leu
65                  70                  75                  80

Glu Thr Ala Pro Ile Val Gly His Met Ser Gly Glu Trp Arg Ala Phe
                85                  90                  95

Thr Leu Asp Ala Glu Arg Thr Gln Leu Val Leu Thr His Asp Phe Val
            100                 105                 110

Thr Arg Ala Ala Gly Asp Asp Gly Leu Val Ala Gly Lys Leu Thr Pro
        115                 120                 125

Asp Glu Ala Arg Glu Met Leu Glu Ala Val Val Glu Arg Asn Ser Val
    130                 135                 140

Ala Asp Leu Asn Ala Val Leu Gly Glu Ala Glu Arg Arg Val Arg Ala
145                 150                 155                 160

Ala Gly Gly Val Gly Thr Val Thr Ala
                165

<210> SEQ ID NO 34
<211> LENGTH: 462
<212> TYPE: DNA
<213> ORGANISM: Actinomadura hibisca
<220> FEATURE:
<221> NAME/KEY: CDS
<222> LOCATION: (1)..(462)
<223> OTHER INFORMATION: pdmD (type: SRPBCC) gene [GenBank ID number
      EF151801.1 Position 23865 to 24326 (nucleotide seq.) encoding a
      'first small molecule foldase' [GenBank ID number ABM21750.1]
```

```
<400> SEQUENCE: 34 atg acg cag tgg cgc acc gac agc gtg atc gtg atc gac gcg ccg ctc    48
Met Thr Gln Trp Arg Thr Asp Ser Val Ile Val Ile Asp Ala Pro Leu
 1               5                  10                  15 gac gtc gtc tgg gac atg acc aac gac gtc gcc tcc tgg ccg gag ctg    96
Asp Val Val Trp Asp Met Thr Asn Asp Val Ala Ser Trp Pro Glu Leu
             20                  25                  30 ttc gac gag tac gcc tcg gcc gag atc ctg gag cgc gac ggc gac acc   144
Phe Asp Glu Tyr Ala Ser Ala Glu Ile Leu Glu Arg Asp Gly Asp Thr
         35                  40                  45 gtc cgc ttc cgg ctg acg atg cac ccc gac gcc gac ggc aac gcc tgg   192
Val Arg Phe Arg Leu Thr Met His Pro Asp Ala Asp Gly Asn Ala Trp
     50                  55                  60 tcg tgg gtg tcg gag cgc acg ccc gac cgc gcc gcg ctc acc gtc aac   240
Ser Trp Val Ser Glu Arg Thr Pro Asp Arg Ala Ala Leu Thr Val Asn
 65                  70                  75                  80 gcg cac cgc gtg gag acc ggc tgg ttc gag cac atg aac ctg cgc tgg   288
Ala His Arg Val Glu Thr Gly Trp Phe Glu His Met Asn Leu Arg Trp
                 85                  90                  95 gac tac cgc gag gtg ccc ggc ggc gtg gag atg cgc tgg cgg cag gac   336
Asp Tyr Arg Glu Val Pro Gly Gly Val Glu Met Arg Trp Arg Gln Asp
            100                 105                 110 ttc gcg atg aag gag gcg tcg ccg gtg tcg ctg gcg gcg atg acc gag   384
Phe Ala Met Lys Glu Ala Ser Pro Val Ser Leu Ala Ala Met Thr Glu
        115                 120                 125 cgc atc cag agc aac tcc ccc gtc cag atg aag ctg atc aag gac aag   432
Arg Ile Gln Ser Asn Ser Pro Val Gln Met Lys Leu Ile Lys Asp Lys
    130                 135                 140 gtg gag cgg gcg gcc cgg ggc gcg cgg tga                            462
Val Glu Arg Ala Ala Arg Gly Ala Arg
145                 150

<210> SEQ ID NO 35
<211> LENGTH: 153
<212> TYPE: PRT
<213> ORGANISM: Actinomadura hibisca

<400> SEQUENCE: 35

Met Thr Gln Trp Arg Thr Asp Ser Val Ile Val Ile Asp Ala Pro Leu
 1               5                  10                  15

Asp Val Val Trp Asp Met Thr Asn Asp Val Ala Ser Trp Pro Glu Leu
             20                  25                  30

Phe Asp Glu Tyr Ala Ser Ala Glu Ile Leu Glu Arg Asp Gly Asp Thr
         35                  40                  45

Val Arg Phe Arg Leu Thr Met His Pro Asp Ala Asp Gly Asn Ala Trp
     50                  55                  60

Ser Trp Val Ser Glu Arg Thr Pro Asp Arg Ala Ala Leu Thr Val Asn
 65                  70                  75                  80

Ala His Arg Val Glu Thr Gly Trp Phe Glu His Met Asn Leu Arg Trp
                 85                  90                  95

Asp Tyr Arg Glu Val Pro Gly Gly Val Glu Met Arg Trp Arg Gln Asp
            100                 105                 110

Phe Ala Met Lys Glu Ala Ser Pro Val Ser Leu Ala Ala Met Thr Glu
        115                 120                 125

Arg Ile Gln Ser Asn Ser Pro Val Gln Met Lys Leu Ile Lys Asp Lys
    130                 135                 140

Val Glu Arg Ala Ala Arg Gly Ala Arg
145                 150
```

<210> SEQ ID NO 36
<211> LENGTH: 456
<212> TYPE: DNA
<213> ORGANISM: Streptomyces sp. SANK 61196
<220> FEATURE:
<221> NAME/KEY: CDS
<222> LOCATION: (1)..(456)
<223> OTHER INFORMATION: sanI (type: SRPBCC) gene [GenBank ID number
      GU937384.1 position 11996 to 12451] encoding a first "small
      molecule foldase" [GenBank ID number ADG86318.1]

<400> SEQUENCE: 36

| | | | | | | | | | | | | | | | | |
|---|---|---|---|---|---|---|---|---|---|---|---|---|---|---|---|---|
| atg | gcg | ctg | acc | gac | aac | acg | atc | gtc | atc | gac | gcg | ccc | atg | gac | ctg | 48 |
| Met | Ala | Leu | Thr | Asp | Asn | Thr | Ile | Val | Ile | Asp | Ala | Pro | Met | Asp | Leu | |
| 1 | | | | 5 | | | | | 10 | | | | | 15 | | |
| gtg | tgg | gag | atg | acc | aac | gac | gtc | gaa | tcc | tgg | ccg | acg | ctc | ttc | tcc | 96 |
| Val | Trp | Glu | Met | Thr | Asn | Asp | Val | Glu | Ser | Trp | Pro | Thr | Leu | Phe | Ser | |
| | | | | 20 | | | | | 25 | | | | | 30 | | |
| gag | tac | gcc | gcg | gcc | gag | atc | ctc | ggc | cgc | acc | ggg | gcc | acc | gtc | cgc | 144 |
| Glu | Tyr | Ala | Ala | Ala | Glu | Ile | Leu | Gly | Arg | Thr | Gly | Ala | Thr | Val | Arg | |
| | | | 35 | | | | | 40 | | | | | 45 | | | |
| ttc | cgg | ctc | acg | ctg | cac | ccg | gac | gag | aac | ggc | gcg | gtc | tgg | agc | tgg | 192 |
| Phe | Arg | Leu | Thr | Leu | His | Pro | Asp | Glu | Asn | Gly | Ala | Val | Trp | Ser | Trp | |
| 50 | | | | | 55 | | | | | 60 | | | | | | |
| gtg | tcg | gag | cgt | act | ccg | gac | ccg | gag | acc | agg | acg | gta | cgc | gcg | cgg | 240 |
| Val | Ser | Glu | Arg | Thr | Pro | Asp | Pro | Glu | Thr | Arg | Thr | Val | Arg | Ala | Arg | |
| 65 | | | | 70 | | | | | 75 | | | | | 80 | | |
| cgc | atc | gag | acg | ggc | ccg | ttc | gag | cac | atg | gac | atc | cac | tgg | aca | tac | 288 |
| Arg | Ile | Glu | Thr | Gly | Pro | Phe | Glu | His | Met | Asp | Ile | His | Trp | Thr | Tyr | |
| | | | | 85 | | | | | 90 | | | | | 95 | | |
| gcc | gac | acc | gac | ggc | ggg | gtg | gag | atg | cgc | tgg | cgg | cag | gag | ttc | acg | 336 |
| Ala | Asp | Thr | Asp | Gly | Gly | Val | Glu | Met | Arg | Trp | Arg | Gln | Glu | Phe | Thr | |
| | | | 100 | | | | | 105 | | | | | 110 | | | |
| gtc | cgt | ccg | ggc | ctg | ccg | ttc | ggc | gac | acg | gag | atg | acc | gag | cgg | ctg | 384 |
| Val | Arg | Pro | Gly | Leu | Pro | Phe | Gly | Asp | Thr | Glu | Met | Thr | Glu | Arg | Leu | |
| | | | 115 | | | | | 120 | | | | | 125 | | | |
| aac | acc | aac | acc | cgc | cgg | gaa | atg | gcc | cgg | atc | aag | ggc | ctg | gtg | gag | 432 |
| Asn | Thr | Asn | Thr | Arg | Arg | Glu | Met | Ala | Arg | Ile | Lys | Gly | Leu | Val | Glu | |
| | | 130 | | | | | 135 | | | | | 140 | | | | |
| cgg | gcc | gcg | gcg | gtg | gcg | cgg | tga | | | | | | | | | 456 |
| Arg | Ala | Ala | Ala | Val | Ala | Arg | | | | | | | | | | |
| 145 | | | | 150 | | | | | | | | | | | | |

<210> SEQ ID NO 37
<211> LENGTH: 151
<212> TYPE: PRT
<213> ORGANISM: Streptomyces sp. SANK 61196

<400> SEQUENCE: 37

Met Ala Leu Thr Asp Asn Thr Ile Val Ile Asp Ala Pro Met Asp Leu
1               5                   10                  15

Val Trp Glu Met Thr Asn Asp Val Glu Ser Trp Pro Thr Leu Phe Ser
            20                  25                  30

Glu Tyr Ala Ala Ala Glu Ile Leu Gly Arg Thr Gly Ala Thr Val Arg
        35                  40                  45

Phe Arg Leu Thr Leu His Pro Asp Glu Asn Gly Ala Val Trp Ser Trp
    50                  55                  60

Val Ser Glu Arg Thr Pro Asp Pro Glu Thr Arg Thr Val Arg Ala Arg
65                  70                  75                  80

Arg Ile Glu Thr Gly Pro Phe Glu His Met Asp Ile His Trp Thr Tyr

```
                85                  90                  95
Ala Asp Thr Asp Gly Val Glu Met Arg Trp Arg Gln Glu Phe Thr
            100                 105                 110

Val Arg Pro Gly Leu Pro Phe Gly Asp Thr Glu Met Thr Glu Arg Leu
        115                 120                 125

Asn Thr Asn Thr Arg Arg Glu Met Ala Arg Ile Lys Gly Leu Val Glu
    130                 135                 140

Arg Ala Ala Ala Val Ala Arg
145                 150

<210> SEQ ID NO 38
<211> LENGTH: 474
<212> TYPE: DNA
<213> ORGANISM: Streptomyces sp. TA-0256
<220> FEATURE:
<221> NAME/KEY: CDS
<222> LOCATION: (1)..(474)
<223> OTHER INFORMATION: pnxD (type: SRPBCC) gene [GenBank ID number
      AB469194.1 position 16730 to 17203] encoding a first 'small
      molecule foldase' [GenBank ID number BAJ52684.1].

<400> SEQUENCE: 38 atg ccg gcg aag acg gag aac tcc gtg gtc atc gac gcg ccc atg gac       48
Met Pro Ala Lys Thr Glu Asn Ser Val Val Ile Asp Ala Pro Met Asp
1               5                   10                  15 ctg gtg tgg cgg atg acc aac gac gtc gcc tcg tgg ccg tcg ctc ttc       96
Leu Val Trp Arg Met Thr Asn Asp Val Ala Ser Trp Pro Ser Leu Phe
                20                  25                  30 gac gag tac gcg gag gcc gag atc ctc gac acc tcg ccc gac ggg acc      144
Asp Glu Tyr Ala Glu Ala Glu Ile Leu Asp Thr Ser Pro Asp Gly Thr
            35                  40                  45 gtc cgc ttc cgg ctg acg atg ttc ccc gac gag gac ggc aag gtc tgg      192
Val Arg Phe Arg Leu Thr Met Phe Pro Asp Glu Asp Gly Lys Val Trp
        50                  55                  60 agc tgg gtc tcg cag cgc agg gcc gac gcc gcc acc cgg agc gtg cgc      240
Ser Trp Val Ser Gln Arg Arg Ala Asp Ala Ala Thr Arg Ser Val Arg
65                  70                  75                  80 gcg cac cgc ctg gag ccg gga ccg ttc gag ttc atg aac atc tcc tgg      288
Ala His Arg Leu Glu Pro Gly Pro Phe Glu Phe Met Asn Ile Ser Trp
                85                  90                  95 gac tac cgc gag acc ggc ggc ggc gtg gag atg cgc tgg gtc cag gag      336
Asp Tyr Arg Glu Thr Gly Gly Gly Val Glu Met Arg Trp Val Gln Glu
            100                 105                 110 ttc cgc gta cgg ccc ggg ctg ccc ttc gac gac gag gcg atg acc gcc      384
Phe Arg Val Arg Pro Gly Leu Pro Phe Asp Asp Glu Ala Met Thr Ala
        115                 120                 125 cac ctg aac acc aac acc aag gtc cag atg gcc cgg atc aag aag ctc      432
His Leu Asn Thr Asn Thr Lys Val Gln Met Ala Arg Ile Lys Lys Leu
    130                 135                 140 gtg gag cag gcg gcc ggc cgg tcg gac ggc ccg gac cga tga              474
Val Glu Gln Ala Ala Gly Arg Ser Asp Gly Pro Asp Arg
145                 150                 155

<210> SEQ ID NO 39
<211> LENGTH: 157
<212> TYPE: PRT
<213> ORGANISM: Streptomyces sp. TA-0256

<400> SEQUENCE: 39

Met Pro Ala Lys Thr Glu Asn Ser Val Val Ile Asp Ala Pro Met Asp
1               5                   10                  15
```

```
Leu Val Trp Arg Met Thr Asn Asp Val Ala Ser Trp Pro Ser Leu Phe
            20                  25                  30

Asp Glu Tyr Ala Glu Ala Glu Ile Leu Asp Thr Ser Pro Asp Gly Thr
            35                  40                  45

Val Arg Phe Arg Leu Thr Met Phe Pro Asp Glu Asp Gly Lys Val Trp
    50                  55                  60

Ser Trp Val Ser Gln Arg Ala Asp Ala Ala Thr Arg Ser Val Arg
65                  70                  75                  80

Ala His Arg Leu Glu Pro Gly Pro Phe Glu Phe Met Asn Ile Ser Trp
            85                  90                  95

Asp Tyr Arg Glu Thr Gly Gly Gly Val Glu Met Arg Trp Val Gln Glu
            100                 105                 110

Phe Arg Val Arg Pro Gly Leu Pro Phe Asp Asp Glu Ala Met Thr Ala
            115                 120                 125

His Leu Asn Thr Asn Thr Lys Val Gln Met Ala Arg Ile Lys Lys Leu
            130                 135                 140

Val Glu Gln Ala Ala Gly Arg Ser Asp Gly Pro Asp Arg
145                 150                 155

<210> SEQ ID NO 40
<211> LENGTH: 468
<212> TYPE: DNA
<213> ORGANISM: Streptomyces tendae
<220> FEATURE:
<221> NAME/KEY: CDS
<222> LOCATION: (1)..(468)
<223> OTHER INFORMATION: llpCI (type: SRPBCC) gene [GenBank ID number
      AM492533.1 position 8866 to 9333] encoding a first 'small molecule
      foldase' [GenBank ID number CAM34342.1]

<400> SEQUENCE: 40 atg tca gga cac acc gac aac tcg acc gtc atc gac gca ccg ctg gac      48
Met Ser Gly His Thr Asp Asn Ser Thr Val Ile Asp Ala Pro Leu Asp
1               5                   10                  15 ctg gtc tgg gac atg acc aac gac gtg gcc tcg tgg ccg gac ctg ttc      96
Leu Val Trp Asp Met Thr Asn Asp Val Ala Ser Trp Pro Asp Leu Phe
            20                  25                  30 agc gag tac gcc gag gcc acc gtc ctg gag cgg gac ggc aac cgg atc     144
Ser Glu Tyr Ala Glu Ala Thr Val Leu Glu Arg Asp Gly Asn Arg Ile
            35                  40                  45 gtc ttc cgc ctg gcg atg cac ccg gac gcg ggc ggc acc gtg tgg agc     192
Val Phe Arg Leu Ala Met His Pro Asp Ala Gly Gly Thr Val Trp Ser
    50                  55                  60 tgg gtg tcc gaa cgc atc ctc gac ccg gtg gcc cgc acc gtc cac gcc     240
Trp Val Ser Glu Arg Ile Leu Asp Pro Val Ala Arg Thr Val His Ala
65                  70                  75                  80 cgc cgg gtg gag acg ggc aac ttc aag tac atg tgg ctg ttc tgg gag     288
Arg Arg Val Glu Thr Gly Asn Phe Lys Tyr Met Trp Leu Phe Trp Glu
            85                  90                  95 tac acc acc gag gac gac ggc gta cgg ctg cgc tgg gtg cag gac ttc     336
Tyr Thr Thr Glu Asp Asp Gly Val Arg Leu Arg Trp Val Gln Asp Phe
            100                 105                 110 gaa ctc aag ccc ggc ctg ccc atg gac gat gcc gcg atg acc gac cgg     384
Glu Leu Lys Pro Gly Leu Pro Met Asp Asp Ala Ala Met Thr Asp Arg
            115                 120                 125 ctc aac gcc aac tcg gtc gcc cag ctc gaa ctg atc aag gag aag atc     432
Leu Asn Ala Asn Ser Val Ala Gln Leu Glu Leu Ile Lys Glu Lys Ile
            130                 135                 140 gag gcc gtg gcc cgc gcg acc gcc gcc aca cgc tga                     468
Glu Ala Val Ala Arg Ala Thr Ala Ala Thr Arg
145                 150
```

<210> SEQ ID NO 41
<211> LENGTH: 155
<212> TYPE: PRT
<213> ORGANISM: Streptomyces tendae

<400> SEQUENCE: 41

```
Met Ser Gly His Thr Asp Asn Ser Thr Val Ile Asp Ala Pro Leu Asp
1               5                   10                  15

Leu Val Trp Asp Met Thr Asn Asp Val Ala Ser Trp Pro Asp Leu Phe
                20                  25                  30

Ser Glu Tyr Ala Glu Ala Thr Val Leu Glu Arg Asp Gly Asn Arg Ile
            35                  40                  45

Val Phe Arg Leu Ala Met His Pro Asp Ala Gly Gly Thr Val Trp Ser
        50                  55                  60

Trp Val Ser Glu Arg Ile Leu Asp Pro Val Ala Arg Thr Val His Ala
65                  70                  75                  80

Arg Arg Val Glu Thr Gly Asn Phe Lys Tyr Met Trp Leu Phe Trp Glu
                85                  90                  95

Tyr Thr Thr Glu Asp Asp Gly Val Arg Leu Arg Trp Val Gln Asp Phe
            100                 105                 110

Glu Leu Lys Pro Gly Leu Pro Met Asp Asp Ala Ala Met Thr Asp Arg
        115                 120                 125

Leu Asn Ala Asn Ser Val Ala Gln Leu Glu Leu Ile Lys Glu Lys Ile
    130                 135                 140

Glu Ala Val Ala Arg Ala Thr Ala Thr Arg
145                 150                 155
```

<210> SEQ ID NO 42
<211> LENGTH: 974
<212> TYPE: DNA
<213> ORGANISM: Streptomyces violaceoruber
<220> FEATURE:
<221> NAME/KEY: CDS
<222> LOCATION: (1)..(972)
<223> OTHER INFORMATION: gra-orf4 (type: 2xSRPBCC) gene [GenBank ID
      number AJ011500.1 position 32006 to 32980] encoding a first small
      molecule foldase [GenBank ID number CAA09656]

<400> SEQUENCE: 42

```
atg gtc cag ccc gcc gcc acc ccc gtc tcc ctg ccc agc ccc acc gtc      48
Met Val Gln Pro Ala Ala Thr Pro Val Ser Leu Pro Ser Pro Thr Val
1               5                   10                  15 cac cgc agc gag cac acc gtg acg gtg gcc gca ccg ccc gag gcg ctc      96
His Arg Ser Glu His Thr Val Thr Val Ala Ala Pro Pro Glu Ala Leu
                20                  25                  30 tac gcg ctc gtc gcc gac gtg acg cgg tgg ccg gcc gtg ttc gag ccg     144
Tyr Ala Leu Val Ala Asp Val Thr Arg Trp Pro Ala Val Phe Glu Pro
            35                  40                  45 acg gtg cac gtg cgg cac ctc gcc cgg gag ggg cgg acc gaa cgg ttc     192
Thr Val His Val Arg His Leu Ala Arg Glu Gly Arg Thr Glu Arg Phe
        50                  55                  60 gag atc tgg gcc gag gtg aac ggc gag atc gcg cac tgg cgt tcg cgc     240
Glu Ile Trp Ala Glu Val Asn Gly Glu Ile Ala His Trp Arg Ser Arg
65                  70                  75                  80 cgc gtt ctc gac ccg gtg cgg cgg tac gtg tcg ttc cgt cag gag cac     288
Arg Val Leu Asp Pro Val Arg Arg Tyr Val Ser Phe Arg Gln Glu His
                85                  90                  95 agc cgg ccg ccg gtg acc tcg atg tcc gga ggg tgg ctg ttc cgc ccg     336
```

-continued

```
                Ser Arg Pro Pro Val Thr Ser Met Ser Gly Gly Trp Leu Phe Arg Pro
                                100                 105                 110 ctg gcc gac ggc cgg acg gag atc gtg ctg cgg cac cgg ttc acc gtc        384
Leu Ala Asp Gly Arg Thr Glu Ile Val Leu Arg His Arg Phe Thr Val
            115                 120                 125 gcc gac gac gac ccg gcc gcc gtg gcc cgt atc gag gag gcc ctc gac        432
Ala Asp Asp Asp Pro Ala Ala Val Ala Arg Ile Glu Glu Ala Leu Asp
130                 135                 140 cgc aac agc gcc cga gaa ctg ggc gcg ctc gcg gcg ctc gcc gag acc        480
Arg Asn Ser Ala Arg Glu Leu Gly Ala Leu Ala Ala Leu Ala Glu Thr
145                 150                 155                 160 ggg cac ccg gtg gac gaa ctg gtc ttc tcc ttc acg gac acc ctc ccg        528
Gly His Pro Val Asp Glu Leu Val Phe Ser Phe Thr Asp Thr Leu Pro
                165                 170                 175 ctc cag ggc gcc gcc cgg gac gcg tac acc ttc gtc gag cgt gcc gag        576
Leu Gln Gly Ala Ala Arg Asp Ala Tyr Thr Phe Val Glu Arg Ala Glu
            180                 185                 190 cgc tgg gcc gag ctg ctg ccg cac gtc gcc caa tgt ggt gct gac cga        624
Arg Trp Ala Glu Leu Leu Pro His Val Ala Gln Cys Gly Ala Asp Arg
        195                 200                 205 gcc gga acc ggg ctc gag cag tgg ctg gag atg gac acc gtg acg gcc        672
Ala Gly Thr Gly Leu Glu Gln Trp Leu Glu Met Asp Thr Val Thr Ala
210                 215                 220 gac ggg tcc acc cac acc acc agg tcg gcg cgc atc tgc cgg gcg ccc        720
Asp Gly Ser Thr His Thr Thr Arg Ser Ala Arg Ile Cys Arg Ala Pro
225                 230                 235                 240 gag tgg atc gcg tac aac gag cag cgc acc ccc cgg ctc gtg tcc ggc        768
Glu Trp Ile Ala Tyr Asn Glu Gln Arg Thr Pro Arg Leu Val Ser Gly
                245                 250                 255 cac agc ggc gag tgg acg ttc gcc cag acc ccc gag ggt ccc gtg gcg        816
His Ser Gly Glu Trp Thr Phe Ala Gln Thr Pro Glu Gly Pro Val Ala
            260                 265                 270 acc gcc cgc cac acc gtc gcc gtc gac ccg agc ggc atc acc gag gtc        864
Thr Ala Arg His Thr Val Ala Val Asp Pro Ser Gly Ile Thr Glu Val
        275                 280                 285 ctc ggc ccg gac gcc acc ctc gcc gac gcc cgg gcc tac ctc cgc gac        912
Leu Gly Pro Asp Ala Thr Leu Ala Asp Ala Arg Ala Tyr Leu Arg Asp
    290                 295                 300 gcc ctg ggc cgc aac agc ctg gcc acg ctg cgg cac gcc gcc gaa gcg        960
Ala Leu Gly Arg Asn Ser Leu Ala Thr Leu Arg His Ala Ala Glu Ala
305                 310                 315                 320 gcc cag cgg gcg ta                                                      974
Ala Gln Arg Ala
```

<210> SEQ ID NO 43
<211> LENGTH: 324
<212> TYPE: PRT
<213> ORGANISM: Streptomyces violaceoruber

<400> SEQUENCE: 43

```
Met Val Gln Pro Ala Ala Thr Pro Val Ser Leu Pro Ser Pro Thr Val
1               5                   10                  15

His Arg Ser Glu His Thr Val Thr Val Ala Ala Pro Glu Ala Leu
            20                  25                  30

Tyr Ala Leu Val Ala Asp Val Thr Arg Trp Pro Ala Val Phe Glu Pro
        35                  40                  45

Thr Val His Val Arg His Leu Ala Arg Glu Gly Arg Thr Glu Arg Phe
    50                  55                  60

Glu Ile Trp Ala Glu Val Asn Gly Glu Ile Ala His Trp Arg Ser Arg
```

```
                65                  70                  75                  80
Arg Val Leu Asp Pro Val Arg Arg Tyr Val Ser Phe Arg Gln Glu His
                85                  90                  95

Ser Arg Pro Pro Val Thr Ser Met Ser Gly Gly Trp Leu Phe Arg Pro
               100                 105                 110

Leu Ala Asp Gly Arg Thr Glu Ile Val Leu Arg His Arg Phe Thr Val
               115                 120                 125

Ala Asp Asp Pro Ala Ala Val Ala Arg Ile Glu Glu Ala Leu Asp
               130                 135                 140

Arg Asn Ser Ala Arg Glu Leu Gly Ala Leu Ala Leu Ala Glu Thr
145                 150                 155                 160

Gly His Pro Val Asp Glu Leu Val Phe Ser Phe Thr Asp Thr Leu Pro
                    165                 170                 175

Leu Gln Gly Ala Ala Arg Asp Ala Tyr Thr Phe Val Glu Arg Ala Glu
                180                 185                 190

Arg Trp Ala Glu Leu Leu Pro His Val Ala Gln Cys Gly Ala Asp Arg
                195                 200                 205

Ala Gly Thr Gly Leu Glu Gln Trp Leu Glu Met Asp Thr Val Thr Ala
                210                 215                 220

Asp Gly Ser Thr His Thr Thr Arg Ser Ala Arg Ile Cys Arg Ala Pro
225                 230                 235                 240

Glu Trp Ile Ala Tyr Asn Glu Gln Arg Thr Pro Arg Leu Val Ser Gly
                245                 250                 255

His Ser Gly Glu Trp Thr Phe Ala Gln Thr Pro Glu Gly Pro Val Ala
                260                 265                 270

Thr Ala Arg His Thr Val Ala Val Asp Pro Ser Gly Ile Thr Glu Val
                275                 280                 285

Leu Gly Pro Asp Ala Thr Leu Ala Asp Ala Arg Ala Tyr Leu Arg Asp
                290                 295                 300

Ala Leu Gly Arg Asn Ser Leu Ala Thr Leu Arg His Ala Ala Glu Ala
305                 310                 315                 320

Ala Gln Arg Ala

<210> SEQ ID NO 44
<211> LENGTH: 954
<212> TYPE: DNA
<213> ORGANISM: Streptomyces fulvissimus
<220> FEATURE:
<221> NAME/KEY: CDS
<222> LOCATION: (1)..(954)
<223> OTHER INFORMATION: schP4/SFUL_4006 (type: 2xSRPBCC) gene [GenBank
      ID number CP005080.1 Position 4477979 to 4478932]) encoding a
      first small molecule foldase [GenBank ID number AGK78908.1]

<400> SEQUENCE: 44 atg aag agc atg acc gac tcc cga ccg cgc gag gtg gag cac gag atc        48
Met Lys Ser Met Thr Asp Ser Arg Pro Arg Glu Val Glu His Glu Ile
1               5                   10                  15 acg gtc tcc gcc ccg gcc gca gag gtg tac cgg ctg atc gcc gag gtc        96
Thr Val Ser Ala Pro Ala Ala Glu Val Tyr Arg Leu Ile Ala Glu Val
                20                  25                  30 gag aac tgg ccg cgg atc ttc ccg ccg acc atc tac gtc gac cac atc       144
Glu Asn Trp Pro Arg Ile Phe Pro Pro Thr Ile Tyr Val Asp His Ile
            35                  40                  45 gag cgc tcc gag ggc gag gag ctc atc cgg atc tgg gcc acg gcc aac       192
Glu Arg Ser Glu Gly Glu Glu Leu Ile Arg Ile Trp Ala Thr Ala Asn
        50                  55                  60
```

```
ggc gag gcc aag aac tgg act tcg cgc cgc ttc ctg gac cgg gag gcg    240
Gly Glu Ala Lys Asn Trp Thr Ser Arg Arg Phe Leu Asp Arg Glu Ala
65                  70                  75                  80 atg cgc atc acc ttc cgc cag cag gtc tcg acc ccg ccc gtc gcc acg    288
Met Arg Ile Thr Phe Arg Gln Gln Val Ser Thr Pro Pro Val Ala Thr
                85                  90                  95 atg ggc ggc acc tgg atc atc gag cca ctc tcc gcc acc gag tcg cgg    336
Met Gly Gly Thr Trp Ile Ile Glu Pro Leu Ser Ala Thr Glu Ser Arg
            100                 105                 110 atc cgg ctc cag cac gac tac acc gcc gtg gac gac gac ccg gcc ggg    384
Ile Arg Leu Gln His Asp Tyr Thr Ala Val Asp Asp Asp Pro Ala Gly
        115                 120                 125 ctc gcc tgg atc gag gag gcc gtc gac cgc aac tcg cgc tcc gag ctg    432
Leu Ala Trp Ile Glu Glu Ala Val Asp Arg Asn Ser Arg Ser Glu Leu
    130                 135                 140 gcc gcc ctg aag acc aac gtc gaa ctg gcc acg gcc tcg gag gag ttg    480
Ala Ala Leu Lys Thr Asn Val Glu Leu Ala Thr Ala Ser Glu Glu Leu
145                 150                 155                 160 acc ttc gcc ttc gag gac acc gtc gag atc gcc ggc tcc gcc aag gac    528
Thr Phe Ala Phe Glu Asp Thr Val Glu Ile Ala Gly Ser Ala Lys Asp
                165                 170                 175 gcc tac gac ttc atc aac gag gcc ggg ctc tgg tcg gag cgg ctg ccg    576
Ala Tyr Asp Phe Ile Asn Glu Ala Gly Leu Trp Ser Glu Arg Leu Pro
            180                 185                 190 cac gtg gcc gtc gtc cgg ctc acc gag gac agc ccc ggg ctc cag acc    624
His Val Ala Val Val Arg Leu Thr Glu Asp Ser Pro Gly Leu Gln Thr
        195                 200                 205 ctg gag atg gac acc cgc gcc aag gac ggc tcc gtg cac acg acg aag    672
Leu Glu Met Asp Thr Arg Ala Lys Asp Gly Ser Val His Thr Thr Lys
    210                 215                 220 tcg tac cgg gtc tgc ctg aac ggc gag aag atc gcg tac aaa cag acc    720
Ser Tyr Arg Val Cys Leu Asn Gly Glu Lys Ile Ala Tyr Lys Gln Thr
225                 230                 235                 240 acc ctg ccc gcc ctg atg aac ctg cac acc ggt gtc tgg acc ttc cgg    768
Thr Leu Pro Ala Leu Met Asn Leu His Thr Gly Val Trp Thr Phe Arg
                245                 250                 255 gag acc ggt gcc ggg gtc gcc gcc acc tcc cag cac acc gtg gtc atc    816
Glu Thr Gly Ala Gly Val Ala Ala Thr Ser Gln His Thr Val Val Ile
            260                 265                 270 cgg gcc gag aac atc gag aag atc ctc ggt cct gag gcg gac gtc gcg    864
Arg Ala Glu Asn Ile Glu Lys Ile Leu Gly Pro Glu Ala Asp Val Ala
        275                 280                 285 cag gcg cgg gag tac gtg aag gcg gcg ctc agc acc aac agc cgc gcc    912
Gln Ala Arg Glu Tyr Val Lys Ala Ala Leu Ser Thr Asn Ser Arg Ala
    290                 295                 300 acc ctc ggc cac gcc aag gac tac gcc gaa gcg cgg cgc tga            954
Thr Leu Gly His Ala Lys Asp Tyr Ala Glu Ala Arg Arg
305                 310                 315

<210> SEQ ID NO 45
<211> LENGTH: 317
<212> TYPE: PRT
<213> ORGANISM: Streptomyces fulvissimus

<400> SEQUENCE: 45

Met Lys Ser Met Thr Asp Ser Arg Pro Arg Glu Val Glu His Glu Ile
1               5                   10                  15

Thr Val Ser Ala Pro Ala Ala Glu Val Tyr Arg Leu Ile Ala Glu Val
            20                  25                  30

Glu Asn Trp Pro Arg Ile Phe Pro Pro Thr Ile Tyr Val Asp His Ile
```

```
                    35                  40                  45
Glu Arg Ser Glu Gly Glu Leu Ile Arg Ile Trp Ala Thr Ala Asn
         50                  55                  60

Gly Glu Ala Lys Asn Trp Thr Ser Arg Arg Phe Leu Asp Arg Glu Ala
 65                  70                  75                  80

Met Arg Ile Thr Phe Arg Gln Gln Val Ser Thr Pro Pro Val Ala Thr
                 85                  90                  95

Met Gly Gly Thr Trp Ile Ile Glu Pro Leu Ser Ala Thr Glu Ser Arg
            100                 105                 110

Ile Arg Leu Gln His Asp Tyr Thr Ala Val Asp Asp Pro Ala Gly
            115                 120                 125

Leu Ala Trp Ile Glu Glu Ala Val Asp Arg Asn Ser Arg Ser Glu Leu
        130                 135                 140

Ala Ala Leu Lys Thr Asn Val Glu Leu Ala Thr Ala Ser Glu Glu Leu
145                 150                 155                 160

Thr Phe Ala Phe Glu Asp Thr Val Glu Ile Ala Gly Ser Ala Lys Asp
                165                 170                 175

Ala Tyr Asp Phe Ile Asn Glu Ala Gly Leu Trp Ser Glu Arg Leu Pro
            180                 185                 190

His Val Ala Val Val Arg Leu Thr Glu Asp Ser Pro Gly Leu Gln Thr
            195                 200                 205

Leu Glu Met Asp Thr Arg Ala Lys Asp Gly Ser Val His Thr Thr Lys
        210                 215                 220

Ser Tyr Arg Val Cys Leu Asn Gly Glu Lys Ile Ala Tyr Lys Gln Thr
225                 230                 235                 240

Thr Leu Pro Ala Leu Met Asn Leu His Thr Gly Val Trp Thr Phe Arg
                245                 250                 255

Glu Thr Gly Ala Gly Val Ala Ala Thr Ser Gln His Thr Val Val Ile
            260                 265                 270

Arg Ala Glu Asn Ile Glu Lys Ile Leu Gly Pro Glu Ala Asp Val Ala
        275                 280                 285

Gln Ala Arg Glu Tyr Val Lys Ala Ala Leu Ser Thr Asn Ser Arg Ala
    290                 295                 300

Thr Leu Gly His Ala Lys Asp Tyr Ala Glu Ala Arg Arg
305                 310                 315

<210> SEQ ID NO 46
<211> LENGTH: 951
<212> TYPE: DNA
<213> ORGANISM: soil bacterium V167
<220> FEATURE:
<221> NAME/KEY: CDS
<222> LOCATION: (1)..(951)
<223> OTHER INFORMATION: Erd4 (bifunc) (type: 2xSRPBCC) gene [GenBank
      ID number FJ719113.1 Position 3913 to 4863) encoding a first small
      molecule foldase [GenBank ID number ACX83620.1]

<400> SEQUENCE: 46 atg acc acg atc cac cgc acc gag cac acc ctg gtc gtc gac gcc ccg      48
Met Thr Thr Ile His Arg Thr Glu His Thr Leu Val Val Asp Ala Pro
 1               5                  10                  15 ccg cgc acc ctc tac gac ctg gtc gcc gac acc acc cgc tgg ccg gcg      96
Pro Arg Thr Leu Tyr Asp Leu Val Ala Asp Thr Thr Arg Trp Pro Ala
                 20                  25                  30 atc ttc ggc ccc agc gtc cac gtc cac cac ctg gag cac ggt gag cgc     144
Ile Phe Gly Pro Ser Val His Val His His Leu Glu His Gly Glu Arg
             35                  40                  45
```

```
gac gag cgc ttc gag atc tgg gcg cag gtc aac ggc gag gtg gtc agc    192
Asp Glu Arg Phe Glu Ile Trp Ala Gln Val Asn Gly Glu Val Val Ser
     50                  55                  60 tgg gtc tcc cgc cgc gtc ctg gac ccc gaa cgg ctc tac atc gcc ttc    240
Trp Val Ser Arg Arg Val Leu Asp Pro Glu Arg Leu Tyr Ile Ala Phe
 65                  70                  75                  80 cgg cag gag cgc agc gca cct ccg ttc gcc tcc atg agc ggc ggc tgg    288
Arg Gln Glu Arg Ser Ala Pro Pro Phe Ala Ser Met Ser Gly Gly Trp
                 85                  90                  95 ctc ttc cgc gcc ctg ccc gga ggc cgc acc gag gtg gtg ctg cgg cac    336
Leu Phe Arg Ala Leu Pro Gly Gly Arg Thr Glu Val Val Leu Arg His
            100                 105                 110 cgg ttc gcc gcg ctc gac gag gac ccg gcg acc ctg gag cgg atc cac    384
Arg Phe Ala Ala Leu Asp Glu Asp Pro Ala Thr Leu Glu Arg Ile His
            115                 120                 125 cgg gcg ctc gac cgc aac agc ccc cag gag ctc gcc gcg ctc gcc cgg    432
Arg Ala Leu Asp Arg Asn Ser Pro Gln Glu Leu Ala Ala Leu Ala Arg
        130                 135                 140 atc gcc caa ctc ggc acc gat gtc gag gag gtg gtg ttc tcc ttc acc    480
Ile Ala Gln Leu Gly Thr Asp Val Glu Glu Val Val Phe Ser Phe Thr
145                 150                 155                 160 gac acc gtg ccg ctg acc ggc acg gcg gcc gcg tac gcc ttc gtc        528
Asp Thr Val Pro Leu Thr Gly Thr Ala Ala Ala Tyr Ala Phe Val
                165                 170                 175 gac cgc gcc gac ctg tgg gcg gag cgt ctc ccg cac gtc tcc cgc gcc    576
Asp Arg Ala Asp Leu Trp Ala Glu Arg Leu Pro His Val Ser Arg Ala
            180                 185                 190 cgt ctc acc gag gac gtc ccg ggc atc cag acc ctg gag atg gac acc    624
Arg Leu Thr Glu Asp Val Pro Gly Ile Gln Thr Leu Glu Met Asp Thr
            195                 200                 205 gtc acc gcc gac ggc agc gcg cac cgc acc cgg tcg gtg cgc gtc tgc    672
Val Thr Ala Asp Gly Ser Ala His Arg Thr Arg Ser Val Arg Val Cys
        210                 215                 220 cgg gag ccg agc tgg atc gcg tac aag cag ctg gag atg ccg cgg ctg    720
Arg Glu Pro Ser Trp Ile Ala Tyr Lys Gln Leu Glu Met Pro Arg Leu
225                 230                 235                 240 ctg agc ggg cac agc ggg ctg tgg acc ttc acg gac ggg ccg gac ggc    768
Leu Ser Gly His Ser Gly Leu Trp Thr Phe Thr Asp Gly Pro Asp Gly
                245                 250                 255 ccg gtc gcc gtc tcc cgg cac acg gtg gcg atc gac ccg tcg gcc gtc    816
Pro Val Ala Val Ser Arg His Thr Val Ala Ile Asp Pro Ser Ala Val
            260                 265                 270 gag gag gtg ctc ggc gcg ggg gcc acg ctc gcc gac gcg cgc cgg tat    864
Glu Glu Val Leu Gly Ala Gly Ala Thr Leu Ala Asp Ala Arg Arg Tyr
        275                 280                 285 ctc cgc gag gcg ctg ggc cgc aac agc ctg acc acg atg acg cac gcg    912
Leu Arg Glu Ala Leu Gly Arg Asn Ser Leu Thr Thr Met Thr His Ala
        290                 295                 300 gcg gcc tac gcg cag gag cac ggc agc gcg gtg cgc tga                951
Ala Ala Tyr Ala Gln Glu His Gly Ser Ala Val Arg
305                 310                 315

<210> SEQ ID NO 47
<211> LENGTH: 316
<212> TYPE: PRT
<213> ORGANISM: soil bacterium V167

<400> SEQUENCE: 47

Met Thr Thr Ile His Arg Thr Glu His Thr Leu Val Val Asp Ala Pro
 1               5                  10                  15
```

Pro Arg Thr Leu Tyr Asp Leu Val Ala Asp Thr Thr Arg Trp Pro Ala
            20                  25                  30

Ile Phe Gly Pro Ser Val His Val His His Leu Glu His Gly Glu Arg
            35                  40                  45

Asp Glu Arg Phe Glu Ile Trp Ala Gln Val Asn Gly Glu Val Val Ser
    50                  55                  60

Trp Val Ser Arg Arg Val Leu Asp Pro Glu Arg Leu Tyr Ile Ala Phe
65                  70                  75                  80

Arg Gln Glu Arg Ser Ala Pro Pro Phe Ala Ser Met Ser Gly Gly Trp
                85                  90                  95

Leu Phe Arg Ala Leu Pro Gly Gly Arg Thr Glu Val Val Leu Arg His
            100                 105                 110

Arg Phe Ala Ala Leu Asp Glu Asp Pro Ala Thr Leu Glu Arg Ile His
            115                 120                 125

Arg Ala Leu Asp Arg Asn Ser Pro Gln Glu Leu Ala Ala Leu Ala Arg
            130                 135                 140

Ile Ala Gln Leu Gly Thr Asp Val Glu Glu Val Val Phe Ser Phe Thr
145                 150                 155                 160

Asp Thr Val Pro Leu Thr Gly Thr Ala Ala Ala Tyr Ala Phe Val
                165                 170                 175

Asp Arg Ala Asp Leu Trp Ala Glu Arg Leu Pro His Val Ser Arg Ala
            180                 185                 190

Arg Leu Thr Glu Asp Val Pro Gly Ile Gln Thr Leu Glu Met Asp Thr
            195                 200                 205

Val Thr Ala Asp Gly Ser Ala His Arg Thr Arg Ser Val Arg Val Cys
    210                 215                 220

Arg Glu Pro Ser Trp Ile Ala Tyr Lys Gln Leu Glu Met Pro Arg Leu
225                 230                 235                 240

Leu Ser Gly His Ser Gly Leu Trp Thr Phe Thr Asp Gly Pro Asp Gly
                245                 250                 255

Pro Val Ala Val Ser Arg His Thr Val Ala Ile Asp Pro Ser Ala Val
            260                 265                 270

Glu Glu Val Leu Gly Ala Gly Ala Thr Leu Ala Asp Ala Arg Arg Tyr
            275                 280                 285

Leu Arg Glu Ala Leu Gly Arg Asn Ser Leu Thr Thr Met Thr His Ala
    290                 295                 300

Ala Ala Tyr Ala Gln Glu His Gly Ser Ala Val Arg
305                 310                 315

<210> SEQ ID NO 48
<211> LENGTH: 957
<212> TYPE: DNA
<213> ORGANISM: Streptomyces sp. AM-7161
<220> FEATURE:
<221> NAME/KEY: CDS
<222> LOCATION: (1)..(957)
<223> OTHER INFORMATION: med-ORF19 (type: 2xSRPBCC) gene [GenBank ID
      number AB103463.1 Position 13942 to 14898) encoding a first small
      molecule foldase [GenBank ID number BAC79027]

<400> SEQUENCE: 48 atg acc cag ccc acc cca cgg gag acc gcc cac gag atc acc gtc cgc        48
Met Thr Gln Pro Thr Pro Arg Glu Thr Ala His Glu Ile Thr Val Arg
1               5                   10                  15 gcg acg gcc gag cgg ctc tac gaa ctg atc gcc gac gtc ggc ggc tgg        96
Ala Thr Ala Glu Arg Leu Tyr Glu Leu Ile Ala Asp Val Gly Gly Trp
            20                  25                  30

```
ccc tcg atc ttc ccg ccc tcg gtc cac gcc gac cac ctg gag cgc ggc    144
Pro Ser Ile Phe Pro Pro Ser Val His Ala Asp His Leu Glu Arg Gly
         35                  40                  45 gac aag gag gag cgc atc cgg ctc tgg gcc acc gtc gac ggg cag gtc    192
Asp Lys Glu Glu Arg Ile Arg Leu Trp Ala Thr Val Asp Gly Gln Val
 50                  55                  60 aag cac tgg acg tcc cgg cgc acc ctg gac cgc gca gga ctc cgc gtc    240
Lys His Trp Thr Ser Arg Arg Thr Leu Asp Arg Ala Gly Leu Arg Val
 65                  70                  75                  80 gac ttc cgg cag gag gtg ccg agt ccg ccg atg gcc gcg atg ggc ggt    288
Asp Phe Arg Gln Glu Val Pro Ser Pro Pro Met Ala Ala Met Gly Gly
                 85                  90                  95 gcc tgg atc atc gaa ccc acg gga ccg ggg gag tgc cgc gta cgg ctg    336
Ala Trp Ile Ile Glu Pro Thr Gly Pro Gly Glu Cys Arg Val Arg Leu
            100                 105                 110 ctg cac gac ttc cgg gcc gtc ggc gac gac ccc ggg acc ctc gac tgg    384
Leu His Asp Phe Arg Ala Val Gly Asp Asp Pro Gly Thr Leu Asp Trp
        115                 120                 125 atc gac cgc gcc gtg gac gcc aac agc cgg tcg gag ctc gcc gcc ctc    432
Ile Asp Arg Ala Val Asp Ala Asn Ser Arg Ser Glu Leu Ala Ala Leu
130                 135                 140 aag cgc cac gcc gaa cgc ggc gcc gac ggc ccg ggc gag ggc gac acc    480
Lys Arg His Ala Glu Arg Gly Ala Asp Gly Pro Gly Glu Gly Asp Thr
145                 150                 155                 160 ttc ctc acc ttc gag gac acc gtc cgc ctc gaa ggc cac gtc aag gac    528
Phe Leu Thr Phe Glu Asp Thr Val Arg Leu Glu Gly His Val Lys Asp
                165                 170                 175 gtc tac gac ttc atc gac cag gcc cag cac tgg gcc gac cgc ctg ccc    576
Val Tyr Asp Phe Ile Asp Gln Ala Gln His Trp Ala Asp Arg Leu Pro
            180                 185                 190 cac gtc acg tcc gtg aac ctg cgg gac gcc ggc ccc ggc cgt cag atc    624
His Val Thr Ser Val Asn Leu Arg Asp Ala Gly Pro Gly Arg Gln Ile
        195                 200                 205 ctg gcc atg gac acg ctc acc aag gac ggc agc ccg cac acc acc gag    672
Leu Ala Met Asp Thr Leu Thr Lys Asp Gly Ser Pro His Thr Thr Glu
210                 215                 220 tcg gtg cgc gtc tgc gtc ccg tac gag cgg atc gtc tac aag cag acc    720
Ser Val Arg Val Cys Val Pro Tyr Glu Arg Ile Val Tyr Lys Gln Thr
225                 230                 235                 240 acc ctg ccc ccg ctg atg gcc ctg cac acc ggc gag tgg agc ttc gcg    768
Thr Leu Pro Pro Leu Met Ala Leu His Thr Gly Glu Trp Ser Phe Ala
                245                 250                 255 gag gac ggc gcc ggc gcc acc gtc gtc acc tcg cgc cac acc gcc gtg    816
Glu Asp Gly Ala Gly Ala Thr Val Val Thr Ser Arg His Thr Ala Val
            260                 265                 270 gtc gag ccc gcc gcc gtc acc cgg gtc ctc ggc gag acc gcc gac ctg    864
Val Glu Pro Ala Ala Val Thr Arg Val Leu Gly Glu Thr Ala Asp Leu
        275                 280                 285 ccg gcg gcg cgt cgc tac ctc cgc gag gcg ctg ggt gcg aac agc ctg    912
Pro Ala Ala Arg Arg Tyr Leu Arg Glu Ala Leu Gly Ala Asn Ser Leu
290                 295                 300 gcc acg ctg agg cac gcc gga gag tac gcc gcg gcc cgc cgc tga        957
Ala Thr Leu Arg His Ala Gly Glu Tyr Ala Ala Ala Arg Arg
305                 310                 315

<210> SEQ ID NO 49
<211> LENGTH: 318
<212> TYPE: PRT
<213> ORGANISM: Streptomyces sp. AM-7161

<400> SEQUENCE: 49
```

Met Thr Gln Pro Thr Pro Arg Glu Thr Ala His Glu Ile Thr Val Arg
1               5                   10                  15

Ala Thr Ala Glu Arg Leu Tyr Glu Leu Ile Ala Asp Val Gly Gly Trp
            20                  25                  30

Pro Ser Ile Phe Pro Pro Ser Val His Ala Asp His Leu Glu Arg Gly
            35                  40                  45

Asp Lys Glu Glu Arg Ile Arg Leu Trp Ala Thr Val Asp Gly Gln Val
        50                  55                  60

Lys His Trp Thr Ser Arg Arg Thr Leu Asp Arg Ala Gly Leu Arg Val
65                  70                  75                  80

Asp Phe Arg Gln Glu Val Pro Ser Pro Met Ala Ala Met Gly Gly
                85                  90                  95

Ala Trp Ile Ile Glu Pro Thr Gly Pro Gly Glu Cys Arg Val Arg Leu
            100                 105                 110

Leu His Asp Phe Arg Ala Val Gly Asp Asp Pro Gly Thr Leu Asp Trp
        115                 120                 125

Ile Asp Arg Ala Val Asp Ala Asn Ser Arg Ser Glu Leu Ala Ala Leu
    130                 135                 140

Lys Arg His Ala Glu Arg Gly Ala Asp Gly Pro Gly Glu Gly Asp Thr
145                 150                 155                 160

Phe Leu Thr Phe Glu Asp Thr Val Arg Leu Glu Gly His Val Lys Asp
                165                 170                 175

Val Tyr Asp Phe Ile Asp Gln Ala Gln His Trp Ala Asp Arg Leu Pro
            180                 185                 190

His Val Thr Ser Val Asn Leu Arg Asp Ala Gly Pro Gly Arg Gln Ile
        195                 200                 205

Leu Ala Met Asp Thr Leu Thr Lys Asp Gly Ser Pro His Thr Thr Glu
210                 215                 220

Ser Val Arg Val Cys Val Pro Tyr Glu Arg Ile Val Tyr Lys Gln Thr
225                 230                 235                 240

Thr Leu Pro Pro Leu Met Ala Leu His Thr Gly Glu Trp Ser Phe Ala
                245                 250                 255

Glu Asp Gly Ala Gly Ala Thr Val Val Thr Ser Arg His Thr Ala Val
            260                 265                 270

Val Glu Pro Ala Ala Val Thr Arg Val Leu Gly Glu Thr Ala Asp Leu
        275                 280                 285

Pro Ala Ala Arg Arg Tyr Leu Arg Glu Ala Leu Gly Ala Asn Ser Leu
    290                 295                 300

Ala Thr Leu Arg His Ala Gly Glu Tyr Ala Ala Ala Arg Arg
305                 310                 315

<210> SEQ ID NO 50
<211> LENGTH: 944
<212> TYPE: DNA
<213> ORGANISM: Streptomyces sp. SF2575
<220> FEATURE:
<221> NAME/KEY: CDS
<222> LOCATION: (1)..(942)
<223> OTHER INFORMATION: ssfY1 (type: 2xSRPBCC) gene [GenBank ID number
      GQ409537.1 Position 9830 to 10774) encoding a first small molecule
      foldase [GenBank ID number ADE34490.1]

<400> SEQUENCE: 50 atg tcc act ggg cag tcc cgg cac acc agc cac gag atc gag atc gat      48
Met Ser Thr Gly Gln Ser Arg His Thr Ser His Glu Ile Glu Ile Asp
1               5                   10                  15

| | | | | | | | | | | | | | | | | |
|---|---|---|---|---|---|---|---|---|---|---|---|---|---|---|---|---|
| gcc | ccc | gcc | gac | gtg | gtc | tac | cgg | gtg | atc | gcg | gac | gtc | acc | gcg | tgg | 96 |
| Ala | Pro | Ala | Asp | Val | Val | Tyr | Arg | Val | Ile | Ala | Asp | Val | Thr | Ala | Trp | |
| | | | 20 | | | | 25 | | | | | 30 | | | | |

| | | | | | | | | | | | | | | | | |
|---|---|---|---|---|---|---|---|---|---|---|---|---|---|---|---|---|
| ccc | ctg | cac | ttc | gcg | ccg | acg | atc | cgc | gtc | gag | cag | acg | caa | ctt | gac | 144 |
| Pro | Leu | His | Phe | Ala | Pro | Thr | Ile | Arg | Val | Glu | Gln | Thr | Gln | Leu | Asp | |
| | | 35 | | | | | 40 | | | | | 45 | | | | |

| | | | | | | | | | | | | | | | | |
|---|---|---|---|---|---|---|---|---|---|---|---|---|---|---|---|---|
| gac | tcc | gcc | gag | cgg | ctg | cgg | atc | tgg | gcc | acc | gcc | aac | ggc | gag | gtc | 192 |
| Asp | Ser | Ala | Glu | Arg | Leu | Arg | Ile | Trp | Ala | Thr | Ala | Asn | Gly | Glu | Val | |
| | 50 | | | | | 55 | | | | | 60 | | | | | |

| | | | | | | | | | | | | | | | | |
|---|---|---|---|---|---|---|---|---|---|---|---|---|---|---|---|---|
| aag | acc | tgg | acc | tcg | cgc | cgg | gtg | cac | gac | aag | gcc | gcc | cgc | cgg | gtg | 240 |
| Lys | Thr | Trp | Thr | Ser | Arg | Arg | Val | His | Asp | Lys | Ala | Ala | Arg | Arg | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gag | ttc | cgc | cag | gag | gtg | tcc | tcg | gcg | ccg | gtg | gcg | gcg | atg | gcc | ggc | 288 |
| Glu | Phe | Arg | Gln | Glu | Val | Ser | Ser | Ala | Pro | Val | Ala | Ala | Met | Ala | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| acc | tgg | atc | gcc | gag | gca | cgc | ccc | gag | ggc | ggc | acc | cgg | ctg | gtg | ctc | 336 |
| Thr | Trp | Ile | Ala | Glu | Ala | Arg | Pro | Glu | Gly | Gly | Thr | Arg | Leu | Val | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| acc | cac | gac | ttc | gcc | gcc | gtc | gac | gac | gac | ccg | gcg | ggc | ctg | gag | tgg | 384 |
| Thr | His | Asp | Phe | Ala | Ala | Val | Asp | Asp | Asp | Pro | Ala | Gly | Leu | Glu | Trp | |
| | | | 115 | | | | | 120 | | | | | 125 | | | |

| | | | | | | | | | | | | | | | | |
|---|---|---|---|---|---|---|---|---|---|---|---|---|---|---|---|---|
| atc | acc | cag | gcc | acc | gac | cgc | aac | agc | gcc | acc | gaa | ctg | ggc | aac | atc | 432 |
| Ile | Thr | Gln | Ala | Thr | Asp | Arg | Asn | Ser | Ala | Thr | Glu | Leu | Gly | Asn | Ile | |
| | 130 | | | | | 135 | | | | | 140 | | | | | |

| | | | | | | | | | | | | | | | | |
|---|---|---|---|---|---|---|---|---|---|---|---|---|---|---|---|---|
| aag | gcg | gtc | gcg | gag | cgc | tgg | gag | cgg | ctg | ggc | gaa | ctg | gtc | ttc | tcc | 480 |
| Lys | Ala | Val | Ala | Glu | Arg | Trp | Glu | Arg | Leu | Gly | Glu | Leu | Val | Phe | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ttc | gag | gac | tcg | gtc | gtc | atc | cag | ggc | tcc | gcc | aag | gag | gtc | tac | gac | 528 |
| Phe | Glu | Asp | Ser | Val | Val | Ile | Gln | Gly | Ser | Ala | Lys | Glu | Val | Tyr | Asp | |
| | | | | 165 | | | | | 170 | | | | | 175 | | |

| | | | | | | | | | | | | | | | | |
|---|---|---|---|---|---|---|---|---|---|---|---|---|---|---|---|---|
| ttc | ctc | tac | cag | gcg | tcc | gag | tgg | ccg | aag | cgg | ctg | ccg | cac | gtg | gcg | 576 |
| Phe | Leu | Tyr | Gln | Ala | Ser | Glu | Trp | Pro | Lys | Arg | Leu | Pro | His | Val | Ala | |
| | | | 180 | | | | | 185 | | | | | 190 | | | |

| | | | | | | | | | | | | | | | | |
|---|---|---|---|---|---|---|---|---|---|---|---|---|---|---|---|---|
| cgc | ctc | gac | ctc | ggc | gag | gac | gtg | ccc | ggc | ctg | cag | acg | atg | tcg | atg | 624 |
| Arg | Leu | Asp | Leu | Gly | Glu | Asp | Val | Pro | Gly | Leu | Gln | Thr | Met | Ser | Met | |
| | | 195 | | | | | 200 | | | | | 205 | | | | |

| | | | | | | | | | | | | | | | | |
|---|---|---|---|---|---|---|---|---|---|---|---|---|---|---|---|---|
| gac | acc | ctc | gcc | cag | gac | ggc | tcg | gtg | cac | acc | acg | gag | tcg | atc | agg | 672 |
| Asp | Thr | Leu | Ala | Gln | Asp | Gly | Ser | Val | His | Thr | Thr | Glu | Ser | Ile | Arg | |
| | 210 | | | | | 215 | | | | | 220 | | | | | |

| | | | | | | | | | | | | | | | | |
|---|---|---|---|---|---|---|---|---|---|---|---|---|---|---|---|---|
| atc | tgc | atg | ccc | gac | gag | ctg | aag | atc | gcc | tac | aag | cag | ctc | gtg | ccg | 720 |
| Ile | Cys | Met | Pro | Asp | Glu | Leu | Lys | Ile | Ala | Tyr | Lys | Gln | Leu | Val | Pro | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ccg | tcg | ctg | atg | acc | gcg | cac | atc | ggc | gag | tgg | acg | atc | acc | gac | acc | 768 |
| Pro | Ser | Leu | Met | Thr | Ala | His | Ile | Gly | Glu | Trp | Thr | Ile | Thr | Asp | Thr | |
| | | | | 245 | | | | | 250 | | | | | 255 | | |

| | | | | | | | | | | | | | | | | |
|---|---|---|---|---|---|---|---|---|---|---|---|---|---|---|---|---|
| gac | gag | ggc | gtg | ctc | gcg | gtc | tcc | cag | cac | acg | gtg | acc | gtc | aac | gag | 816 |
| Asp | Glu | Gly | Val | Leu | Ala | Val | Ser | Gln | His | Thr | Val | Thr | Val | Asn | Glu | |
| | | | 260 | | | | | 265 | | | | | 270 | | | |

| | | | | | | | | | | | | | | | | |
|---|---|---|---|---|---|---|---|---|---|---|---|---|---|---|---|---|
| gcg | aac | atc | acc | aag | gtg | ctg | ggc | gag | gcg | ggc | acg | gtg | gcc | tcc | gcc | 864 |
| Ala | Asn | Ile | Thr | Lys | Val | Leu | Gly | Glu | Ala | Gly | Thr | Val | Ala | Ser | Ala | |
| | | 275 | | | | | 280 | | | | | 285 | | | | |

| | | | | | | | | | | | | | | | | |
|---|---|---|---|---|---|---|---|---|---|---|---|---|---|---|---|---|
| cgg | gac | ttc | atc | cgc | cgc | gcc | gcc | ggc | ggc | aac | agc | ctg | tcc | acg | ctc | 912 |
| Arg | Asp | Phe | Ile | Arg | Arg | Ala | Ala | Gly | Gly | Asn | Ser | Leu | Ser | Thr | Leu | |
| | 290 | | | | | 295 | | | | | 300 | | | | | |

| | | | | | | | | | |
|---|---|---|---|---|---|---|---|---|---|
| aag | cac | gcc | aag | gcg | ttc | gtg | gag | gcc | ggc | tg | 944 |
| Lys | His | Ala | Lys | Ala | Phe | Val | Glu | Ala | Gly | | |
| 305 | | | | | 310 | | | | | | |

<210> SEQ ID NO 51
<211> LENGTH: 314

<212> TYPE: PRT
<213> ORGANISM: Streptomyces sp. SF2575

<400> SEQUENCE: 51

```
Met Ser Thr Gly Gln Ser Arg His Thr Ser His Glu Ile Glu Ile Asp
1               5                   10                  15

Ala Pro Ala Asp Val Val Tyr Arg Val Ile Ala Asp Val Thr Ala Trp
            20                  25                  30

Pro Leu His Phe Ala Pro Thr Ile Arg Val Glu Gln Thr Gln Leu Asp
        35                  40                  45

Asp Ser Ala Glu Arg Leu Arg Ile Trp Ala Thr Ala Asn Gly Glu Val
    50                  55                  60

Lys Thr Trp Thr Ser Arg Arg Val His Asp Lys Ala Ala Arg Arg Val
65                  70                  75                  80

Glu Phe Arg Gln Glu Val Ser Ser Ala Pro Val Ala Ala Met Ala Gly
                85                  90                  95

Thr Trp Ile Ala Glu Ala Arg Pro Glu Gly Gly Thr Arg Leu Val Leu
            100                 105                 110

Thr His Asp Phe Ala Ala Val Asp Asp Pro Ala Gly Leu Glu Trp
        115                 120                 125

Ile Thr Gln Ala Thr Asp Arg Asn Ser Ala Thr Glu Leu Gly Asn Ile
130                 135                 140

Lys Ala Val Ala Glu Arg Trp Glu Arg Leu Gly Glu Leu Val Phe Ser
145                 150                 155                 160

Phe Glu Asp Ser Val Val Ile Gln Gly Ser Ala Lys Glu Val Tyr Asp
                165                 170                 175

Phe Leu Tyr Gln Ala Ser Glu Trp Pro Lys Arg Leu Pro His Val Ala
            180                 185                 190

Arg Leu Asp Leu Gly Glu Asp Val Pro Gly Leu Gln Thr Met Ser Met
        195                 200                 205

Asp Thr Leu Ala Gln Asp Gly Ser Val His Thr Thr Glu Ser Ile Arg
    210                 215                 220

Ile Cys Met Pro Asp Glu Leu Lys Ile Ala Tyr Lys Gln Leu Val Pro
225                 230                 235                 240

Pro Ser Leu Met Thr Ala His Ile Gly Glu Trp Thr Ile Thr Asp Thr
                245                 250                 255

Asp Glu Gly Val Leu Ala Val Ser Gln His Thr Val Thr Val Asn Glu
            260                 265                 270

Ala Asn Ile Thr Lys Val Leu Gly Glu Ala Gly Thr Val Ala Ser Ala
        275                 280                 285

Arg Asp Phe Ile Arg Arg Ala Ala Gly Gly Asn Ser Leu Ser Thr Leu
    290                 295                 300

Lys His Ala Lys Ala Phe Val Glu Ala Gly
305                 310
```

<210> SEQ ID NO 52
<211> LENGTH: 953
<212> TYPE: DNA
<213> ORGANISM: Streptomyces rimosus
<220> FEATURE:
<221> NAME/KEY: CDS
<222> LOCATION: (1)..(951)
<223> OTHER INFORMATION: oxyK (type: 2xSRPBCC) gene [GenBank ID number DQ143963.2 Position 11443 to 12396) encoding a small molecule foldase [GenBank ID number AAZ78334.2]

<400> SEQUENCE: 52

-continued

```
atg ccc gca ccc aca tcc cac cgc gcc gtg cac cgc acg gag atc gac        48
Met Pro Ala Pro Thr Ser His Arg Ala Val His Arg Thr Glu Ile Asp
1               5                   10                  15 gcc ccg gcc gac cgg gtg tac gcc ctg atc agg gac gcc gcc gag tgg        96
Ala Pro Ala Asp Arg Val Tyr Ala Leu Ile Arg Asp Ala Ala Glu Trp
            20                  25                  30 ccc cgg cac ttc acc ccg acc gtc cac gtc gag cgc gcg gag ctc gac       144
Pro Arg His Phe Thr Pro Thr Val His Val Glu Arg Ala Glu Leu Asp
        35                  40                  45 gcc cgc agc gag cgg ctg cgg atc tgg gcc acc gcc aac ggc gag gtc       192
Ala Arg Ser Glu Arg Leu Arg Ile Trp Ala Thr Ala Asn Gly Glu Val
50                  55                  60 aag cac tgg acg tcg cac cgc gcc ctg gac ccc gaa ggg cag agc gtc       240
Lys His Trp Thr Ser His Arg Ala Leu Asp Pro Glu Gly Gln Ser Val
65                  70                  75                  80 cgg ttc cgg cag gag gtg tgt tcg cct ccg gtg gcc gcg atg agc ggt       288
Arg Phe Arg Gln Glu Val Cys Ser Pro Pro Val Ala Ala Met Ser Gly
                85                  90                  95 gaa tgg gtc ctc cgg gac ctt ccg ggg cgg tgc gag ctg acg ctg           336
Glu Trp Val Leu Arg Asp Leu Pro Gly Gly Arg Cys Glu Leu Thr Leu
            100                 105                 110 cac cac acg ttc gcc gcg gtg gac gac cgc ccg gag gac gtg gag tgg       384
His His Thr Phe Ala Ala Val Asp Asp Arg Pro Glu Asp Val Glu Trp
        115                 120                 125 atc acc acc gcg acc gac cgc aac agc cgt acc gag ctg gcg aac atc       432
Ile Thr Thr Ala Thr Asp Arg Asn Ser Arg Thr Glu Leu Ala Asn Ile
130                 135                 140 aag gcg ctg gcc gag gcc gcg ggg tcc gac gcg gag ctg ctg ttc tcg       480
Lys Ala Leu Ala Glu Ala Ala Gly Ser Asp Ala Glu Leu Leu Phe Ser
145                 150                 155                 160 ttc gag gac tcc gag acg gtg cac gcc ccg gcc gag gcg gtg tac gcg       528
Phe Glu Asp Ser Glu Thr Val His Ala Pro Ala Glu Ala Val Tyr Ala
                165                 170                 175 ttc ctc gcg gag gcc ggg aag tgg ccc gac cgg ctg ccg cac gtc tcc       576
Phe Leu Ala Glu Ala Gly Lys Trp Pro Asp Arg Leu Pro His Val Ser
            180                 185                 190 cgg ctc gac ctc acc gag ccg tcc gac ggc gtg cag gtg atg acc atg       624
Arg Leu Asp Leu Thr Glu Pro Ser Asp Gly Val Gln Val Met Thr Met
        195                 200                 205 gtc acc cgg gcc aac gac ggc tcg gag cac acg acg gag tcg gtg cgg       672
Val Thr Arg Ala Asn Asp Gly Ser Glu His Thr Thr Glu Ser Val Arg
210                 215                 220 gtc tgc ttc ccc gac gaa ctg cgc atc gtc tac aag cag atc ggc acc       720
Val Cys Phe Pro Asp Glu Leu Arg Ile Val Tyr Lys Gln Ile Gly Thr
225                 230                 235                 240 ccg ccg ctg atg acc ctg cac acc ggt gag tgg tcg ata cgg gac acc       768
Pro Pro Leu Met Thr Leu His Thr Gly Glu Trp Ser Ile Arg Asp Thr
                245                 250                 255 ggg gac ggg ctg ctc gtc acc tcc cag cac acc atc cgg atc aac gaa       816
Gly Asp Gly Leu Leu Val Thr Ser Gln His Thr Ile Arg Ile Asn Glu
            260                 265                 270 tcc gcc atc ccg gag atc ctc ggc gcg gac gcc acg gcg gcc gac gcg       864
Ser Ala Ile Pro Glu Ile Leu Gly Ala Asp Ala Thr Ala Ala Asp Ala
        275                 280                 285 cgg gcc cgg gtg cgc gcg gcg gtc ggc ggc aac agc gcg gcc acc ctg       912
Arg Ala Arg Val Arg Ala Ala Val Gly Gly Asn Ser Ala Ala Thr Leu
290                 295                 300 gcc ctc gcc aag cgc ttc gcg gag gcc ccg cat gcc gcc tg                953
Ala Leu Ala Lys Arg Phe Ala Glu Ala Pro His Ala Ala
305                 310                 315
```

<210> SEQ ID NO 53
<211> LENGTH: 317
<212> TYPE: PRT
<213> ORGANISM: Streptomyces rimosus

<400> SEQUENCE: 53

```
Met Pro Ala Pro Thr Ser His Arg Ala Val His Arg Thr Glu Ile Asp
1               5                   10                  15

Ala Pro Ala Asp Arg Val Tyr Ala Leu Ile Arg Asp Ala Ala Glu Trp
            20                  25                  30

Pro Arg His Phe Thr Pro Thr Val His Val Glu Arg Ala Glu Leu Asp
        35                  40                  45

Ala Arg Ser Glu Arg Leu Arg Ile Trp Ala Thr Ala Asn Gly Glu Val
    50                  55                  60

Lys His Trp Thr Ser His Arg Ala Leu Asp Pro Glu Gly Gln Ser Val
65                  70                  75                  80

Arg Phe Arg Gln Glu Val Cys Ser Pro Val Ala Ala Met Ser Gly
                85                  90                  95

Glu Trp Val Leu Arg Asp Leu Pro Gly Gly Arg Cys Glu Leu Thr Leu
            100                 105                 110

His His Thr Phe Ala Ala Val Asp Asp Arg Pro Glu Asp Val Glu Trp
        115                 120                 125

Ile Thr Thr Ala Thr Asp Arg Asn Ser Arg Thr Glu Leu Ala Asn Ile
    130                 135                 140

Lys Ala Leu Ala Glu Ala Ala Gly Ser Asp Ala Glu Leu Leu Phe Ser
145                 150                 155                 160

Phe Glu Asp Ser Glu Thr Val His Ala Pro Ala Glu Ala Val Tyr Ala
                165                 170                 175

Phe Leu Ala Glu Ala Gly Lys Trp Pro Asp Arg Leu Pro His Val Ser
            180                 185                 190

Arg Leu Asp Leu Thr Glu Pro Ser Asp Gly Val Gln Val Met Thr Met
        195                 200                 205

Val Thr Arg Ala Asn Asp Gly Ser Glu His Thr Thr Glu Ser Val Arg
    210                 215                 220

Val Cys Phe Pro Asp Glu Leu Arg Ile Val Tyr Lys Gln Ile Gly Thr
225                 230                 235                 240

Pro Pro Leu Met Thr Leu His Thr Gly Glu Trp Ser Ile Arg Asp Thr
                245                 250                 255

Gly Asp Gly Leu Leu Val Thr Ser Gln His Thr Ile Arg Ile Asn Glu
            260                 265                 270

Ser Ala Ile Pro Glu Ile Leu Gly Ala Asp Ala Thr Ala Ala Asp Ala
        275                 280                 285

Arg Ala Arg Val Arg Ala Ala Val Gly Gly Asn Ser Ala Ala Thr Leu
    290                 295                 300

Ala Leu Ala Lys Arg Phe Ala Glu Ala Pro His Ala Ala
305                 310                 315
```

<210> SEQ ID NO 54
<211> LENGTH: 950
<212> TYPE: DNA
<213> ORGANISM: Streptomyces coelicolor
<220> FEATURE:
<221> NAME/KEY: CDS
<222> LOCATION: (1)..(948)
<223> OTHER INFORMATION: Act_ARO-CYC_actVII (type: 2xSRPBCC) gene
    [GenBank ID number AL939122.1 Position 162706 to 163656) encoding -continued a first small molecule foldase [GenBank ID number Q02055]

<400> SEQUENCE: 54

| | | | | | | | | | | | | | | | | |
|---|---|---|---|---|---|---|---|---|---|---|---|---|---|---|---|---|
| atg | agc | cgg | ccg | gga | gaa | cac | cgg | gtg | gtc | cac | acc | ctg | agg | acc | cag | 48 |
| Met | Ser | Arg | Pro | Gly | Glu | His | Arg | Val | Val | His | Thr | Leu | Arg | Thr | Gln | |
| 1 | | | | 5 | | | | | 10 | | | | | 15 | | |

| gcc | ccg | gcg | cgg | cgg | ctc | tac | gag | ctg | gtc | gca | cgc | gtc | gaa | gac | tgg | 96 |
|---|---|---|---|---|---|---|---|---|---|---|---|---|---|---|---|---|
| Ala | Pro | Ala | Arg | Arg | Leu | Tyr | Glu | Leu | Val | Ala | Arg | Val | Glu | Asp | Trp | |
| | | | 20 | | | | | 25 | | | | | 30 | | | |

| ccg | gcc | gtc | ttc | gaa | ccc | acc | gtg | cac | gta | cag | gtc | ctg | gag | cgc | ggc | 144 |
|---|---|---|---|---|---|---|---|---|---|---|---|---|---|---|---|---|
| Pro | Ala | Val | Phe | Glu | Pro | Thr | Val | His | Val | Gln | Val | Leu | Glu | Arg | Gly | |
| | | 35 | | | | | 40 | | | | | 45 | | | | |

| ccg | ggc | acc | gaa | cgc | ttc | cgg | atc | tgg | gcg | cgc | gtg | ggc | ggc | cgg | gtg | 192 |
|---|---|---|---|---|---|---|---|---|---|---|---|---|---|---|---|---|
| Pro | Gly | Thr | Glu | Arg | Phe | Arg | Ile | Trp | Ala | Arg | Val | Gly | Gly | Arg | Val | |
| | 50 | | | | | 55 | | | | | 60 | | | | | |

| aag | acc | tgg | acg | tcc | cgc | cgg | acg | ctg | gat | ccc | gac | acc | ctg | agg | gtg | 240 |
|---|---|---|---|---|---|---|---|---|---|---|---|---|---|---|---|---|
| Lys | Thr | Trp | Thr | Ser | Arg | Arg | Thr | Leu | Asp | Pro | Asp | Thr | Leu | Arg | Val | |
| 65 | | | | | 70 | | | | | 75 | | | | | 80 | |

| acg | ttc | cgc | cag | gag | ctc | acc | cag | ccg | ccc | atc | gcc | tcg | atg | ggc | ggg | 288 |
|---|---|---|---|---|---|---|---|---|---|---|---|---|---|---|---|---|
| Thr | Phe | Arg | Gln | Glu | Leu | Thr | Gln | Pro | Pro | Ile | Ala | Ser | Met | Gly | Gly | |
| | | | | 85 | | | | | 90 | | | | | 95 | | |

| agc | tgg | gag | ttc | cgg | ggc | gac | ggc | gac | ggc | acc | gaa | gtc | gtg | ctg | acc | 336 |
|---|---|---|---|---|---|---|---|---|---|---|---|---|---|---|---|---|
| Ser | Trp | Glu | Phe | Arg | Gly | Asp | Gly | Asp | Gly | Thr | Glu | Val | Val | Leu | Thr | |
| | | | | 100 | | | | | 105 | | | | | 110 | | |

| cac | gac | ttc | gcc | gcg | gtc | gac | gaa | gcc | gcc | ctg | ccg | gga | ctg | cgc | gag | 384 |
|---|---|---|---|---|---|---|---|---|---|---|---|---|---|---|---|---|
| His | Asp | Phe | Ala | Ala | Val | Asp | Glu | Ala | Ala | Leu | Pro | Gly | Leu | Arg | Glu | |
| | | | 115 | | | | | 120 | | | | | 125 | | | |

| gcg | ctg | gac | gcg | aac | agc | ggg | aag | gag | ctg | gcc | gcg | ctg | gtc | gcg | ctg | 432 |
|---|---|---|---|---|---|---|---|---|---|---|---|---|---|---|---|---|
| Ala | Leu | Asp | Ala | Asn | Ser | Gly | Lys | Glu | Leu | Ala | Ala | Leu | Val | Ala | Leu | |
| | 130 | | | | | 135 | | | | | 140 | | | | | |

| gcg | gag | cgc | cgg | cag | ccg | ccc | gag | gag | ctg | gtc | ttc | acg | ttc | gag | gac | 480 |
|---|---|---|---|---|---|---|---|---|---|---|---|---|---|---|---|---|
| Ala | Glu | Arg | Arg | Gln | Pro | Pro | Glu | Glu | Leu | Val | Phe | Thr | Phe | Glu | Asp | |
| 145 | | | | | 150 | | | | | 155 | | | | | 160 | |

| acg | ctc | cgg | gtg | ccg | tcc | ggg | gac | gac | gcc | tac | gcc | ttc | atc | gag | cgc | 528 |
|---|---|---|---|---|---|---|---|---|---|---|---|---|---|---|---|---|
| Thr | Leu | Arg | Val | Pro | Ser | Gly | Asp | Asp | Ala | Tyr | Ala | Phe | Ile | Glu | Arg | |
| | | | | 165 | | | | | 170 | | | | | 175 | | |

| agc | gac | ctg | tgg | cag | gaa | cgg | ctg | ccg | cac | gtg | cgg | aag | gtg | aca | ctc | 576 |
|---|---|---|---|---|---|---|---|---|---|---|---|---|---|---|---|---|
| Ser | Asp | Leu | Trp | Gln | Glu | Arg | Leu | Pro | His | Val | Arg | Lys | Val | Thr | Leu | |
| | | | 180 | | | | | 185 | | | | | 190 | | | |

| acc | gag | gag | gcg | gcg | ggt | acc | ggc | ccc | gcc | gag | acg | cgg | gac | atg | acc | 624 |
|---|---|---|---|---|---|---|---|---|---|---|---|---|---|---|---|---|
| Thr | Glu | Glu | Ala | Ala | Gly | Thr | Gly | Pro | Ala | Glu | Thr | Arg | Asp | Met | Thr | |
| | | 195 | | | | | 200 | | | | | 205 | | | | |

| gtc | cag | gac | atg | acc | atg | gag | acg | gtg | acc | acc | gac | ggc | ggt | acc | cac | 672 |
|---|---|---|---|---|---|---|---|---|---|---|---|---|---|---|---|---|
| Val | Gln | Asp | Met | Thr | Met | Glu | Thr | Val | Thr | Thr | Asp | Gly | Gly | Thr | His | |
| | 210 | | | | | 215 | | | | | 220 | | | | | |

| acc | acc | cgt | tcg | atc | cgg | ctc | tgc | gtc | ccc | gcg | agg | agc | atc | gtg | tac | 720 |
|---|---|---|---|---|---|---|---|---|---|---|---|---|---|---|---|---|
| Thr | Thr | Arg | Ser | Ile | Arg | Leu | Cys | Val | Pro | Ala | Arg | Ser | Ile | Val | Tyr | |
| 225 | | | | | 230 | | | | | 235 | | | | | 240 | |

| aag | cag | ctc | gtc | ccg | ccc | gcc | ctg | ctc | tcc | ggg | cac | tgc | ggc | gcc | tgg | 768 |
|---|---|---|---|---|---|---|---|---|---|---|---|---|---|---|---|---|
| Lys | Gln | Leu | Val | Pro | Pro | Ala | Leu | Leu | Ser | Gly | His | Cys | Gly | Ala | Trp | |
| | | | | 245 | | | | | 250 | | | | | 255 | | |

| acc | ttc | ggc | gag | gac | acg | gtc | acc | gcc | cgc | cac | acc | gtg | gcg | atc | gac | 816 |
|---|---|---|---|---|---|---|---|---|---|---|---|---|---|---|---|---|
| Thr | Phe | Gly | Glu | Asp | Thr | Val | Thr | Ala | Arg | His | Thr | Val | Ala | Ile | Asp | |
| | | | 260 | | | | | 265 | | | | | 270 | | | |

| ccg | gcc | cgc | gtg | gaa | gag | gtc | ctg | ggc | aaa | ggc | gcg | acc | gtc | gcg | gac | 864 |
|---|---|---|---|---|---|---|---|---|---|---|---|---|---|---|---|---|
| Pro | Ala | Arg | Val | Glu | Glu | Val | Leu | Gly | Lys | Gly | Ala | Thr | Val | Ala | Asp | |
| | 275 | | | | | 280 | | | | | 285 | | | | | |

| gcc | cgt | acc | cat | ctg | cgc | gag | gtg | ctc | ggt | gcc | aac | agc | cgg | gcc | acg | 912 |
|---|---|---|---|---|---|---|---|---|---|---|---|---|---|---|---|---|
| Ala | Arg | Thr | His | Leu | Arg | Glu | Val | Leu | Gly | Ala | Asn | Ser | Arg | Ala | Thr | |
| 290 | | | | | 295 | | | | | 300 | | | | | | |

```
ctc cgc cac gcg gcg gcc gcc gcc ggg ccg gcg tca tg              950
Leu Arg His Ala Ala Ala Ala Ala Gly Pro Ala Ser
305                 310                 315

<210> SEQ ID NO 55
<211> LENGTH: 316
<212> TYPE: PRT
<213> ORGANISM: Streptomyces coelicolor

<400> SEQUENCE: 55

Met Ser Arg Pro Gly Glu His Arg Val Val His Thr Leu Arg Thr Gln
1               5                   10                  15

Ala Pro Ala Arg Arg Leu Tyr Glu Leu Val Ala Arg Val Glu Asp Trp
            20                  25                  30

Pro Ala Val Phe Glu Pro Thr Val His Val Gln Val Leu Glu Arg Gly
        35                  40                  45

Pro Gly Thr Glu Arg Phe Arg Ile Trp Ala Arg Val Gly Gly Arg Val
    50                  55                  60

Lys Thr Trp Thr Ser Arg Arg Thr Leu Asp Pro Asp Thr Leu Arg Val
65                  70                  75                  80

Thr Phe Arg Gln Glu Leu Thr Gln Pro Pro Ile Ala Ser Met Gly Gly
                85                  90                  95

Ser Trp Glu Phe Arg Gly Asp Gly Asp Gly Thr Glu Val Val Leu Thr
            100                 105                 110

His Asp Phe Ala Ala Val Asp Glu Ala Leu Pro Gly Leu Arg Glu
        115                 120                 125

Ala Leu Asp Ala Asn Ser Gly Lys Glu Leu Ala Ala Leu Val Ala Leu
    130                 135                 140

Ala Glu Arg Arg Gln Pro Pro Glu Glu Leu Val Phe Thr Phe Glu Asp
145                 150                 155                 160

Thr Leu Arg Val Pro Ser Gly Asp Asp Ala Tyr Ala Phe Ile Glu Arg
                165                 170                 175

Ser Asp Leu Trp Gln Glu Arg Leu Pro His Val Arg Lys Val Thr Leu
            180                 185                 190

Thr Glu Glu Ala Ala Gly Thr Gly Pro Ala Glu Thr Arg Asp Met Thr
        195                 200                 205

Val Gln Asp Met Thr Met Glu Thr Val Thr Thr Asp Gly Gly Thr His
    210                 215                 220

Thr Thr Arg Ser Ile Arg Leu Cys Val Pro Ala Arg Ser Ile Val Tyr
225                 230                 235                 240

Lys Gln Leu Val Pro Pro Ala Leu Leu Ser Gly His Cys Gly Ala Trp
                245                 250                 255

Thr Phe Gly Glu Asp Thr Val Thr Ala Arg His Thr Val Ala Ile Asp
            260                 265                 270

Pro Ala Arg Val Glu Glu Val Leu Gly Lys Gly Ala Thr Val Ala Asp
        275                 280                 285

Ala Arg Thr His Leu Arg Glu Val Leu Gly Ala Asn Ser Arg Ala Thr
    290                 295                 300

Leu Arg His Ala Ala Ala Ala Gly Pro Ala Ser
305                 310                 315

<210> SEQ ID NO 56
<211> LENGTH: 306
<212> TYPE: DNA
<213> ORGANISM: Cannabis sativa
<220> FEATURE:
```

```
<221> NAME/KEY: CDS
<222> LOCATION: (1)..(306)
<223> OTHER INFORMATION: AOC (type: DABB) gene [GenBank ID number
      JN679224.1 Position 36..341) encoding a first small molecule
      foldase [GenBank ID number AFN42527]

<400> SEQUENCE: 56 atg gca gtg aag cat ttg att gta ttg aag ttc aaa gat gaa atc aca        48
Met Ala Val Lys His Leu Ile Val Leu Lys Phe Lys Asp Glu Ile Thr
1               5                   10                  15 gaa gcc caa aag gaa gaa ttt ttc aag acg tat gtg aat ctt gtg aat        96
Glu Ala Gln Lys Glu Glu Phe Phe Lys Thr Tyr Val Asn Leu Val Asn
            20                  25                  30 atc atc cca gcc atg aaa gat gta tac tgg ggt aaa gat gtg act caa       144
Ile Ile Pro Ala Met Lys Asp Val Tyr Trp Gly Lys Asp Val Thr Gln
        35                  40                  45 aag aat aag gaa gaa ggg tac act cac ata gtt gag gta aca ttt gag       192
Lys Asn Lys Glu Glu Gly Tyr Thr His Ile Val Glu Val Thr Phe Glu
    50                  55                  60 agt gtg gag act att cag gac tac att att cat cct gcc cat gtt gga       240
Ser Val Glu Thr Ile Gln Asp Tyr Ile Ile His Pro Ala His Val Gly
65                  70                  75                  80 ttt gga gat gtc tat cgt tct ttc tgg gaa aaa ctt ctc att ttt gac       288
Phe Gly Asp Val Tyr Arg Ser Phe Trp Glu Lys Leu Leu Ile Phe Asp
                85                  90                  95 tac aca cca cga aag tag                                                306
Tyr Thr Pro Arg Lys
            100

<210> SEQ ID NO 57
<211> LENGTH: 101
<212> TYPE: PRT
<213> ORGANISM: Cannabis sativa

<400> SEQUENCE: 57

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Val Asn
            20                  25                  30

Ile Ile Pro Ala Met Lys Asp Val Tyr Trp Gly Lys Asp Val Thr Gln
        35                  40                  45

Lys Asn Lys Glu Glu Gly Tyr Thr His Ile Val Glu Val Thr Phe Glu
    50                  55                  60

Ser Val Glu Thr Ile Gln Asp Tyr Ile Ile His Pro Ala His Val Gly
65                  70                  75                  80

Phe Gly Asp Val Tyr Arg Ser Phe Trp Glu Lys Leu Leu Ile Phe Asp
                85                  90                  95

Tyr Thr Pro Arg Lys
            100

<210> SEQ ID NO 58
<211> LENGTH: 1095
<212> TYPE: DNA
<213> ORGANISM: Aspergillus nidulan
<220> FEATURE:
<221> NAME/KEY: CDS
<222> LOCATION: (1)..(1095)
<223> OTHER INFORMATION: wA-PT (type: PT domain) synthetic gene encoding
      a first small molecule foldase [GenBank ID number CAA46695
      position 1276 to 1651]

<400> SEQUENCE: 58
```

| | | |
|---|---|---|
| atg ttg act acc tct gct caa aga gtt gtc gaa tct aga gat gat ggt<br>Met Leu Thr Thr Ser Ala Gln Arg Val Val Glu Ser Arg Asp Asp Gly<br>1                          5                      10                 15 | 48 | |
| ttg act gct act gtt gtt gtt cat aac gat att gcc gat cca gat ttg<br>Leu Thr Ala Thr Val Val Val His Asn Asp Ile Ala Asp Pro Asp Leu<br>                20                      25                      30 | 96 | |
| aac aga gtt atc caa ggt cat aag gtt aat ggt gct gct ttg tgt cca<br>Asn Arg Val Ile Gln Gly His Lys Val Asn Gly Ala Ala Leu Cys Pro<br>        35                      40                      45 | 144 | |
| tct tca tta tat gct gat tcc gct caa act ttg gcc gaa tac ttg att<br>Ser Ser Leu Tyr Ala Asp Ser Ala Gln Thr Leu Ala Glu Tyr Leu Ile<br>  50                      55                      60 | 192 | |
| gaa aag tac aag cca gaa ttg aag ggt tct ggt ttg gat gtc tgt aat<br>Glu Lys Tyr Lys Pro Glu Leu Lys Gly Ser Gly Leu Asp Val Cys Asn<br>65                        70                      75                  80 | 240 | |
| gtt act gtt cca aag cca ttg att gcc aag act ggt aaa gaa caa ttc<br>Val Thr Val Pro Lys Pro Leu Ile Ala Lys Thr Gly Lys Glu Gln Phe<br>                85                      90                      95 | 288 | |
| aga att tct gct acc gct aac tgg gtt gat aag cac gtt tct gtt caa<br>Arg Ile Ser Ala Thr Ala Asn Trp Val Asp Lys His Val Ser Val Gln<br>               100                     105                 110 | 336 | |
| gtt ttc tct gtt act gct gaa ggt aaa aag ttg att gat cat gct cac<br>Val Phe Ser Val Thr Ala Glu Gly Lys Lys Leu Ile Asp His Ala His<br>          115                     120                 125 | 384 | |
| tgc gaa gtc aag ttg ttt gat tgc atg gct gct gat ttg gaa tgg aaa<br>Cys Glu Val Lys Leu Phe Asp Cys Met Ala Ala Asp Leu Glu Trp Lys<br>130                       135                    140 | 432 | |
| aga ggt tct tac ttg gtc aag aga tcc atc gaa tta ttg gaa aac tct<br>Arg Gly Ser Tyr Leu Val Lys Arg Ser Ile Glu Leu Leu Glu Asn Ser<br>145                       150                    155              160 | 480 | |
| gcc gtt aag ggt gat gct cat aga ttg aga aga ggt atg gtt tac aag<br>Ala Val Lys Gly Asp Ala His Arg Leu Arg Arg Gly Met Val Tyr Lys<br>               165                     170                 175 | 528 | |
| ttg ttc tcc gct ttg gtt gat tac gac gaa aac tac caa tcc atc aga<br>Leu Phe Ser Ala Leu Val Asp Tyr Asp Glu Asn Tyr Gln Ser Ile Arg<br>          180                     185                 190 | 576 | |
| gaa gtt atc ttg gat tcc gaa cat cat gaa gct act gct ttg gtt aag<br>Glu Val Ile Leu Asp Ser Glu His His Glu Ala Thr Ala Leu Val Lys<br>          195                     200                 205 | 624 | |
| ttt caa gct cca caa gct aac ttc cat aga aac cca tat tgg atc gat<br>Phe Gln Ala Pro Gln Ala Asn Phe His Arg Asn Pro Tyr Trp Ile Asp<br>210                       215                    220 | 672 | |
| tcc ttc ggt cat ttg tct ggt ttc att atg aat gcc tct gat ggt act<br>Ser Phe Gly His Leu Ser Gly Phe Ile Met Asn Ala Ser Asp Gly Thr<br>225                       230                    235              240 | 720 | |
| gac tcc aag tct caa gtt ttt gtt aat cac ggt tgg gac tct atg aga<br>Asp Ser Lys Ser Gln Val Phe Val Asn His Gly Trp Asp Ser Met Arg<br>               245                     250                 255 | 768 | |
| tgc ttg aaa aag ttt tct gcc gat gtt acc tac aga acc tac gtt aga<br>Cys Leu Lys Lys Phe Ser Ala Asp Val Thr Tyr Arg Thr Tyr Val Arg<br>          260                     265                 270 | 816 | |
| atg caa cct tgg aga gat tct att tgg gct ggt aac gtt tac atc ttc<br>Met Gln Pro Trp Arg Asp Ser Ile Trp Ala Gly Asn Val Tyr Ile Phe<br>          275                     280                 285 | 864 | |
| gaa ggt gat gat att atc gct gtt ttc ggt ggt gtc aaa ttc caa gct<br>Glu Gly Asp Asp Ile Ile Ala Val Phe Gly Gly Val Lys Phe Gln Ala<br>290                       295                    300 | 912 | |
| ttg tcc aga aag att ttg gat att gct ttg cca cca gcc ggt ttg tct<br>Leu Ser Arg Lys Ile Leu Asp Ile Ala Leu Pro Pro Ala Gly Leu Ser<br>305                       310                    315              320 | 960 | |

```
aaa gct caa act agt cca att caa tcc tct gct cca caa aag cca att        1008
Lys Ala Gln Thr Ser Pro Ile Gln Ser Ser Ala Pro Gln Lys Pro Ile
                325                 330                 335 gaa act gct aaa cct act tct aga cca gct cca cca gtt act atg aag        1056
Glu Thr Ala Lys Pro Thr Ser Arg Pro Ala Pro Pro Val Thr Met Lys
            340                 345                 350 tct ttc gtt aag aaa tct gcc ggt cca tca gtt gtt gtt                    1095
Ser Phe Val Lys Lys Ser Ala Gly Pro Ser Val Val Val
                355                 360                 365

<210> SEQ ID NO 59
<211> LENGTH: 365
<212> TYPE: PRT
<213> ORGANISM: Aspergillus nidulan

<400> SEQUENCE: 59

Met Leu Thr Thr Ser Ala Gln Arg Val Val Glu Ser Arg Asp Asp Gly
1               5                   10                  15

Leu Thr Ala Thr Val Val His Asn Asp Ile Ala Asp Pro Asp Leu
            20                  25                  30

Asn Arg Val Ile Gln Gly His Lys Val Asn Gly Ala Ala Leu Cys Pro
        35                  40                  45

Ser Ser Leu Tyr Ala Asp Ser Ala Gln Thr Leu Ala Glu Tyr Leu Ile
    50                  55                  60

Glu Lys Tyr Lys Pro Glu Leu Lys Gly Ser Gly Leu Asp Val Cys Asn
65                  70                  75                  80

Val Thr Val Pro Lys Pro Leu Ile Ala Lys Thr Gly Lys Glu Gln Phe
                85                  90                  95

Arg Ile Ser Ala Thr Ala Asn Trp Val Asp Lys His Val Ser Val Gln
            100                 105                 110

Val Phe Ser Val Thr Ala Glu Gly Lys Lys Leu Ile Asp His Ala His
        115                 120                 125

Cys Glu Val Lys Leu Phe Asp Cys Met Ala Ala Asp Leu Glu Trp Lys
    130                 135                 140

Arg Gly Ser Tyr Leu Val Lys Arg Ser Ile Glu Leu Leu Glu Asn Ser
145                 150                 155                 160

Ala Val Lys Gly Asp Ala His Arg Leu Arg Arg Gly Met Val Tyr Lys
                165                 170                 175

Leu Phe Ser Ala Leu Val Asp Tyr Asp Glu Asn Tyr Gln Ser Ile Arg
            180                 185                 190

Glu Val Ile Leu Asp Ser Glu His His Glu Ala Thr Ala Leu Val Lys
        195                 200                 205

Phe Gln Ala Pro Gln Ala Asn Phe His Arg Asn Pro Tyr Trp Ile Asp
    210                 215                 220

Ser Phe Gly His Leu Ser Gly Phe Ile Met Asn Ala Ser Asp Gly Thr
225                 230                 235                 240

Asp Ser Lys Ser Gln Val Phe Val Asn His Gly Trp Asp Ser Met Arg
                245                 250                 255

Cys Leu Lys Lys Phe Ser Ala Asp Val Thr Tyr Arg Thr Tyr Val Arg
            260                 265                 270

Met Gln Pro Trp Arg Asp Ser Ile Trp Ala Gly Asn Val Tyr Ile Phe
        275                 280                 285

Glu Gly Asp Asp Ile Ile Ala Val Phe Gly Gly Val Lys Phe Gln Ala
    290                 295                 300

Leu Ser Arg Lys Ile Leu Asp Ile Ala Leu Pro Pro Ala Gly Leu Ser
```

```
305                 310                 315                 320
Lys Ala Gln Thr Ser Pro Ile Gln Ser Ser Ala Pro Gln Lys Pro Ile
                325                 330                 335

Glu Thr Ala Lys Pro Thr Ser Arg Pro Ala Pro Val Thr Met Lys
                340                 345                 350

Ser Phe Val Lys Lys Ser Ala Gly Pro Ser Val Val Val
                355                 360                 365

<210> SEQ ID NO 60
<211> LENGTH: 1122
<212> TYPE: DNA
<213> ORGANISM: Fusarium fujikuroi
<220> FEATURE:
<221> NAME/KEY: CDS
<222> LOCATION: (1)..(1122)
<223> OTHER INFORMATION: BIK1-PT (type: PT domain)  synthetic gene
      encoding a first small molecule synthase [ GenBank ID number
      CAB92399 Position 1252 to 1632]

<400> SEQUENCE: 60 atg aga ttg tcc gat tcc gtt cac aac gtt atc gaa caa gtt cat ggt     48
Met Arg Leu Ser Asp Ser Val His Asn Val Ile Glu Gln Val His Gly
1               5                   10                  15 gac aag aga tcc tct att acc gtt gaa tct gat atg cac gat cca tcc     96
Asp Lys Arg Ser Ser Ile Thr Val Glu Ser Asp Met His Asp Pro Ser
            20                  25                  30 ttg ttg gct att gct caa aat cat aga gtt aac ggt ttg acc atg gct    144
Leu Leu Ala Ile Ala Gln Asn His Arg Val Asn Gly Leu Thr Met Ala
        35                  40                  45 cca tct act ttg ttt gct gat att gct ttc act ttg gcc aag cac ttg    192
Pro Ser Thr Leu Phe Ala Asp Ile Ala Phe Thr Leu Ala Lys His Leu
    50                  55                  60 att caa aat cac ggt ttg gat acc cat acc aac ttg cca tct att aac    240
Ile Gln Asn His Gly Leu Asp Thr His Thr Asn Leu Pro Ser Ile Asn
65                  70                  75                  80 aac atg gct gtt gaa aag gct ttg atc gtt ggt gaa act ggt cct caa    288
Asn Met Ala Val Glu Lys Ala Leu Ile Val Gly Glu Thr Gly Pro Gln
                85                  90                  95 tta ttc aga gct tct ttg gat atg gat tgg act act atg aga ggt tcc    336
Leu Phe Arg Ala Ser Leu Asp Met Asp Trp Thr Thr Met Arg Gly Ser
            100                 105                 110 gtt aga att ttt tcc gtt ggt gct aat ggt aag caa act aca ttg cat    384
Val Arg Ile Phe Ser Val Gly Ala Asn Gly Lys Gln Thr Thr Leu His
        115                 120                 125 gct gtt tgt gat gtt gcc gtt gaa aat cca tct tcc cat aga gaa tct    432
Ala Val Cys Asp Val Ala Val Glu Asn Pro Ser Ser His Arg Glu Ser
    130                 135                 140 tgg caa tct aac gct tac ttg atc caa aga ggt atc aag caa ttg gtt    480
Trp Gln Ser Asn Ala Tyr Leu Ile Gln Arg Gly Ile Lys Gln Leu Val
145                 150                 155                 160 caa ggt gct tct gat ggt tct gct cat atg atg aga aga ggt ttg ttg    528
Gln Gly Ala Ser Asp Gly Ser Ala His Met Met Arg Arg Gly Leu Leu
                165                 170                 175 tac aag atc ttc tcc aac tct gtt caa tac ggt tct gct ttc caa ggt    576
Tyr Lys Ile Phe Ser Asn Ser Val Gln Tyr Gly Ser Ala Phe Gln Gly
            180                 185                 190 ata gaa caa gtt tgg ttc gat tcc gaa ggt ttg gaa ggt act ggt aaa    624
Ile Glu Gln Val Trp Phe Asp Ser Glu Gly Leu Glu Gly Thr Gly Lys
        195                 200                 205 gtt ttt atg cca tct ggt aag gat acc ttc gct ttg aat cca tac tgt    672
Val Phe Met Pro Ser Gly Lys Asp Thr Phe Ala Leu Asn Pro Tyr Cys
```

```
                210                 215                 220
tgt gat tcc ttg ggt cat att acc ggt ttc att atg aac tgc tct gac         720
Cys Asp Ser Leu Gly His Ile Thr Gly Phe Ile Met Asn Cys Ser Asp
225                 230                 235                 240 tcc ttg gat ttg gat gat cat gtt tac atc aac cac ggt tgg aga act         768
Ser Leu Asp Leu Asp Asp His Val Tyr Ile Asn His Gly Trp Arg Thr
                    245                 250                 255 ttg aga ttg gtt gaa cca tac caa tgc gac gtt caa tat caa acc tac         816
Leu Arg Leu Val Glu Pro Tyr Gln Cys Asp Val Gln Tyr Gln Thr Tyr
                260                 265                 270 gtt aag atg caa gcc gtt ggt tct gat gat tct act tat tct ggt gat         864
Val Lys Met Gln Ala Val Gly Ser Asp Asp Ser Thr Tyr Ser Gly Asp
            275                 280                 285 gtt cac gtc ttg aga gat ggt aag att att ggt att tgt ggt ggt gtc         912
Val His Val Leu Arg Asp Gly Lys Ile Ile Gly Ile Cys Gly Gly Val
        290                 295                 300 acc ttc aag aaa gtt gct aga aaa gtc ttg gaa atg ttg ttg cca aaa         960
Thr Phe Lys Lys Val Ala Arg Lys Val Leu Glu Met Leu Leu Pro Lys
305                 310                 315                 320 cca tct ggt gct aaa gct aaa cat ggt gtt gtc aaa cat gtt gct cca        1008
Pro Ser Gly Ala Lys Ala Lys His Gly Val Val Lys His Val Ala Pro
                    325                 330                 335 gaa cca gtt aag cac gtt gtt ttg act cca cca tct act act tct cat        1056
Glu Pro Val Lys His Val Val Leu Thr Pro Pro Ser Thr Thr Ser His
                340                 345                 350 tct gtt ggt act aca tct cca cca gaa cct act gaa tct cca gtt ggt        1104
Ser Val Gly Thr Thr Ser Pro Pro Glu Pro Thr Glu Ser Pro Val Gly
            355                 360                 365 tca gct tct ggt ttg att                                                 1122
Ser Ala Ser Gly Leu Ile
    370

<210> SEQ ID NO 61
<211> LENGTH: 374
<212> TYPE: PRT
<213> ORGANISM: Fusarium fujikuroi

<400> SEQUENCE: 61

Met Arg Leu Ser Asp Ser Val His Asn Val Ile Glu Gln Val His Gly
1               5                   10                  15

Asp Lys Arg Ser Ser Ile Thr Val Glu Ser Asp Met His Asp Pro Ser
            20                  25                  30

Leu Leu Ala Ile Ala Gln Asn His Arg Val Asn Gly Leu Thr Met Ala
        35                  40                  45

Pro Ser Thr Leu Phe Ala Asp Ile Ala Phe Thr Leu Ala Lys His Leu
    50                  55                  60

Ile Gln Asn His Gly Leu Asp Thr His Thr Asn Leu Pro Ser Ile Asn
65                  70                  75                  80

Asn Met Ala Val Glu Lys Ala Leu Ile Val Gly Glu Thr Gly Pro Gln
                85                  90                  95

Leu Phe Arg Ala Ser Leu Asp Met Asp Trp Thr Thr Met Arg Gly Ser
            100                 105                 110

Val Arg Ile Phe Ser Val Gly Ala Asn Gly Lys Gln Thr Thr Leu His
        115                 120                 125

Ala Val Cys Asp Val Ala Val Glu Asn Pro Ser Ser His Arg Glu Ser
    130                 135                 140

Trp Gln Ser Asn Ala Tyr Leu Ile Gln Arg Gly Ile Lys Gln Leu Val
145                 150                 155                 160
```

```
Gln Gly Ala Ser Asp Gly Ser Ala His Met Met Arg Arg Gly Leu Leu
                165                 170                 175

Tyr Lys Ile Phe Ser Asn Ser Val Gln Tyr Gly Ser Ala Phe Gln Gly
            180                 185                 190

Ile Glu Gln Val Trp Phe Asp Ser Glu Gly Leu Glu Gly Thr Gly Lys
        195                 200                 205

Val Phe Met Pro Ser Gly Lys Asp Thr Phe Ala Leu Asn Pro Tyr Cys
    210                 215                 220

Cys Asp Ser Leu Gly His Ile Thr Gly Phe Ile Met Asn Cys Ser Asp
225                 230                 235                 240

Ser Leu Asp Leu Asp Asp His Val Tyr Ile Asn His Gly Trp Arg Thr
                245                 250                 255

Leu Arg Leu Val Glu Pro Tyr Gln Cys Asp Val Gln Tyr Gln Thr Tyr
            260                 265                 270

Val Lys Met Gln Ala Val Gly Ser Asp Ser Thr Tyr Ser Gly Asp
        275                 280                 285

Val His Val Leu Arg Asp Gly Lys Ile Ile Gly Ile Cys Gly Gly Val
    290                 295                 300

Thr Phe Lys Lys Val Ala Arg Lys Val Leu Glu Met Leu Leu Pro Lys
305                 310                 315                 320

Pro Ser Gly Ala Lys Ala Lys His Gly Val Val Lys His Val Ala Pro
                325                 330                 335

Glu Pro Val Lys His Val Val Leu Thr Pro Pro Ser Thr Thr Ser His
            340                 345                 350

Ser Val Gly Thr Thr Ser Pro Pro Glu Pro Thr Glu Ser Pro Val Gly
        355                 360                 365

Ser Ala Ser Gly Leu Ile
        370
```

<210> SEQ ID NO 62
<211> LENGTH: 1167
<212> TYPE: DNA
<213> ORGANISM: Fusarium graminearum
<220> FEATURE:
<221> NAME/KEY: CDS
<222> LOCATION: (1)..(1167)
<223> OTHER INFORMATION: PGL1_PT (type: PT domain) synthetic gene
      encoding a first

```
                      85                  90                   95
gct ttg att ttg aga ggt gat ggt tct aag caa cct att caa gct cat   336
Ala Leu Ile Leu Arg Gly Asp Gly Ser Lys Gln Pro Ile Gln Ala His
            100                 105                 110 gct gaa gca gat tgg ttg tct caa tct gtt gct atc aag ttc atg tcc   384
Ala Glu Ala Asp Trp Leu Ser Gln Ser Val Ala Ile Lys Phe Met Ser
        115                 120                 125 ttc gat aac aag ggt aac ttg caa gaa cat tct gct tgc gtt gtt aga   432
Phe Asp Asn Lys Gly Asn Leu Gln Glu His Ser Ala Cys Val Val Arg
130                 135                 140 tac aag gat aga act cat caa aag acc ttg caa tcc gaa gct caa caa   480
Tyr Lys Asp Arg Thr His Gln Lys Thr Leu Gln Ser Glu Ala Gln Gln
145                 150                 155                 160 act aag aga aag atc caa aac ttg aga gat caa gtt acc acc gat gaa   528
Thr Lys Arg Lys Ile Gln Asn Leu Arg Asp Gln Val Thr Thr Asp Glu
                165                 170                 175 tcc gct aga ttc aat aga cca atg gtt tac aga atg atc aga cca ttg   576
Ser Ala Arg Phe Asn Arg Pro Met Val Tyr Arg Met Ile Arg Pro Leu
            180                 185                 190 gct aga ttc cac gat gat tac aga gct atc gat gaa gtt gtc ttg aac   624
Ala Arg Phe His Asp Asp Tyr Arg Ala Ile Asp Glu Val Val Leu Asn
        195                 200                 205 tct gaa act ttg gaa gcc tcc tct aag att tct ttc ggt act gtt aag   672
Ser Glu Thr Leu Glu Ala Ser Ser Lys Ile Ser Phe Gly Thr Val Lys
210                 215                 220 aga gaa ggt gac tat cat act cat cca gcc gtt att gat tct ttg act   720
Arg Glu Gly Asp Tyr His Thr His Pro Ala Val Ile Asp Ser Leu Thr
225                 230                 235                 240 caa tct tgt ggt ttc gcc atg aac tgt aac gat cat acc gat att gat   768
Gln Ser Cys Gly Phe Ala Met Asn Cys Asn Asp His Thr Asp Ile Asp
                245                 250                 255 gtc gac gtt tac atg aat cat ggt tgg ggt tct ttg gaa tta ttc gaa   816
Val Asp Val Tyr Met Asn His Gly Trp Gly Ser Leu Glu Leu Phe Glu
            260                 265                 270 gct ttg gac ttc gaa aaa gaa tac act acc tac acc caa atg cat gct   864
Ala Leu Asp Phe Glu Lys Glu Tyr Thr Thr Tyr Thr Gln Met His Ala
        275                 280                 285 ggt gaa gat aag ttg tgg tac ggt gat gtt act gtt ttc gat ggt gat   912
Gly Glu Asp Lys Leu Trp Tyr Gly Asp Val Thr Val Phe Asp Gly Asp
290                 295                 300 aga gtt gtc gct ttc ttt ggt caa att gcc att caa ggt gtt cct aga   960
Arg Val Val Ala Phe Phe Gly Gln Ile Ala Ile Gln Gly Val Pro Arg
305                 310                 315                 320 aga gtt ttg aag gtc atc ttg tcc att gaa tct ggt aaa aag ggt caa   1008
Arg Val Leu Lys Val Ile Leu Ser Ile Glu Ser Gly Lys Lys Gly Gln
                325                 330                 335 cct caa aga cca gtt caa gat aag cca caa act act tct aaa cca tct   1056
Pro Gln Arg Pro Val Gln Asp Lys Pro Gln Thr Thr Ser Lys Pro Ser
            340                 345                 350 gct aca cca tct cca aaa cct act caa aac aaa cca gct gct aaa atg   1104
Ala Thr Pro Ser Pro Lys Pro Thr Gln Asn Lys Pro Ala Ala Lys Met
        355                 360                 365 gaa cct act aag ttc tct acc gcc ttg aga att atc tct gaa gaa tcc   1152
Glu Pro Thr Lys Phe Ser Thr Ala Leu Arg Ile Ile Ser Glu Glu Ser
370                 375                 380 ggt atc gaa att agt                                               1167
Gly Ile Glu Ile Ser
385
```

<210> SEQ ID NO 63
<211> LENGTH: 389
<212> TYPE: PRT
<213> ORGANISM: Fusarium graminearum

<400> SEQUENCE: 63

```
Met Pro Ala Tyr Ser Trp Glu Leu Lys Asp Tyr Trp Ile Asn Thr Thr
1               5                   10                  15

Ile His Arg Val Val Glu Glu Gly Asp Ser Asn Lys Ile His Ile
            20                  25                  30

Ile Val Glu Ala Asp Ile Ala Arg Lys Asp Leu Ser Pro Leu Val Gln
            35                  40                  45

Gly His Glu Val Asp Gly Ile Pro Leu Cys Thr Pro Ser Val Tyr Ala
        50                  55                  60

Asp Ile Gly Leu Thr Leu Gly Lys Tyr Leu Leu Glu Lys Tyr Gln Pro
65                  70                  75                  80

Gln Asn Arg Asp Asn Met Val Val Ser Asp Met Thr Val Ser Lys
                85                  90                  95

Ala Leu Ile Leu Arg Gly Asp Gly Ser Lys Gln Pro Ile Gln Ala His
            100                 105                 110

Ala Glu Ala Asp Trp Leu Ser Gln Ser Val Ala Ile Lys Phe Met Ser
        115                 120                 125

Phe Asp Asn Lys Gly Asn Leu Gln Glu His Ser Ala Cys Val Val Arg
130                 135                 140

Tyr Lys Asp Arg Thr His Gln Lys Thr Leu Gln Ser Glu Ala Gln Gln
145                 150                 155                 160

Thr Lys Arg Lys Ile Gln Asn Leu Arg Asp Gln Val Thr Thr Asp Glu
                165                 170                 175

Ser Ala Arg Phe Asn Arg Pro Met Val Tyr Arg Met Ile Arg Pro Leu
            180                 185                 190

Ala Arg Phe His Asp Asp Tyr Arg Ala Ile Asp Glu Val Val Leu Asn
        195                 200                 205

Ser Glu Thr Leu Glu Ala Ser Ser Lys Ile Ser Phe Gly Thr Val Lys
210                 215                 220

Arg Glu Gly Asp Tyr His Thr His Pro Ala Val Ile Asp Ser Leu Thr
225                 230                 235                 240

Gln Ser Cys Gly Phe Ala Met Asn Cys Asn Asp His Thr Asp Ile Asp
                245                 250                 255

Val Asp Val Tyr Met Asn His Gly Trp Gly Ser Leu Glu Leu Phe Glu
            260                 265                 270

Ala Leu Asp Phe Glu Lys Glu Tyr Thr Thr Tyr Thr Gln Met His Ala
        275                 280                 285

Gly Glu Asp Lys Leu Trp Tyr Gly Asp Val Thr Val Phe Asp Gly Asp
290                 295                 300

Arg Val Val Ala Phe Phe Gly Gln Ile Ala Ile Gln Gly Val Pro Arg
305                 310                 315                 320

Arg Val Leu Lys Val Ile Leu Ser Ile Glu Ser Gly Lys Lys Gly Gln
                325                 330                 335

Pro Gln Arg Pro Val Gln Asp Lys Pro Gln Thr Thr Ser Lys Pro Ser
            340                 345                 350

Ala Thr Pro Ser Pro Lys Pro Thr Gln Asn Lys Pro Ala Ala Lys Met
        355                 360                 365

Glu Pro Thr Lys Phe Ser Thr Ala Leu Arg Ile Ile Ser Glu Glu Ser
370                 375                 380
```

Gly Ile Glu Ile Ser
385

<210> SEQ ID NO 64
<211> LENGTH: 1215
<212> TYPE: DNA
<213> ORGANISM: Aspergillus nidulans
<220> FEATURE:
<221> NAME/KEY: CDS
<222> LOCATION: (1)..(1215)
<223> OTHER INFORMATION: mpdG_PT (type: PT domain) synthetic gene
    encoding a first small molecule foldase [GenBank ID number
    XP_657754.1 position 1335 to 1739]

<400> SEQUENCE: 64

| | | | | | | | | | | | | | | | |
|---|---|---|---|---|---|---|---|---|---|---|---|---|---|---|---|
| atg | tct | ggt | ttg | aga | act | tcc | acc | gtt | caa | caa | atc | atc | gaa | gaa | tct | 48 |
| Met | Ser | Gly | Leu | Arg | Thr | Ser | Thr | Val | Gln | Gln | Ile | Ile | Glu | Glu | Ser | |
| 1 | | | | 5 | | | | | 10 | | | | | 15 | | |

| ttt | aac | ggt | tcc | gct | ggt | aag | gtt | gtt | atg | caa | tct | gat | atg | atg | caa | 96 |
| Phe | Asn | Gly | Ser | Ala | Gly | Lys | Val | Val | Met | Gln | Ser | Asp | Met | Met | Gln | |
| | | | 20 | | | | | 25 | | | | | 30 | | | |

| cca | gat | ttc | ttg | gat | gct | gct | cat | ggt | cat | aag | atg | aat | ggt | tgt | ggt | 144 |
| Pro | Asp | Phe | Leu | Asp | Ala | Ala | His | Gly | His | Lys | Met | Asn | Gly | Cys | Gly | |
| | | 35 | | | | | 40 | | | | | 45 | | | | |

| gtt | gtt | acc | tcc | tct | att | cat | ggt | gat | att | ggt | ttt | act | ttg | ggt | ggt | 192 |
| Val | Val | Thr | Ser | Ser | Ile | His | Gly | Asp | Ile | Gly | Phe | Thr | Leu | Gly | Gly | |
| | 50 | | | | | 55 | | | | | 60 | | | | | |

| tac | ttg | tac | aaa | aac | ttg | gtt | aag | ggt | ggt | aag | gct | cca | gat | atg | aat | 240 |
| Tyr | Leu | Tyr | Lys | Asn | Leu | Val | Lys | Gly | Gly | Lys | Ala | Pro | Asp | Met | Asn | |
| 65 | | | | | 70 | | | | | 75 | | | | | 80 | |

| atg | gct | aat | ttg | gtt | gtc | ttg | aga | ggt | ttg | gtt | gct | caa | aag | aac | act | 288 |
| Met | Ala | Asn | Leu | Val | Val | Leu | Arg | Gly | Leu | Val | Ala | Gln | Lys | Asn | Thr | |
| | | | | 85 | | | | | 90 | | | | | 95 | | |

| aag | aag | cca | caa | tat | atc | aga | gtc | acc | att | tct | acc | acc | gat | atc | aat | 336 |
| Lys | Lys | Pro | Gln | Tyr | Ile | Arg | Val | Thr | Ile | Ser | Thr | Thr | Asp | Ile | Asn | |
| | | | 100 | | | | | 105 | | | | | 110 | | | |

| tct | ggt | gtt | gcc | gaa | ttg | att | tgg | caa | aac | gtt | ttg | aat | gat | aac | acc | 384 |
| Ser | Gly | Val | Ala | Glu | Leu | Ile | Trp | Gln | Asn | Val | Leu | Asn | Asp | Asn | Thr | |
| | | | 115 | | | | | 120 | | | | | 125 | | | |

| gct | gat | gaa | cca | ttt | gct | tca | gct | tct | atc | ttg | tat | gat | gat | gct | gct | 432 |
| Ala | Asp | Glu | Pro | Phe | Ala | Ser | Ala | Ser | Ile | Leu | Tyr | Asp | Asp | Ala | Ala | |
| | 130 | | | | | 135 | | | | | 140 | | | | | |

| ttg | tgg | ttg | aag | tct | tgg | att | cca | tct | act | cat | ttg | gtc | caa | ggt | aga | 480 |
| Leu | Trp | Leu | Lys | Ser | Trp | Ile | Pro | Ser | Thr | His | Leu | Val | Gln | Gly | Arg | |
| 145 | | | | | 150 | | | | | 155 | | | | | 160 | |

| att | gaa | gcc | ttg | gaa | aga | ttg | gct | gaa | gat | ggt | att | gct | aac | aga | ttc | 528 |
| Ile | Glu | Ala | Leu | Glu | Arg | Leu | Ala | Glu | Asp | Gly | Ile | Ala | Asn | Arg | Phe | |
| | | | 165 | | | | | 170 | | | | | 175 | | | |

| act | aga | aac | atg | gcc | tac | ttg | ttg | ttc | gct | aac | aac | ttg | gtt | gat | tac | 576 |
| Thr | Arg | Asn | Met | Ala | Tyr | Leu | Leu | Phe | Ala | Asn | Asn | Leu | Val | Asp | Tyr | |
| | | | 180 | | | | | 185 | | | | | 190 | | | |

| gcc | caa | aag | tat | aga | ggt | atg | caa | tca | gtt | gtc | ttg | cat | gaa | ttg | gaa | 624 |
| Ala | Gln | Lys | Tyr | Arg | Gly | Met | Gln | Ser | Val | Val | Leu | His | Glu | Leu | Glu | |
| | | 195 | | | | | 200 | | | | | 205 | | | | |

| gct | ttc | gct | gat | att | acc | ttg | tct | act | gaa | aaa | tct | ggt | act | tgg | act | 672 |
| Ala | Phe | Ala | Asp | Ile | Thr | Leu | Ser | Thr | Glu | Lys | Ser | Gly | Thr | Trp | Thr | |
| | 210 | | | | | 215 | | | | | 220 | | | | | |

| atc | cca | cca | tac | ttc | att | gat | tct | gtt | gct | cat | ttg | gct | ggt | ttc | gtc | 720 |
| Ile | Pro | Pro | Tyr | Phe | Ile | Asp | Ser | Val | Ala | His | Leu | Ala | Gly | Phe | Val | |
| 225 | | | | | 230 | | | | | 235 | | | | | 240 | |

| atg | aat | gtt | tct | gat | gct | att | gat | acc | aag | gcc | aac | tat | tgt | gtt | act | 768 |
| Met | Asn | Val | Ser | Asp | Ala | Ile | Asp | Thr | Lys | Ala | Asn | Tyr | Cys | Val | Thr | |

```
cca ggt tgg aag tct ttg aga ttt gct aaa cca ttg gtt gct ggt gct    816
Pro Gly Trp Lys Ser Leu Arg Phe Ala Lys Pro Leu Val Ala Gly Ala
        260                 265                 270 aag tat aga tcc tac gtt aag atg atc caa acc gaa gaa gat cca act    864
Lys Tyr Arg Ser Tyr Val Lys Met Ile Gln Thr Glu Glu Asp Pro Thr
            275                 280                 285 gtt tat ttg ggt gat gtc tac att atg caa gat ggt gcc att att ggt    912
Val Tyr Leu Gly Asp Val Tyr Ile Met Gln Asp Gly Ala Ile Ile Gly
        290                 295                 300 atg tgc ggt ggt att caa ttc aga aga tac cca aga atc ttg ttg aat    960
Met Cys Gly Gly Ile Gln Phe Arg Arg Tyr Pro Arg Ile Leu Leu Asn
305                 310                 315                 320 aga ttc ttc acc gct cct gaa gaa gct ggt gca att tct cat gct gct   1008
Arg Phe Phe Thr Ala Pro Glu Glu Ala Gly Ala Ile Ser His Ala Ala
                325                 330                 335 gct tca tct act cca gct cca aga aca aaa cca gaa cca gtt cca gtt   1056
Ala Ser Ser Thr Pro Ala Pro Arg Thr Lys Pro Glu Pro Val Pro Val
            340                 345                 350 gct aca cca gct aca gct gct gct cca gtt gca caa tct cca gca gct   1104
Ala Thr Pro Ala Thr Ala Ala Ala Pro Val Ala Gln Ser Pro Ala Ala
        355                 360                 365 cca gct tct gtt act cct gct cca gca cca gcc cca gct cca ggt cca   1152
Pro Ala Ser Val Thr Pro Ala Pro Ala Pro Ala Pro Ala Pro Gly Pro
370                 375                 380 act cct gct gct gcc cca gct gcc gct ggt gaa tct gat tca gtt gct   1200
Thr Pro Ala Ala Ala Pro Ala Ala Ala Gly Glu Ser Asp Ser Val Ala
385                 390                 395                 400 gct aaa gct ttg gtc                                                1215
Ala Lys Ala Leu Val
                405
```

<210> SEQ ID NO 65
<211> LENGTH: 405
<212> TYPE: PRT
<213> ORGANISM: Aspergillus nidulans

<400> SEQUENCE: 65

```
Met Ser Gly Leu Arg Thr Ser Thr Val Gln Gln Ile Ile Glu Glu Ser
1               5                   10                  15

Phe Asn Gly Ser Ala Gly Lys Val Val Met Gln Ser Asp Met Met Gln
            20                  25                  30

Pro Asp Phe Leu Asp Ala Ala His Gly His Lys Met Asn Gly Cys Gly
        35                  40                  45

Val Val Thr Ser Ser Ile His Gly Asp Ile Gly Phe Thr Leu Gly Gly
    50                  55                  60

Tyr Leu Tyr Lys Asn Leu Val Lys Gly Gly Lys Ala Pro Asp Met Asn
65                  70                  75                  80

Met Ala Asn Leu Val Val Leu Arg Gly Leu Val Ala Gln Lys Asn Thr
                85                  90                  95

Lys Lys Pro Gln Tyr Ile Arg Val Thr Ile Ser Thr Thr Asp Ile Asn
            100                 105                 110

Ser Gly Val Ala Glu Leu Ile Trp Gln Asn Val Leu Asn Asp Asn Thr
        115                 120                 125

Ala Asp Glu Pro Phe Ala Ser Ala Ser Ile Leu Tyr Asp Asp Ala Ala
    130                 135                 140

Leu Trp Leu Lys Ser Trp Ile Pro Ser Thr His Leu Val Gln Gly Arg
145                 150                 155                 160
```

```
Ile Glu Ala Leu Glu Arg Leu Ala Glu Asp Gly Ile Ala Asn Arg Phe
            165                 170                 175

Thr Arg Asn Met Ala Tyr Leu Leu Phe Ala Asn Asn Leu Val Asp Tyr
            180                 185                 190

Ala Gln Lys Tyr Arg Gly Met Gln Ser Val Val Leu His Glu Leu Glu
            195                 200                 205

Ala Phe Ala Asp Ile Thr Leu Ser Thr Glu Lys Ser Gly Thr Trp Thr
            210                 215                 220

Ile Pro Pro Tyr Phe Ile Asp Ser Val Ala His Leu Ala Gly Phe Val
225                 230                 235                 240

Met Asn Val Ser Asp Ala Ile Asp Thr Lys Ala Asn Tyr Cys Val Thr
            245                 250                 255

Pro Gly Trp Lys Ser Leu Arg Phe Ala Lys Pro Leu Val Ala Gly Ala
            260                 265                 270

Lys Tyr Arg Ser Tyr Val Lys Met Ile Gln Thr Glu Glu Asp Pro Thr
            275                 280                 285

Val Tyr Leu Gly Asp Val Tyr Ile Met Gln Asp Gly Ala Ile Ile Gly
            290                 295                 300

Met Cys Gly Gly Ile Gln Phe Arg Arg Tyr Pro Arg Ile Leu Leu Asn
305                 310                 315                 320

Arg Phe Phe Thr Ala Pro Glu Glu Ala Gly Ala Ile Ser His Ala Ala
            325                 330                 335

Ala Ser Ser Thr Pro Ala Pro Arg Thr Lys Pro Glu Pro Val Pro Val
            340                 345                 350

Ala Thr Pro Ala Thr Ala Ala Ala Pro Val Ala Gln Ser Pro Ala Ala
            355                 360                 365

Pro Ala Ser Val Thr Pro Ala Pro Ala Pro Ala Pro Ala Pro Gly Pro
            370                 375                 380

Thr Pro Ala Ala Ala Pro Ala Ala Ala Gly Glu Ser Asp Ser Val Ala
385                 390                 395                 400

Ala Lys Ala Leu Val
            405

<210> SEQ ID NO 66
<211> LENGTH: 720
<212> TYPE: DNA
<213> ORGANISM: Aspergillus nidulans
<220> FEATURE:
<221> NAME/KEY: CDS
<222> LOCATION: (1)..(720)
<223> OTHER INFORMATION: ZhuI-1 (type: SRPBCC) gene [GenBank ID number
      ANIA_10642) encoding a first small molecule foldase [GenBank ID
      number CBF80957]

<400> SEQUENCE: 66 atg aac cac ctg ctt gca cca cgg tct att ttc tac cta aat tca aaa        48
Met Asn His Leu Leu Ala Pro Arg Ser Ile Phe Tyr Leu Asn Ser Lys
1               5                   10                  15 gtg cct acg ata cgg cca gaa atc tta cga tgt cgc ctc ttt tgc tac        96
Val Pro Thr Ile Arg Pro Glu Ile Leu Arg Cys Arg Leu Phe Cys Tyr
            20                  25                  30 acc tcc agg ctt caa ggg tta ccg caa caa ccc tct tat aga caa agt       144
Thr Ser Arg Leu Gln Gly Leu Pro Gln Gln Pro Ser Tyr Arg Gln Ser
        35                  40                  45 tat aac cct caa ttt cag tct cga att gaa aaa cga act ttt ttg tcg       192
Tyr Asn Pro Gln Phe Gln Ser Arg Ile Glu Lys Arg Thr Phe Leu Ser
    50                  55                  60
```

| | | | | | | | | | | | | | | | |
|---|---|---|---|---|---|---|---|---|---|---|---|---|---|---|---|
| tca | ttt | atc | cct | tct | ccg | ccc | caa | gct | tct | aac | aat | ggg | gac | gga | aat | 240 |
| Ser | Phe | Ile | Pro | Ser | Pro | Pro | Gln | Ala | Ser | Asn | Asn | Gly | Asp | Gly | Asn |
| 65 | | | | 70 | | | | | 75 | | | | | 80 |

```
ggc aac aac aaa gcc cgc atc ctg aca gcc tcc cgc aca ctt ccc tac      288
Gly Asn Asn Lys Ala Arg Ile Leu Thr Ala Ser Arg Thr Leu Pro Tyr
             85                  90                  95 ccg cca tcc ccc tta ttc aac gta ata tcc tcc gtt gaa tcc tac gcc      336
Pro Pro Ser Pro Leu Phe Asn Val Ile Ser Ser Val Glu Ser Tyr Ala
            100                 105                 110 gag ttc ctc ccc ttc ctc acc gcg tcc act gtt acg gcc cgt gac ccc      384
Glu Phe Leu Pro Phe Leu Thr Ala Ser Thr Val Thr Ala Arg Asp Pro
        115                 120                 125 gag aca cgg tat ccg acg cag gcg tat ctc aca gtc gga tat ggg cct      432
Glu Thr Arg Tyr Pro Thr Gln Ala Tyr Leu Thr Val Gly Tyr Gly Pro
        130                 135                 140 ctt agc gag acg ttt acg tcg aag gtt gac tgt aat cgg gag agt tgg      480
Leu Ser Glu Thr Phe Thr Ser Lys Val Asp Cys Asn Arg Glu Ser Trp
145                 150                 155                 160 gtt gtt gag gcg cgg agc ggg gaa agg ttt ggg atc ttc gag tat ctg      528
Val Val Glu Ala Arg Ser Gly Glu Arg Phe Gly Ile Phe Glu Tyr Leu
                165                 170                 175 agc acg agg tgg gag ttg gtt ccg gag act gct tct gag ggg gga gac      576
Ser Thr Arg Trp Glu Leu Val Pro Glu Thr Ala Ser Glu Gly Gly Asp
            180                 185                 190 gcg agg acc acg gtt aat ctg gag atc cgg ttt gag ttt aag agt cag      624
Ala Arg Thr Thr Val Asn Leu Glu Ile Arg Phe Glu Phe Lys Ser Gln
        195                 200                 205 ttg tat gcg agt atg atg agt gca gtg gaa ggg cag atg gcg ggg att      672
Leu Tyr Ala Ser Met Met Ser Ala Val Glu Gly Gln Met Ala Gly Ile
    210                 215                 220 atg atc gag gca ttc gaa aag agg att aga gaa gtg cat ggg agg tga      720
Met Ile Glu Ala Phe Glu Lys Arg Ile Arg Glu Val His Gly Arg
225                 230                 235
```

<210> SEQ ID NO 67
<211> LENGTH: 239
<212> TYPE: PRT
<213> ORGANISM: Aspergillus nidulans

<400> SEQUENCE: 67

```
Met Asn His Leu Leu Ala Pro Arg Ser Ile Phe Tyr Leu Asn Ser Lys
1               5                   10                  15

Val Pro Thr Ile Arg Pro Glu Ile Leu Arg Cys Arg Leu Phe Cys Tyr
            20                  25                  30

Thr Ser Arg Leu Gln Gly Leu Pro Gln Gln Pro Ser Tyr Arg Gln Ser
        35                  40                  45

Tyr Asn Pro Gln Phe Gln Ser Arg Ile Glu Lys Arg Thr Phe Leu Ser
    50                  55                  60

Ser Phe Ile Pro Ser Pro Pro Gln Ala Ser Asn Asn Gly Asp Gly Asn
65                  70                  75                  80

Gly Asn Asn Lys Ala Arg Ile Leu Thr Ala Ser Arg Thr Leu Pro Tyr
                85                  90                  95

Pro Pro Ser Pro Leu Phe Asn Val Ile Ser Ser Val Glu Ser Tyr Ala
            100                 105                 110

Glu Phe Leu Pro Phe Leu Thr Ala Ser Thr Val Thr Ala Arg Asp Pro
        115                 120                 125

Glu Thr Arg Tyr Pro Thr Gln Ala Tyr Leu Thr Val Gly Tyr Gly Pro
    130                 135                 140
```

```
Leu Ser Glu Thr Phe Thr Ser Lys Val Asp Cys Asn Arg Glu Ser Trp
145                 150                 155                 160

Val Val Glu Ala Arg Ser Gly Glu Arg Phe Gly Ile Phe Glu Tyr Leu
                165                 170                 175

Ser Thr Arg Trp Glu Leu Val Pro Glu Thr Ala Ser Glu Gly Gly Asp
            180                 185                 190

Ala Arg Thr Thr Val Asn Leu Glu Ile Arg Phe Glu Phe Lys Ser Gln
        195                 200                 205

Leu Tyr Ala Ser Met Met Ser Ala Val Glu Gly Gln Met Ala Gly Ile
    210                 215                 220

Met Ile Glu Ala Phe Glu Lys Arg Ile Arg Glu Val His Gly Arg
225                 230                 235

<210> SEQ ID NO 68
<211> LENGTH: 621
<212> TYPE: DNA
<213> ORGANISM: Aspergillus nidulans
<220> FEATURE:
<221> NAME/KEY: CDS
<222> LOCATION: (1)..(621)
<223> OTHER INFORMATION: ZhuI-2 (type: SRPBCC) gene [GenBank ID number
      AN3000.2) encoding a first small molecule foldase [GenBank ID
      number XP_660604.1]

<400> SEQUENCE: 68 atg tcg tct ctc aac cat ccc gat acc ccg aac att ccc tct tcc tcc      48
Met Ser Ser Leu Asn His Pro Asp Thr Pro Asn Ile Pro Ser Ser Ser
1               5                   10                  15 gcc atc ctc ggc atc cag agc tcc act ctc att gat gcc ccc atc caa      96
Ala Ile Leu Gly Ile Gln Ser Ser Thr Leu Ile Asp Ala Pro Ile Gln
            20                  25                  30 gtc gtc tgg agc gct ctt aca gac aca tct acc tac ccg aga tgg aac     144
Val Val Trp Ser Ala Leu Thr Asp Thr Ser Thr Tyr Pro Arg Trp Asn
        35                  40                  45 cga ttt gta ccg cgg gtg acc gtt cgc gag cag cct gac tca ggc aac     192
Arg Phe Val Pro Arg Val Thr Val Arg Glu Gln Pro Asp Ser Gly Asn
    50                  55                  60 gag gat gca atc ctg aga aac gga aca aga ttc acg ttc cac gtc aac     240
Glu Asp Ala Ile Leu Arg Asn Gly Thr Arg Phe Thr Phe His Val Asn
65                  70                  75                  80 atg tac ccc gaa gca gat gac gaa ccg cag ccg caa aat aaa aat ctc     288
Met Tyr Pro Glu Ala Asp Asp Glu Pro Gln Pro Gln Asn Lys Asn Leu
                85                  90                  95 cgc gac acg ttc ctg aaa att ata gag gtc gag ccg ccg gcg tca aca     336
Arg Asp Thr Phe Leu Lys Ile Ile Glu Val Glu Pro Pro Ala Ser Thr
            100                 105                 110 gaa ccc gct gat agt ggc ttg agg aaa ggc aaa att gta tgg gcg tcg     384
Glu Pro Ala Asp Ser Gly Leu Arg Lys Gly Lys Ile Val Trp Ala Ser
        115                 120                 125 gac ccc gct gca gac gga tat gtc ata tct tca ttg ttg acc gcc gag     432
Asp Pro Ala Ala Asp Gly Tyr Val Ile Ser Ser Leu Leu Thr Ala Glu
    130                 135                 140 cgc gtc cat gag ctg gaa gag gtg ata gac ggc aat ggg aag aga atg     480
Arg Val His Glu Leu Glu Glu Val Ile Asp Gly Asn Gly Lys Arg Met
145                 150                 155                 160 aca atg gtg aca aat tgg gaa tcg cag gtg ggt ggt ctg gct tat gtg     528
Thr Met Val Thr Asn Trp Glu Ser Gln Val Gly Gly Leu Ala Tyr Val
                165                 170                 175 gtg aaa tgg atg ttt ggg ggc agg tta aaa ggg aat ttc aca att tgg     576
Val Lys Trp Met Phe Gly Gly Arg Leu Lys Gly Asn Phe Thr Ile Trp
            180                 185                 190
```

```
gag aat ggc ctg aag gaa tac gcc gaa cgg aac tgg gag aat tag        621
Glu Asn Gly Leu Lys Glu Tyr Ala Glu Arg Asn Trp Glu Asn
        195                 200                 205

<210> SEQ ID NO 69
<211> LENGTH: 206
<212> TYPE: PRT
<213> ORGANISM: Aspergillus nidulans

<400> SEQUENCE: 69

Met Ser Ser Leu Asn His Pro Asp Thr Pro Asn Ile Pro Ser Ser Ser
1               5                   10                  15

Ala Ile Leu Gly Ile Gln Ser Ser Thr Leu Ile Asp Ala Pro Ile Gln
            20                  25                  30

Val Val Trp Ser Ala Leu Thr Asp Thr Ser Thr Tyr Pro Arg Trp Asn
        35                  40                  45

Arg Phe Val Pro Arg Val Thr Val Arg Glu Gln Pro Asp Ser Gly Asn
    50                  55                  60

Glu Asp Ala Ile Leu Arg Asn Gly Thr Arg Phe Thr Phe His Val Asn
65                  70                  75                  80

Met Tyr Pro Glu Ala Asp Asp Glu Pro Gln Pro Gln Asn Lys Asn Leu
                85                  90                  95

Arg Asp Thr Phe Leu Lys Ile Ile Glu Val Glu Pro Pro Ala Ser Thr
            100                 105                 110

Glu Pro Ala Asp Ser Gly Leu Arg Lys Gly Lys Ile Val Trp Ala Ser
        115                 120                 125

Asp Pro Ala Ala Asp Gly Tyr Val Ile Ser Ser Leu Leu Thr Ala Glu
    130                 135                 140

Arg Val His Glu Leu Glu Glu Val Ile Asp Gly Asn Gly Lys Arg Met
145                 150                 155                 160

Thr Met Val Thr Asn Trp Glu Ser Gln Val Gly Gly Leu Ala Tyr Val
                165                 170                 175

Val Lys Trp Met Phe Gly Gly Arg Leu Lys Gly Asn Phe Thr Ile Trp
            180                 185                 190

Glu Asn Gly Leu Lys Glu Tyr Ala Glu Arg Asn Trp Glu Asn
        195                 200                 205

<210> SEQ ID NO 70
<211> LENGTH: 336
<212> TYPE: DNA
<213> ORGANISM: Aspergillus nidulans
<220> FEATURE:
<221> NAME/KEY: CDS
<222> LOCATION: (1)..(336)
<223> OTHER INFORMATION: AOC-1 (type: Dabb) gene [GenBank ID number
      AN8584.2) encoding a first small molecule synthase [GenBank ID
      number XP_681853.1]

<400> SEQUENCE: 70 atg tct gtg aca cat atc gtt gtc ttc cgc ttc aag gat gga acg agt    48
Met Ser Val Thr His Ile Val Val Phe Arg Phe Lys Asp Gly Thr Ser
1               5                   10                  15 gac gag aag atc gaa gag gtg tgc cgt gag gtt gta gcc ctc aag gag    96
Asp Glu Lys Ile Glu Glu Val Cys Arg Glu Val Val Ala Leu Lys Glu
            20                  25                  30 aag tgc att ttg cca cgg acc cag aag ccc tac att aaa tcc tac gtt   144
Lys Cys Ile Leu Pro Arg Thr Gln Lys Pro Tyr Ile Lys Ser Tyr Val
        35                  40                  45 ggt ggc aaa gac cac tcc cct gaa ggc gcc cag cat ggg atg acg cat   192
```

```
Gly Gly Lys Asp His Ser Pro Glu Gly Ala Gln His Gly Met Thr His
        50              55                  60 gcg ttt gtg gcc cag ttc gag agc cga gag gat cgc gac tac tac gtc        240
Ala Phe Val Ala Gln Phe Glu Ser Arg Glu Asp Arg Asp Tyr Tyr Val
 65              70                  75                  80 tcc aag gat ccc gtc cac ctg gaa ctt gga ccc cga att gcg ccg gtg        288
Ser Lys Asp Pro Val His Leu Glu Leu Gly Pro Arg Ile Ala Pro Val
                    85                  90                  95 gtc gag aca ttt ctg tgc cta gac ttc act cct ggg ctc att ctg tga        336
Val Glu Thr Phe Leu Cys Leu Asp Phe Thr Pro Gly Leu Ile Leu
                100                 105                 110

<210> SEQ ID NO 71
<211> LENGTH: 111
<212> TYPE: PRT
<213> ORGANISM: Aspergillus nidulans

<400> SEQUENCE: 71

Met Ser Val Thr His Ile Val Val Phe Arg Phe Lys Asp Gly Thr Ser
  1               5                  10                  15

Asp Glu Lys Ile Glu Glu Val Cys Arg Glu Val Val Ala Leu Lys Glu
                 20                  25                  30

Lys Cys Ile Leu Pro Arg Thr Gln Lys Pro Tyr Ile Lys Ser Tyr Val
             35                  40                  45

Gly Gly Lys Asp His Ser Pro Glu Gly Ala Gln His Gly Met Thr His
        50              55                  60

Ala Phe Val Ala Gln Phe Glu Ser Arg Glu Asp Arg Asp Tyr Tyr Val
 65              70                  75                  80

Ser Lys Asp Pro Val His Leu Glu Leu Gly Pro Arg Ile Ala Pro Val
                    85                  90                  95

Val Glu Thr Phe Leu Cys Leu Asp Phe Thr Pro Gly Leu Ile Leu
                100                 105                 110

<210> SEQ ID NO 72
<211> LENGTH: 333
<212> TYPE: DNA
<213> ORGANISM: Aspergillus nidulans
<220> FEATURE:
<221> NAME/KEY: CDS
<222> LOCATION: (1)..(333)
<223> OTHER INFORMATION: AOC-2 (type: Dabb) gene [GenBank ID number
      ANIA_01204) encoding a first small molecule foldase [GenBank ID
      number CBF87939.1]

<400> SEQUENCE: 72 atg ccc atc acg cac att gtt atg ttc caa gtc aag cag ggc ctc agc         48
Met Pro Ile Thr His Ile Val Met Phe Gln Val Lys Gln Gly Leu Ser
  1               5                  10                  15 gcc gaa acc gtc aac gac ctg tgt ttg cgg atg ctg tcc ctc aaa gac         96
Ala Glu Thr Val Asn Asp Leu Cys Leu Arg Met Leu Ser Leu Lys Asp
                 20                  25                  30 aaa tgc atc cac cct gtt tcc cag aag ccg tat att att tcc tca tcc        144
Lys Cys Ile His Pro Val Ser Gln Lys Pro Tyr Ile Ile Ser Ser Ser
             35                  40                  45 ggt ggc ata gat aac tcc ccc gaa ggg atg cag aac ggt atc acg cac        192
Gly Gly Ile Asp Asn Ser Pro Glu Gly Met Gln Asn Gly Ile Thr His
        50              55                  60 gct ttt gtg gtt gag ttc gcc aat gaa gag gac agg gct tat tat ctc        240
Ala Phe Val Val Glu Phe Ala Asn Glu Glu Asp Arg Ala Tyr Tyr Leu
 65              70                  75                  80 gag aag gac cct gcg cat ctg gaa ttt gtg ggc agt ttg aag gac gta        288
Glu Lys Asp Pro Ala His Leu Glu Phe Val Gly Ser Leu Lys Asp Val
```

```
                Glu Lys Asp Pro Ala His Leu Glu Phe Val Gly Ser Leu Lys Asp Val
                                85                  90                  95 att gag aag gcg cag gtc gtc gac ttc acc aac ggt gtg ttt tga               333
Ile Glu Lys Ala Gln Val Val Asp Phe Thr Asn Gly Val Phe
            100                 105                 110

<210> SEQ ID NO 73
<211> LENGTH: 110
<212> TYPE: PRT
<213> ORGANISM: Aspergillus nidulans

<400> SEQUENCE: 73

Met Pro Ile Thr His Ile Val Met Phe Gln Val Lys Gln Gly Leu Ser
1               5                   10                  15

Ala Glu Thr Val Asn Asp Leu Cys Leu Arg Met Leu Ser Leu Lys Asp
                20                  25                  30

Lys Cys Ile His Pro Val Ser Gln Lys Pro Tyr Ile Ser Ser Ser
            35                  40                  45

Gly Gly Ile Asp Asn Ser Pro Glu Gly Met Gln Asn Gly Ile Thr His
        50                  55                  60

Ala Phe Val Val Glu Phe Ala Asn Glu Glu Asp Arg Ala Tyr Tyr Leu
65                  70                  75                  80

Glu Lys Asp Pro Ala His Leu Glu Phe Val Gly Ser Leu Lys Asp Val
                85                  90                  95

Ile Glu Lys Ala Gln Val Val Asp Phe Thr Asn Gly Val Phe
            100                 105                 110

<210> SEQ ID NO 74
<211> LENGTH: 486
<212> TYPE: DNA
<213> ORGANISM: Aspergillus nidulans
<220> FEATURE:
<221> NAME/KEY: CDS
<222> LOCATION: (1)..(486)
<223> OTHER INFORMATION: AOC-3 (type: Dabb) gene [GenBank ID number
      ANIA_10997) encodign a first small molecule synthase [GenBank ID
      number CBF79774.1]

<400> SEQUENCE: 74 atg ctg aac gat gat gca gtg ctt ttc aaa ttc cgc tcc ggt gtc act   48
Met Leu Asn Asp Asp Ala Val Leu Phe Lys Phe Arg Ser Gly Val Thr
1               5                   10                  15 tta gag cag aag aac aag ttt att cga gag ctc aag aca ctg aag aat   96
Leu Glu Gln Lys Asn Lys Phe Ile Arg Glu Leu Lys Thr Leu Lys Asn
                20                  25                  30 cta cct tca gtc aag aat gga cgg ctc att gtc ggt agc ccc agc gcc  144
Leu Pro Ser Val Lys Asn Gly Arg Leu Ile Val Gly Ser Pro Ser Ala
            35                  40                  45 acg gat ccc att gaa cga agc aaa ggg ttt caa ata gct ctt gtg agt  192
Thr Asp Pro Ile Glu Arg Ser Lys Gly Phe Gln Ile Ala Leu Val Ser
        50                  55                  60 tac cac gaa aac ctg gcg gct ctg gca gaa tac caa gcc agc gag gac  240
Tyr His Glu Asn Leu Ala Ala Leu Ala Glu Tyr Gln Ala Ser Glu Asp
65                  70                  75                  80 cat cac cgg gta acg tct aca tac ttc att ccg tac aag gag gat ttg  288
His His Arg Val Thr Ser Thr Tyr Phe Ile Pro Tyr Lys Glu Asp Leu
                85                  90                  95 att cga ttt gat ttt gag gta gat gtt gag gac gaa tat atg tgt ggt  336
Ile Arg Phe Asp Phe Glu Val Asp Val Glu Asp Glu Tyr Met Cys Gly
            100                 105                 110 ggc aac cgg ttc ggg agc tcc gct aac cta acg gat ctt ctc cgt cag  384
```

```
Gly Asn Arg Phe Gly Ser Ser Ala Asn Leu Thr Asp Leu Leu Arg Gln
            115                 120                 125 acc ttt ttc tcc aca tct tct act tcc aca ggc tcg ttt acg tac ggg      432
Thr Phe Phe Ser Thr Ser Ser Thr Ser Thr Gly Ser Phe Thr Tyr Gly
130                 135                 140 cgc aat tgt caa gac gta agc acc aga ttt aca att gga cat tta gag      480
Arg Asn Cys Gln Asp Val Ser Thr Arg Phe Thr Ile Gly His Leu Glu
145                 150                 155                 160 gcc taa                                                              486
Ala

<210> SEQ ID NO 75
<211> LENGTH: 161
<212> TYPE: PRT
<213> ORGANISM: Aspergillus nidulans

<400> SEQUENCE: 75

Met Leu Asn Asp Asp Ala Val Leu Phe Lys Phe Arg Ser Gly Val Thr
1               5                   10                  15

Leu Glu Gln Lys Asn Lys Phe Ile Arg Glu Leu Lys Thr Leu Lys Asn
                20                  25                  30

Leu Pro Ser Val Lys Asn Gly Arg Leu Ile Val Gly Ser Pro Ser Ala
            35                  40                  45

Thr Asp Pro Ile Glu Arg Ser Lys Gly Phe Gln Ile Ala Leu Val Ser
    50                  55                  60

Tyr His Glu Asn Leu Ala Ala Leu Ala Glu Tyr Gln Ala Ser Glu Asp
65                  70                  75                  80

His His Arg Val Thr Ser Thr Tyr Phe Ile Pro Tyr Lys Glu Asp Leu
                85                  90                  95

Ile Arg Phe Asp Phe Glu Val Asp Val Glu Asp Glu Tyr Met Cys Gly
            100                 105                 110

Gly Asn Arg Phe Gly Ser Ser Ala Asn Leu Thr Asp Leu Leu Arg Gln
            115                 120                 125

Thr Phe Phe Ser Thr Ser Ser Thr Ser Thr Gly Ser Phe Thr Tyr Gly
130                 135                 140

Arg Asn Cys Gln Asp Val Ser Thr Arg Phe Thr Ile Gly His Leu Glu
145                 150                 155                 160

Ala

<210> SEQ ID NO 76
<211> LENGTH: 309
<212> TYPE: DNA
<213> ORGANISM: Aspergillus nidulans
<220> FEATURE:
<221> NAME/KEY: CDS
<222> LOCATION: (1)..(309)
<223> OTHER INFORMATION: AOC-4 (type: Dabb) gene [GenBank ID number
      ANIA_11021] encoding a first small molecule foldase [GenBank ID
      number CBF80167.1]

<400> SEQUENCE: 76 atg ccg gta tat cac gtc gcc cta ttc aaa ctc aaa cca gac gcc gac      48
Met Pro Val Tyr His Val Ala Leu Phe Lys Leu Lys Pro Asp Ala Asp
1               5                   10                  15 cct aac cgt atc tgt tta tgg cag gag ctc gcg cac gca atg gtc ggc      96
Pro Asn Arg Ile Cys Leu Trp Gln Glu Leu Ala His Ala Met Val Gly
                20                  25                  30 aag gta cct ggc cta ctg gat ctg caa gct ggg cct ccc ctc gac ttc      144
Lys Val Pro Gly Leu Leu Asp Leu Gln Ala Gly Pro Pro Leu Asp Phe
            35                  40                  45
```

```
acg gct cga ctg gcg aaa ggg ttt gat atg ggt gta gtc gtg ctg cta    192
Thr Ala Arg Leu Ala Lys Gly Phe Asp Met Gly Val Val Val Leu Leu
         50                  55                  60 gac tat gtg gag tct ctc gct acc atg ttt acg cat ccg agc cat gac    240
Asp Tyr Val Glu Ser Leu Ala Thr Met Phe Thr His Pro Ser His Asp
 65                  70                  75                  80 caa gtt cac gaa ttg tac cag gag gtt tgc gag gac ggg agt act gtt    288
Gln Val His Glu Leu Tyr Gln Glu Val Cys Glu Asp Gly Ser Thr Val
                 85                  90                  95 ggt tac gat att gaa ttc tag                                        309
Gly Tyr Asp Ile Glu Phe
            100

<210> SEQ ID NO 77
<211> LENGTH: 102
<212> TYPE: PRT
<213> ORGANISM: Aspergillus nidulans

<400> SEQUENCE: 77

Met Pro Val Tyr His Val Ala Leu Phe Lys Leu Lys Pro Asp Ala Asp
 1               5                  10                  15

Pro Asn Arg Ile Cys Leu Trp Gln Glu Leu Ala His Ala Met Val Gly
             20                  25                  30

Lys Val Pro Gly Leu Leu Asp Leu Gln Ala Gly Pro Pro Leu Asp Phe
         35                  40                  45

Thr Ala Arg Leu Ala Lys Gly Phe Asp Met Gly Val Val Val Leu Leu
     50                  55                  60

Asp Tyr Val Glu Ser Leu Ala Thr Met Phe Thr His Pro Ser His Asp
 65                  70                  75                  80

Gln Val His Glu Leu Tyr Gln Glu Val Cys Glu Asp Gly Ser Thr Val
                 85                  90                  95

Gly Tyr Asp Ile Glu Phe
            100

<210> SEQ ID NO 78
<211> LENGTH: 315
<212> TYPE: DNA
<213> ORGANISM: Aspergillus nidulans
<220> FEATURE:
<221> NAME/KEY: CDS
<222> LOCATION: (1)..(315)
<223> OTHER INFORMATION: AOC-5 (type: Dabb) gene [GenBank ID number
      AN1979.2) encoding a first small molecule foldase [GenBank ID
      number XP_659583.1]

<400> SEQUENCE: 78 atg gcc ccc atc gag cgc atc acc ctt ttc aag atc ccc gac gaa gca     48
Met Ala Pro Ile Glu Arg Ile Thr Leu Phe Lys Ile Pro Asp Glu Ala
 1               5                  10                  15 gcc cga gat cgt gtg ctg gag cag tac aag gtc ctt gcg aag acg gct     96
Ala Arg Asp Arg Val Leu Glu Gln Tyr Lys Val Leu Ala Lys Thr Ala
             20                  25                  30 gtt aag gac ggc aaa ccg tac att gtc tcc gcc gca gga ccg acg            144
Val Lys Asp Gly Lys Pro Tyr Ile Val Ser Ala Ala Gly Pro Thr
         35                  40                  45 atc ccg gac ccg cga tgt aaa ggt ttc aat ctc tcc gtt aag aca acg    192
Ile Pro Asp Pro Arg Cys Lys Gly Phe Asn Leu Ser Val Lys Thr Thr
     50                  55                  60 ttc gca tcg ctg gag gat atg aag tac tat gat aca gag tgt gag gcg    240
Phe Ala Ser Leu Glu Asp Met Lys Tyr Tyr Asp Thr Glu Cys Glu Ala
 65                  70                  75                  80
```

```
cac aag gcg ttg aag gcg gtt gcg gcg ccg gtg aag gag gat gtt ttg    288
His Lys Ala Leu Lys Ala Val Ala Ala Pro Val Lys Glu Asp Val Leu
                 85                  90                  95 acg act tac ttc gag agt gtg ctt tga                                315
Thr Thr Tyr Phe Glu Ser Val Leu
            100
```

<210> SEQ ID NO 79
<211> LENGTH: 104
<212> TYPE: PRT
<213> ORGANISM: Aspergillus nidulans

<400> SEQUENCE: 79

```
Met Ala Pro Ile Glu Arg Ile Thr Leu Phe Lys Ile Pro Asp Glu Ala
1                5                  10                  15

Ala Arg Asp Arg Val Leu Glu Gln Tyr Lys Val Leu Ala Lys Thr Ala
             20                  25                  30

Val Lys Asp Gly Lys Pro Tyr Ile Val Ser Ala Ala Gly Pro Thr
         35                  40                  45

Ile Pro Asp Pro Arg Cys Lys Gly Phe Asn Leu Ser Val Lys Thr Thr
50                  55                  60

Phe Ala Ser Leu Glu Asp Met Lys Tyr Tyr Asp Thr Glu Cys Glu Ala
65                  70                  75                  80

His Lys Ala Leu Lys Ala Val Ala Ala Pro Val Lys Glu Asp Val Leu
                85                  90                  95

Thr Thr Tyr Phe Glu Ser Val Leu
            100
```

<210> SEQ ID NO 80
<211> LENGTH: 771
<212> TYPE: DNA
<213> ORGANISM: Streptomyces sp. R1128
<220> FEATURE:
<221> NAME/KEY: CDS
<222> LOCATION: (1)..(771)
<223> OTHER INFORMATION: ZhuJ gene [GenBank ID number AF293442.1)
      encoding cylase [GenBank ID number AAG30196.1]

<400> SEQUENCE: 80

```
atg agc ggc cgc aag acg ttc ctc gac ctg agc ttc gcg acc cgg gac    48
Met Ser Gly Arg Lys Thr Phe Leu Asp Leu Ser Phe Ala Thr Arg Asp
1                5                  10                  15 acc ccc agc gag gcc acc ccg gtc gtc gtc gac ctg ctc gac cac gtg    96
Thr Pro Ser Glu Ala Thr Pro Val Val Val Asp Leu Leu Asp His Val
             20                  25                  30 acc ggc gcg acg gtg ctc ggg ctg agc ccc gag gac ttc ccc gac ggc   144
Thr Gly Ala Thr Val Leu Gly Leu Ser Pro Glu Asp Phe Pro Asp Gly
         35                  40                  45 atg gcc atc tcg aac gag acg gtc acc ctc acc acg cac acc ggc acg   192
Met Ala Ile Ser Asn Glu Thr Val Thr Leu Thr Thr His Thr Gly Thr
50                  55                  60 cac atg gac gcg ccg ctg cac tac ggc ccg ctc agc ggc ggc gtg ccg   240
His Met Asp Ala Pro Leu His Tyr Gly Pro Leu Ser Gly Gly Val Pro
65                  70                  75                  80 gcc aag tcg atc gac cag gtc ccg ctg gag tgg tgc tac ggc ccg ggc   288
Ala Lys Ser Ile Asp Gln Val Pro Leu Glu Trp Cys Tyr Gly Pro Gly
                85                  90                  95 gtg cgc ctg gac gtg cgg cac gtg ccg gcc ggc gac ggc atc acc gtc   336
Val Arg Leu Asp Val Arg His Val Pro Ala Gly Asp Gly Ile Thr Val
                100                 105                 110
```

```
gac cac ctc aac gcc gcg ctc gac gcc gcc gag cac gac ctg gcg ccc      384
Asp His Leu Asn Ala Ala Leu Asp Ala Ala Glu His Asp Leu Ala Pro
        115                 120                 125 ggc gac atc gtc atg ttg tgg acc ggc gcg gac gcc ctg tgg ggc acc      432
Gly Asp Ile Val Met Leu Trp Thr Gly Ala Asp Ala Leu Trp Gly Thr
130                 135                 140 cgc gag tac ctg tcc acc ttc ccc gga ctg acc ggc aag gga acg cag      480
Arg Glu Tyr Leu Ser Thr Phe Pro Gly Leu Thr Gly Lys Gly Thr Gln
145                 150                 155                 160 ttc ctg gtc gag gcg ggc gtg aag gtg atc ggc atc gac gcg tgg ggc      528
Phe Leu Val Glu Ala Gly Val Lys Val Ile Gly Ile Asp Ala Trp Gly
                165                 170                 175 ctg gac cgg ccg atg gcc gcg atg atc gag gag tac cgg cgt acc ggc      576
Leu Asp Arg Pro Met Ala Ala Met Ile Glu Glu Tyr Arg Arg Thr Gly
            180                 185                 190 gac aag ggc gcc ttg tgg ccg gcg cac gtc tac ggg cgc acc cgc gaa      624
Asp Lys Gly Ala Leu Trp Pro Ala His Val Tyr Gly Arg Thr Arg Glu
        195                 200                 205 tac ctc cag ttg gag aag ctc aac aac ctg ggc gcg ctg ccc ggc gcc      672
Tyr Leu Gln Leu Glu Lys Leu Asn Asn Leu Gly Ala Leu Pro Gly Ala
210                 215                 220 acc gga tac gac atc agt tgc ttc ccg gtc gcc gtc gcg ggc acc ggt      720
Thr Gly Tyr Asp Ile Ser Cys Phe Pro Val Ala Val Ala Gly Thr Gly
225                 230                 235                 240 gcg ggc tgg acc cgg gtg gtc gcc gtg ttc gag cag gaa gag gag gac      768
Ala Gly Trp Thr Arg Val Val Ala Val Phe Glu Gln Glu Glu Glu Asp
                245                 250                 255 tag                                                                   771
```

<210> SEQ ID NO 81
<211> LENGTH: 256
<212> TYPE: PRT
<213> ORGANISM: Streptomyces sp. R1128

<400> SEQUENCE: 81

```
Met Ser Gly Arg Lys Thr Phe Leu Asp Leu Ser Phe Ala Thr Arg Asp
1               5                   10                  15

Thr Pro Ser Glu Ala Thr Pro Val Val Asp Leu Leu Asp His Val
            20                  25                  30

Thr Gly Ala Thr Val Leu Gly Leu Ser Pro Glu Asp Phe Pro Asp Gly
        35                  40                  45

Met Ala Ile Ser Asn Glu Thr Val Leu Thr Thr His Thr Gly Thr
    50                  55                  60

His Met Asp Ala Pro Leu His Tyr Gly Pro Leu Ser Gly Gly Val Pro
65                  70                  75                  80

Ala Lys Ser Ile Asp Gln Val Pro Leu Glu Trp Cys Tyr Gly Pro Gly
                85                  90                  95

Val Arg Leu Asp Val Arg His Val Pro Ala Gly Asp Gly Ile Thr Val
            100                 105                 110

Asp His Leu Asn Ala Ala Leu Asp Ala Ala Glu His Asp Leu Ala Pro
        115                 120                 125

Gly Asp Ile Val Met Leu Trp Thr Gly Ala Asp Ala Leu Trp Gly Thr
    130                 135                 140

Arg Glu Tyr Leu Ser Thr Phe Pro Gly Leu Thr Gly Lys Gly Thr Gln
145                 150                 155                 160

Phe Leu Val Glu Ala Gly Val Lys Val Ile Gly Ile Asp Ala Trp Gly
                165                 170                 175
```

```
Leu Asp Arg Pro Met Ala Ala Met Ile Glu Glu Tyr Arg Arg Thr Gly
            180                 185                 190

Asp Lys Gly Ala Leu Trp Pro Ala His Val Tyr Gly Arg Thr Arg Glu
        195                 200                 205

Tyr Leu Gln Leu Glu Lys Leu Asn Asn Leu Gly Ala Leu Pro Gly Ala
            210                 215                 220

Thr Gly Tyr Asp Ile Ser Cys Phe Pro Val Val Ala Gly Thr Gly
225                 230                 235                 240

Ala Gly Trp Thr Arg Val Val Ala Val Phe Glu Gln Glu Glu Glu Asp
                245                 250                 255

<210> SEQ ID NO 82
<211> LENGTH: 774
<212> TYPE: DNA
<213> ORGANISM: Streptomyces rimosus
<220> FEATURE:
<221> NAME/KEY: CDS
<222> LOCATION: (1)..(774)
<223> OTHER INFORMATION: oxyN gene [GenBank ID number DQ143963.2
      position 14855 to 15628) encoding  cylase [GenBank ID number
      AAZ78337.1]

<400> SEQUENCE: 82 atg cgc atc atc gat ctg tcg aca acc gtg gac gcc ggc cgg tgg gag        48
Met Arg Ile Ile Asp Leu Ser Thr Thr Val Asp Ala Gly Arg Trp Glu
1               5                   10                  15 gtc gat ccg gtc gaa cac gaa atc ctc acc ccg gcc gag ggc ggc cgg        96
Val Asp Pro Val Glu His Glu Ile Leu Thr Pro Ala Glu Gly Gly Arg
            20                  25                  30 cac atg gcc gag ggg atg cgg cgc cac cac ggc atc gac ttc gac ccc       144
His Met Ala Glu Gly Met Arg Arg His His Gly Ile Asp Phe Asp Pro
        35                  40                  45 gcc gac ctc ccg gac ggc gaa ctg ctg tcc ctc gac acc ctg cgg ctg       192
Ala Asp Leu Pro Asp Gly Glu Leu Leu Ser Leu Asp Thr Leu Arg Leu
    50                  55                  60 acc acc cac acc ggc acc cac gtc gac gcc ccg tcg cac tac ggg tcc       240
Thr Thr His Thr Gly Thr His Val Asp Ala Pro Ser His Tyr Gly Ser
65                  70                  75                  80 cgc gcg cgc tac ggc acg ccg cgc cac atc gac cag atg cca ctg gac       288
Arg Ala Arg Tyr Gly Thr Pro Arg His Ile Asp Gln Met Pro Leu Asp
                85                  90                  95 tgg ttt ctg cgg ccg ggc ctc aag ctc gac ctt acc gac gag ccg gtg       336
Trp Phe Leu Arg Pro Gly Leu Lys Leu Asp Leu Thr Asp Glu Pro Val
            100                 105                 110 ggc gcc atc gga gcc gac cgg ata cgg cgg gcc ctc gac gaa gcg ggc       384
Gly Ala Ile Gly Ala Asp Arg Ile Arg Arg Ala Leu Asp Glu Ala Gly
        115                 120                 125 cgc gac ccg cgt ccg tac gac atc gtg ctg ctg cac acc ggc gcg gac       432
Arg Asp Pro Arg Pro Tyr Asp Ile Val Leu Leu His Thr Gly Ala Asp
    130                 135                 140 cgg cgg gcc gga aag ccg gag tac ttc acc gag ttc gcc ggc ctg gac       480
Arg Arg Ala Gly Lys Pro Glu Tyr Phe Thr Glu Phe Ala Gly Leu Asp
145                 150                 155                 160 gcc gcg gcg acc cac ctg ctg ctc gac ttc ggc gtc cgg gtc atc ggc       528
Ala Ala Ala Thr His Leu Leu Leu Asp Phe Gly Val Arg Val Ile Gly
                165                 170                 175 acc gac gcc ttc agc ctc gac gcc ccg ttc ggg cac atg atc aag gag       576
Thr Asp Ala Phe Ser Leu Asp Ala Pro Phe Gly His Met Ile Lys Glu
            180                 185                 190 tac cag cgc acc ggc gac cgc ggt gtg ctg tgg ccc gcc cac ttc gtg       624
Tyr Gln Arg Thr Gly Asp Arg Gly Val Leu Trp Pro Ala His Phe Val
        195                 200                 205
```

|  |  |  |  |  | 195 |  |  |  | 200 |  |  |  | 205 |  |  |  |
|---|---|---|---|---|---|---|---|---|---|---|---|---|---|---|---|---|
| gga | cgg | gag | cgc | gag | tac | tgc | cag | atc | gag | cgg | ctg | gac | aac | ctc | ggc | 672 |
| Gly | Arg | Glu | Arg | Glu | Tyr | Cys | Gln | Ile | Glu | Arg | Leu | Asp | Asn | Leu | Gly |  |
|  | 210 |  |  |  |  | 215 |  |  |  |  | 220 |  |  |  |  |  |
| gcg | ctg | ccc | gga | ccg | gac | ggc | ttg | gtc | tcc | tgc | ttt | ccg | ttc | aag |  | 720 |
| Ala | Leu | Pro | Gly | Pro | Asp | Gly | Phe | Leu | Val | Ser | Cys | Phe | Pro | Phe | Lys |  |
| 225 |  |  |  |  | 230 |  |  |  |  | 235 |  |  |  |  | 240 |  |
| atc | gcg | gga | gcg | ggg | gcg | ggg | tgg | acg | cgg | gcg | gtg | gcg | gtg | gtg | gag | 768 |
| Ile | Ala | Gly | Ala | Gly | Ala | Gly | Trp | Thr | Arg | Ala | Val | Ala | Val | Val | Glu |  |
|  |  |  |  | 245 |  |  |  |  | 250 |  |  |  |  | 255 |  |  |
| gag | tag |  |  |  |  |  |  |  |  |  |  |  |  |  |  | 774 |
| Glu |  |  |  |  |  |  |  |  |  |  |  |  |  |  |  |  |

<210> SEQ ID NO 83
<211> LENGTH: 257
<212> TYPE: PRT
<213> ORGANISM: Streptomyces rimosus

<400> SEQUENCE: 83

```
Met Arg Ile Ile Asp Leu Ser Thr Thr Val Asp Ala Gly Arg Trp Glu
1               5                   10                  15

Val Asp Pro Val Glu His Glu Ile Leu Thr Pro Ala Glu Gly Gly Arg
            20                  25                  30

His Met Ala Glu Gly Met Arg Arg His His Gly Ile Asp Phe Asp Pro
        35                  40                  45

Ala Asp Leu Pro Asp Gly Glu Leu Leu Ser Leu Asp Thr Leu Arg Leu
    50                  55                  60

Thr Thr His Thr Gly Thr His Val Asp Ala Pro Ser His Tyr Gly Ser
65                  70                  75                  80

Arg Ala Arg Tyr Gly Thr Pro Arg His Ile Asp Gln Met Pro Leu Asp
                85                  90                  95

Trp Phe Leu Arg Pro Gly Leu Lys Leu Asp Leu Thr Asp Glu Pro Val
            100                 105                 110

Gly Ala Ile Gly Ala Asp Arg Ile Arg Arg Ala Leu Asp Glu Ala Gly
        115                 120                 125

Arg Asp Pro Arg Pro Tyr Asp Ile Val Leu Leu His Thr Gly Ala Asp
    130                 135                 140

Arg Arg Ala Gly Lys Pro Glu Tyr Phe Thr Glu Phe Ala Gly Leu Asp
145                 150                 155                 160

Ala Ala Ala Thr His Leu Leu Leu Asp Phe Gly Val Arg Val Ile Gly
                165                 170                 175

Thr Asp Ala Phe Ser Leu Asp Ala Pro Phe Gly His Met Ile Lys Glu
            180                 185                 190

Tyr Gln Arg Thr Gly Asp Arg Gly Val Leu Trp Pro Ala His Phe Val
        195                 200                 205

Gly Arg Glu Arg Glu Tyr Cys Gln Ile Glu Arg Leu Asp Asn Leu Gly
    210                 215                 220

Ala Leu Pro Gly Pro Asp Gly Phe Leu Val Ser Cys Phe Pro Phe Lys
225                 230                 235                 240

Ile Ala Gly Ala Gly Ala Gly Trp Thr Arg Ala Val Ala Val Val Glu
                245                 250                 255

Glu
```

<210> SEQ ID NO 84
<211> LENGTH: 330
<212> TYPE: DNA

```
<213> ORGANISM: Streptomyces venezuelae
<220> FEATURE:
<221> NAME/KEY: CDS
<222> LOCATION: (1)..(330)
<223> OTHER INFORMATION: jadI gene [GenBank ID number AAD37852.1
      position 2020 to 2349 ) encoding a polyketide cyclase [GenBank ID
      number AF126429.1]

<400> SEQUENCE: 84 atg cac agc act ctg atc gtg gcc cga atg gaa ccc gga tcg agc acc      48
Met His Ser Thr Leu Ile Val Ala Arg Met Glu Pro Gly Ser Ser Thr
1               5                   10                  15 gac gtg gcg aag ctg ttc gcc gaa ttc gac gcc tcc gag atg ccg cat      96
Asp Val Ala Lys Leu Phe Ala Glu Phe Asp Ala Ser Glu Met Pro His
            20                  25                  30 ctc atg ggg acg cga cgc gtc cag ctg ttc tcg tac cgc ggc ctc tac     144
Leu Met Gly Thr Arg Arg Arg Gln Leu Phe Ser Tyr Arg Gly Leu Tyr
        35                  40                  45 ttc cac ctc cag gac ttc gac gcc gac aac ggc ggc gag ctc atc gag     192
Phe His Leu Gln Asp Phe Asp Ala Asp Asn Gly Gly Glu Leu Ile Glu
    50                  55                  60 cgg gcc aag acc gac ccc cgc ttc gtg ggc atc agc gag gac ctg aag     240
Arg Ala Lys Thr Asp Pro Arg Phe Val Gly Ile Ser Glu Asp Leu Lys
65                  70                  75                  80 ccg ttc atc gag gcc tac gac ccg gcc acc tgg cgc tcg ccc gcc gac     288
Pro Phe Ile Glu Ala Tyr Asp Pro Ala Thr Trp Arg Ser Pro Ala Asp
                85                  90                  95 gcc atg gcc acc cgc ttc tac aac tgg gag gcg aac gcg tga             330
Ala Met Ala Thr Arg Phe Tyr Asn Trp Glu Ala Asn Ala
            100                 105

<210> SEQ ID NO 85
<211> LENGTH: 109
<212> TYPE: PRT
<213> ORGANISM: Streptomyces venezuelae

<400> SEQUENCE: 85

Met His Ser Thr Leu Ile Val Ala Arg Met Glu Pro Gly Ser Ser Thr
1               5                   10                  15

Asp Val Ala Lys Leu Phe Ala Glu Phe Asp Ala Ser Glu Met Pro His
            20                  25                  30

Leu Met Gly Thr Arg Arg Arg Gln Leu Phe Ser Tyr Arg Gly Leu Tyr
        35                  40                  45

Phe His Leu Gln Asp Phe Asp Ala Asp Asn Gly Gly Glu Leu Ile Glu
    50                  55                  60

Arg Ala Lys Thr Asp Pro Arg Phe Val Gly Ile Ser Glu Asp Leu Lys
65                  70                  75                  80

Pro Phe Ile Glu Ala Tyr Asp Pro Ala Thr Trp Arg Ser Pro Ala Asp
                85                  90                  95

Ala Met Ala Thr Arg Phe Tyr Asn Trp Glu Ala Asn Ala
            100                 105

<210> SEQ ID NO 86
<211> LENGTH: 330
<212> TYPE: DNA
<213> ORGANISM: Streptomyces globisporus
<220> FEATURE:
<221> NAME/KEY: CDS
<222> LOCATION: (1)..(330)
<223> OTHER INFORMATION: LndF gene [GenBank ID number AY659997.1)
      encoding a polyketide cyclase [GenBank ID number AAU04837.1]

<400> SEQUENCE: 86
```

```
atg cac agc aca ctg atc gtc gcc cgg atg gac ccc gcg tcg agc atc      48
Met His Ser Thr Leu Ile Val Ala Arg Met Asp Pro Ala Ser Ser Ile
1               5                   10                  15 gac gtg gcg gaa ctc ttc ggc gag ttc gac cgc acc gag atg ccc cac      96
Asp Val Ala Glu Leu Phe Gly Glu Phe Asp Arg Thr Glu Met Pro His
            20                  25                  30 cgc atg ggc acc agg cgt cgg cag ctc ttc tcg tat cgc gga ctg tac     144
Arg Met Gly Thr Arg Arg Gln Leu Phe Ser Tyr Arg Gly Leu Tyr
        35                  40                  45 ttc cac ctg cag gac ttc gac tcc gac aac ggc gga gag ctg atc gag     192
Phe His Leu Gln Asp Phe Asp Ser Asp Asn Gly Gly Glu Leu Ile Glu
    50                  55                  60 gag gcc aag agc gac ccg cgc ttc gcg gcg atc agc cag gac ctg aag     240
Glu Ala Lys Ser Asp Pro Arg Phe Ala Ala Ile Ser Gln Asp Leu Lys
65                  70                  75                  80 ccc ttc atc gaa gcg tac gac ccg gcc acc tgg cgt tcc ccg gcc gat     288
Pro Phe Ile Glu Ala Tyr Asp Pro Ala Thr Trp Arg Ser Pro Ala Asp
                85                  90                  95 gcg atg gcc acc cgc ttc tac aac tgg acg acg tcg tca taa             330
Ala Met Ala Thr Arg Phe Tyr Asn Trp Thr Thr Ser Ser
                100                 105

<210> SEQ ID NO 87
<211> LENGTH: 109
<212> TYPE: PRT
<213> ORGANISM: Streptomyces globisporus

<400> SEQUENCE: 87

Met His Ser Thr Leu Ile Val Ala Arg Met Asp Pro Ala Ser Ser Ile
1               5                   10                  15

Asp Val Ala Glu Leu Phe Gly Glu Phe Asp Arg Thr Glu Met Pro His
            20                  25                  30

Arg Met Gly Thr Arg Arg Gln Leu Phe Ser Tyr Arg Gly Leu Tyr
        35                  40                  45

Phe His Leu Gln Asp Phe Asp Ser Asp Asn Gly Gly Glu Leu Ile Glu
    50                  55                  60

Glu Ala Lys Ser Asp Pro Arg Phe Ala Ala Ile Ser Gln Asp Leu Lys
65                  70                  75                  80

Pro Phe Ile Glu Ala Tyr Asp Pro Ala Thr Trp Arg Ser Pro Ala Asp
                85                  90                  95

Ala Met Ala Thr Arg Phe Tyr Asn Trp Thr Thr Ser Ser
                100                 105

<210> SEQ ID NO 88
<211> LENGTH: 336
<212> TYPE: DNA
<213> ORGANISM: Streptomyces coelicoflavus
<220> FEATURE:
<221> NAME/KEY: CDS
<222> LOCATION: (1)..(336)
<223> OTHER INFORMATION: pgaF gene [GenBank ID number AHGS01000054.1
      position 6389 to 6724) encoding a polyketide cyclase [GenBank ID
      number EHN79050.1]

<400> SEQUENCE: 88 atg gtc gcg cga atg gac gcg gcg aat tcc acg gaa gtg tcg agg ctg      48
Met Val Ala Arg Met Asp Ala Ala Asn Ser Thr Glu Val Ser Arg Leu
1               5                   10                  15 ttc tcc gcg tcg gac gcc acg tcc ctg ccg cac gat ctc ggc gtg cgc      96
Phe Ser Ala Ser Asp Ala Thr Ser Leu Pro His Asp Leu Gly Val Arg
            20                  25                  30
```

```
ggg cgt cgg ctc ttt cgc tat cac ggc ctg tac ttc cat ctc gtc gaa     144
Gly Arg Arg Leu Phe Arg Tyr His Gly Leu Tyr Phe His Leu Val Glu
            35                  40                  45 ttc gac ggc acc cac acc gac ccg gtg gcc gtg gcc cgc ggc cgt gcg     192
Phe Asp Gly Thr His Thr Asp Pro Val Ala Val Ala Arg Gly Arg Ala
 50                  55                  60 gac ttc cag cgg ctc agc gag gaa ctg agc ccg ttc gtg ctg ccc ttc     240
Asp Phe Gln Arg Leu Ser Glu Glu Leu Ser Pro Phe Val Leu Pro Phe
 65                  70                  75                  80 gaa ccg gcg acc tgg cgg ggg ccg gag tcg gcc atg gcg gag gag ttc     288
Glu Pro Ala Thr Trp Arg Gly Pro Glu Ser Ala Met Ala Glu Glu Phe
                 85                  90                  95 tac tcc tgg acc gcc gcc ccg gcg gtg ccc ccc cgg ccc gcg ggc tga     336
Tyr Ser Trp Thr Ala Ala Pro Ala Val Pro Pro Arg Pro Ala Gly
            100                 105                 110

<210> SEQ ID NO 89
<211> LENGTH: 111
<212> TYPE: PRT
<213> ORGANISM: Streptomyces coelicoflavus

<400> SEQUENCE: 89

Met Val Ala Arg Met Asp Ala Ala Asn Ser Thr Glu Val Ser Arg Leu
 1               5                  10                  15

Phe Ser Ala Ser Asp Ala Thr Ser Leu Pro His Asp Leu Gly Val Arg
             20                  25                  30

Gly Arg Arg Leu Phe Arg Tyr His Gly Leu Tyr Phe His Leu Val Glu
         35                  40                  45

Phe Asp Gly Thr His Thr Asp Pro Val Ala Val Ala Arg Gly Arg Ala
 50                  55                  60

Asp Phe Gln Arg Leu Ser Glu Glu Leu Ser Pro Phe Val Leu Pro Phe
 65                  70                  75                  80

Glu Pro Ala Thr Trp Arg Gly Pro Glu Ser Ala Met Ala Glu Glu Phe
                 85                  90                  95

Tyr Ser Trp Thr Ala Ala Pro Ala Val Pro Pro Arg Pro Ala Gly
            100                 105                 110

<210> SEQ ID NO 90
<211> LENGTH: 894
<212> TYPE: DNA
<213> ORGANISM: Streptomyces coelicolor
<220> FEATURE:
<221> NAME/KEY: CDS
<222> LOCATION: (1)..(894)
<223> OTHER INFORMATION: Act_CYC gene [GenBank ID number X63449.1
      Position 3830 to 4723) encoding GenBank ID number CAA45047.1

<400> SEQUENCE: 90 atg acg gtc gag gtc cgt gag gtc gcc gag ggt gtc tac gcc tac gag     48
Met Thr Val Glu Val Arg Glu Val Ala Glu Gly Val Tyr Ala Tyr Glu
 1               5                  10                  15 cag gcc ccc ggc ggc tgg tgc gtc agc aac gcg ggc atc gtg gtg ggc     96
Gln Ala Pro Gly Gly Trp Cys Val Ser Asn Ala Gly Ile Val Val Gly
             20                  25                  30 ggc gac ggc gcg ctc gtc gtc gac acg ctg tcg acg atc ccg agg gcg     144
Gly Asp Gly Ala Leu Val Val Asp Thr Leu Ser Thr Ile Pro Arg Ala
         35                  40                  45 cgg cgg ctg gcg gag tgg gtc gac aag ctc gcc gcg ggc ccc ggc cgt     192
Arg Arg Leu Ala Glu Trp Val Asp Lys Leu Ala Ala Gly Pro Gly Arg
 50                  55                  60
```

| | | |
|---|---|---|
| acc gtg gtc aac acc cac ttc cac ggc gac cac gcc ttc ggc aac cag<br>Thr Val Val Asn Thr His Phe His Gly Asp His Ala Phe Gly Asn Gln<br>65                      70                      75                     80 | 240 |
| gtc ttc gcg ccg ggg acg cgg atc atc gcg cac gag gac atg cgg tcc<br>Val Phe Ala Pro Gly Thr Arg Ile Ile Ala His Glu Asp Met Arg Ser<br>                  85                      90                     95 | 288 |
| gcc atg gtg acg acc ggc ctg gcc ctc acc ggg ctc tgg ccg cgg gtc<br>Ala Met Val Thr Thr Gly Leu Ala Leu Thr Gly Leu Trp Pro Arg Val<br>              100                      105                    110 | 336 |
| gac tgg ggc gag atc gag ctg agg ccg ccg aac gtg acc ttc cgc gac<br>Asp Trp Gly Glu Ile Glu Leu Arg Pro Pro Asn Val Thr Phe Arg Asp<br>        115                      120                    125 | 384 |
| cgg ttg acc ctg cac gtc ggc gag cga cag gtc gaa ctg atc tgc gtc<br>Arg Leu Thr Leu His Val Gly Glu Arg Gln Val Glu Leu Ile Cys Val<br>130                      135                    140 | 432 |
| ggc ccc gcg cac acc gat cac gac gtg gtg gtc tgg ctg ccc gag gag<br>Gly Pro Ala His Thr Asp His Asp Val Val Val Trp Leu Pro Glu Glu<br>145                      150                    155                    160 | 480 |
| cgg gtg ctg ttc gcg ggg gac gtc gtc atg tcg ggc gtc act ccg ttc<br>Arg Val Leu Phe Ala Gly Asp Val Val Met Ser Gly Val Thr Pro Phe<br>                  165                      170                    175 | 528 |
| gcc ctc ttc ggt tcg gtg gcc ggc acg ctg gcc gcg ctc gac cgg ctg<br>Ala Leu Phe Gly Ser Val Ala Gly Thr Leu Ala Ala Leu Asp Arg Leu<br>                  180                      185                    190 | 576 |
| gcg gag ctg gag ccc gag gtg gtc gtc ggc ggg cac ggc ccg gtg gcg<br>Ala Glu Leu Glu Pro Glu Val Val Val Gly Gly His Gly Pro Val Ala<br>        195                      200                    205 | 624 |
| gga ccc gag gtg atc gac gcc aac cgg gac tat ctg cgc tgg gtc cag<br>Gly Pro Glu Val Ile Asp Ala Asn Arg Asp Tyr Leu Arg Trp Val Gln<br>210                      215                    220 | 672 |
| cgc ctc gcc gcc gat gcg gtc gac cgc cgg ctg aca ccg ttg cag gcc<br>Arg Leu Ala Ala Asp Ala Val Asp Arg Arg Leu Thr Pro Leu Gln Ala<br>225                      230                    235                    240 | 720 |
| gcg cgc cgg gcg gac ctc ggc gcc ttc gcc ggg ctg ctg gac gcg gag<br>Ala Arg Arg Ala Asp Leu Gly Ala Phe Ala Gly Leu Leu Asp Ala Glu<br>                  245                      250                    255 | 768 |
| cgc ctc gtc gcg aac ctg cac cgg gcc cac gag gag ctg ctg ggc ggg<br>Arg Leu Val Ala Asn Leu His Arg Ala His Glu Glu Leu Leu Gly Gly<br>                  260                      265                    270 | 816 |
| cac gtg cgt gac gcc atg gag atc ttc gcg gag ctg gtc gcc tac aac<br>His Val Arg Asp Ala Met Glu Ile Phe Ala Glu Leu Val Ala Tyr Asn<br>        275                      280                    285 | 864 |
| ggt ggg cag ctg ccc acc tgc ctc gcc tag<br>Gly Gly Gln Leu Pro Thr Cys Leu Ala<br>290                      295 | 894 |

<210> SEQ ID NO 91
<211> LENGTH: 297
<212> TYPE: PRT
<213> ORGANISM: Streptomyces coelicolor

<400> SEQUENCE: 91

Met Thr Val Glu Val Arg Glu Val Ala Glu Gly Val Tyr Ala Tyr Glu
1                 5                    10                    15

Gln Ala Pro Gly Gly Trp Cys Val Ser Asn Ala Gly Ile Val Val Gly
                20                    25                    30

Gly Asp Gly Ala Leu Val Val Asp Thr Leu Ser Thr Ile Pro Arg Ala
                35                    40                    45

Arg Arg Leu Ala Glu Trp Val Asp Lys Leu Ala Ala Gly Pro Gly Arg
50                      55                    60

```
Thr Val Val Asn Thr His Phe His Gly Asp His Ala Phe Gly Asn Gln
 65                  70                  75                  80

Val Phe Ala Pro Gly Thr Arg Ile Ile Ala His Glu Asp Met Arg Ser
             85                  90                  95

Ala Met Val Thr Thr Gly Leu Ala Leu Thr Gly Leu Trp Pro Arg Val
            100                 105                 110

Asp Trp Gly Glu Ile Glu Leu Arg Pro Pro Asn Val Thr Phe Arg Asp
            115                 120                 125

Arg Leu Thr Leu His Val Gly Glu Arg Gln Val Glu Leu Ile Cys Val
            130                 135                 140

Gly Pro Ala His Thr Asp His Asp Val Val Trp Leu Pro Glu Glu
145                 150                 155                 160

Arg Val Leu Phe Ala Gly Asp Val Val Met Ser Gly Val Thr Pro Phe
                165                 170                 175

Ala Leu Phe Gly Ser Val Ala Gly Thr Leu Ala Ala Leu Asp Arg Leu
                180                 185                 190

Ala Glu Leu Glu Pro Glu Val Val Gly Gly His Gly Pro Val Ala
            195                 200                 205

Gly Pro Glu Val Ile Asp Ala Asn Arg Asp Tyr Leu Arg Trp Val Gln
210                 215                 220

Arg Leu Ala Ala Asp Ala Val Asp Arg Arg Leu Thr Pro Leu Gln Ala
225                 230                 235                 240

Ala Arg Arg Ala Asp Leu Gly Ala Phe Ala Gly Leu Leu Asp Ala Glu
                245                 250                 255

Arg Leu Val Ala Asn Leu His Arg Ala His Glu Glu Leu Leu Gly Gly
                260                 265                 270

His Val Arg Asp Ala Met Glu Ile Phe Ala Glu Leu Val Ala Tyr Asn
                275                 280                 285

Gly Gly Gln Leu Pro Thr Cys Leu Ala
        290                 295

<210> SEQ ID NO 92
<211> LENGTH: 570
<212> TYPE: DNA
<213> ORGANISM: Streptomyces ansochromogenes
<220> FEATURE:
<221> NAME/KEY: CDS
<222> LOCATION: (1)..(570)
<223> OTHER INFORMATION: sanE gene [GenBank ID number AF228524.1
      position 15 to 584] encoding a cyclase [ GenBank ID number
      AAF61923.1]

<400> SEQUENCE: 92 atg gct cgg cct ggc cgc gtg ctg cgc ggg gac ggc ccc tgt cgg tcg    48
Met Ala Arg Pro Gly Arg Leu Arg Gly Asp Gly Pro Cys Arg Ser
1               5                   10                  15 ggt tcc tca cgc ggc cca ccc ggc cgg tgg cgg cgc ccg cgg ccg cgc    96
Gly Ser Ser Arg Gly Pro Pro Gly Arg Trp Arg Arg Pro Arg Pro Arg
                20                  25                  30 cgc tgc ggc gga tcg tcg tcg gcg gga tca gcg gcg cgg gca aga cga   144
Arg Cys Gly Gly Ser Ser Ser Ala Gly Ser Ala Ala Arg Ala Arg Arg
            35                  40                  45 cgc tgg ccg ccg ccc tgg ccg ggg cgc tgg aca tca ggc aca tcg aga   192
Arg Trp Pro Pro Pro Trp Pro Gly Arg Trp Thr Ser Gly Thr Ser Arg
50                  55                  60 tgg acg cgc tct acc acg gtc ccg gct gga ccc acc ggg cgg agt tcg   240
Trp Thr Arg Ser Thr Thr Val Pro Ala Gly Pro Thr Gly Arg Ser Ser
65                  70                  75                  80
```

```
cgg acg acg tgg agc gcg cca cgc ggg cac cgg cgt gga tct gcg acg      288
Arg Thr Thr Trp Ser Ala Pro Arg Gly His Arg Arg Gly Ser Ala Thr
            85                  90                  95 ccc agt acc act ggg tcg tcg gcg acc tgc tcg gcg agc gcg ccg aca      336
Pro Ser Thr Thr Gly Ser Ser Ala Thr Cys Ser Ala Ser Ala Pro Thr
            100                 105                 110 cgt tcg tct ggc tcg acc tgc ccc gcc gga ccg tca tgc gcc gcg tgc      384
Arg Ser Ser Gly Ser Thr Cys Pro Ala Gly Pro Ser Cys Ala Ala Cys
            115                 120                 125 tgc ggc gct cgg tgg tcc ggg ccg cca cgg gcc ggg aac tgt ggc acg      432
Cys Gly Ala Arg Trp Ser Gly Pro Pro Arg Ala Gly Asn Cys Gly Thr
    130                 135                 140 gca acc ggg aga cct ggc ggt cga tgc tgc gca acc cgc gcc acc cgc      480
Ala Thr Gly Arg Pro Gly Gly Arg Cys Cys Ala Thr Arg Ala Thr Arg
145                 150                 155                 160 tgc gct ggg cct ggt ccc agc acg cca ccc ggc ggg ccg aga cgg ccg      528
Cys Ala Gly Pro Gly Pro Ser Thr Pro Pro Gly Gly Pro Arg Arg Pro
            165                 170                 175 ctt tcc tcg gcc tgc acc ccg gcc tca ccg tcg tcc acc tga              570
Leu Ser Ser Ala Cys Thr Pro Ala Ser Pro Ser Ser Thr
            180                 185

<210> SEQ ID NO 93
<211> LENGTH: 189
<212> TYPE: PRT
<213> ORGANISM: Streptomyces ansochromogenes

<400> SEQUENCE: 93

Met Ala Arg Pro Gly Arg Arg Leu Arg Gly Asp Gly Pro Cys Arg Ser
1               5                   10                  15

Gly Ser Ser Arg Gly Pro Pro Gly Arg Trp Arg Arg Pro Arg
            20                  25                  30

Arg Cys Gly Gly Ser Ser Ala Gly Ser Ala Ala Arg Ala Arg Arg
            35                  40                  45

Arg Trp Pro Pro Pro Trp Pro Gly Arg Trp Thr Ser Gly Thr Ser Arg
    50                  55                  60

Trp Thr Arg Ser Thr Thr Val Pro Ala Gly Pro Thr Gly Arg Ser Ser
65                  70                  75                  80

Arg Thr Thr Trp Ser Ala Pro Arg Gly His Arg Arg Gly Ser Ala Thr
            85                  90                  95

Pro Ser Thr Thr Gly Ser Ser Ala Thr Cys Ser Ala Ser Ala Pro Thr
            100                 105                 110

Arg Ser Ser Gly Ser Thr Cys Pro Ala Gly Pro Ser Cys Ala Ala Cys
            115                 120                 125

Cys Gly Ala Arg Trp Ser Gly Pro Pro Arg Ala Gly Asn Cys Gly Thr
    130                 135                 140

Ala Thr Gly Arg Pro Gly Gly Arg Cys Cys Ala Thr Arg Ala Thr Arg
145                 150                 155                 160

Cys Ala Gly Pro Gly Pro Ser Thr Pro Pro Gly Gly Pro Arg Arg Pro
            165                 170                 175

Leu Ser Ser Ala Cys Thr Pro Ala Ser Pro Ser Ser Thr
            180                 185

<210> SEQ ID NO 94
<211> LENGTH: 324
<212> TYPE: DNA
<213> ORGANISM: Streptomyces sp. TA-0256
<220> FEATURE:
```

<221> NAME/KEY: CDS
<222> LOCATION: (1)..(324)
<223> OTHER INFORMATION: pnxK gene [GenBank ID number AB469194.1
      position 13057 to 13380) enclding a polyketide cyclase [GenBank ID
      number BAJ52679.1]

<400> SEQUENCE: 94

```
atg tat cag aac ctg atc gtc gcc cgg atg gat cct gcg gag gcg gac      48
Met Tyr Gln Asn Leu Ile Val Ala Arg Met Asp Pro Ala Glu Ala Asp
1               5                  10                  15 tcc gtc gcg aag atc ttc gcg gaa tcg gac gct tcc gac ttg ccg cac      96
Ser Val Ala Lys Ile Phe Ala Glu Ser Asp Ala Ser Asp Leu Pro His
            20                  25                  30 agg atc gga gtg tcc cgg cgg acg ctg tgg cgc ttc cac gat ctg tac     144
Arg Ile Gly Val Ser Arg Arg Thr Leu Trp Arg Phe His Asp Leu Tyr
        35                  40                  45 ttc cac ctc gtg gag ggc gag gag gac atc acg ccg aac ctc tac cgg     192
Phe His Leu Val Glu Gly Glu Glu Asp Ile Thr Pro Asn Leu Tyr Arg
    50                  55                  60 gcg cgc agc cac ccg ctc tac gag gac atc cac gtg aag ctc gcc agg     240
Ala Arg Ser His Pro Leu Tyr Glu Asp Ile His Val Lys Leu Ala Arg
65                  70                  75                  80 cac atc cgg ccg tac gac ccc gcg tgg agc gag ccg aag gac gcc atg     288
His Ile Arg Pro Tyr Asp Pro Ala Trp Ser Glu Pro Lys Asp Ala Met
                85                  90                  95 gcc agc ccg ttc tac acc tgg gag aac cgg cgg tga                     324
Ala Ser Pro Phe Tyr Thr Trp Glu Asn Arg Arg
            100                 105
```

<210> SEQ ID NO 95
<211> LENGTH: 107
<212> TYPE: PRT
<213> ORGANISM: Streptomyces sp. TA-0256

<400> SEQUENCE: 95

```
Met Tyr Gln Asn Leu Ile Val Ala Arg Met Asp Pro Ala Glu Ala Asp
1               5                  10                  15

Ser Val Ala Lys Ile Phe Ala Glu Ser Asp Ala Ser Asp Leu Pro His
            20                  25                  30

Arg Ile Gly Val Ser Arg Arg Thr Leu Trp Arg Phe His Asp Leu Tyr
        35                  40                  45

Phe His Leu Val Glu Gly Glu Glu Asp Ile Thr Pro Asn Leu Tyr Arg
    50                  55                  60

Ala Arg Ser His Pro Leu Tyr Glu Asp Ile His Val Lys Leu Ala Arg
65                  70                  75                  80

His Ile Arg Pro Tyr Asp Pro Ala Trp Ser Glu Pro Lys Asp Ala Met
                85                  90                  95

Ala Ser Pro Phe Tyr Thr Trp Glu Asn Arg Arg
            100                 105
```

<210> SEQ ID NO 96
<211> LENGTH: 525
<212> TYPE: DNA
<213> ORGANISM: Streptomyces sp. TA-0256
<220> FEATURE:
<221> NAME/KEY: CDS
<222> LOCATION: (1)..(525)
<223> OTHER INFORMATION: pnxL gene [GenBank ID number AB469194.1
      position 13377 to 13901 ) encoding Cupin_2 type cyclase [GenBank
      ID number BAJ52680.1]

<400> SEQUENCE: 96

| | | |
|---|---|---|
| atg agc ccc gac gcg acc aag gcg acc aag ccg acg gca acc aag gcg<br>Met Ser Pro Asp Ala Thr Lys Ala Thr Lys Pro Thr Ala Thr Lys Ala<br>1                      5                      10                    15 | 48 | |
| acc gac gtg acc ccg gca ccc gaa gtg acc cag gtg acg aac gtg acc<br>Thr Asp Val Thr Pro Ala Pro Glu Val Thr Gln Val Thr Asn Val Thr<br>                    20                      25                    30 | 96 | |
| aag gtg gcc ttc acc gac atc aag ccg aac cgg cgc agg ggc ggc gac<br>Lys Val Ala Phe Thr Asp Ile Lys Pro Asn Arg Arg Arg Gly Gly Asp<br>                35                      40                    45 | 144 | |
| gtc cgc gtc ctg ctg agc ccg ctg acg gcc ggt gcc acc tcg ggg ttc<br>Val Arg Val Leu Leu Ser Pro Leu Thr Ala Gly Ala Thr Ser Gly Phe<br>50                      55                      60 | 192 | |
| atg ggc acg gtg acg ctg gag ccc ggc gag cac gtc tgc gag cac tac<br>Met Gly Thr Val Thr Leu Glu Pro Gly Glu His Val Cys Glu His Tyr<br>65                      70                      75                    80 | 240 | |
| cac ccg tac tcc gag gag ttc gtc cac ctg gtc cgc ggg acc gtc gtg<br>His Pro Tyr Ser Glu Glu Phe Val His Leu Val Arg Gly Thr Val Val<br>                    85                      90                    95 | 288 | |
| ctc acc atc ggc ggc acc acg ctc acc ctg gag ccc ggg gac tcg gcc<br>Leu Thr Ile Gly Gly Thr Thr Leu Thr Leu Glu Pro Gly Asp Ser Ala<br>                    100                 105                 110 | 336 | |
| ctg gtc ccc atc ggt gtg cgc cac cgg ctg gtg aac gcc ggc tct gta<br>Leu Val Pro Ile Gly Val Arg His Arg Leu Val Asn Ala Gly Ser Val<br>                115                 120                 125 | 384 | |
| gcg gca cag gcc gtc ttc cat ctg ggg ccg ctg gcg ccc cgc ccg gaa<br>Ala Ala Gln Ala Val Phe His Leu Gly Pro Leu Ala Pro Arg Pro Glu<br>130                     135                 140 | 432 | |
| ctc ggc cac gtc gac acc gag ttc ctg ccc ggc gcc cgc gac gag ccc<br>Leu Gly His Val Asp Thr Glu Phe Leu Pro Gly Ala Arg Asp Glu Pro<br>145                     150                 155                 160 | 480 | |
| gtg ctc gaa gtc ggc gga ggc gga acc ccc ggg gcg ggc tca tga<br>Val Leu Glu Val Gly Gly Gly Gly Thr Pro Gly Ala Gly Ser<br>                    165                 170 | 525 | |

<210> SEQ ID NO 97
<211> LENGTH: 174
<212> TYPE: PRT
<213> ORGANISM: Streptomyces sp. TA-0256

<400> SEQUENCE: 97

Met Ser Pro Asp Ala Thr Lys Ala Thr Lys Pro Thr Ala Thr Lys Ala
1                   5                     10                    15

Thr Asp Val Thr Pro Ala Pro Glu Val Thr Gln Val Thr Asn Val Thr
                  20                     25                    30

Lys Val Ala Phe Thr Asp Ile Lys Pro Asn Arg Arg Arg Gly Gly Asp
                35                     40                    45

Val Arg Val Leu Leu Ser Pro Leu Thr Ala Gly Ala Thr Ser Gly Phe
50                      55                     60

Met Gly Thr Val Thr Leu Glu Pro Gly Glu His Val Cys Glu His Tyr
65                   70                     75                    80

His Pro Tyr Ser Glu Glu Phe Val His Leu Val Arg Gly Thr Val Val
                85                     90                    95

Leu Thr Ile Gly Gly Thr Thr Leu Thr Leu Glu Pro Gly Asp Ser Ala
                 100                 105                 110

Leu Val Pro Ile Gly Val Arg His Arg Leu Val Asn Ala Gly Ser Val
                115                 120                 125

Ala Ala Gln Ala Val Phe His Leu Gly Pro Leu Ala Pro Arg Pro Glu
    130                     135                 140

```
Leu Gly His Val Asp Thr Glu Phe Leu Pro Gly Ala Arg Asp Glu Pro
145                 150                 155                 160

Val Leu Glu Val Gly Gly Gly Thr Pro Gly Ala Gly Ser
                165                 170
```

<210> SEQ ID NO 98
<211> LENGTH: 429
<212> TYPE: DNA
<213> ORGANISM: Streptomyces tendae
<220> FEATURE:
<221> NAME/KEY: CDS
<222> LOCATION: (1)..(429)
<223> OTHER INFORMATION: llpCII gene [GenBank ID number AM492533.1 position 12120 to 12548) encoding a Cupin_2 enzyme [GenBank ID number CAM34346.1]

<400> SEQUENCE: 98

```
atg acc gcg gag cgc agg ctg aag gtc aac gcg cgg gag gtc tcc gcg      48
Met Thr Ala Glu Arg Arg Leu Lys Val Asn Ala Arg Glu Val Ser Ala
1               5                   10                  15 aac cgc agg cgc ggc gga gag ctg cgg gtg acc gtc agc ccc agg acg      96
Asn Arg Arg Arg Gly Gly Glu Leu Arg Val Thr Val Ser Pro Arg Thr
                20                  25                  30 gtc ggc tgc acc tcc gga ttc ggc ggc ctg ctg agg ctg gag ccc ggt     144
Val Gly Cys Thr Ser Gly Phe Gly Gly Leu Leu Arg Leu Glu Pro Gly
            35                  40                  45 gag ttc gtc acc gag cac tac cac ccg tac tcc gag gag ttc ctg cac     192
Glu Phe Val Thr Glu His Tyr His Pro Tyr Ser Glu Glu Phe Leu His
        50                  55                  60 gtg atc tcg ggc cgg ctg gag atg acc ctg gac ggc gaa ccg gtc cgg     240
Val Ile Ser Gly Arg Leu Glu Met Thr Leu Asp Gly Glu Pro Val Arg
65                  70                  75                  80 ctc ggc ccc gga gac tcg ctg tac gtc ccg atc ggg gtg cgg cac cgg     288
Leu Gly Pro Gly Asp Ser Leu Tyr Val Pro Ile Gly Val Arg His Arg
                85                  90                  95 ctg gtg aac acc ggc gac gaa ccg gcg acc ggc gtg ttc cac ctc tcg     336
Leu Val Asn Thr Gly Asp Glu Pro Ala Thr Gly Val Phe His Leu Ser
            100                 105                 110 ccc ctg gca ccg cgg ccc gaa ctc ggc cac gtc gac acc gag ccg gtg     384
Pro Leu Ala Pro Arg Pro Glu Leu Gly His Val Asp Thr Glu Pro Val
        115                 120                 125 ccg gcg gcc gac gag gcg cta ccg gac gtc ggg acc gcg acg tga         429
Pro Ala Ala Asp Glu Ala Leu Pro Asp Val Gly Thr Ala Thr
130                 135                 140
```

<210> SEQ ID NO 99
<211> LENGTH: 142
<212> TYPE: PRT
<213> ORGANISM: Streptomyces tendae

<400> SEQUENCE: 99

```
Met Thr Ala Glu Arg Arg Leu Lys Val Asn Ala Arg Glu Val Ser Ala
1               5                   10                  15

Asn Arg Arg Arg Gly Gly Glu Leu Arg Val Thr Val Ser Pro Arg Thr
                20                  25                  30

Val Gly Cys Thr Ser Gly Phe Gly Gly Leu Leu Arg Leu Glu Pro Gly
            35                  40                  45

Glu Phe Val Thr Glu His Tyr His Pro Tyr Ser Glu Glu Phe Leu His
        50                  55                  60

Val Ile Ser Gly Arg Leu Glu Met Thr Leu Asp Gly Glu Pro Val Arg
65                  70                  75                  80
```

```
Leu Gly Pro Gly Asp Ser Leu Tyr Val Pro Ile Gly Val Arg His Arg
                85                  90                  95

Leu Val Asn Thr Gly Asp Glu Pro Ala Thr Gly Val Phe His Leu Ser
            100                 105                 110

Pro Leu Ala Pro Arg Pro Glu Leu Gly His Val Asp Thr Glu Pro Val
        115                 120                 125

Pro Ala Ala Asp Glu Ala Leu Pro Asp Val Gly Thr Ala Thr
    130                 135                 140

<210> SEQ ID NO 100
<211> LENGTH: 336
<212> TYPE: DNA
<213> ORGANISM: Streptomyces tendae
<220> FEATURE:
<221> NAME/KEY: CDS
<222> LOCATION: (1)..(336)
<223> OTHER INFORMATION: llpCIII gene [GenBank ID number AM492533.1
      position 12545 to 12880] enclding a  Polyketide cyclase [GenBank
      ID number CAM34347.1]

<400> SEQUENCE: 100 atg cac cgc acc ctg atc gtc gcc agg ctg aaa acc ggc aat ccc gcc      48
Met His Arg Thr Leu Ile Val Ala Arg Leu Lys Thr Gly Asn Pro Ala
1               5                   10                  15 cgg atc gcg gag gtg ttc ggc gca tcg gac gcg acg gag ctg ccg cac      96
Arg Ile Ala Glu Val Phe Gly Ala Ser Asp Ala Thr Glu Leu Pro His
                20                  25                  30 atg gtc ggc gtg tcc cgg cgg acc ctg ttc acc ttc cac gac ctg tac     144
Met Val Gly Val Ser Arg Arg Thr Leu Phe Thr Phe His Asp Leu Tyr
            35                  40                  45 ttc cac ctc gtc gag gcc gac gag gac atc acc ccg aac ctg tac cgg     192
Phe His Leu Val Glu Ala Asp Glu Asp Ile Thr Pro Asn Leu Tyr Arg
        50                  55                  60 gcc cgc agc cac ccg ctg tac gcc gac gtc aac aaa cgg ctc ggc gaa     240
Ala Arg Ser His Pro Leu Tyr Ala Asp Val Asn Lys Arg Leu Gly Glu
65                  70                  75                  80 ctc gtc gcg ccc tac gac ccc ggc tgg aag gaa ccg aag gac gcc atg     288
Leu Val Ala Pro Tyr Asp Pro Gly Trp Lys Glu Pro Lys Asp Ala Met
                85                  90                  95 gca tca ccg ttc tac acc tgg acc gcc gag cag ggc agg atc cgg tga     336
Ala Ser Pro Phe Tyr Thr Trp Thr Ala Glu Gln Gly Arg Ile Arg
            100                 105                 110

<210> SEQ ID NO 101
<211> LENGTH: 111
<212> TYPE: PRT
<213> ORGANISM: Streptomyces tendae

<400> SEQUENCE: 101

Met His Arg Thr Leu Ile Val Ala Arg Leu Lys Thr Gly Asn Pro Ala
1               5                   10                  15

Arg Ile Ala Glu Val Phe Gly Ala Ser Asp Ala Thr Glu Leu Pro His
                20                  25                  30

Met Val Gly Val Ser Arg Arg Thr Leu Phe Thr Phe His Asp Leu Tyr
            35                  40                  45

Phe His Leu Val Glu Ala Asp Glu Asp Ile Thr Pro Asn Leu Tyr Arg
        50                  55                  60

Ala Arg Ser His Pro Leu Tyr Ala Asp Val Asn Lys Arg Leu Gly Glu
65                  70                  75                  80

Leu Val Ala Pro Tyr Asp Pro Gly Trp Lys Glu Pro Lys Asp Ala Met
                85                  90                  95
```

```
Ala Ser Pro Phe Tyr Thr Trp Thr Ala Glu Gln Gly Arg Ile Arg
            100                 105                 110

<210> SEQ ID NO 102
<211> LENGTH: 1032
<212> TYPE: DNA
<213> ORGANISM: Aspergillus nidulans
<220> FEATURE:
<221> NAME/KEY: CDS
<222> LOCATION: (1)..(1032)
<223> OTHER INFORMATION: ZhuJ-1 gene [GenBank ID number AN5060.2)
      encoding a Cyclase [GenBank ID number XP_662664.1]

<400> SEQUENCE: 102 atg tct gaa tac acc aac ctg ccc gac tac gac tcc ctc ccg ccc gtc      48
Met Ser Glu Tyr Thr Asn Leu Pro Asp Tyr Asp Ser Leu Pro Pro Val
1               5                   10                  15 aaa ggc atg ccc cgt ggc tgc gca tgg ggt att ttc gac aaa gac ggc      96
Lys Gly Met Pro Arg Gly Cys Ala Trp Gly Ile Phe Asp Lys Asp Gly
                20                  25                  30 aag aaa gac cat atc ggg tgt ctg aac ctg ctt acg ccg tct gtg gtg     144
Lys Lys Asp His Ile Gly Cys Leu Asn Leu Leu Thr Pro Ser Val Val
            35                  40                  45 cgc gcg gcc ttg aag gaa gcg gag acg ggc cag tcg gtc tcg ctg aac     192
Arg Ala Ala Leu Lys Glu Ala Glu Thr Gly Gln Ser Val Ser Leu Asn
        50                  55                  60 tgg ccc atc aac gct atc cat aag cct ggg ttc cag cgc gcg gga ctc     240
Trp Pro Ile Asn Ala Ile His Lys Pro Gly Phe Gln Arg Ala Gly Leu
65                  70                  75                  80 gag cat aag gtc tct tcg ttc cag gac acg ccc ttc aag tta cat ggg     288
Glu His Lys Val Ser Ser Phe Gln Asp Thr Pro Phe Lys Leu His Gly
                85                  90                  95 ttc gac gac gag gtc gcg ttc aat act cag tgc tcc agc cag tgg gat     336
Phe Asp Asp Glu Val Ala Phe Asn Thr Gln Cys Ser Ser Gln Trp Asp
                100                 105                 110 agc ttg gta cat ttc gcg cac cag ccg tcc ggg ttc agc tat aat gga     384
Ser Leu Val His Phe Ala His Gln Pro Ser Gly Phe Ser Tyr Asn Gly
            115                 120                 125 gtc aag cca acg aag gag gcg ctg ctg cag gca gac gcg ccc ttc cac     432
Val Lys Pro Thr Lys Glu Ala Leu Leu Gln Ala Asp Ala Pro Phe His
        130                 135                 140 aaa gac acc gac ctg ccc acg ctt gac cac tgg cat tcg cgc ggc ggc     480
Lys Asp Thr Asp Leu Pro Thr Leu Asp His Trp His Ser Arg Gly Gly
145                 150                 155                 160 ctc gtc ggt cgc ggt gtc ctg ctc gac tac caa gcg tac gca gac gcg     528
Leu Val Gly Arg Gly Val Leu Leu Asp Tyr Gln Ala Tyr Ala Asp Ala
                165                 170                 175 cac ggc cgg aag tac tct ccc ttt gag acg cac aaa atc act gtc gcc     576
His Gly Arg Lys Tyr Ser Pro Phe Glu Thr His Lys Ile Thr Val Ala
            180                 185                 190 gat ctc gag gct gtg gct caa tgg gag aat gtt gag ttg cgc cag ggc     624
Asp Leu Glu Ala Val Ala Gln Trp Glu Asn Val Glu Leu Arg Gln Gly
        195                 200                 205 gat att gtc atc atc cgg tcc ggg ttc aca aag ggg ctg cag gaa gct     672
Asp Ile Val Ile Ile Arg Ser Gly Phe Thr Lys Gly Leu Gln Glu Ala
    210                 215                 220 gcc acg cca gag aaa cag gca gag tgc atg gcc agc cac cga act gtc     720
Ala Thr Pro Glu Lys Gln Ala Glu Cys Met Ala Ser His Arg Thr Val
225                 230                 235                 240 ggg gtg gaa ggc aac gag gct acg gcg aag tgg ttc tgg aac aag cat     768
Gly Val Glu Gly Asn Glu Ala Thr Ala Lys Trp Phe Trp Asn Lys His
```

```
            245                 250                 255
ttt gcg gct gtt gcg ggc gat gcc atc gcg ttc gag tgt ctg ccg ccg    816
Phe Ala Ala Val Ala Gly Asp Ala Ile Ala Phe Glu Cys Leu Pro Pro
        260                 265                 270 tcg aaa gaa gat ggg aca gag ggg tcg att gga gat ctg gtg ctg cat    864
Ser Lys Glu Asp Gly Thr Glu Gly Ser Ile Gly Asp Leu Val Leu His
            275                 280                 285 cag tac ttc ctc ggc ctg ttc ggg ctg aat atc ggc gag ctg tgg gat    912
Gln Tyr Phe Leu Gly Leu Phe Gly Leu Asn Ile Gly Glu Leu Trp Asp
        290                 295                 300 ctt gag gcg ctg tcg aag ctt tgt gct gag aag aag cga tac tcg ttc    960
Leu Glu Ala Leu Ser Lys Leu Cys Ala Glu Lys Lys Arg Tyr Ser Phe
305                 310                 315                 320 ttg ctc aca agc tgt ccg ctc aac gtg cca ggc agc gtc ggg agc cca   1008
Leu Leu Thr Ser Cys Pro Leu Asn Val Pro Gly Ser Val Gly Ser Pro
                325                 330                 335 ccg aat gcg ctt gcg att ttt tag                                   1032
Pro Asn Ala Leu Ala Ile Phe
            340
```

<210> SEQ ID NO 103
<211> LENGTH: 343
<212> TYPE: PRT
<213> ORGANISM: Aspergillus nidulans

<400> SEQUENCE: 103

```
Met Ser Glu Tyr Thr Asn Leu Pro Asp Tyr Asp Ser Leu Pro Pro Val
1               5                   10                  15

Lys Gly Met Pro Arg Gly Cys Ala Trp Gly Ile Phe Asp Lys Asp Gly
            20                  25                  30

Lys Lys Asp His Ile Gly Cys Leu Asn Leu Leu Thr Pro Ser Val Val
        35                  40                  45

Arg Ala Ala Leu Lys Glu Ala Glu Thr Gly Gln Ser Val Ser Leu Asn
    50                  55                  60

Trp Pro Ile Asn Ala Ile His Lys Pro Gly Phe Gln Arg Ala Gly Leu
65                  70                  75                  80

Glu His Lys Val Ser Ser Phe Gln Asp Thr Pro Phe Lys Leu His Gly
                85                  90                  95

Phe Asp Asp Glu Val Ala Phe Asn Thr Gln Cys Ser Ser Gln Trp Asp
            100                 105                 110

Ser Leu Val His Phe Ala His Gln Pro Ser Gly Phe Ser Tyr Asn Gly
        115                 120                 125

Val Lys Pro Thr Lys Glu Ala Leu Leu Gln Ala Asp Ala Pro Phe His
    130                 135                 140

Lys Asp Thr Asp Leu Pro Thr Leu Asp His Trp His Ser Arg Gly Gly
145                 150                 155                 160

Leu Val Gly Arg Gly Val Leu Leu Asp Tyr Gln Ala Tyr Ala Asp Ala
                165                 170                 175

His Gly Arg Lys Tyr Ser Pro Phe Glu Thr His Lys Ile Thr Val Ala
            180                 185                 190

Asp Leu Glu Ala Val Ala Gln Trp Glu Asn Val Glu Leu Arg Gln Gly
        195                 200                 205

Asp Ile Val Ile Ile Arg Ser Gly Phe Thr Lys Gly Leu Gln Glu Ala
    210                 215                 220

Ala Thr Pro Glu Lys Gln Ala Glu Cys Met Ala Ser His Arg Thr Val
225                 230                 235                 240
```

-continued

```
Gly Val Glu Gly Asn Glu Ala Thr Ala Lys Trp Phe Trp Asn Lys His
            245                 250                 255

Phe Ala Ala Val Ala Gly Asp Ala Ile Ala Phe Glu Cys Leu Pro Pro
        260                 265                 270

Ser Lys Glu Asp Gly Thr Glu Gly Ser Ile Gly Asp Leu Val Leu His
    275                 280                 285

Gln Tyr Phe Leu Gly Leu Phe Gly Leu Asn Ile Gly Glu Leu Trp Asp
290                 295                 300

Leu Glu Ala Leu Ser Lys Leu Cys Ala Glu Lys Lys Arg Tyr Ser Phe
305                 310                 315                 320

Leu Leu Thr Ser Cys Pro Leu Asn Val Pro Gly Ser Val Gly Ser Pro
            325                 330                 335

Pro Asn Ala Leu Ala Ile Phe
            340
```

<210> SEQ ID NO 104
<211> LENGTH: 1014
<212> TYPE: DNA
<213> ORGANISM: Aspergillus nidulans
<220> FEATURE:
<221> NAME/KEY: CDS
<222> LOCATION: (1)..(1014)
<223> OTHER INFORMATION: ZhuJ-2 gene [GenBank ID number ANIA_11053) encoding a cyclase [GenBank ID number CBF74060.1]

<400> SEQUENCE: 104

```
atg gca ccc ctg cct tct att ccc acc ttc gac aac ctg acc ctc gac      48
Met Ala Pro Leu Pro Ser Ile Pro Thr Phe Asp Asn Leu Thr Leu Asp
1               5                   10                  15 ccc aat ggt ccc cct ggc aac gca tgg ggt cta ttt gga cct aat aat      96
Pro Asn Gly Pro Pro Gly Asn Ala Trp Gly Leu Phe Gly Pro Asn Asn
            20                  25                  30 gaa ctt ggg atg ctt aat ttg ctc acc ccc gag gta gtt aag aga gca     144
Glu Leu Gly Met Leu Asn Leu Leu Thr Pro Glu Val Val Lys Arg Ala
        35                  40                  45 gcc tcc gag gaa atc cgc gag ggg gtc cga ata tct ctt gat ctt cct     192
Ala Ser Glu Glu Ile Arg Glu Gly Val Arg Ile Ser Leu Asp Leu Pro
    50                  55                  60 cta aat cga ctc tcg cat ccg agc ttc aac cgg aaa ccc ttc atc caa     240
Leu Asn Arg Leu Ser His Pro Ser Phe Asn Arg Lys Pro Phe Ile Gln
65                  70                  75                  80 gag ctg gtt aat aag gca ccg agg att gtc aat gat gat atc ttg acg     288
Glu Leu Val Asn Lys Ala Pro Arg Ile Val Asn Asp Asp Ile Leu Thr
                85                  90                  95 ttc aat acg cag tcg agc acg cag tgg gat ggg ttt agg cat tac gga     336
Phe Asn Thr Gln Ser Ser Thr Gln Trp Asp Gly Phe Arg His Tyr Gly
            100                 105                 110 aac cag acg cat ggg tgt tac ttt aat ggc cat tcg ctg gat gag ctg     384
Asn Gln Thr His Gly Cys Tyr Phe Asn Gly His Ser Leu Asp Glu Leu
        115                 120                 125 aga gag tcg agg gtt atc gga att gac gca tgg tcc aac agc ggc ggc     432
Arg Glu Ser Arg Val Ile Gly Ile Asp Ala Trp Ser Asn Ser Gly Gly
    130                 135                 140 att gtc ggc cgg ggc att cta att gat tac gcg acc tgg gcg cag aga     480
Ile Val Gly Arg Gly Ile Leu Ile Asp Tyr Ala Thr Trp Ala Gln Arg
145                 150                 155                 160 aac tcc att gcc cta acg ccc ttc caa acg tct aca atc ccc ctc tca     528
Asn Ser Ile Ala Leu Thr Pro Phe Gln Thr Ser Thr Ile Pro Leu Ser
                165                 170                 175 tcc att cag cag ata atc cac gaa acc tcc cta acc ccc cgc cca ggc     576
```

```
Ser Ile Gln Gln Ile Ile His Glu Thr Ser Leu Thr Pro Arg Pro Gly
                180                 185                 190 gac atc ctc ttc atc cgc aca ggc ttc aca gaa gcc tac aac aag ctc       624
Asp Ile Leu Phe Ile Arg Thr Gly Phe Thr Glu Ala Tyr Asn Lys Leu
            195                 200                 205 acg ccg gac gaa gaa gca gcc att gcc gcg cga cca aca cca aac ttt       672
Thr Pro Asp Glu Glu Ala Ala Ile Ala Ala Arg Pro Thr Pro Asn Phe
210                 215                 220 gcg ggc gtc gag aac ggc aag aac aca ttg cgc tgg ttg tgg gag aac       720
Ala Gly Val Glu Asn Gly Lys Asn Thr Leu Arg Trp Leu Trp Glu Asn
225                 230                 235                 240 cag ttt gcg gca atc gcg agt gac agt cca gct ttt gaa ccg gcg ccg       768
Gln Phe Ala Ala Ile Ala Ser Asp Ser Pro Ala Phe Glu Pro Ala Pro
                245                 250                 255 ctg ttt agg ccc gag cag ggg gtt gga cat gag gtg acg ctg cat cag       816
Leu Phe Arg Pro Glu Gln Gly Val Gly His Glu Val Thr Leu His Gln
            260                 265                 270 tgg tgt ctg agt gcg tgg gga atg ccg atc ggg gag tac ttt gat ctg       864
Trp Cys Leu Ser Ala Trp Gly Met Pro Ile Gly Glu Tyr Phe Asp Leu
        275                 280                 285 gaa gag ctt gca aaa tat tgt agg gag aag ggg agg tgg agt ttc ttc       912
Glu Glu Leu Ala Lys Tyr Cys Arg Glu Lys Gly Arg Trp Ser Phe Phe
290                 295                 300 ttg agc agt att ccg ctt aag gtt tgt tat tta cct ttt tca ttt tat       960
Leu Ser Ser Ile Pro Leu Lys Val Cys Tyr Leu Pro Phe Ser Phe Tyr
305                 310                 315                 320 att ttt ttt gtt tct tat ttt gtt ttg ggc tat gta gtt tgc tgc aat      1008
Ile Phe Phe Val Ser Tyr Phe Val Leu Gly Tyr Val Val Cys Cys Asn
                325                 330                 335 tgc tga                                                              1014
Cys

<210> SEQ ID NO 105
<211> LENGTH: 337
<212> TYPE: PRT
<213> ORGANISM: Aspergillus nidulans

<400> SEQUENCE: 105

Met Ala Pro Leu Pro Ser Ile Pro Thr Phe Asp Asn Leu Thr Leu Asp
1               5                   10                  15

Pro Asn Gly Pro Pro Gly Asn Ala Trp Gly Leu Phe Gly Pro Asn Asn
            20                  25                  30

Glu Leu Gly Met Leu Asn Leu Leu Thr Pro Glu Val Val Lys Arg Ala
        35                  40                  45

Ala Ser Glu Glu Ile Arg Glu Gly Val Arg Ile Ser Leu Asp Leu Pro
    50                  55                  60

Leu Asn Arg Leu Ser His Pro Ser Phe Asn Arg Lys Pro Phe Ile Gln
65                  70                  75                  80

Glu Leu Val Asn Lys Ala Pro Arg Ile Val Asn Asp Ile Leu Thr
                85                  90                  95

Phe Asn Thr Gln Ser Ser Thr Gln Trp Asp Gly Phe Arg His Tyr Gly
            100                 105                 110

Asn Gln Thr His Gly Cys Tyr Phe Asn Gly His Ser Leu Asp Glu Leu
        115                 120                 125

Arg Glu Ser Arg Val Ile Gly Ile Asp Ala Trp Ser Asn Ser Gly Gly
    130                 135                 140

Ile Val Gly Arg Gly Ile Leu Ile Asp Tyr Ala Thr Trp Ala Gln Arg
145                 150                 155                 160
```

```
Asn Ser Ile Ala Leu Thr Pro Phe Gln Thr Ser Thr Ile Pro Leu Ser
                165                 170                 175

Ser Ile Gln Gln Ile Ile His Glu Thr Ser Leu Thr Pro Arg Pro Gly
            180                 185                 190

Asp Ile Leu Phe Ile Arg Thr Gly Phe Thr Glu Ala Tyr Asn Lys Leu
        195                 200                 205

Thr Pro Asp Glu Glu Ala Ala Ile Ala Ala Arg Pro Thr Pro Asn Phe
    210                 215                 220

Ala Gly Val Glu Asn Gly Lys Asn Thr Leu Arg Trp Leu Trp Glu Asn
225                 230                 235                 240

Gln Phe Ala Ala Ile Ala Ser Asp Ser Pro Ala Phe Glu Pro Ala Pro
                245                 250                 255

Leu Phe Arg Pro Glu Gln Gly Val Gly His Glu Val Thr Leu His Gln
            260                 265                 270

Trp Cys Leu Ser Ala Trp Gly Met Pro Ile Gly Glu Tyr Phe Asp Leu
        275                 280                 285

Glu Glu Leu Ala Lys Tyr Cys Arg Glu Lys Gly Arg Trp Ser Phe Phe
    290                 295                 300

Leu Ser Ser Ile Pro Leu Lys Val Cys Tyr Leu Pro Phe Ser Phe Tyr
305                 310                 315                 320

Ile Phe Phe Val Ser Tyr Phe Val Leu Gly Tyr Val Val Cys Cys Asn
                325                 330                 335

Cys

<210> SEQ ID NO 106
<211> LENGTH: 975
<212> TYPE: DNA
<213> ORGANISM: Aspergillus nidulans
<220> FEATURE:
<221> NAME/KEY: CDS
<222> LOCATION: (1)..(975)
<223> OTHER INFORMATION: ZhuJ-3 gene [GenBank ID number ANIA_10146)
      encoding cyclase [GenBank ID number CBF88175.1]

<400> SEQUENCE: 106 atg act act ttc gac cta cca gag aca ttt gat gac ctc ccc aac aag      48
Met Thr Thr Phe Asp Leu Pro Glu Thr Phe Asp Asp Leu Pro Asn Lys
1               5                   10                  15 cgc caa tac tgg cct gct ccg aaa ggc tcg ccc gaa gag ggc cta ggc      96
Arg Gln Tyr Trp Pro Ala Pro Lys Gly Ser Pro Glu Glu Gly Leu Gly
            20                  25                  30 atg ctc cgt atc ctg acc ccg gac atc gtt gcc aat gca gcc cgc caa     144
Met Leu Arg Ile Leu Thr Pro Asp Ile Val Ala Asn Ala Ala Arg Gln
        35                  40                  45 atc caa acg ggc gag cgg gta tgt ctg aac tgg gat att gag aac ttg     192
Ile Gln Thr Gly Glu Arg Val Cys Leu Asn Trp Asp Ile Glu Asn Leu
    50                  55                  60 aat cct cca ggt ttc aaa cgc aag ccc ttt gag cac agg ata aaa tgg     240
Asn Pro Pro Gly Phe Lys Arg Lys Pro Phe Glu His Arg Ile Lys Trp
65                  70                  75                  80 gtc gca gaa ggc gtg gct ttt gat gac gaa tat cac ttc aat cca cag     288
Val Ala Glu Gly Val Ala Phe Asp Asp Glu Tyr His Phe Asn Pro Gln
                85                  90                  95 cag tca tct caa tgg gac ggc ctc cgt cac cac aat ggg ccc gca cca     336
Gln Ser Ser Gln Trp Asp Gly Leu Arg His His Asn Gly Pro Ala Pro
            100                 105                 110 acg gcc gaa gat ccc aac tgc cga ctt ttc tac gga gga acg agc gca     384
Thr Ala Glu Asp Pro Asn Cys Arg Leu Phe Tyr Gly Gly Thr Ser Ala
```

```
             115                 120                 125
gaa gaa att caa gac cct aag aat ccc cgt atc gga atg ggg tac tgg      432
Glu Glu Ile Gln Asp Pro Lys Asn Pro Arg Ile Gly Met Gly Tyr Trp
    130                 135                 140 gcg aag aag ggc att gca gga cgc ggc gtc ctt atc gat ttc gtc tcg      480
Ala Lys Lys Gly Ile Ala Gly Arg Gly Val Leu Ile Asp Phe Val Ser
145                 150                 155                 160 tgg gct gaa aag aag gga atc ccc gtc aat gcc tta aca cag cag gag      528
Trp Ala Glu Lys Lys Gly Ile Pro Val Asn Ala Leu Thr Gln Gln Glu
                165                 170                 175 gtt tca cta gac act gtg cac gag att gcg cga gag tgc aag gtt gaa      576
Val Ser Leu Asp Thr Val His Glu Ile Ala Arg Glu Cys Lys Val Glu
            180                 185                 190 ttc caa cac ggc gac atc ttc ttc ctc aga gtc ggt ctg ccg caa aca      624
Phe Gln His Gly Asp Ile Phe Phe Leu Arg Val Gly Leu Pro Gln Thr
        195                 200                 205 tgg gcg gcc atg aac gat gag cag aaa caa gcg tac agc aag cag gcg      672
Trp Ala Ala Met Asn Asp Glu Gln Lys Gln Ala Tyr Ser Lys Gln Ala
    210                 215                 220 acc cca aaa cat gcc ggg atc gag caa agt gag cgt gtg cta cgg ttc      720
Thr Pro Lys His Ala Gly Ile Glu Gln Ser Glu Arg Val Leu Arg Phe
225                 230                 235                 240 ttt tgg gac aac cac ttt gcg gcg gtt gcg tca gac gcg gtc agt ttc      768
Phe Trp Asp Asn His Phe Ala Ala Val Ala Ser Asp Ala Val Ser Phe
                245                 250                 255 gag gtg tac cca cca ctt aac ccg gac ttt gat ctg cat cat cat cta      816
Glu Val Tyr Pro Pro Leu Asn Pro Asp Phe Asp Leu His His His Leu
            260                 265                 270 ctt gcg ggg tgg gga gta cct atc ggc gag atg ttt gat ttg gat ggg      864
Leu Ala Gly Trp Gly Val Pro Ile Gly Glu Met Phe Asp Leu Asp Gly
        275                 280                 285 ttg gcg gag atg tgt ata caa cat ggt cgc tgg acg ttt ttc gtc tcg      912
Leu Ala Glu Met Cys Ile Gln His Gly Arg Trp Thr Phe Phe Val Ser
    290                 295                 300 agt agc cct ttg aac tgt gcg aat ggg gtc tcg agt ccc ccg aac act      960
Ser Ser Pro Leu Asn Cys Ala Asn Gly Val Ser Ser Pro Pro Asn Thr
305                 310                 315                 320 atg gct att ttt tga                                                  975
Met Ala Ile Phe <210> SEQ ID NO 107
<211> LENGTH: 324
<212> TYPE: PRT
<213> ORGANISM: Aspergillus nidulans

<400> SEQUENCE: 107

Met Thr Thr Phe Asp Leu Pro Glu Thr Phe Asp Asp Leu Pro Asn Lys
1               5                   10                  15

Arg Gln Tyr Trp Pro Ala Pro Lys Gly Ser Pro Glu Glu Gly Leu Gly
            20                  25                  30

Met Leu Arg Ile Leu Thr Pro Asp Ile Val Ala Asn Ala Ala Arg Gln
        35                  40                  45

Ile Gln Thr Gly Glu Arg Val Cys Leu Asn Trp Asp Ile Glu Asn Leu
    50                  55                  60

Asn Pro Pro Gly Phe Lys Arg Lys Pro Phe Glu His Arg Ile Lys Trp
65                  70                  75                  80

Val Ala Glu Gly Val Ala Phe Asp Asp Glu Tyr His Phe Asn Pro Gln
                85                  90                  95
```

```
Gln Ser Ser Gln Trp Asp Gly Leu Arg His His Asn Gly Pro Ala Pro
                100                 105                 110

Thr Ala Glu Asp Pro Asn Cys Arg Leu Phe Tyr Gly Thr Ser Ala
        115                 120                 125

Glu Glu Ile Gln Asp Pro Lys Asn Pro Arg Ile Gly Met Gly Tyr Trp
        130                 135                 140

Ala Lys Lys Gly Ile Ala Gly Arg Gly Val Leu Ile Asp Phe Val Ser
145                 150                 155                 160

Trp Ala Glu Lys Lys Gly Ile Pro Val Asn Ala Leu Thr Gln Gln Glu
                165                 170                 175

Val Ser Leu Asp Thr Val His Glu Ile Ala Arg Glu Cys Lys Val Glu
            180                 185                 190

Phe Gln His Gly Asp Ile Phe Phe Leu Arg Val Gly Leu Pro Gln Thr
        195                 200                 205

Trp Ala Ala Met Asn Asp Glu Gln Lys Gln Ala Tyr Ser Lys Gln Ala
    210                 215                 220

Thr Pro Lys His Ala Gly Ile Glu Gln Ser Arg Val Leu Arg Phe
225                 230                 235                 240

Phe Trp Asp Asn His Phe Ala Ala Val Ala Ser Asp Ala Val Ser Phe
                245                 250                 255

Glu Val Tyr Pro Pro Leu Asn Pro Asp Phe Asp Leu His His His Leu
            260                 265                 270

Leu Ala Gly Trp Gly Val Pro Ile Gly Glu Met Phe Asp Leu Asp Gly
            275                 280                 285

Leu Ala Glu Met Cys Ile Gln His Gly Arg Trp Thr Phe Phe Val Ser
    290                 295                 300

Ser Ser Pro Leu Asn Cys Ala Asn Gly Val Ser Ser Pro Pro Asn Thr
305                 310                 315                 320

Met Ala Ile Phe

<210> SEQ ID NO 108
<211> LENGTH: 1044
<212> TYPE: DNA
<213> ORGANISM: Aspergillus nidulans
<220> FEATURE:
<221> NAME/KEY: CDS
<222> LOCATION: (1)..(1044)
<223> OTHER INFORMATION: ZhuJ-4 gene [GenBank ID number AN5068.2)
      encoding cyclase [GenBank ID number XP_662672.1]

<400> SEQUENCE: 108 atg gca gac agc aag ttg tcc cag tcg ccc tac gac att ccc tat gat      48
Met Ala Asp Ser Lys Leu Ser Gln Ser Pro Tyr Asp Ile Pro Tyr Asp
1               5                   10                  15 gag cta gcc aac ccc aga cag gtg tgg gta gga gag ccc gga agc gaa      96
Glu Leu Ala Asn Pro Arg Gln Val Trp Val Gly Glu Pro Gly Ser Glu
            20                  25                  30 gag gaa gga aag gca aag ctc ggc atg ctg acc cca gag gtg gtt cac     144
Glu Glu Gly Lys Ala Lys Leu Gly Met Leu Thr Pro Glu Val Val His
        35                  40                  45 ggg gcg gca gcg tcc gaa att cgg act ggc cgt cgc gtt acc atg ggg     192
Gly Ala Ala Ala Ser Glu Ile Arg Thr Gly Arg Arg Val Thr Met Gly
    50                  55                  60 tgg aca ttg acg gaa ttg ggg tat ccc aat ctc ggt cga cag ccg tgt     240
Trp Thr Leu Thr Glu Leu Gly Tyr Pro Asn Leu Gly Arg Gln Pro Cys
65                  70                  75                  80 aaa cat cga atc gtg cca ctg cta gac ggt ttg gcg ttc gat gac tat     288
Lys His Arg Ile Val Pro Leu Leu Asp Gly Leu Ala Phe Asp Asp Tyr
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 85  |     |     |     |     | 90  |     |     |     |     | 95  |     |     |      |
| tac | gaa | ttc | aat | ccg | caa | cag | agt | agc | caa | tgg | gac | ggg | ctt | cga | cat | 336  |
| Tyr | Glu | Phe | Asn | Pro | Gln | Gln | Ser | Ser | Gln | Trp | Asp | Gly | Leu | Arg | His |      |
|     |     |     | 100 |     |     |     |     | 105 |     |     |     |     | 110 |     |     |      |
| ttt | tcc | cag | acc | gtt | cct | gga | cag | agc | gag | cgt | gtc | ttc | tat | ggc | ggt | 384  |
| Phe | Ser | Gln | Thr | Val | Pro | Gly | Gln | Ser | Glu | Arg | Val | Phe | Tyr | Gly | Gly |      |
|     |     | 115 |     |     |     |     | 120 |     |     |     |     | 125 |     |     |     |      |
| aca | aca | gct | gcc | gag | atc | tac | gat | cgg | aag | aat | gac | cgc | atc | ggc | atg | 432  |
| Thr | Thr | Ala | Ala | Glu | Ile | Tyr | Asp | Arg | Lys | Asn | Asp | Arg | Ile | Gly | Met |      |
|     | 130 |     |     |     |     | 135 |     |     |     |     | 140 |     |     |     |     |      |
| cag | cat | tgg | gcc | aag | gaa | ggc | att | gca | ggc | cgc | ggc | gtc | ttg | att | gac | 480  |
| Gln | His | Trp | Ala | Lys | Glu | Gly | Ile | Ala | Gly | Arg | Gly | Val | Leu | Ile | Asp |      |
| 145 |     |     |     |     | 150 |     |     |     |     | 155 |     |     |     |     | 160 |      |
| tac | gcc | agt | tgg | gcg | aag | aag | aaa | ggg | atc | aag | tac | agc | acc | ttc | tcg | 528  |
| Tyr | Ala | Ser | Trp | Ala | Lys | Lys | Lys | Gly | Ile | Lys | Tyr | Ser | Thr | Phe | Ser |      |
|     |     |     |     | 165 |     |     |     |     | 170 |     |     |     |     | 175 |     |      |
| acc | cat | caa | gtc | cgc | ctg | tcg | gat | ata | cag | gag | att | gcc | aaa | gaa | tgc | 576  |
| Thr | His | Gln | Val | Arg | Leu | Ser | Asp | Ile | Gln | Glu | Ile | Ala | Lys | Glu | Cys |      |
|     |     |     | 180 |     |     |     |     | 185 |     |     |     |     | 190 |     |     |      |
| gag | att | gaa | ttc | aag | aag | ggc | gat | atc | cta | ttt | gtg | cgg | att | ggg | gtt | 624  |
| Glu | Ile | Glu | Phe | Lys | Lys | Gly | Asp | Ile | Leu | Phe | Val | Arg | Ile | Gly | Val |      |
|     |     | 195 |     |     |     |     | 200 |     |     |     |     | 205 |     |     |     |      |
| acc | gaa | gaa | tgg | gat | act | atg | acg | gag | gcc | cag | aag | caa | gag | tat | tcc | 672  |
| Thr | Glu | Glu | Trp | Asp | Thr | Met | Thr | Glu | Ala | Gln | Lys | Gln | Glu | Tyr | Ser |      |
|     | 210 |     |     |     |     | 215 |     |     |     |     | 220 |     |     |     |     |      |
| aac | aac | agc | aaa | ccc | tta | cac | gcc | ggc | gtg | gaa | gcc | acc | gag | gat | atg | 720  |
| Asn | Asn | Ser | Lys | Pro | Leu | His | Ala | Gly | Val | Glu | Ala | Thr | Glu | Asp | Met |      |
| 225 |     |     |     |     | 230 |     |     |     |     | 235 |     |     |     |     | 240 |      |
| ctg | cgg | tgg | cta | tgg | aat | gag | aaa | ttc | gct | gcg | att | gcc | agt | gac | gct | 768  |
| Leu | Arg | Trp | Leu | Trp | Asn | Glu | Lys | Phe | Ala | Ala | Ile | Ala | Ser | Asp | Ala |      |
|     |     |     |     | 245 |     |     |     |     | 250 |     |     |     |     | 255 |     |      |
| atc | agt | tgg | gag | gtt | tat | ccg | cct | cag | tcc | gat | att | ttc | ctg | cat | gag | 816  |
| Ile | Ser | Trp | Glu | Val | Tyr | Pro | Pro | Gln | Ser | Asp | Ile | Phe | Leu | His | Glu |      |
|     |     |     | 260 |     |     |     |     | 265 |     |     |     |     | 270 |     |     |      |
| tac | gtt | ctg | gct | gga | tgg | gga | atg | cca | att | ggc | gaa | ctt | ttc | gat | ctg | 864  |
| Tyr | Val | Leu | Ala | Gly | Trp | Gly | Met | Pro | Ile | Gly | Glu | Leu | Phe | Asp | Leu |      |
|     |     | 275 |     |     |     |     | 280 |     |     |     |     | 285 |     |     |     |      |
| gaa | gct | cta | gct | cga | atg | tgc | att | gaa | cac | aag | cgc | tgg | agc | ttc | ttc | 912  |
| Glu | Ala | Leu | Ala | Arg | Met | Cys | Ile | Glu | His | Lys | Arg | Trp | Ser | Phe | Phe |      |
|     | 290 |     |     |     |     | 295 |     |     |     |     | 300 |     |     |     |     |      |
| gta | gcg | tcg | att | cca | ctc | aac | atg | cca | ggg | gtg | ccc | gcc | aca | ccc | aaa | 960  |
| Val | Ala | Ser | Ile | Pro | Leu | Asn | Met | Pro | Gly | Val | Pro | Ala | Thr | Pro | Lys |      |
| 305 |     |     |     |     | 310 |     |     |     |     | 315 |     |     |     |     | 320 |      |
| gct | cct | gaa | gtg | ctt | gac | cag | agc | aac | atc | agc | aag | ttt | cag | cac | gcc | 1008 |
| Ala | Pro | Glu | Val | Leu | Asp | Gln | Ser | Asn | Ile | Ser | Lys | Phe | Gln | His | Ala |      |
|     |     |     |     | 325 |     |     |     |     | 330 |     |     |     |     | 335 |     |      |
| tcg | atc | gtg | atg | gat | gta | ttt | gaa | acc | aga | gga | tag |     |     |     |     | 1044 |
| Ser | Ile | Val | Met | Asp | Val | Phe | Glu | Thr | Arg | Gly |     |     |     |     |     |      |
|     |     |     | 340 |     |     |     |     | 345 |     |     |     |     |     |     |     |      |

<210> SEQ ID NO 109
<211> LENGTH: 347
<212> TYPE: PRT
<213> ORGANISM: Aspergillus nidulans

<400> SEQUENCE: 109

| Met | Ala | Asp | Ser | Lys | Leu | Ser | Gln | Ser | Pro | Tyr | Asp | Ile | Pro | Tyr | Asp |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |

| Glu | Leu | Ala | Asn | Pro | Arg | Gln | Val | Trp | Val | Gly | Glu | Pro | Gly | Ser | Glu |
| --- | --- | --- | --- | --- | --- | --- | --- | --- | --- | --- | --- | --- | --- | --- | --- |
|     |     |     | 20  |     |     |     |     | 25  |     |     |     |     | 30  |     |     |

Glu Gly Lys Ala Lys Leu Gly Met Leu Thr Pro Glu Val His
            35                  40                  45

Gly Ala Ala Ser Glu Ile Arg Thr Gly Arg Arg Val Thr Met Gly
 50                  55                  60

Trp Thr Leu Thr Glu Leu Gly Tyr Pro Asn Leu Gly Arg Gln Pro Cys
 65                  70                  75                  80

Lys His Arg Ile Val Pro Leu Leu Asp Gly Leu Ala Phe Asp Asp Tyr
                 85                  90                  95

Tyr Glu Phe Asn Pro Gln Ser Ser Gln Trp Asp Gly Leu Arg His
            100                 105                 110

Phe Ser Gln Thr Val Pro Gly Gln Ser Glu Arg Val Phe Tyr Gly Gly
            115                 120                 125

Thr Thr Ala Ala Glu Ile Tyr Asp Arg Lys Asn Asp Arg Ile Gly Met
    130                 135                 140

Gln His Trp Ala Lys Glu Gly Ile Ala Gly Arg Gly Val Leu Ile Asp
145                 150                 155                 160

Tyr Ala Ser Trp Ala Lys Lys Gly Ile Lys Tyr Ser Thr Phe Ser
                165                 170                 175

Thr His Gln Val Arg Leu Ser Asp Ile Gln Glu Ile Ala Lys Glu Cys
            180                 185                 190

Glu Ile Glu Phe Lys Lys Gly Asp Ile Leu Phe Val Arg Ile Gly Val
            195                 200                 205

Thr Glu Glu Trp Asp Thr Met Thr Glu Ala Gln Lys Gln Glu Tyr Ser
    210                 215                 220

Asn Asn Ser Lys Pro Leu His Ala Gly Val Glu Ala Thr Glu Asp Met
225                 230                 235                 240

Leu Arg Trp Leu Trp Asn Glu Lys Phe Ala Ala Ile Ala Ser Asp Ala
                245                 250                 255

Ile Ser Trp Glu Val Tyr Pro Pro Gln Ser Asp Ile Phe Leu His Glu
            260                 265                 270

Tyr Val Leu Ala Gly Trp Gly Met Pro Ile Gly Glu Leu Phe Asp Leu
    275                 280                 285

Glu Ala Leu Ala Arg Met Cys Ile Glu His Lys Arg Trp Ser Phe Phe
290                 295                 300

Val Ala Ser Ile Pro Leu Asn Met Pro Gly Val Pro Ala Thr Pro Lys
305                 310                 315                 320

Ala Pro Glu Val Leu Asp Gln Ser Asn Ile Ser Lys Phe Gln His Ala
                325                 330                 335

Ser Ile Val Met Asp Val Phe Glu Thr Arg Gly
            340                 345

<210> SEQ ID NO 110
<211> LENGTH: 42
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(42)
<223> OTHER INFORMATION: Sc_Gh_2-PS-F

<400> SEQUENCE: 110
atcaacgggu aaaaatgggt tcctactctt ctgatgatgt tg                                42

<210> SEQ ID NO 111

```
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(40)
<223> OTHER INFORMATION: Sc_Gh_2-PS-R primer

<400> SEQUENCE: 111
cgtgcgautt agttaccatt agcaacagca gcagtaactc                                40

<210> SEQ ID NO 112
<211> LENGTH: 42
<212> TYPE: DNA
<213> ORGANISM: Aloe arborescens
<220> FEATURE:
<221> NAME/KEY: primer_bind
<222> LOCATION: (1)..(42)
<223> OTHER INFORMATION: Sc_AaOKS-F primer

<400> SEQUENCE: 112
atcaacgggd uaaaaatgag tagtttatca aatgccagtc ac                            42

<210> SEQ ID NO 113
<211> LENGTH: 37
<212> TYPE: DNA
<213> ORGANISM: Aloe arborescens
<220> FEATURE:
<221> NAME/KEY: primer_bind
<222> LOCATION: (1)..(37)
<223> OTHER INFORMATION: Sc_AaOKS-R primer

<400> SEQUENCE: 113
cgtgcgadut tacatcaatg gcaaggaatg caataag                                  37

<210> SEQ ID NO 114
<211> LENGTH: 39
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(39)
<223> OTHER INFORMATION: Sc_Aa_PCS-F

<400> SEQUENCE: 114
atcaacgggu aaaaatgtcc tccttgtcta attccttgc                                39

<210> SEQ ID NO 115
<211> LENGTH: 31
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(31)
<223> OTHER INFORMATION: Sc_Aa_PCS-R primer

<400> SEQUENCE: 115
cgtgcgautt acatcaaagg caaagaatgc a                                        31

<210> SEQ ID NO 116
<211> LENGTH: 38
<212> TYPE: DNA
<213> ORGANISM: Artificial Sequence
```

```
<220> FEATURE:
<223> OTHER INFORMATION: synthetic
<220> FEATURE:
<221> NAME/KEY: primer_bind
<222> LOCATION: (1)..(38)
<223> OTHER INFORMATION: Sc_DluHKS-F primer

<400> SEQUENCE: 116
atcaacgggu aaaaatggct tcgttgaag gtatgggt                                   38

<210> SEQ ID NO 117
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(37)
<223> OTHER INFORMATION: Sc_DluHKS-R

<400> SEQUENCE: 117
cgtgcgautt agttgttgat tgggaaggat ctcaaga                                   37

<210> SEQ ID NO 118
<211> LENGTH: 41
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(41)
<223> OTHER INFORMATION: Sc_AaPKS3/ALS-F

<400> SEQUENCE: 118
atcaacgggu aaaaatgggt tccttgtctg attctactcc a                              41

<210> SEQ ID NO 119
<211> LENGTH: 34
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(34)
<223> OTHER INFORMATION: Sc_AaPKS3/ALS-R primer

<400> SEQUENCE: 119
cgtgcgautt agactggtgg caaagaatgc aaca                                      34

<210> SEQ ID NO 120
<211> LENGTH: 33
<212> TYPE: DNA
<213> ORGANISM: Saccharomyces cerevisiae
<220> FEATURE:
<221> NAME/KEY: primer_bind
<222> LOCATION: (1)..(33)
<223> OTHER INFORMATION: PGK1-d primer (Phosphoglycerate kinase 1 gene)

<400> SEQUENCE: 120
acccgttgad ugccgcttgt tttatatttg ttg                                       33

<210> SEQ ID NO 121
<211> LENGTH: 30
<212> TYPE: DNA
<213> ORGANISM: Saccharomyces cerevisiae
<220> FEATURE:
```

```
<221> NAME/KEY: primer_bind
<222> LOCATION: (1)..(30)
<223> OTHER INFORMATION: PGK1-F primer (Phosphoglycerate kinase 1 gene)

<400> SEQUENCE: 121
cacgcgadug gcctggaagt accttcaaag                                           30

<210> SEQ ID NO 122
<211> LENGTH: 42
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(42)
<223> OTHER INFORMATION: Sc_ZhuI-F primer

<400> SEQUENCE: 122
agcgatacgu aaaaatgaga cacgttgaac acacagttac cg                             42

<210> SEQ ID NO 123
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(37)
<223> OTHER INFORMATION: Sc_ZhuI-R primer

<400> SEQUENCE: 123
cacgcgautt attatgcagt tacggtacca acaccac                                   37

<210> SEQ ID NO 124
<211> LENGTH: 39
<212> TYPE: DNA
<213> ORGANISM: Fusarium graminearum
<220> FEATURE:
<221> NAME/KEY: primer_bind
<222> LOCATION: (1)..(39)
<223> OTHER INFORMATION: Sc_BIK1-PT-F primer - Fusarium graminearum BIK1
      gene

<400> SEQUENCE: 124
agcgatacgu aaaaatgaga ttgtccgatt ccgttcaca                                 39

<210> SEQ ID NO 125
<211> LENGTH: 37
<212> TYPE: DNA
<213> ORGANISM: Fusarium graminearum
<220> FEATURE:
<221> NAME/KEY: primer_bind
<222> LOCATION: (1)..(37)
<223> OTHER INFORMATION: Sc_BIK1-PT-R primer from Fusarium graminearum
      BIK1 gene

<400> SEQUENCE: 125
cacgcgautt aaatcaaacc agaagctgaa ccaactg                                   37

<210> SEQ ID NO 126
<211> LENGTH: 36
<212> TYPE: DNA
<213> ORGANISM: Artificial Sequence
<220> FEATURE:
<223> OTHER INFORMATION: synthetic
<220> FEATURE:
<221> NAME/KEY: primer_bind
```

```
<222> LOCATION: (1)..(36)
<223> OTHER INFORMATION: Sc_gra-orf4-F primer

<400> SEQUENCE: 126
agcgatacgu aaaaatggct agaactgctg ctttgc                         36

<210> SEQ ID NO 127
<211> LENGTH: 32
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(32)
<223> OTHER INFORMATION: Sc_gra-orf4-R primer

<400> SEQUENCE: 127
cacgcgautt aacctgcttc agcagcttca gc                             32

<210> SEQ ID NO 128
<211> LENGTH: 47
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(47)
<223> OTHER INFORMATION: Sc_ZhuJ-F primer

<400> SEQUENCE: 128
agcgatacgu aaaaatgtcc ggtagaaaga ccttttttaga tttgtca            47

<210> SEQ ID NO 129
<211> LENGTH: 41
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(41)
<223> OTHER INFORMATION: Sc_ZhuJ-R primer

<400> SEQUENCE: 129
cacgcgautt attaatcttc ttcttcttgt tcgaaaacag c                   41

<210> SEQ ID NO 130
<211> LENGTH: 36
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(36)
<223> OTHER INFORMATION: OKS-Forward

<400> SEQUENCE: 130
ggcttaauat gagttcactc tccaacgctt cccatc                         36

<210> SEQ ID NO 131
<211> LENGTH: 41
<212> TYPE: DNA
<213> ORGANISM: Artificial Sequence
<220> FEATURE:
<223> OTHER INFORMATION: synthetic
<220> FEATURE:
```

```
<221> NAME/KEY: primer_bind
<222> LOCATION: (1)..(41)
<223> OTHER INFORMATION: OKS-Reverse primer

<400> SEQUENCE: 131
ggtttaautt acatgagagg caggctgtgg agaaggatag t                              41

<210> SEQ ID NO 132
<211> LENGTH: 26
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(26)
<223> OTHER INFORMATION: ZhuI-Forward primer

<400> SEQUENCE: 132
ggcttaauat gaggcatgtc gagcat                                              26

<210> SEQ ID NO 133
<211> LENGTH: 31
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(31)
<223> OTHER INFORMATION: ZhuI-Reverse primer

<400> SEQUENCE: 133
ggtttaautt atgccgtgac agttccgaca c                                         31

<210> SEQ ID NO 134
<211> LENGTH: 26
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(26)
<223> OTHER INFORMATION: ZhuJ-Forward primer

<400> SEQUENCE: 134
ggcttaauat gtccggacgt aagacg                                              26

<210> SEQ ID NO 135
<211> LENGTH: 31
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(31)
<223> OTHER INFORMATION: ZhuJ-Reverse primer

<400> SEQUENCE: 135
ggtttaautt aatcttcctc ctcctgttca a                                         31

<210> SEQ ID NO 136
<211> LENGTH: 26
<212> TYPE: DNA
<213> ORGANISM: Artificial Sequence
<220> FEATURE:
<223> OTHER INFORMATION: synthetic
```

```
<220> FEATURE:
<221> NAME/KEY: primer_bind
<222> LOCATION: (1)..(26)
<223> OTHER INFORMATION: CYC-Forward primer

<400> SEQUENCE: 136
ggcttaauat gactgttgaa gttcgt                                          26

<210> SEQ ID NO 137
<211> LENGTH: 31
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(31)

<400> SEQUENCE: 137
ggtttaautt aagccaagca agtaggaagt t                                    31

<210> SEQ ID NO 138
<211> LENGTH: 26
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(26)
<223> OTHER INFORMATION: CYC_DH-Forward primer

<400> SEQUENCE: 138
ggcttaauat gtcaagacct ggagaa                                          26

<210> SEQ ID NO 139
<211> LENGTH: 26
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(26)
<223> OTHER INFORMATION: CYC_DH-Reverse primer

<400> SEQUENCE: 139
ggtttaautt agcttgccgg cccagc                                          26

<210> SEQ ID NO 140
<211> LENGTH: 36
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(36)
<223> OTHER INFORMATION: KR-Forward primer

<400> SEQUENCE: 140
ggcttaauat ggcaacccag gatagcgaag ttgcac                               36

<210> SEQ ID NO 141
<211> LENGTH: 41
<212> TYPE: DNA
<213> ORGANISM: Artificial Sequence
<220> FEATURE:
<223> OTHER INFORMATION: synthetic
```

```
<220> FEATURE:
<221> NAME/KEY: primer_bind
<222> LOCATION: (1)..(41)
<223> OTHER INFORMATION: KR-Reverse

<400> SEQUENCE: 141
ggtttaautt aatagttgcc cagaccacca caaacattca g                        41

<210> SEQ ID NO 142
<211> LENGTH: 29
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(29)
<223> OTHER INFORMATION: HpPKS2-Forward primer

<400> SEQUENCE: 142
ggcttaauat gggttccctt gacaatggt                                      29

<210> SEQ ID NO 143
<211> LENGTH: 31
<212> TYPE: DNA
<213> ORGANISM: Artificial Sequence
<220> FEATURE:
<223> OTHER INFORMATION: synthetic
<220> FEATURE:
<221> NAME/KEY: primer_bind
<222> LOCATION: (1)..(31)
<223> OTHER INFORMATION: HpPKS2-Reverse primer

<400> SEQUENCE: 143
ggtttaautt agagaggcac acttcggaga a                                   31

<210> SEQ ID NO 144
<211> LENGTH: 39
<212> TYPE: DNA
<213> ORGANISM: Aspergillus nidulans
<220> FEATURE:
<221> NAME/KEY: primer_bind
<222> LOCATION: (1)..(39)
<223> OTHER INFORMATION: Sc_mdpG-PT-F primer from Aspergillus nidulans
      mdpG-PT gene

<400> SEQUENCE: 144
agcgatacgu aaaaatgtct ggtttgagaa cttccaccg                           39

<210> SEQ ID NO 145
<211> LENGTH: 36
<212> TYPE: DNA
<213> ORGANISM: Aspergillus nidulans
<220> FEATURE:
<221> NAME/KEY: primer_bind
<222> LOCATION: (1)..(36)
<223> OTHER INFORMATION: Sc_mdpG-PT-R primer from Aspergillus nidulans
      mdpG-PT gene

<400> SEQUENCE: 145
cacgcgautt agaccaaagc tttagcagca actgaa                              36
```

UNITED STATES PATENT AND TRADEMARK OFFICE
CERTIFICATE OF CORRECTION

PATENT NO. : 10,519,460 B2  
APPLICATION NO. : 15/735023  
DATED : December 31, 2019  
INVENTOR(S) : Rasmus John Normand Frandsen et al.

It is certified that error appears in the above-identified patent and that said Letters Patent is hereby corrected as shown below:

On the Title Page  
Item (71), "CHR, HANSEN NATURAL COLORS A/S" should read -- CHR. HANSEN NATURAL COLORS A/S --.

In the Claims  
Column 247, Claim 2, Line 47, "PhID" should read -- Ph1D --.  
Column 248, Claim 4, Line 34, delete the second instance of "heterologous".  
Column 249, Claim 7, Line 28, delete the second instance of "heterologous".  
Column 249, Claim 7, Line 66, "PGL1 PT" should read -- PGL1_PT --.  
Column 250, Claim 12, Lines 38-39, delete the second instance of "heterologous".  
Column 251, Claim 15, Line 23, delete the second instance of "heterologous".  
Column 252, Claim 16, Line 18, delete the second instance of "heterologous".

Signed and Sealed this  
Second Day of February, 2021

Drew Hirshfeld  
*Performing the Functions and Duties of the*  
*Under Secretary of Commerce for Intellectual Property and*  
*Director of the United States Patent and Trademark Office*